United States Patent
Guenaga et al.

(10) Patent No.: US 11,149,082 B2
(45) Date of Patent: Oct. 19, 2021

(54) MULTISPECIFIC ANTIBODIES TARGETING HUMAN IMMUNODEFICIENCY VIRUS AND METHODS OF USING THE SAME

(71) Applicants: UNIVERSITY OF MARYLAND, COLLEGE PARK, College Park, MD (US); THE UNITED STATES OF AMERICA, AS REPRESENTED BY THE SECRETARY, DEPARTMENT OF HEALTH AND HUMAN SERVICES, Bethesda, MD (US); INTERNATIONAL AIDS VACCINE INITIATIVE, New York, NY (US)

(72) Inventors: Javier Guenaga, San Diego, CA (US); Yuxing Li, Boyds, MD (US); James Steinhardt, Westminster, MD (US); John R. Mascola, Rockville, MD (US)

(73) Assignees: University of Maryland, College Park, College Park, MD (US); The United States of America, As Represented By, Bethesda, MD (US); International AIDS Vaccine Initiative, New York, NY (US)

( * ) Notice: Subject to any disclaimer, the term of this patent is extended or adjusted under 35 U.S.C. 154(b) by 0 days.

(21) Appl. No.: 16/342,962

(22) PCT Filed: Oct. 17, 2017

(86) PCT No.: PCT/US2017/057053
§ 371 (c)(1),
(2) Date: Apr. 17, 2019

(87) PCT Pub. No.: WO2018/075564
PCT Pub. Date: Apr. 26, 2018

(65) Prior Publication Data
US 2020/0123236 A1 Apr. 23, 2020

Related U.S. Application Data

(60) Provisional application No. 62/409,097, filed on Oct. 17, 2016.

(51) Int. Cl.
| | |
|---|---|
| A61K 39/00 | (2006.01) |
| C07K 16/10 | (2006.01) |
| C07K 16/28 | (2006.01) |
| C07K 16/30 | (2006.01) |
| A61K 39/21 | (2006.01) |
| A61K 47/68 | (2017.01) |
| A61P 31/18 | (2006.01) |

(52) U.S. Cl.
CPC ...... *C07K 16/1063* (2013.01); *A61K 47/6841* (2017.08); *A61P 31/18* (2018.01); *C07K 16/2812* (2013.01); *C07K 2317/31* (2013.01); *C07K 2317/35* (2013.01); *C07K 2317/52* (2013.01); *C07K 2317/55* (2013.01); *C07K 2317/622* (2013.01); *C07K 2317/732* (2013.01); *C07K 2317/76* (2013.01); *C07K 2317/92* (2013.01)

(58) Field of Classification Search
CPC .............. A61K 2039/505; A61K 39/21; C07K 16/1063; C07K 2317/92; C07K 2317/21
See application file for complete search history.

(56) References Cited

U.S. PATENT DOCUMENTS

| | | | |
|---|---|---|---|
| 4,816,467 A | 3/1989 | Doria et al. | |
| 4,946,778 A | 8/1990 | Ladner et al. | |
| 6,117,655 A | 9/2000 | Capon et al. | |
| 8,673,307 B1 | 3/2014 | Nussenzweig et al. | |
| 2010/0166806 A1 | 7/2010 | Castor | |
| 2010/0324034 A1 | 12/2010 | Hazuda et al. | |
| 2012/0203014 A1 | 8/2012 | Dinarello et al. | |
| 2012/0244166 A1 | 9/2012 | Mascola et al. | |
| 2015/0037334 A1 | 2/2015 | Kufer et al. | |
| 2016/0213779 A1 | 7/2016 | Barouch | |

FOREIGN PATENT DOCUMENTS

| | | |
|---|---|---|
| WO | 2010112193 A1 | 10/2010 |
| WO | 2012030904 A2 | 3/2012 |
| WO | 2012158948 A1 | 11/2012 |
| WO | 2013163427 A1 | 10/2013 |
| WO | WO2013163427 | * 10/2013 |
| WO | 2014063059 A1 | 4/2014 |
| WO | 2015117008 A2 | 8/2015 |
| WO | 2016014484 A1 | 1/2016 |
| WO | 2016037154 A1 | 3/2016 |
| WO | 2017079479 A1 | 5/2017 |

OTHER PUBLICATIONS

Ahmad ZA, et al., scFv antibody: principles and clinical application. Clin Dev Immunol 2012, 980250 (2012).
Ainavarapu SR, et al. Contour length and refolding rate of a small protein controlled by engineered disulfide bonds. Biophys J 92, 225-233 (2007).
Ananworanich J, Broadly neutralizing antibody and the HIV reservoir in acute HIV infection: a strategy toward HIV remission; Curr Opin HIV AIDS 10, 198-206 (2015).
Asokan M, et al. Bispecific Antibodies Targeting Different Epitopes on the HIV-1 Envelope Exhibit Broad and Potent Neutralization. J Virol 89, 12501-12512 (2015).
Balazs AB, etal., Antibody-based protection against HIV infection by vectored immunoprophylaxis. Nature 481:81-84 (2012).

(Continued)

*Primary Examiner* — Barry A Chestnut
(74) *Attorney, Agent, or Firm* — Carter, DeLuca & Farrell LLP

(57) ABSTRACT

The present disclosure relates to multispecific antibodies targeting the human immunodeficiency virus-1 (HIV-1) envelope, methods for their production, pharmaceutical compositions containing said antibodies and uses thereof in treatment and prevention of HIV infection.

18 Claims, 68 Drawing Sheets
Specification includes a Sequence Listing.

(56) References Cited

OTHER PUBLICATIONS

Balazs AB, et al., Vectored immunoprophylaxis protects humanized mice from mucosa. HIV transmission. Nat Med 20:296-300 (2014).
Bar KJ, et al. Effect of HIV Antibody VRC01 on Viral Rebound after Treatment Interruption. N Engl J Med 375, 2037-2050 (2016).
Barouch DH, et al., Immunologic strategies for HIV-1 remission and eradication. Science 345, 169-174 (2014).
Barouch DH, et al., Therapeutic efficacy of potent neutralizing HIV-I-specific monoclonal antibodies in SHIV-infected rhesus monkeys. Nature 503:224-228 (2013).
Barre-Sinoussi F, et al., Isolation of a T-lymphotropic retrovirus from a patient at risk for acquired immune deficiency syndrome (AIDS). Science 220:868-871 (1983).
Bolton DL, et al., Human Immunodeficiency Virus Type 1 Monoclonal Antibodies Suppress Acute Simian-Human Immunodeficiency Virus Viremia and Limit Seeding of Cell-Associated Viral Reservoirs. J Virol 90:1321-1332 (2016).
Bournazos S, et al., Bispecific Anti-HIV-1 Antibodies with Enhanced Breadth and Potency. Cell 165, 1609-1620 (2016).
Buchacher A, et al. Generation of human monoclonal antibodies against HIV-1 proteins; electrofusion and Epstein-Barr virus transformation for peripheral blood lymphocyte immortalization. AIDS Res Hum Retroviruses 10, 359-369 (1994).
Burton DR, et al., A large array of human monoclonal antibodies to type 1 human immunodeficiency ; virus from combinatorial libraries of asymptomatic seropositive individuals. Proc Natl Acad Sci U S A 88, 10134-10137 (1991).
Burton DR, Mascola JR. Antibody responses to envelope glycoproteins in HIV-1 infection. Nat Immunol 16, 571-576 (2015).
Burton DR. Antibodies, viruses and vaccines. Nat Rev Immunol 2, 706-713 (2002).
Caskey M, et al. Antibody 10-1074 suppresses viremia in HIV-1-infected individuals. Nat Med 23, 185-191 (2017).
Caskey M, et al.. Viraemia suppressed in HIV-1-infected humans by broadly neutralizing antibody 3BNC117. Nature 522, 487-491 (2015).
Chen X, et al., Fusion protein linkers: property, design and functionality. Adv Drug Deliv Rev 65, 1357-1369 (2013).
Cristina J, et al., Genetic variability and molecular evolution of hepatitis A virus. Virus Res 127, 151-157 (2007).
Dietzshold B, et al., Genotypic and phenotypic diversity of rabies virus variants involved in human rabies: ; implications for postexposure prophylaxis. J Hum Virol 3, 50-57 (2000).
Diskin R, et al., Restricting HIV-1 pathways for escape using rationally designed anti-HIV-I antibodies. J Exp Med 210:1235-1249 (2013).
Doria-Rose NA, et al., HIV-1 neutralization coverage is improved by combining monoclonal antibodies that target independent epitopes. J Virol 86, 3393-3397 (2012).
Galimidi RP, et al. Intra-spike crosslinking overcomes antibody evasion by HIV-1. Cell 160, 433-446 (2015).
Gallo RC, et al., Frequent detection and isolation of cytopathic retroviruses (HTLV-111) from patients with AIDS and at risk for AIDS. Science 224:500-503 (1984).
Gardner MR, et al. AAV-expressed eCD4-lg provides durable protection from multiple SHIV challenges. Nature 519, 87-91 (2015).
Graham BS, et al., History of passive antibody administration for prevention and treatment of infectious diseases. Curr Opin HIV AIDS 10, 129-134 (2015).
Guenaga J, et al. Structure-Guided Redesign Increases the Propensity of HIV Env to Generate Highly Stable Soluble Trimers. J Virol 90, 2806-2817 (2015).
Hessell AJ, et al. Early short-term treatment with neutralizing human monoclonal antibodies halts SHIV infection in infant macaques. Nat Med 22, 362-368 (2016).
Hollinger P, et al.. Engineered antibody fragments and the rise of single domains. Nat Biotechnol 23, 1126-1136 (2005).
Horwitz JA, et al., HIV-1 suppression and durable control by combining single broadly neutralizing antibodies and antiretroviral drugs in humanized mice. Proc Natl Acad Sci U S A 110, 16538-16543 (2013).
Hu Q, et al., Recent advances of cocktail chemotherapy by combination drug delivery systems. Adv Drug Deliv Rev 98, 19-34 (2016).
Huang J, et al., Broad and potent neutralization of HIV-1 by a gp41-specific human antibody. Nature 491, 406-412 (2012).
Huang J, et al., Identification of a CD4-Binding-Site Antibody to HIV that Evolved Near-Pan Neutralization Breadth. Immunity 45, 1108-1121 (2016).
Huang J, et al., Broad and potent HIV-I neutralization by a human antibody that binds the gp41-gp120 interface. Nature 515: 138-142.
Huang Y, et al., Engineered Bispecific Antibodies with Exquisite HIV-1-Neutralizing Activity. Cell 165, 1621-1631 (2016).
International Search Report and The Written Opinion of the International Searching Authority, dated Mar. 1, 2018, corresponding to counterpart International Application No. PCT/US17/57053; 20 total pages.
Irimia A, et al. Lipid interactions and angle of approach to the HIV-1 viral membrane of broadly neutralizing antibody 10E8: Insights for vaccine and therapeutic design. PLoS Pathog 13, e1006212 (2017).
Klein C, et al., The use of Cross MAb technology for the generation of bi- and multispecific antibodies. MAbs, 0 (2016).
Klein F, et al., HIV therapy by a combination of broadly neutralizing antibodies in humanized mice. Nature 492:118-122 (2012).
Kong R, et al., Improving neutralization potency and breadth by combining broadly reactive HIV-1 antibodies targeting major neutralization epitopes. J Virol 89, 2659-2671 (2015).
Korber B, et al., Timing the ancestor of the HIV-1 pandemic strains. Science 288, 1789-1796 (2000).
Korber B, et al., Evolutionary and immunological implications of contemporary HIV-1 variation. Br Med Bull 58, 19-42 (2001).
Kowalski M, et al., Functional regions of the envelope glycoprotein of human immunodeficiency virus type 1. Science 237:1351-1355 (1987).
Kriangkum J, et al., Bispecific and bifunctional single chain recombinant antibodies. Biomol Eng 18, 31-40 (2001).
Kwon YD, et al., Optimization of the Solubility of HIV-1-Neutralizing Angibody 10E8 through somatic Variation and Structure-Based Design. J Virol 90, 5899-5914 (2016).
Kwong PD, et al., Broadly neutralizing antibodies and the search for an HIV-1 vaccine: the end of the beginning. Nat Rev Immunol 13:693-701 (2013).
Lander GC, et al., Appoin: an integrated, database-driven pipeline to facilitate EM image processing. J Struct Biol 166, 95-102 (2009).
Ledgerwood JE, et al., Safety, pharmacokinetics and neutralization of the broadly neutralizing HIV-1 human monoclonal antibody VRC01 in healthy adults; Clin Exp Immunol 182, 289-301 (2015).
Lee JH, et al., Cryo-EM structure of a native, fully glycosylated, cleaved HIV-1 envelope trimer. Science 351:1043-1048 (2016).
Li M, et al., Human immunodeficiency virus type I env clones from acute and early subtype B infections for standardized assessments of vaccine-elicited neutralizing antibodies. J virol 79, 10108-10125 (2005).
Lin CL, et al., Hepatitis B virus genotypes and variants. Cold Spring Harb Perspect Med 5, a021436 (2015).
Lu M, et al., A trimeric structural domain of the HIV-1 transmembrane glycoprotein. Nat Struct Biol 2:1075-1082 (1995).
Lynch RM, et al., HIV-1 fitness cost associated with escape from the VRC01 class of CD4 binding site neutralizing antibodies. J Virol 89, 4201-4213 (2015).
Lynch RM, et al., Virologic effects of broadly neutralizing antibody VRC01 administration during chronic HIV-1 infection. Sci Transl Med 7, 319ra206 (2015).
Nisimura Y, et al., Early antibody therapy can induce long-lasting immunity to SHIV. Nature 543, 559-563 (2017).
Ogura T, et al., Topology representing network enables highly accurate classification of protein images taken by cryo; electron-microscope without masking. J Struct Biol 143, 185-200 (2003).

(56) References Cited

OTHER PUBLICATIONS

Pace CS, et al., Bispecific antibodies directed to CD4 domain 2 and HIV envelope exhibit exceptional breadth and picomolar potency against HIV-1. Pro Natl Acad Sci UDA 110, 13540-13545 (2013).
Pancera M, et al., Structure and immune recognition of trimeric pre-fusion HIV-1 Env. Nature 514:455-461 (2014).
Pegu A, et al., Neutralizing antibodies to HIV-1 envelope protect more effectively in vivo than those to the CD4 receptor. Sci Transl Med 6:243ra288 (2014).
Pettersen EF, et al., UCSF Chimera—a visualization system for exploratory research and analysis. J Comput Chem 25, 1606-1612 (2004).
Pietzsch J, et al., Human anti-HIV-neutralizing antibodies frequently target a conserved epitope essential for viral fitness. J Exp Med 207, 1995-2002 (2010).
Potter CS, et al., Leginon: a system for fully automated acquisition of 1000 electron micrographs a day. Ultramicroscopy 77, 153-161 (1999).
Ridgway JB, et al., 'Knobs-into-holes' engineering of antibody CH3 domains for heavy chain heterodimerization. Protein Eng 9, 617-621 (1996).
Rudicell RS, et al., Enhanced potency of a broadly neutralizing HIV-1 antibody in vitro improves protection against lentiviral infection in vivo. J Virol 88, 12669-12682 (2014).
Sather DN, et al., Broadly neutralizing antibodies developed by an HIV-positive elite neutralizer exact a replication fitness cost on the contemporaneous virus. J Virol 86, 12676-12685 (2012).
Scheid JF, et al., Sequence and structural convergence of broad and potent HIV antibodies that mimic CD4 binding. Science 333, 1633-1637 (2011).
Seaman MS, et al.,Tiered categorization of a diverse panel of HIV-1 Env pseudoviruses for assessment of neutralizing antibodies. J Virol 84, 1439-1452 (2010).
Shingai M, et al., Antibody-mediated immunotherapy of macaques chronically infected with SHIV suppresses viraemia. Nature 503:277-280 (2013).
Sievers SA, et al., Antibody engineering for increased potency, breadth and half-life. Curr Opin HIV AIDS 10, 151-159 (2015).

Stewart-Jones GB, et al., Trimeric HIV-1-Env Structures Define Glycan Shields from Clades A, B, and G. Cell 165, 813-826 (2016).
Sullender WM, et al., Antigenic and genetic diversity among the attachment proteins of group A respiratory syncytial viruses that have caused repeat infections in children. J Infect Dis 178, 925-932 (1998).
Sun M, et al.. Rational design and characterization of the novel, broad and potent bispecific HIV-1 neutralizing antibody iMabm36. J Acquir Immune Defic Syndr 66, 473-483 (2014).
Tebit DM, et al., HIV diversity, recombination and disease progression: how does fitness "fit" into the puzzle? AIDS Rev 9, 75-87 (2007).
Vidarsson G, et al., IgG subclasses and allotypes: from structure to effector functions. Front Immunol 5, 520 (2014).
Voss NR, et al., DoG Picker and TiltPicker: software tools to facilitate particle selection in single particle electron microscopy; J Struct Biol 166, 205-213 (2009).
Wagh K, et al., Optimal Combinations of Broadly Neutralizing Antibodies for Prevention and Treatment of HIV-1 Clade C Infection. PLoS Pathog 12, e1005520 (2016).
Walker LM, et al., Broad neutralization coverage of HIV by multiple highly potent antibodies. Nature 477, 466-470 (2011).
Wu X, et al., Rational design of envelope identifies broadly neutralizing human monoclonal antibodies to HIV-1. Science 329, 856-861 (2010).
Wyatt R, et al., The HIV-I envelope glycoproteins: fusogens, antigens, and immunogens. Science 280:1884-1888 (1998).
European Partial Supplementary Search Report dated May 7, 2020, corresponding to counterpart European Application No. 17862065.4; 17 total pages.
Nicole Welsh, "Abstracts of the HIV Research for Prevention Meeting 2016", HIVR4P Partnering for Prevention, Oct. 17-21, 2016; AIDS Research and Human Retroviruses; pp. 1-409.
Ming Sun et al., "Rational Design and Characterization of the Novel, Broad and Potent Bispecific HIV-1 Neutralizing Antibody iMabm36," Journal of Acquired Immune Deficiency Syndromes, vol. 66, No. 5, Aug. 1, 2014; pp. 473-483.
Bournazos et al., "Bispecific Anti-HIV-1 Antibodies with Enhanced Breadth and Potency," Cell, vol. 165, Jun. 16, 2016; pp. 1609-1620.

* cited by examiner

FIG. 5C

| | 5X-PGT121/ScFv | 5X-PGT121/ScFv | 5X-VRC01/ScFv | 4X-VRC01/ScFv | 5X-ScFv | 3X-ScFv | 5X-PGT121/IgG | 5X-IgG | 5X-IgG | 1.4X-VRC01/IgG | 3X-VRC01/IgG | PGT121 |
|---|---|---|---|---|---|---|---|---|---|---|---|---|
| # Viruses | 20 | 20 | 20 | 20 | 20 | 20 | 20 | 20 | 20 | 20 | 20 | 20 |
| Total VS Neutralized | | | | | | | | | | | | |
| IC50 <50µg/ml | 18 | 20 | 17 | 17 | 17 | 17 | 18 | 18 | 17 | 17 | 16 | 13 |
| IC50 <1µg/ml | 12 | 13 | 11 | 11 | 10 | 10 | 10 | 10 | 12 | 10 | 10 | 7 |
| % VS Neutralized | | | | | | | | | | | | |
| IC50 <50µg/ml | 90 | 100 | 85 | 85 | 85 | 85 | 90 | 90 | 85 | 85 | 80 | 65 |
| IC50 <1µg/ml | 60 | 65 | 55 | 55 | 50 | 50 | 50 | 50 | 60 | 50 | 50 | 35 |
| Median IC50 | 0.251 | 0.331 | 0.285 | 0.357 | 0.416 | 0.357 | 0.344 | 0.064 | 0.309 | 0.490 | 0.414 | 0.751 | 0.061 |
| Geometric Mean | 0.330 | 0.504 | 0.326 | 0.337 | 0.419 | 0.419 | 1.406 | 1.100 | 0.332 | 0.483 | 0.536 | 0.697 | 0.545 |

Scale
0.01-0.1
0.1-1.00
1.00-10.0
>10.0

| virus | clade | VRC01-5X-PGT121 ScFv | dVRC01-5X-PGT121 ScFv | PGT121-5X-VRC01 ScFv | PGT121-4X-VRC01 ScFv | PGT121-3X-VRC01 ScFv | VRC01 | PGT121 |
|---|---|---|---|---|---|---|---|---|
| Q769.d22.SG3 | A | 0.160 | 0.245 | 2.61 | 3.37 | 3.48 | 0.080 | >50 |
| 6095.V1.C10.SG3 | ACD | 0.024 | 0.053 | 0.018 | 0.031 | 0.034 | 0.444 | 1.20 |
| Q168.a2.SG3 | AD | 0.030 | 0.038 | 0.392 | 0.451 | 1.13 | 0.113 | >50 |
|

| virus | clade | VRC01-5X-PGT121 IgG | dVRC01-5X-PGT121 IgG | PGT121-5X-VRC01 IgG | PGT121-4X-VRC01 IgG | PGT121-3X-VRC01 IgG | VRC01 | PGT121 |
|---|---|---|---|---|---|---|---|---|
| Q769.d22.SG3 | A | 0.765 | 0.461 | 4.76 | 10.2 | 25.0 | 0.050 | >50 |
| 6095.V1.C10.SG3 | ACD | 0.198 | 0.159 | 0.035 | 0.041 | 0.055 | 0.444 | 1.20 |
| Q168.a2.SG3 | AD | 0.322 | 0.225 | 0.309 | 0.490 | 0.505 | 0.113 | >50 |
| BJOX009000.02.4.SG3 | AE | 2.35 | 1.51 | 0.175 | 0.166 | 0.322 | 3.32 | 7.07 |
| 242-14.SG3 | AG | >50 | >50 | >50 | >50 | >50 | >50 | >50 |
| T251-18.SG3 | AG | 41.7 | 30.2 | 13.0 | 25.9 | 41.7 | 8.59 | >50 |
| 7165.18.SG3 | B | 0.528 | 0.341 | 0.041 | 0.047 | 0.051 | >50 | 0.024 |
| AC10.29.SG3 | B | 0.600 | 0.266 | 0.058 | 0.090 | 0.080 | 2.71 | 0.121 |
| BG1168.01.SG3 | B | 6.08 | 4.61 | >50 | >50 | >50 | 0.911 | >50 |
| JRFL.JB.SG3 | B | 0.174 | 0.175 | 0.030 | 0.119 | 0.102 | 0.022 | 0.029 |
| QH0692.42.SG3 | B | 8.02 | 6.67 | 0.872 | 1.08 | 1.61 | 3.82 | 7.01 |
| 3637.V5.C3.SG3 | C | >50 | >50 | >50 | >50 | >50 | 14.9 | >50 |
| CAP210.E8.SG3 | C | 13.2 | 11.4 | 4.69 | 2.40 | 4.11 | >50 | 48.2 |
| DU172.17.SG3 | C | 0.965 | 0.883 | 0.178 | 0.207 | 0.254 | >50 | 0.089 |
| DU422.01.SG3 | C | 0.351 | 0.378 | 0.068 | 0.074 | 0.091 | >50 | 0.195 |
| TZA125.17.SG3 | C | 8.69 | 12.1 | 1.61 | 1.72 | 2.64 | >50 | 14.2 |
| ZM214.15.SG3 | C | 5.31 | 2.46 | 0.536 | 1.07 | 0.741 | 0.590 | 0.661 |
| ZM249.1.SG3 | C | 0.923 | 0.844 | 8.55 | 11.1 | >50 | 0.100 | >50 |
| 57128.vrc15.SG3 | D | 2.76 | 2.26 | 0.838 | 0.789 | 1.36 | >50 | 4.74 |
| X2088.c9.SG3 | G | 0.186 | 0.077 | 0.016 | 0.015 | 0.031 | >50 | 0.002 |

| Scale |
|---|
| <0.001 |
| .001-.01 |
| .01-.100 |
| .100-1.00 |
| 1.00-10.0 |
| >10.0 |

| | dVRC01-5X-PGT121 scFv | dVRC01-5X-PGT121 IgG | VRC01 | PGT121 |
|---|---|---|---|---|
| # Viruses | 200 | 200 | 200 | 208 |
| Total VS Neutralized | | | | |
| IC50 <50ug/ml | 193 | 192 | 182 | 131 |
| IC50 <10ug/ml | 189 | 187 | 178 | 125 |
| IC50 <1.0ug/ml | 157 | 142 | 146 | 108 |
| IC50 <0.1ug/ml | 110 | 57 | 39 | 94 |
| IC50 <0.01ug/ml | 23 | 0 | 0 | 58 |
| % VS Neutralized | | | | |
| IC50 <50ug/ml | 97 | 96 | 91 | 63 |
| IC50 <10ug/ml | 95 | 94 | 89 | 60 |
| IC50 <1.0ug/ml | 79 | 71 | 73 | 52 |
| IC50 <0.1ug/ml | 55 | 29 | 20 | 45 |
| IC50 <0.01ug/ml | 12 | 0 | 0 | 28 |
| Median IC50 | 0.0700 | 0.1975 | 0.2855 | 0.0130 |
| Geometric Mean | 0.1045 | 0.2385 | 0.3031 | 0.0237 |

FIG. 6B

| Virus ID | Clade | Bispecific | | Parental | |
|---|---|---|---|---|---|
| | | dVRC01-5X-PGT121 ScFv | dVRC01-5X-PGT121 IgG | VRC01 | PGT121 |
| BJOX025000.01.1 | AE | >50 | >50 | 20.2 | >25 |
| CNE3 | AE | >50 | >50 | 1.79 | >25 |
| 6322.V4.C1 | C | 15.2 | 5.00 | >50 | >25 |
| 6631.V3.C10 | C | 1.91 | 2.63 | >50 | >25 |
| CAP210.E8 | C | 2.55 | 4.88 | >50 | >25 |
| 3817.v2.c59 | CD | 7.23 | 1.16 | >50 | >25 |

| Virus ID | Clade | dVRC01-5X-PGT121 ScFv | dVRC01-5X-PGT121 IgG1 | VRC01 | PGT121 |
|---|---|---|---|---|---|
| CNE7 | BC | 0.053 | 0.175 | 0.137 | 1.02 |
| 286.36 | C | | 0.097 | 0.223 | |
| 288.38 | C | 0.160 | 0.105 | 1.38 | |
| 001395.1.11 | C | 0.208 | 0.684 | 0.106 | >50 |
| 001428.2.42 | C | 0.324 | 0.685 | 0.104 | 0.023 |
| 0077.V1.C16 | C | | 0.492 | 0.113 | 31.8 |
| 00836.2.5 | C | 0.169 | 0.447 | 0.122 | >50 |
| 0921.V2.C14 | C | 0.752 | 0.135 | 0.230 | 1.02 |
| 16055-2.3 | C | 0.015 | 0.090 | 0.100 | 9.41 |
| 16845-2.22 | C | 1.99 | 5.21 | 1.35 | |
| 16936-2.21 | C | 0.021 | 0.038 | 0.154 | |
| 25710-2.43 | C | 0.053 | 0.054 | 0.042 | |
| 25711-2.4 | C | 0.678 | 1.103 | 0.559 | 0.139 |
| 25925-2.22 | C | 0.780 | 0.188 | 0.350 | 0.153 |
| 26191-2.48 | C | 0.107 | 0.406 | 0.183 | >50 |
| 3168.V4.C10 | C | 11.4 | 18.9 | 1.97 | >50 |
| 3637.V5.C3 | C | 0.372 | 1.48 | 2.81 | >50 |
| 3873.V1.C24 | C | 15.2 | 5.00 | >50 | >50 |
| 4736 | C | 0.169 | 0.053 | 1.93 | 0.016 |
| 6322.V4.C1 | C | 1.91 | 3.63 | >50 | 0.119 |
| 6471.V1.C16 | C | 0.122 | 0.243 | 0.143 | 0.119 |
| 6631.V3.C10 | C | 0.109 | 0.149 | 0.253 | >50 |
| 6644.V2.C33 | C | 0.026 | 0.080 | 0.086 | 0.018 |
| 6785.V5.C14 | C | 0.053 | 0.013 | 0.528 | 0.018 |
| 6838.V1.C35 | C | 0.028 | | >50 | |
| 962H651.01 | C | 1.55 | 4.83 | 1.34 | >50 |
| BR025.9 | C | 3.45 | 1.28 | 1.07 | >50 |
| CAP210.E8 | C | 0.251 | 0.100 | 6.75 | 2.00 |
| CAP244.D3 | C | 0.166 | 0.375 | 1.25 | |
| CAP255.206.C9 | C | 0.061 | 0.020 | | 0.015 |
| CAP45.C3 | C | | | | |
| Ce1176.A3 | C | | | | |

| virus | clade | 35O22-5X-10E8 IgG1 | 10E8 | 35O22 |
|---|---|---|---|---|
| Q769.d22.SG3 | A | 0.009 | 0.78 | 0.053 |
| 3589.V1.C4.SG3 | AC | 0.014 | 3.19 | >50 |
| T251-18.SG3 | AG | 0.058 | 0.42 | >50 |
| AC10.29.SG3 | B | 0.089 | 0.14 | >50 |
| QH0692.42.SG3 | B | 0.086 | 0.52 | >50 |
| ZM106.9.SG3 | C | 15.30 | 34.02 | >50 |
| ZM214.15.SG3 | C | 0.042 | 1.75 | >50 |

FIG. 9C

| virus | clade | VRC01-5X-PGT121 ScFv | dVRC01-5X-PGT121 ScFv | PGT121-5X-VRC01 ScFv | PGT121-6X-VRC01 ScFv | PGT121-3X-VRC01 ScFv | VRC01 | PGT 121 |
|---|---|---|---|---|---|---|---|---|
| Q769.d22.SG3 | A | 0.160 | 8.245 | 7.61 | 3.37 | 3.48 | 0.050 | >50 |
| 6095.V1.C10.SG3 | ACD | 0.023 | 0.050 | 0.046 | 0.053 | 0.027 | 0.044 | 1.30 |
| Q168.a2.SG3 | AD | 10.30 | 0.086 | 0.092 | 0.451 | 1.13 | 0.102 | >50 |
| BJOX009000.02.4.SG3 | AE | 0.83 | 0.330 | 0.138 | 0.357 | 0.316 | 3.33 | 7.07 |
| 242-14.SG3 | AG | >50 | 19.4 | >50 | >50 | >50 | >50 | >50 |
| T251-18.SG3 | AG | 14.3 | 8.53 | 9.46 | 8.28 | 15.9 | 8.59 | >50 |
| 7165.18.SG3 | B | 10.90 | 0.105 | 0.074 | 0.053 | 0.021 | >50 | 0.024 |
| AC10.29.SG3 | B | 0.62 | 0.067 | 0.076 | 0.009 | 0.016 | 2.71 | 0.101 |
| BG1168.01.SG3 | B | 0.68 | 2.38 | >50 | >50 | >50 | 0.051 | >50 |
| JRFL.JB.SG3 | B | 0.044 | 0.050 | 0.014 | 0.072 | 0.002 | 0.072 | 0.059 |
| QH0692.42.SG3 | B | 2.06 | 1.83 | 3.36 | 0.374 | 0.666 | 3.82 | 7.01 |
| 3637.V5.C3.SG3 | C | >50 | 49.4 | >50 | >50 | >50 | 14.9 | >50 |
| CAP210.E8.SG3 | C | 6.10 | 3.06 | 13.3 | 11.8 | 22.9 | >50 | 48.2 |
| DU172.17.SG3 | C | 0.152 | 0.310 | 0.107 | 0.073 | 0.081 | >50 | 0.085 |
| DU422.01.SG3 | C | 0.060 | 0.091 | 0.045 | 0.056 | 0.085 | >50 | 0.105 |
| TZA125.17.SG3 | C | 3.07 | 3.44 | 5.27 | 3.32 | 5.51 | >50 | 14.2 |
| ZM214.15.SG3 | C | 0.144 | 0.710 | 0.098 | 0.274 | 0.101 | 0.890 | 0.661 |
| ZM249.1.SG3 | C | 0.19 | 0.225 | 3.46 | 4.93 | 6.29 | 3.01 | >50 |
| 5712B.vf15.SG3 | D | 1.02 | 0.564 | 19.3 | 10.5 | 15.2 | >50 | 4.74 |
| X2088.c9.SG3 | G | 10.70 | 0.025 | 0.056 | 0.040 | 0.046 | >50 | 0.053 |

| Sensitivity | N | VRC01 | PGT121 | Potency (μg/mL) Bi-ScFv* | Bi-NAb |
|---|---|---|---|---|---|
| VRC01(S) × PGT121(S) | 125 | 0.27 | 0.019 | 0.144 (2.1x, 0.1x) | 0.131(1.9x, 0.1x) |
| VRC01(R) × PGT121(S) | 8 | >50 | 0.11 | 0.174 (0.7x) | 0.164 (0.7x) |
| VRC01(S) × PGT121(R) | 63 | 0.30 | >50 | 1.46 (0.1x) | 1.28 (0.2x) |
| VRC01(R) × PGT121(R) | 12 | >50 | >50 | 21.7 (NA, NA) | 4.9 (NA, NA) |
| All Viruses | 208 | 0.29 | 0.013 | 0.210 (1.4x, 0.1x) | 0.198 (1.3x, 0.1x) |

| Sensitivity | N | VRC01 | PGT121 | Potency (μg/mL) 10E8 | Tri-NAb |
|---|---|---|---|---|---|
| VRC01(S) × PGT121(S) × 10E8(S) | 122 | 0.274 | 0.013 | 0.392 | 0.037 (7.5x, 0.3x, 10.7x) |
| VRC01(R) × PGT121(S) × 10E8(S) | 7 | >50 | 0.03 | 0.224 | 0.98 (0.3x, 2.3x) |
| VRC01(S) × PGT121(R) × 10E8(S) | 62 | 0.299 | >50 | 0.394 | 0.170 (1.8x, 2.3x) |
| VRC01(S) × PGT121(S) × 10E8(R) | 3 | 0.487 | 0.118 | >50 | 0.131 (3.7x, 0.9x) |
| VRC01(R) × PGT121(R) × 10E8(S) | 12 | >50 | >50 | 0.746 | 2.36 (0.4x) |
| VRC01(R) × PGT121(S) × 10E8(R) | 1 | >50 | 0.001 | >50 | 0.017 (0.0x) |
| VRC01(S) × PGT121(R) × 10E8(R) | 1 | 0.512 | >50 | >50 | 0.772 (0.7x) |
| VRC01(R) × PGT121(R) × 10E8(R) | 0 | NA | NA | NA | NA |
| All Viruses | 208 | 0.2865 | 0.013 | 0.392 | 0.063 (4.5x, 0.2x, 6.2x) |

FIG. 17E

| | | Bi-ScFv | Bi-NAb | Tri-NAb | Tetra-NAb1 | Tetra-NAb2 | Parental mAbs | | |
|---|---|---|---|---|---|---|---|---|---|
| Virus ID | Clade | dVRC01-5X-PGT121 ScFv | dVRC01-5X-PGT121 Fc | 10E8/dVRC01-5X-PGT121 | 10E8-5X-35O22/dVRC01-5X-PGT121 | 35O22-5X-10E8/dVRC01-5X-PGT121 | VRC01 | PGT121 | 10E8 | 35O22 |
| 0260.v5.c36 | A | 0.124 | 0.416 | 0.170 | 0.131 | 0.062 | 0.523 | 0.039 | 9.87 | 0.078 |
| 0330.v4.c3 | A | 0.062 | 0.241 | 0.092 | 0.055 | 0.054 | 0.066 | 0.004 | 1.12 | >50 |
| 0439.v5.c1 | A | 1.57 | 2.93 | 0.471 | 1.02 | 0.215 | 0.228 | >50 | 1.23 | 0.120 |
| 3365.v2.c20 | A | 0.070 | 0.232 | 0.078 | 0.077 | 0.063 | 0.060 | 0.039 | 1.60 | >50 |
| 3415.v1.c1 | A | 0.354 | 0.847 | 0.312 | 0.425 | 0.300 | 0.087 | >50 | 4.69 | >50 |
| 3718.v3.c11 | A | 0.116 | 0.295 | 0.147 | 0.123 | 0.141 | 0.411 | 1.40 | 0.838 | >50 |
| 398-F1_F6_20 | A | 0.015 | 0.147 | 0.105 | 0.017 | 0.019 | 0.102 | >50 | 0.704 | >50 |
| BB201.B42 | A | 0.015 | 0.063 | 0.049 | 0.094 | 0.051 | 0.262 | >50 | 0.613 | >50 |
| BB539.2B13 | A | 1.82 | 1.29 | 0.296 | 0.835 | 0.415 | 0.105 | >50 | 0.591 | >50 |
| BG505.W6M.C2 | A | 0.065 | 0.134 | 0.089 | 0.131 | 0.077 | 0.037 | 0.032 | 0.689 | >50 |
| BI369.9A | A | 0.087 | 0.103 | 0.072 | 0.237 | 0.081 | 0.147 | >50 | 0.136 | >50 |
| BS208.B1 | A | 0.061 | 0.096 | 0.026 | 0.093 | 0.033 | 0.027 | >50 | 0.219 | >50 |
| KER2008.12 | A | 0.067 | 0.233 | 0.131 | 0.148 | 0.036 | 0.487 | 2.22 | >50 | >50 |
| KER2018.11 | A | 0.064 | 0.271 | 0.211 | 0.279 | 0.131 | 0.348 | >50 | 1.89 | 0.062 |
| KNH1209.18 | A | 0.014 | 0.049 | 0.034 | 0.051 | 0.045 | 0.119 | 0.019 | 0.406 | 0.040 |
| MB201.A1 | A | 0.070 | 0.036 | 0.030 | 0.023 | 0.023 | 0.241 | 0.004 | 0.411 | >50 |
| MB539.2B7 | A | 1.94 | 4.16 | 0.772 | 2.33 | 1.14 | 0.512 | >50 | >50 | 1.49 |
| MI369.A5 | A | 0.056 | 0.155 | 0.107 | 0.150 | 0.075 | 0.236 | 0.021 | 0.671 | 0.042 |
| MS208.A1 | A | 0.504 | 0.994 | 0.405 | 0.755 | 1.17 | 0.174 | >50 | 0.187 | >50 |
| Q23.17 | A | 0.080 | 0.131 | 0.038 | 0.041 | 0.036 | 0.099 | 0.014 | 0.461 | 0.013 |
| Q259.17 | A | 0.013 | 0.093 | 0.042 | 0.646 | 0.149 | 0.095 | >50 | 4.76 | 0.053 |
| Q769.d22 | A | 0.175 | 0.489 | 0.315 | 0.254 | 0.126 | 0.035 | >50 | 1.91 | 0.635 |
| Q769.h5 | A | 0.094 | 0.325 | 0.229 | 0.168 | 0.827 | 0.032 | >50 | 2.89 | 0.006 |
| Q842.d12 | A | 0.030 | 0.139 | 0.048 | 0.039 | 0.070 | 0.034 | 0.016 | 2.82 | >50 |
| QH209.14M.A2 | A | 0.125 | 0.456 | 0.168 | 0.161 | 0.072 | 0.026 | >50 | 1.30 | >50 |
| RW020.2 | A | 0.066 | 0.032 | 0.021 | 0.033 | 0.022 | 0.217 | 0.022 | 0.902 | 0.139 |
| UG037.8 | A | 0.104 | 0.333 | 0.092 | 0.138 | 0.084 | 0.073 | 0.065 | 0.048 | 0.195 |
| 246-F3.C10.2 | AC | 0.028 | 0.092 | 0.037 | 0.099 | 0.017 | 0.254 | >50 | 0.210 | 0.121 |
| 3301.V1.C24 | AC | 0.023 | 0.065 | 0.070 | 0.075 | 0.066 | 0.095 | 0.024 | 1.91 | 0.057 |
| 3589.V1.C4 | AC | 0.127 | 0.475 | 0.208 | 0.230 | 0.112 | 0.051 | >50 | 5.77 | 0.006 |
| 6540.v4.c1 | AC | >50 | >50 | 28.7 | >50 | >50 | >50 | >50 | 2.24 | >50 |

| | | Bi-ScFv | Bi-NAb | Tri-NAb | Tetra-NAb1 | Tetra-NAb2 | Parental mAbs | | | |
|---|---|---|---|---|---|---|---|---|---|---|
| Virus ID | Clade | dVRC01-5X-PGT121 ScFv | dVRC01-5X-PGT121 Fc | 10E8/dVRC01-5X-PGT121 | 10E8-5X-35O22/dVRC01-5X-PGT121 | 35O22-5X-10E8/dVRC01-5X-PGT121 | VRC01 | PGT121 | 10E8 | 35O22 |
| 6545.V4.C1 | AC | >50 | >50 | 5.56 | 9.91 | 1.51 | >50 | >50 | 2.54 | >50 |
| 0815.V3.C3 | ACD | 0.031 | 0.109 | 0.058 | 0.071 | 0.033 | 0.029 | 0.020 | 0.491 | 0.012 |
| 6095.V1.C10 | ACD | 0.146 | 0.331 | 0.012 | 0.047 | 0.063 | 0.631 | 37.3 | | >50 |
| 3468.V1.C12 | AD | 0.085 | 0.045 | 0.025 | 0.022 | 0.019 | 0.053 | 0.042 | 0.381 | |
| Q168.a2 | AD | 0.057 | 0.14 | 0.126 | 0.184 | 0.095 | 0.101 | >50 | 0.463 | 0.051 |
| Q461.e2 | AD | 3.28 | 6.73 | 4.41 | 5.04 | 0.208 | 0.420 | >50 | 2.29 | |
| 620345.c1 | AE | >50 | >50 | 26.3 | >50 | >50 | >50 | >50 | 0.988 | >50 |
| BJOX009000.02.4 | AE | 0.226 | 0.654 | 0.063 | 0.115 | 0.180 | 1.74 | 14.7 | 0.251 | >50 |
| BJOX010000.06.2 | AE | 4.85 | 18.8 | 0.177 | 0.409 | 0.326 | 8.40 | >50 | 0.080 | 3.00 |
| BJOX025000.01.1 | AE | >50 | >50 | 0.357 | 0.113 | 0.100 | 20.2 | >50 | 0.226 | 3.00 |
| BJOX028000.10.3 | AE | 0.152 | 0.285 | 0.076 | 0.077 | 0.066 | 0.185 | >50 | 0.167 | |
| C1080.c3 | AE | 6.87 | 5.02 | 0.077 | 0.069 | 0.071 | 2.63 | >50 | 0.108 | 0.077 |
| C2101.c1 | AE | 1.47 | 1.86 | 0.138 | 0.293 | 0.051 | 0.269 | >50 | 1.10 | |
| C3347.c11 | AE | 1.77 | 1.73 | 0.205 | 0.011 | 0.057 | 0.213 | >50 | 0.019 | 0.044 |
| C4118.09 | AE | 2.00 | 2.26 | 0.113 | 0.077 | 0.020 | 0.285 | >50 | 0.421 | |
| CM244.ec1 | AE | 0.237 | 0.857 | 0.117 | 0.142 | 0.139 | 0.116 | >50 | 0.353 | 0.023 |
| CNE3 | AE | >50 | >50 | 3.85 | 3.12 | 0.479 | 1.79 | >50 | 1.37 | 0.020 |
| CNE5 | AE | 1.01 | 4.59 | 0.163 | 0.40 | 0.192 | 0.358 | >50 | 1.17 | >50 |
| CNE55 | AE | 1.78 | 5.74 | 0.233 | 0.340 | 0.229 | 0.358 | >50 | 0.108 | >50 |
| CNE56 | AE | 2.74 | 6.54 | 0.476 | 1.02 | 0.754 | 0.525 | >50 | 0.068 | >50 |
| CNE59 | AE | 2.83 | 2.26 | 0.065 | 0.331 | 0.603 | 0.363 | >50 | 0.060 | >50 |
| CNE8 | AE | 0.356 | 1.14 | 0.031 | 0.025 | 0.095 | 0.209 | >50 | 0.353 | >50 |
| M02138 | AE | 4.92 | 7.18 | 0.055 | 0.138 | 0.221 | 0.858 | >50 | 0.014 | >50 |
| R1166.c1 | AE | 4.58 | 10.6 | 0.557 | 0.124 | 0.275 | 2.09 | >50 | 0.488 | >50 |
| R2184.c4 | AE | 0.791 | 2.33 | 0.894 | 0.859 | 0.525 | 0.206 | >50 | 0.576 | 0.052 |
| R3265.c6 | AE | 2.87 | 6.81 | 0.015 | 1.16 | 0.773 | 0.382 | >50 | 1.58 | >50 |
| TH023.6 | AE | 5.07 | 1.05 | 0.027 | 0.042 | 0.056 | 0.546 | >50 | | 0.046 |
| TH966.8 | AE | 2.29 | 3.47 | 0.256 | 0.135 | 0.227 | 0.390 | >50 | 0.039 | >50 |
| TH976.17 | AE | 1.05 | 2.96 | 0.067 | 0.370 | 0.282 | 0.259 | >50 | 0.292 | 1.00 |
| 235-47 | AG | 0.083 | 0.246 | 0.067 | 0.094 | 0.086 | 0.843 | 0.10 | 0.244 | >50 |
| 242.14 | AG | 33.2 | >50 | 1.23 | 19.3 | 3.01 | >50 | >50 | 0.568 | >50 |

| Virus ID | Clade | Bi-ScFv dVRC01-5X-PGT121 ScFv | Bi-NAb dVRC01-5X-PGT121 Fc | Tri-NAb 10E8/dVRC01-5X-PGT121 | Tetra-NAb1 dVRC01-5X-10E8-5X-PGT121 | Tetra-NAb2 35O22-5X-10E8-5X-PGT121 | VRC01 | PGT121 | 10E8 | 35O22 |
|---|---|---|---|---|---|---|---|---|---|---|
| 263-8 | AG | 0.250 | 0.683 | 0.227 | 0.133 | 0.112 | 0.176 | 1.23 | 0.229 | >50 |
| 269-12 | AG | 0.656 | 0.239 | 0.063 | 0.069 | 0.055 | 0.333 | 0.164 | 0.124 | >50 |
| 271-11 | AG | 0.105 | 0.032 | 0.020 | 0.024 | 0.012 | 0.059 | 11.7 | 0.891 | 0.030 |
| 928-28 | AG | 1.16 | 2.63 | 0.089 | 0.206 | 0.349 | 0.394 | 31.0 | 0.073 | >50 |
| DJ263.8 | AG | 0.010 | 0.100 | 0.004 | 0.038 | 0.055 | 0.047 | 0.064 | 0.009 | 0.030 |
| T250-4 | AG | 0.047 | 0.028 | 0.025 | 0.035 | 0.016 | >50 | 0.062 | 1.07 | >50 |
| T251-18 | AG | 2.86 | 8.32 | 0.032 | 0.084 | 0.046 | 4.21 | 10.8 | 0.666 | >50 |
| T253-11 | AG | 0.717 | 2.29 | 0.239 | 0.243 | 0.128 | 0.397 | >50 | 1.21 | 2.89 |
| T255-34 | AG | 0.034 | 0.089 | 0.013 | 0.016 | 0.036 | 0.980 | >50 | 0.228 | 0.012 |
| T257-31 | AG | 0.480 | 1.71 | 0.247 | 0.250 | 0.194 | 1.72 | >50 | 0.336 | >50 |
| T266-60 | AG | 0.534 | 1.40 | 0.694 | 0.418 | 0.282 | 1.81 | 0.160 | >50 | >50 |
| T278-50 | AG | >50 | >50 | 2.36 | 1.51 | 0.165 | >50 | >50 | 0.357 | 2.27 |
| T280-5 | AG | 0.014 | 0.050 | 0.004 | 0.047 | 0.038 | 0.032 | 0.107 | 0.715 | >50 |
| T33-7 | AG | 0.033 | 0.180 | 0.105 | 0.079 | 0.044 | 0.018 | >50 | 0.618 | 1.10 |
| 3988.25 | B | 0.058 | 0.038 | 0.033 | 0.045 | 0.055 | 0.494 | 0.147 | 0.071 | 0.609 |
| 5768.04 | B | 0.042 | 0.103 | 0.124 | 0.108 | 0.074 | 0.365 | 0.039 | 1.63 | 0.074 |
| 6101.10 | B | 0.018 | 0.036 | 0.010 | 0.016 | 0.015 | 0.055 | 0.032 | 0.009 | >50 |
| 6535.3 | B | 0.033 | 0.03 | 0.07 | 0.017 | 0.023 | 1.93 | 0.03 | 0.130 | >50 |
| 7165.18 | B | 0.085 | 0.196 | 0.055 | 0.106 | 0.116 | 28.2 | 0.019 | 0.659 | >50 |
| 45_01dG5 | B | 0.016 | 0.051 | 0.015 | 0.020 | 0.013 | 0.018 | 0.02 | 0.106 | >50 |
| 89.6.DG | B | 0.124 | 0.160 | 0.128 | 0.020 | 0.023 | 0.762 | 0.016 | 0.312 | >50 |
| AC10.29 | B | 0.179 | 0.534 | 0.128 | 0.289 | 0.308 | 1.81 | 0.028 | 0.102 | >50 |
| ADA.DG | B | 0.075 | 0.193 | 0.022 | 0.094 | 0.082 | 0.470 | 0.197 | 0.03 | >50 |
| Bal.01 | B | 0.107 | 0.028 | 0.031 | 0.032 | 0.034 | 0.095 | 0.011 | 0.421 | >50 |
| BaL.26 | B | 0.023 | 0.080 | 0.036 | 0.062 | 0.031 | 0.042 | 0.010 | 0.519 | 0.03 |
| BG1168.01 | B | 2.03 | 2.27 | 0.580 | 1.54 | 1.46 | 0.869 | >50 | 0.396 | >50 |
| BL01.DG | B | >50 | >50 | 4.01 | 10.5 | 1.70 | >50 | >50 | 0.352 | 0.03 |
| BR07.DG | B | 0.162 | 0.333 | 0.091 | 0.070 | 0.049 | 1.57 | 0.04 | 0.118 | 0.03 |
| BX08.16 | B | 0.055 | 0.053 | 0.020 | 0.077 | 0.082 | 0.274 | 0.07 | 0.203 | 0.040 |
| CAAN.A2 | B | 0.052 | 0.104 | 0.055 | 0.040 | 0.026 | 1.03 | 0.03 | 1.45 | 0.03 |
| CNE10 | B | 0.074 | 0.090 | 0.018 | 0.029 | 0.027 | 0.565 | 0.03 | 0.014 | >50 |

IC50 (ug/mL): <0.10 / 0.10-1.00 / 1.00-10.0 / >10.0

Parental mAbs

FIG. 18C

| Virus ID | Clade | Bi-ScFv dVRC01-5X-PGT121 ScFv | Bi-NAb dVRC01-5X-PGT121 Fc | Tri-NAb 10E8-5X/dVRC01-5X-PGT121 | Tetra-NAb1 10E8-5X-35O22/dVRC01-5X-PGT121 | Tetra-NAb2 35O22-5X-10E8/dVRC01-5X-PGT121 | VRC01 | PGT121 | 10E8 | 35O22 |
|---|---|---|---|---|---|---|---|---|---|---|
| CNE12 | B | 0.023 | 0.073 | 0.021 | 0.031 | 0.025 | 0.866 | 0.182 | 0.301 | 0.010 |
| CNE14 | B | 0.012 | 0.048 | 0.008 | 0.021 | 0.018 | 0.275 | 0.062 | 0.151 | 13.45 |
| CNE4 | B | 0.359 | 0.966 | 0.063 | 0.187 | 0.100 | 0.910 | 11.5 | 0.059 | 17.3 |
| CNE57 | B | 0.050 | 0.155 | 0.029 | 0.075 | 0.066 | 0.553 | 14.4 | 0.059 | 3.070 |
| HO86.8 | B | >50 | >50 | 5.94 | 4.32 | 0.527 | >50 | >50 | 0.326 | >50 |
| HT593.1 | B | 0.445 | 1.10 | 0.094 | 0.370 | 0.416 | 0.476 | >50 | 0.049 | >50 |
| HXB2.DG | B | 0.024 | 0.065 | 0.004 | 0.019 | 0.017 | 0.034 | >50 | 0.707 | 17.3 |
| JRCSF.JB | B | 0.036 | 0.278 | 0.158 | 0.167 | 0.145 | 0.362 | 0.063 | 0.429 | 3.070 |
| JRFL.JB | B | 0.021 | 0.087 | 0.053 | 0.081 | 0.053 | 0.828 | 0.013 | 0.174 | 3.020 |
| MN.3 | B | 0.057 | 0.057 | 0.016 | 0.027 | 0.036 | 0.020 | >50 | 0.115 | 3.059 |
| PVO.04 | B | 0.497 | 1.26 | 0.732 | 0.858 | 0.302 | 0.531 | 0.132 | 1.60 | 45.0 |
| QH0515.01 | B | 0.462 | 1.29 | 0.335 | 0.445 | 0.354 | 1.01 | 8.70 | 2.25 | >50 |
| QH0692.42 | B | 0.966 | 1.70 | 0.331 | 0.524 | 0.323 | 1.54 | 0.940 | 0.531 | 3.110 |
| REJO.67 | B | 0.046 | 0.178 | 0.072 | 0.091 | 0.049 | 0.072 | 8.87 | 0.302 | 3.020 |
| RHPA.7 | B | 0.035 | 0.110 | 0.065 | 0.036 | 0.058 | 0.034 | 0.014 | 1.01 | >50 |
| SC422.8 | B | 0.167 | 0.488 | 0.166 | 0.220 | 0.198 | 0.127 | 0.006 | 0.343 | >50 |
| SF162.15 | B | 0.017 | 0.037 | 0.013 | 0.031 | 0.005 | 0.207 | 0.03 | 0.245 | >50 |
| SS1196.01 | B | 0.017 | 0.063 | 0.014 | 0.013 | 0.018 | 0.904 | 0.022 | 0.244 | 0.055 |
| THRO.18 | B | 1.70 | 2.60 | 0.316 | 0.664 | 0.458 | 3.16 | >50 | 0.092 | >50 |
| TRJO.58 | B | 0.321 | 0.820 | 0.377 | 0.411 | 0.098 | 0.101 | 4.31 | 1.13 | 3.21 |
| TRO.11 | B | 0.093 | 0.138 | 0.033 | 0.058 | 0.066 | 0.469 | 0.016 | 0.028 | >50 |
| WITO.33 | B | 0.298 | 0.893 | 0.080 | 0.160 | 0.123 | 0.102 | 0.797 | 0.031 | 7.24 |
| X2278.C2.B6 | B | 0.064 | 0.183 | 0.051 | 0.082 | 0.026 | 0.151 | 0.182 | 0.442 | 3.339 |
| YU2.DG | B | 0.049 | 0.200 | 0.049 | 0.074 | 0.070 | 0.096 | 0.068 | 1.17 | >50 |
| BJOX002000.03.2 | BC | 0.046 | 0.132 | 0.066 | 0.081 | 0.021 | >50 | 0.018 | 0.384 | 45.0 |
| CH038.12 | BC | 0.043 | 0.104 | 0.024 | 0.033 | 0.043 | 0.447 | 0.04 | 0.271 | >50 |
| CH070.1 | BC | 0.039 | 0.095 | 0.024 | 0.031 | 0.037 | 14.0 | 0.01 | 6.65 | >50 |
| CH117.4 | BC | 0.024 | 0.058 | 0.018 | 0.021 | 0.013 | 0.105 | >50 | 0.270 | >50 |
| CH119.10 | BC | 0.046 | 0.173 | 0.023 | 0.041 | 0.033 | 0.833 | 0.029 | 0.591 | 38.2 |
| CH181.12 | BC | 0.046 | 0.124 | 0.063 | 0.061 | 0.053 | 0.487 | 0.037 | 0.754 | 10.6 |
| CNE15 | BC | 0.105 | 0.359 | 0.036 | 0.038 | 0.024 | 0.141 | 19.0 | 0.844 | >50 |

FIG. 18D

| | Bi-ScFv | Bi-NAb | Tri-NAb | Tetra-NAb1 | Tetra-NAb2 | Parental mAbs | | | |
|---|---|---|---|---|---|---|---|---|---|
| Virus ID | Clade | dVRC01-5X-PGT121 ScFv | dVRC01-5X-PGT121 Fc | 10E8/dVRC01-5X-PGT121 | 10E8-5X-dVRC01-5X-PGT121 | 35O22-5X-dVRC01-5X-PGT121 | VRC01 | PGT121 | 10E8 | 35O22 |
| CNE19 | BC | 0.012 | 0.030 | 0.007 | 0.019 | 0.019 | 0.247 | 1.007 | 0.251 | 0.019 |
| CNE20 | BC | 0.052 | 0.017 | 0.018 | 0.028 | 0.023 | 7.39 | 3.072 | 0.131 | >50 |
| CNE21 | BC | 0.026 | 0.096 | 0.031 | 0.041 | 0.042 | 0.274 | 0.005 | 0.979 | 0.063 |
| CNE40 | BC | 0.234 | 0.440 | 0.065 | 0.025 | 0.063 | 0.433 | 0.224 | 0.018 | 0.063 |
| CNE7 | BC | 0.055 | 0.175 | 0.033 | 0.098 | 0.091 | 0.187 | 0.032 | 0.130 | 0.018 |
| 286.36 | C | 0.036 | 0.031 | 0.007 | 0.015 | 0.012 | 0.223 | 0.008 | 1.19 | >50 |
| 288.38 | C | 0.030 | 0.085 | 0.007 | 0.023 | 0.017 | 1.33 | 0.006 | 0.435 | 0.038 |
| 0013095-2.11 | C | 0.306 | 0.064 | 0.004 | 0.011 | 0.014 | 0.086 | >50 | 0.019 | 0.096 |
| 001428-2.42 | C | 0.018 | 0.085 | 0.038 | 0.065 | 0.025 | 0.034 | 0.023 | 1.71 | >50 |
| 0077_V1.C16 | C | 0.224 | 0.462 | 0.171 | 0.185 | 0.147 | 1.19 | >50 | 1.86 | >50 |
| 00836-2.5 | C | 0.002 | 0.040 | 0.024 | 0.014 | 0.003 | 0.122 | 31.8 | 0.666 | >50 |
| 0921.V2.C14 | C | 0.050 | 0.135 | 0.093 | 0.092 | 0.064 | 0.230 | >50 | 0.908 | >50 |
| 16055-2.3 | C | 0.016 | 0.070 | 0.047 | 0.048 | 0.041 | 0.100 | 1.02 | 1.10 | >50 |
| 16845-2.22 | C | 2.99 | 5.21 | 0.068 | 0.189 | 0.510 | 2.95 | 9.41 | 0.070 | 0.030 |
| 16936-2.21 | C | 0.011 | 0.038 | 0.001 | 0.033 | 0.009 | 0.154 | 0.018 | 0.264 | >50 |
| 25710-2.43 | C | 0.034 | 0.154 | 0.032 | 0.055 | 0.049 | 0.487 | 0.031 | 2.04 | >50 |
| 25711-2.4 | C | 0.028 | 0.103 | 0.063 | 0.036 | 0.049 | 0.559 | 0.020 | 0.516 | >50 |
| 25925-2.22 | C | 0.080 | 0.188 | 0.072 | 0.076 | 0.061 | 0.550 | 0.024 | 0.402 | >50 |
| 26191-2.48 | C | 0.107 | 0.406 | 0.136 | 0.142 | 0.115 | 0.183 | 0.150 | 1.83 | >50 |
| 3168.V4.C10 | C | 0.638 | 1.68 | 0.544 | 0.583 | 0.232 | 0.129 | 0.485 | 2.83 | >50 |
| 3637.V5.C3 | C | 11.4 | 18.9 | 2.07 | 8.72 | 6.20 | 1.97 | >50 | 2.12 | >50 |
| 3873.V1.C24 | C | 0.322 | 1.48 | 0.063 | 0.031 | 0.068 | 2.81 | 0.015 | 5.51 | >50 |
| 425c | C | 0.419 | 0.953 | 0.428 | 0.466 | 0.298 | 1.93 | 0.005 | 0.445 | >50 |
| 6322.V4.C1 | C | 15.2 | 5.00 | 1.67 | >50 | 0.029 | >50 | >50 | 0.923 | >50 |
| 6471.V1.C16 | C | >50 | >50 | >50 | 1.82 | >50 | >50 | >50 | 4.98 | >50 |
| 6631.V3.C10 | C | 1.91 | 2.63 | 1.39 | 0.094 | 0.075 | 0.129 | >50 | 0.934 | >50 |
| 6644.V2.C33 | C | 0.021 | 0.143 | 0.027 | 0.031 | 0.025 | 1.97 | 0.008 | 0.019 | 0.037 |
| 6785.V5.C14 | C | 0.054 | 0.149 | 0.134 | 0.125 | 0.036 | 0.193 | 0.088 | 0.701 | >50 |
| 6838.V1.C35 | C | 0.092 | 0.015 | 0.032 | 0.038 | 0.009 | 0.253 | 0.019 | 0.292 | >50 |
| 96ZM651.02 | C | 0.026 | 0.076 | 0.021 | 0.017 | 0.035 | 0.288 | 0.119 | 0.053 | 0.019 |
| BR025.9 | C | 0.019 | 0.033 | 0.014 | 0.035 | 0.015 | 0.528 | 0.010 | 0.307 | 0.035 |

| Virus ID | Clade | Bi-ScFv dVRC01-5X-PGT121 ScFv | Bi-NAb dVRC01-5X-PGT121 Fc | Tri-NAb 10E8/ dVRC01-5X-PGT121 | Tetra-NAb1 10E8-5X-35O22/ dVRC01-5X-PGT121 | Tetra-NAb2 35O22-5X-10E8/ dVRC01-5X-PGT121 | VRC01 | PGT121 | 10E8 | 35O22 |
|---|---|---|---|---|---|---|---|---|---|---|
| CAP210.E8 | C | 2.55 | 4.88 | 0.526 | 0.303 | 0.23 | >50 | >50 | 0.474 | 0.019 |
| CAP244.D3 | C | 0.455 | 1.28 | 0.013 | 0.034 | 0.057 | 1.34 | >50 | 0.369 | >50 |
| CAP256.206.C9 | C | 0.054 | 0.103 | 0.049 | 0.045 | 0.021 | 1.07 | 0.010 | 0.713 | 0.033 |
| CAP45.G3 | C | 0.166 | 0.373 | 0.188 | 0.122 | 0.083 | 6.75 | 2.08 | 0.722 | 0.016 |
| Ce1176.A3 | C | 0.051 | 0.120 | 0.071 | 0.052 | 0.049 | 1.85 | 0.016 | 0.252 | 0.005 |
| CE703010217.B6 | C | 0.004 | 0.035 | 0.018 | 0.023 | 0.019 | 0.195 | 0.003 | 0.096 | >50 |
| CNE30 | C | 0.224 | 0.608 | 0.084 | 0.152 | 0.172 | 0.693 | 0.061 | 0.456 | >50 |
| CNE31 | C | 0.713 | 2.30 | 1.01 | 0.528 | 0.392 | 0.772 | 0.789 | 1.32 | >50 |
| CNE53 | C | 0.050 | 0.106 | 0.010 | 0.028 | 0.038 | 0.112 | 0.022 | 0.213 | >50 |
| CNE58 | C | 0.970 | 2.32 | 0.366 | 0.735 | 0.651 | 0.252 | >50 | 0.229 | >50 |
| DU123.06 | C | 0.053 | 0.199 | 0.007 | 0.021 | 0.044 | 5.70 | 0.033 | 0.132 | 0.070 |
| DU151.02 | C | 0.011 | 0.024 | 0.059 | 0.085 | 0.067 | 10.5 | 0.007 | 0.461 | 8.00 |
| DU156.12 | C | 0.025 | 0.036 | 0.015 | 0.036 | 0.028 | 0.077 | 0.015 | 0.075 | >50 |
| DU172.17 | C | 0.059 | 0.140 | 0.053 | 0.061 | 0.113 | >50 | 0.104 | 0.057 | >50 |
| DU422.01 | C | 0.057 | 0.18 | 0.82 | 0.290 | 0.267 | >50 | 0.164 | 0.224 | >50 |
| MW965.26 | C | 0.012 | 0.05 | 0.005 | 0.011 | 0.022 | 0.043 | 0.011 | 0.041 | 5.60 |
| SO18.18 | C | 0.004 | 0.022 | 0.003 | 0.005 | 0.007 | 0.052 | 0.012 | 1.60 | >50 |
| TV1.29 | C | 0.319 | 0.473 | 1.17 | 1.57 | 0.774 | >50 | 0.118 | 0.243 | >50 |
| TZA125.17 | C | 2.11 | 5.14 | 0.428 | 0.557 | 0.746 | >50 | 9.96 | 0.217 | >50 |
| TZBD.02 | C | 0.037 | 0.055 | 0.017 | 0.023 | 0.02 | 0.043 | 0.003 | 1.41 | >50 |
| ZA012.29 | C | 0.023 | 0.062 | 0.060 | 0.164 | 0.059 | 0.327 | 0.005 | 1.47 | >50 |
| ZM106.9 | C | 0.023 | 0.095 | 0.049 | 0.070 | 0.045 | 0.264 | 0.008 | >50 | >50 |
| ZM109.4 | C | 0.091 | 0.351 | 0.060 | 0.094 | 0.07 | 0.142 | 13.7 | 0.161 | >50 |
| ZM135.10a | C | 1.20 | 2.12 | 0.002 | 0.019 | 0.076 | 1.40 | 1.50 | 0.093 | >50 |
| ZM176.66 | C | 0.071 | 0.221 | 0.080 | 0.071 | 0.060 | 0.045 | 13.8 | 0.267 | >50 |
| ZM197.7 | C | 1.14 | 4.15 | 0.161 | 0.410 | 0.484 | 0.532 | >50 | 0.055 | >50 |
| ZM214.15 | C | 0.857 | 2.30 | 0.533 | 0.509 | 0.417 | 0.957 | 0.682 | 2.22 | >50 |
| ZM215.8 | C | 0.021 | 0.100 | 0.023 | 0.031 | 0.02 | 0.362 | 0.014 | 0.064 | 0.015 |
| ZM233.6 | C | 0.070 | 0.268 | 0.060 | 0.12 | 0.04 | 1.98 | 4.14 | 0.270 | >50 |
| ZM249.1 | C | 0.486 | 0.811 | 0.279 | 0.211 | 0.056 | 0.107 | >50 | 0.830 | >50 |
| ZM53.12 | C | 0.005 | 0.010 | 0.011 | 0.014 | 0.010 | 0.792 | 0.001 | 2.62 | >50 |

| | | Bi-ScFv | Bi-NAb | Tri-NAb | Tetra-NAb1 | Tetra-NAb2 | Parental mAbs | | | |
|---|---|---|---|---|---|---|---|---|---|---|
| Virus ID | Clade | dVRCO1-5X-PGT121 ScFv | dVRCO1-5X-PGT121 Fc | 10E8/ dVRCO1-5X-PGT121 | 10E8-5X-35O22/ dVRCO1-5X-PGT121 | 35O22-5X-10E8/ dVRCO1-5X-PGT121 | VRC01 | PGT121 | 10E8 | 35O22 |
| ZM55.28a | C | 0.137 | 0.407 | 0.212 | 0.240 | 0.155 | 0.241 | 0.070 | 2.34 | >50 |
| 3326.V4.C3 | CD | NA | 0.017 | 0.048 | 0.020 | 0.017 | 0.107 | >50 | 1.40 | >50 |
| 3337.V2.C6 | CD | 0.051 | 0.110 | 0.089 | 0.054 | 0.037 | 0.105 | 21.1 | 1.09 | |
| 3817.v2.c59 | CD | 7.23 | 11.6 | 0.230 | 0.446 | 0.407 | >50 | >50 | 0.229 | >50 |
| 191821.E6.1 | D | 0.487 | 1.57 | 0.921 | 0.724 | 0.342 | 0.438 | >50 | 1.91 | >50 |
| 231965.c1 | D | 1.31 | 1.41 | 0.261 | 0.269 | 0.074 | 0.392 | >50 | 11.0 | >50 |
| 247-23 | D | 19.5 | 18.3 | 0.639 | 0.695 | 0.113 | 1.63 | >50 | 0.344 | |
| 3016.v5.c45 | D | 0.043 | 0.078 | 0.037 | 0.052 | 0.041 | 0.117 | >50 | 0.710 | >50 |
| 57128.vrc15 | D | 0.434 | 0.875 | 0.094 | 0.136 | 0.129 | >50 | 2.16 | 0.212 | 0.042 |
| 6405.v4.c34 | D | 0.092 | 0.259 | 0.103 | 0.104 | 0.056 | 1.69 | 0.019 | 0.461 | |
| A03349M1.vrc4a | D | 0.071 | 0.194 | 0.189 | 0.136 | 0.045 | 4.42 | 0.013 | 0.270 | |
| A07412M1.vrc12 | D | 0.011 | 0.057 | 0.041 | 0.037 | 0.017 | 0.101 | 0.012 | 0.140 | >50 |
| NKU3006.ec1 | D | 3.28 | 8.54 | 1.91 | 3.65 | 0.904 | 0.460 | >50 | 0.673 | |
| UG021.16 | D | 0.275 | 0.340 | 0.016 | 0.055 | 0.093 | 0.451 | 2.41 | 8.046 | >50 |
| UG024.2 | D | 2.28 | 0.830 | 0.035 | 0.119 | 0.126 | 0.219 | >50 | 8.053 | >50 |
| P0402.c2.11 | G | 0.024 | 0.021 | 0.026 | 0.020 | 0.025 | 0.207 | 1.04 | 0.057 | |
| P1981.C5.3 | G | 0.006 | 0.024 | 0.025 | 0.052 | 0.032 | 0.336 | 0.044 | 0.024 | |
| X1193.c1 | G | 0.128 | 0.239 | 0.065 | 0.032 | 0.031 | 0.124 | 0.032 | 0.341 | 0.020 |
| X1254.c3 | G | 0.072 | 0.158 | 0.017 | 0.054 | 0.062 | 0.055 | 0.024 | 3.67 | |
| X1632.S2.B10 | G | 0.088 | 0.178 | 0.016 | 0.066 | 0.055 | 0.131 | >50 | 0.387 | 0.564 |
| X2088.c9 | G | 0.016 | 0.029 | 0.017 | 0.033 | 0.032 | >50 | 0.043 | >50 | |
| X2131.C1.B5 | G | 0.023 | 0.079 | 0.016 | 0.031 | 0.026 | 0.467 | 0.012 | 0.039 | |
| SIVmac251.30.SG3 | NA | >50 | >50 | >50 | >50 | >50 | >50 | >50 | >50 | >50 |
| SVA.MLV | NA | >50 | >50 | >50 | >50 | >50 | >50 | >50 | >50 | >50 |

IC50 (ug/mL) legend: <0.1; 0.1-1.00; 1.00-10.0; >10.0

| | Bi-ScFv | Bi-NAb | Tri-NAb | Tetra-NAb1 | Tetra-NAb2 | Parental mAbs | | | |
|---|---|---|---|---|---|---|---|---|---|
| | dVRC01-5X-PGT121 ScFv | dVRC01-5X-PGT121 Fc | 10E8/dVRC01-5X-PGT121 | 10E8-5X-35O22/dVRC01-5X-PGT121 | 35O22-5X-10E8/dVRC01-5X-PGT121 | VRC01 | PGT121 | 10E8 | 35O22 |
| # Viruses | 208 | 208 | 208 | 208 | 208 | 208 | 208 | 208 | 208 |
| Total VS Neutralized | | | | | | | | | |
| IC50 <50ug/ml | 199 | 198 | 207 | 205 | 205 | 188 | 133 | 203 | 94 |
| IC50 <10ug/ml | 195 | 193 | 205 | 203 | 205 | 184 | 122 | 202 | 89 |
| IC50 <1.0ug/ml | 162 | 147 | 192 | 189 | 198 | 152 | 108 | 152 | 79 |
| IC50 <0.1ug/ml | 112 | 58 | 131 | 117 | 133 | 40 | 93 | 42 | 75 |
| IC50 <0.01ug/ml | 23 | 0 | 24 | 3 | 5 | 0 | 47 | 10 | 45 |
| % VS Neutralized | | | | | | | | | |
| IC50 <50ug/ml | 95.7 | 95.2 | 99.5 | 98.6 | 98.6 | 90 | 64 | 97.6 | 45 |
| IC50 <10ug/ml | 94 | 93 | 99 | 98 | 99 | 88 | 59 | 97 | 43 |
| IC50 <1.0ug/ml | 78 | 71 | 92 | 91 | 95 | 73 | 52 | 73 | 38 |
| IC50 <0.1ug/ml | 54 | 28 | 63 | 56 | 64 | 19 | 45 | 20 | 36 |
| IC50 <0.01ug/ml | 11 | 0 | 12 | 1 | 2 | 0 | 23 | 5 | 22 |
| Median IC50 | 0.071 | 0.198 | 0.063 | 0.079 | 0.063 | 0.287 | 0.019 | 0.392 | 0.010 |
| Geometric Mean | 0.108 | 0.297 | 0.069 | 0.101 | 0.077 | 0.301 | 0.045 | 0.299 | 0.025 |

Note: Median and Geometric Mean titers are calculated only for samples with IC50 <50ug/ml

FIG. 18H

| | | Bi-ScFv | Bi-NAb | Tri-NAb | Tetra-NAb1 | Tetra-NAb2 | Parental mAbs | | | |
|---|---|---|---|---|---|---|---|---|---|---|
| Virus ID | Clade | dVRC01-5X-PGT121 ScFv | 5X-PGT121 Fc | 10E8-5X-dVRC01-5X-PGT121 | 10E8-5X-35O22-PGT121 | 35O22-5X-dVRC01-5X-PGT121 | VRC01 | PGT121 | 10E8 | 35O22 |
| 0260.v5.c36 | A | 0.378 | 0.953 | 0.716 | 0.458 | 0.224 | 1.35 | 0.143 | 21.7 | >50 |
| 0330.v4.c3 | A | 0.216 | 0.619 | 0.403 | 0.391 | 0.216 | 0.202 | 0.194 | 3.64 | >50 |
| 0439.v5.c1 | A | 2.60 | 7.07 | 2.27 | 3.39 | 0.829 | 0.438 | >50 | 3.95 | >50 |
| 3365.v2.c20 | A | 0.150 | 0.534 | 0.301 | 0.773 | 0.210 | 0.125 | 1.34 | 4.56 | >50 |
| 3415.v1.c1 | A | 0.752 | 2.18 | 1.40 | 1.33 | 0.850 | 0.177 | >50 | 11.5 | >50 |
| 3718.v3.c11 | A | 0.337 | 0.653 | 0.573 | 0.470 | 0.448 | 5.58 | 8.64 | 4.42 | >50 |
| 398-F1.F6_20 | A | 0.049 | 0.322 | 0.037 | 0.066 | 0.062 | 0.479 | 0.011 | 6.17 | >50 |
| BB201.B42 | A | 0.053 | 0.137 | 0.161 | 0.182 | 0.148 | 0.614 | 0.011 | 1.96 | >50 |
| BB539.2B13 | A | 3.17 | 3.46 | 1.97 | 2.73 | 2.02 | 0.407 | >50 | 13.0 | >50 |
| BG505.W6M.C2 | A | 0.130 | 0.338 | 0.293 | 0.457 | 0.276 | 0.125 | 0.256 | 2.14 | >50 |
| BI369.9A | A | 0.418 | 0.563 | 0.340 | 1.19 | 0.477 | 0.532 | 0.043 | 1.29 | >50 |
| BS208.B1 | A | 0.139 | 0.245 | 0.114 | 0.124 | 0.125 | 0.080 | >50 | 3.27 | 0.167 |
| KER2008.12 | A | 0.221 | 0.673 | 0.421 | 0.451 | 0.115 | 1.46 | >50 | >50 | 0.281 |
| KER2018.11 | A | 0.213 | 0.800 | 0.979 | 1.05 | 0.442 | 0.976 | >50 | 7.16 | >50 |
| KNH1209.18 | A | 0.087 | 0.10 | 0.101 | 0.159 | 0.121 | 0.298 | 0.067 | 2.39 | >50 |
| MB201.A1 | A | 0.025 | 0.089 | 0.077 | 0.078 | 0.074 | 0.452 | 0.026 | 1.36 | >50 |
| MB539.2B7 | A | 4.72 | 11.0 | 2.45 | 6.80 | 4.08 | 1.24 | >50 | >50 | >50 |
| MI369.A5 | A | 0.204 | 0.309 | 0.642 | 0.450 | 0.342 | 0.843 | 0.087 | 1.77 | 0.819 |
| MS208.A1 | A | 1.94 | 3.39 | 1.79 | 3.16 | 4.51 | 0.593 | >50 | 1.14 | >50 |
| Q23.17 | A | 0.117 | 0.352 | 0.149 | 0.167 | 0.115 | 0.212 | 0.019 | 1.60 | 0.080 |
| Q259.17 | A | 0.052 | 0.080 | 0.147 | 0.174 | 0.107 | 0.242 | >50 | 12.0 | >50 |
| Q769.d22 | A | 0.435 | 1.14 | 1.11 | 1.08 | 0.530 | 0.098 | >50 | 4.47 | >50 |
| Q769.h5 | A | 0.223 | 0.703 | 0.650 | 0.728 | 0.464 | 0.145 | 7.44 | >50 |
| Q842.d12 | A | 0.096 | 0.351 | 0.169 | 0.156 | 0.083 | 0.075 | 0.047 | 7.58 | >50 |
| QH209.14M.A2 | A | 0.577 | 1.48 | 0.705 | 0.663 | 0.281 | 0.094 | >50 | 4.09 | >50 |
| RW020.2 | A | 0.021 | 0.076 | 0.073 | 0.096 | 0.069 | 0.647 | 0.019 | 2.92 | >50 |
| UG037.8 | A | 0.339 | 0.990 | 0.483 | 0.741 | 0.286 | 0.186 | 0.237 | 0.353 | >50 |
| 246-F3.C10.2 | AC | 0.108 | 0.301 | 0.181 | 0.179 | 0.052 | 0.650 | >50 | 1.49 | >50 |
| 3301.V1.C24 | AC | 0.070 | 0.170 | 0.207 | 0.222 | 0.165 | 0.223 | 0.030 | 9.50 | >50 |
| 3589.V1.C4 | AC | 0.315 | 1.10 | 0.709 | 0.774 | 0.369 | 0.199 | >50 | 11.7 | >50 |
| 6540.v4.c1 | AC | >50 | >50 | >50 | >50 | >50 | >50 | >50 | 7.01 | >50 |

| Virus ID | Clade | Bi-ScFv dVRC01-5X-PGT121 ScFv | Bi-NAb 5X-PGT121 Fc | Tri-NAb 10E8/dVRC01-5X-PGT121 | Tetra-NAb1 10E8-5X-35O22/ dVRC01-5X-PGT121 | Tetra-NAb2 35O22-5X-10E8/ dVRC01-5X-PGT121 | VRC01 | PGT121 | 10E8 | 35O22 |
|---|---|---|---|---|---|---|---|---|---|---|
| 6545.V4.C1 | AC | >50 | >50 | 31.4 | >50 | 30.1 | >50 | >50 | 7.50 | >50 |
| 0815.V3.C3 | ACD | 0.082 | 0.356 | 0.186 | 0.244 | 0.115 | 0.135 | 0.072 | 1.81 | 0.018 |
| 6095.V1.C10 | ACD | 0.557 | 0.933 | 0.048 | 0.153 | 0.230 | 2.04 | >50 | 0.019 | >50 |
| 3468.V1.C12 | AD | 0.049 | 0.101 | 0.072 | 0.074 | 0.034 | 0.111 | 1.05 | 2.04 | 6.66 |
| Q168.a2 | AD | 0.127 | 0.377 | 0.382 | 0.510 | 0.329 | 0.230 | >50 | 2.88 | >50 |
| Q461.e2 | AD | 7.51 | 17.0 | 11.5 | 16.4 | 1.18 | 1.02 | >50 | 4.68 | 0.169 |
| 620345.c1 | AE | >50 | >50 | >50 | >50 | >50 | >50 | >50 | 3.73 | >50 |
| BJOX009000.02.4 | AE | 0.762 | 1.92 | 0.279 | 0.504 | 0.675 | 4.80 | >50 | 1.47 | >50 |
| BJOX010000.06.2 | AE | 15.5 | >50 | 1.70 | 4.19 | 2.52 | 20.9 | >50 | 0.476 | >50 |
| BJOX025000.01.1 | AE | >50 | 6.10 | 2.98 | 8.47 | 8.29 | >50 | >50 | 1.54 | >50 |
| BJOX028000.10.3 | AE | 0.804 | 1.01 | 0.432 | 0.414 | 0.206 | 1.03 | >50 | 0.876 | >50 |
| C1080.c3 | AE | 18.1 | 22.4 | 0.973 | 0.895 | 0.415 | 9.98 | >50 | 0.613 | >50 |
| C2101.c1 | AE | 3.46 | 4.64 | 0.816 | 0.521 | 0.271 | 0.581 | >50 | 4.12 | 0.090 |
| C3347.c11 | AE | 3.82 | 3.88 | 0.080 | 0.183 | 0.302 | 0.452 | >50 | 0.089 | >50 |
| C4118.09 | AE | 5.11 | 7.21 | 1.04 | 0.648 | 0.109 | 0.720 | >50 | 2.30 | 0.041 |
| CM244.ec1 | AE | 0.701 | 2.48 | 0.913 | 1.20 | 1.05 | 0.452 | >50 | 1.46 | >50 |
| CNE3 | AE | >50 | >50 | 20.9 | 17.2 | 3.12 | 11.0 | >50 | 4.01 | >50 |
| CNE5 | AE | 3.00 | 11.0 | 1.67 | 1.57 | 1.07 | 0.914 | >50 | 2.52 | >50 |
| CNE55 | AE | 4.29 | 17.1 | 1.44 | 2.77 | 1.28 | 0.933 | >50 | 0.605 | >50 |
| CNE56 | AE | 7.51 | 28.5 | 2.06 | 5.04 | 3.27 | 1.30 | >50 | 0.314 | >50 |
| CNE59 | AE | 11.8 | 9.43 | 0.339 | 1.47 | 2.62 | 1.70 | >50 | 0.012 | >50 |
| CNE8 | AE | 1.46 | 4.45 | 0.025 | 0.123 | 0.441 | 0.265 | >50 | 1.42 | >50 |
| M02138 | AE | 21.4 | 25.8 | 0.135 | 0.718 | 1.18 | 3.02 | >50 | 0.126 | >50 |
| R1166.c1 | AE | 13.7 | 44.6 | 0.463 | 1.11 | 1.90 | 5.39 | >50 | 2.02 | >50 |
| R2184.c4 | AE | 2.26 | 6.10 | 1.94 | 3.18 | 1.87 | 0.288 | >50 | 2.20 | >50 |
| R3265.c6 | AE | 9.74 | 19.7 | 4.97 | 7.77 | 4.54 | 1.41 | >50 | 9.28 | >50 |
| TH023.6 | AE | 21.1 | 4.46 | 0.115 | 0.301 | 0.481 | 5.75 | >50 | 0.034 | >50 |
| TH966.8 | AE | 5.60 | 12.7 | 0.180 | 0.558 | 1.35 | 0.983 | >50 | 0.291 | >50 |
| TH976.17 | AE | 2.93 | 7.63 | 1.18 | 1.84 | 1.22 | 0.726 | >50 | 1.75 | >50 |
| 235-47 | AG | 0.265 | 0.857 | 0.309 | 0.320 | 0.310 | 0.154 | 0.842 | 0.786 | >50 |
| 242-14 | AG | >50 | >50 | 8.76 | >50 | 34.7 | >50 | >50 | 3.17 | >50 |

| Virus ID | Clade | Bi-ScFv dVRCO1-5X-PGT121 ScFv | Bi-NAb 5X-PGT121 Fc | Tri-NAb 10E8/dVRCO1-5X-PGT121 | Tetra-NAb1 10E8-5X-dVRCO1-5X-PGT121 | Tetra-NAb2 35O22-5X-dVRCO1-5X-PGT121 | VRC01 | PGT121 | 10E8 | 35O22 |
|---|---|---|---|---|---|---|---|---|---|---|
| 263-8 | AG | 0.674 | 2.34 | 1.00 | 0.889 | 0.525 | 0.536 | 7.73 | 0.991 | >50 |
| 269-12 | AG | 0.155 | 0.632 | 0.308 | 0.223 | 0.191 | 0.679 | 1.26 | 0.475 | >50 |
| 271-11 | AG | 0.028 | 0.096 | 0.076 | 0.079 | 0.065 | 0.200 | >50 | 4.34 | >50 |
| 928-28 | AG | 2.92 | 7.95 | 0.877 | 1.86 | 1.35 | 0.968 | >50 | 0.365 | 12.0 |
| DJ263.8 | AG | 0.090 | 0.328 | 0.061 | 0.180 | 0.158 | 0.490 | 0.202 | 0.100 | >50 |
| T250-4 | AG | 0.024 | 0.078 | 0.092 | 0.058 | 0.044 | >50 | 0.012 | 3.45 | >50 |
| T251-18 | AG | 8.52 | 26.9 | 0.951 | 0.736 | 0.225 | 12.0 | >50 | 2.55 | >50 |
| T253-11 | AG | 0.603 | 5.03 | 1.16 | 1.14 | 0.536 | 1.23 | >50 | 4.05 | >50 |
| T255-34 | AG | 0.141 | 0.312 | 0.160 | 0.120 | 0.077 | 1.31 | >50 | 1.14 | >50 |
| T257-31 | AG | 1.21 | 4.87 | 1.16 | 1.43 | 1.12 | 4.55 | 0.820 | 1.58 | >50 |
| T266-60 | AG | 1.64 | 5.19 | 3.57 | 2.43 | 1.51 | 5.78 | >50 | >50 | >50 |
| T278-50 | AG | >50 | >50 | >50 | >50 | 7.64 | >50 | >50 | 2.10 | >50 |
| T280-5 | AG | 0.083 | 0.129 | 0.103 | 0.216 | 0.065 | 0.094 | 0.10 | 4.77 | >50 |
| T33-7 | AG | 0.236 | 0.545 | 0.367 | 0.311 | 0.166 | 0.067 | >50 | 2.83 | >50 |
| 3988.25 | B | 0.858 | 0.118 | 0.084 | 0.132 | 0.065 | 1.12 | 0.033 | 0.293 | >50 |
| 5768.04 | B | 0.109 | 0.245 | 0.318 | 0.291 | 0.193 | 0.956 | 0.697 | 5.26 | >50 |
| 6101.10 | B | 0.057 | 0.132 | 0.038 | 0.068 | 0.052 | 0.112 | 0.038 | 0.055 | 0.040 |
| 6535.3 | B | 0.023 | 0.122 | 0.031 | 0.074 | 0.053 | 5.77 | 0.011 | 1.28 | 0.025 |
| 7165.18 | B | 0.218 | 0.489 | 0.355 | 0.402 | 0.336 | >50 | 0.074 | 2.71 | >50 |
| 45_01dG5 | B | 0.032 | 0.131 | 0.058 | 0.086 | 0.060 | 0.042 | 0.054 | 0.703 | 0.040 |
| 89.6.DG | B | 0.410 | 0.444 | 0.052 | 0.093 | 0.099 | 2.03 | 0.077 | 1.48 | >50 |
| AC10.29 | B | 0.475 | 1.21 | 0.349 | 0.898 | 0.952 | 2.76 | 0.118 | 0.512 | >50 |
| ADA.DG | B | 0.225 | 0.474 | 0.097 | 0.274 | 0.281 | 1.32 | 0.085 | 0.358 | >50 |
| BaL.01 | B | 0.023 | 0.073 | 0.079 | 0.099 | 0.046 | 0.407 | 0.044 | 1.91 | 0.040 |
| BaL.26 | B | 0.065 | 0.100 | 0.132 | 0.165 | 0.084 | 0.138 | 0.058 | 2.39 | 0.025 |
| BG1168.01 | B | 5.61 | 5.88 | 1.68 | 3.76 | 3.82 | 3.57 | >50 | 1.48 | >50 |
| BL01.DG | B | >50 | >50 | 22.8 | >50 | 10.1 | >50 | >50 | 1.57 | 0.049 |
| BR07.DG | B | 0.492 | 0.998 | 0.171 | 0.308 | 0.176 | 4.69 | 0.333 | 0.445 | 0.049 |
| BX08.16 | B | 0.198 | 0.223 | 0.102 | 0.313 | 0.367 | 1.09 | 0.037 | 1.30 | >50 |
| CAAN.A2 | B | 0.116 | 0.300 | 0.170 | 0.155 | 0.077 | 3.71 | 0.022 | 5.70 | 0.027 |
| CNE10 | B | 0.065 | 0.207 | 0.094 | 0.108 | 0.092 | 1.59 | 0.027 | 0.169 | >50 |

IC80 (ug/mL): <0.01, 0.01-0.1, 0.10-1.00, 1.00-10.0, >10.0

| Virus ID | Clade | Bi-ScFv dVRC01-5X-PGT121 ScFv | Bi-NAb 5X-PGT121 Fc | Tri-NAb 10E8/dVRC01-5X-PGT121 | Tetra-NAb1 10E8-5X-dVRC01-5X-35O22 | Tetra-NAb2 35O22-5X-10E8/dVRC01-5X-PGT121 | VRC01 | PGT121 | 10E8 | 35O22 |
|---|---|---|---|---|---|---|---|---|---|---|
| CNE12 | B | 0.063 | 0.169 | 0.102 | 0.096 | 0.085 | 2.14 | 0.014 | 1.09 | 10.0 |
| CNE14 | B | 0.095 | 0.109 | 0.071 | 0.069 | 0.053 | 0.613 | 0.067 | 0.649 | >50 |
| CNE4 | B | 1.19 | 2.69 | 0.579 | 0.914 | 0.358 | 2.96 | >50 | 0.437 | >50 |
| CNE57 | B | 0.117 | 0.427 | 0.163 | 0.271 | 0.225 | 1.26 | 0.035 | 0.317 | >50 |
| HO86.8 | B | >50 | >50 | 45.9 | >50 | 4.72 | >50 | >50 | 1.52 | >50 |
| HT593.1 | B | 1.47 | 3.63 | 0.441 | 1.41 | 1.53 | 1.67 | >50 | 0.285 | >50 |
| HXB2.DG | B | 0.024 | 0.166 | 0.028 | 0.056 | 0.041 | 0.093 | >50 | 0.015 | >50 |
| JRCSF.JB | B | 0.126 | 0.747 | 0.452 | 0.573 | 0.369 | 0.925 | 0.219 | 1.89 | >50 |
| JRFL.JB | B | 0.062 | 0.223 | 0.156 | 0.250 | 0.166 | 0.067 | 0.071 | 0.768 | 49.0 |
| MN.3 | B | 0.035 | 0.138 | 0.086 | 0.098 | 0.119 | 0.033 | >50 | 0.030 | 0.030 |
| PVO.04 | B | 1.21 | 3.10 | 2.37 | 2.97 | 1.06 | 1.20 | 0.436 | 6.43 | >50 |
| QH0515.01 | B | 1.08 | 2.99 | 1.91 | 1.56 | 1.18 | 2.85 | >50 | 5.54 | >50 |
| QH0692.42 | B | 2.41 | 4.40 | 1.59 | 1.86 | 1.06 | 3.98 | 9.70 | 2.35 | 0.040 |
| REJO.67 | B | 0.105 | 0.415 | 0.154 | 0.353 | 0.136 | 0.180 | >50 | 1.18 | >50 |
| RHPA.7 | B | 0.102 | 0.300 | 0.246 | 0.347 | 0.267 | 0.112 | 0.046 | 5.10 | >50 |
| SC422.8 | B | 0.474 | 1.10 | 0.934 | 1.25 | 0.662 | 0.321 | 0.362 | 1.15 | >50 |
| SF162.LS | B | 0.024 | 0.041 | 0.053 | 0.033 | 0.038 | 0.080 | 0.017 | 1.06 | >50 |
| SS1196.01 | B | 0.055 | 0.144 | 0.034 | 0.040 | 0.070 | 0.679 | 0.011 | 1.25 | 4.18 |
| THRO.18 | B | 5.69 | 12.5 | 1.13 | 3.22 | 2.11 | 9.91 | >50 | 0.587 | >50 |
| TRJO.58 | B | 0.777 | 2.25 | 1.02 | 1.14 | 0.231 | 0.231 | >50 | 4.18 | 25.0 |
| TRO.11 | B | 0.058 | 0.326 | 0.150 | 0.160 | 0.169 | 1.19 | 0.032 | 0.286 | >50 |
| WITO.33 | B | 0.800 | 2.98 | 0.353 | 0.699 | 0.553 | 0.295 | 3.25 | 0.305 | >50 |
| X2278.C2.B6 | B | 0.140 | 0.410 | 0.196 | 0.273 | 0.064 | 0.356 | 0.034 | 2.24 | 0.030 |
| YU2.DG | B | 0.111 | 0.500 | 0.181 | 0.324 | 0.191 | 0.198 | 0.178 | 5.46 | >50 |
| BJOX002000.03.2 | BC | 0.129 | 0.337 | 0.273 | 0.304 | 0.280 | >50 | 0.068 | 1.56 | >50 |
| CH038.12 | BC | 0.109 | 0.241 | 0.094 | 0.122 | 0.119 | 1.04 | 0.030 | 1.41 | >50 |
| CH070.1 | BC | 0.116 | 0.272 | 0.034 | 0.039 | 0.034 | >50 | 0.015 | 13.5 | >50 |
| CH117.4 | BC | 0.036 | 0.125 | 0.080 | 0.065 | 0.038 | 0.241 | >50 | 0.859 | >50 |
| CH119.10 | BC | 0.176 | 0.514 | 0.153 | 0.150 | 0.113 | 2.15 | 0.116 | 2.36 | >50 |
| CH181.12 | BC | 0.124 | 0.334 | 0.253 | 0.263 | 0.195 | 1.22 | 0.039 | 2.79 | >50 |
| CNE15 | BC | 0.225 | 0.709 | 0.062 | 0.119 | 0.152 | 0.373 | >50 | 2.97 | >50 |

FIG. 19D

| | | Bi-ScFv | Bi-NAb | Tri-NAb | Tetra-NAb1 | Tetra-NAb2 | Parental mAbs | | | |
|---|---|---|---|---|---|---|---|---|---|---|
| Virus ID | Clade | dVRC01-5X-PGT121 ScFv | 5X-PGT121 Fc | 10E8/dVRC01-5X-PGT121 | 10E8-5X-35O22/dVRC01-5X-PGT121 | 35O22-5X-10E8/dVRC01-5X-PGT121 | VRC01 | PGT121 | 10E8 | 35O22 |
| CNE19 | BC | 0.049 | 0.044 | 0.024 | 0.023 | 0.018 | 0.659 | 0.083 | 1.11 | >50 |
| CNE20 | BC | 0.009 | 0.036 | 0.039 | 0.092 | 0.054 | >50 | 0.048 | 0.732 | >50 |
| CNE21 | BC | 0.081 | 0.236 | 0.119 | 0.159 | 0.146 | 0.903 | 0.018 | 3.25 | >50 |
| CNE40 | BC | 0.855 | 1.29 | 0.046 | 0.114 | 0.192 | 4.55 | 1.85 | 0.012 | 0.070 |
| CNE7 | BC | 0.146 | 0.558 | 0.206 | 0.391 | 0.307 | 0.605 | 0.096 | 0.609 | 0.013 |
| 286.36 | C | 0.023 | 0.085 | 0.054 | 0.046 | 0.043 | 0.715 | 0.005 | 5.00 | >50 |
| 288.38 | C | 0.106 | 0.176 | 0.022 | 0.061 | 0.091 | 3.46 | 0.035 | 3.08 | >50 |
| 0013095-2.11 | C | 0.659 | 2.57 | 0.025 | 0.046 | 0.099 | 0.287 | >50 | 0.077 | 0.038 |
| 001428-2.42 | C | 0.022 | 0.217 | 0.144 | 0.135 | 0.102 | 0.036 | 0.076 | 6.28 | >50 |
| 0077_V1C16 | C | 0.697 | 1.82 | 1.12 | 0.841 | 0.453 | 3.10 | >50 | 7.11 | >50 |
| 00836-2.5 | C | 0.021 | 0.07 | 0.078 | 0.054 | 0.035 | 0.462 | >50 | 1.77 | >50 |
| 0921.V2.C14 | C | 0.090 | 0.325 | 0.280 | 0.289 | 0.182 | 0.519 | >50 | 3.03 | >50 |
| 16055-2.3 | C | 0.046 | 0.159 | 0.125 | 0.127 | 0.101 | 0.224 | 12.2 | 3.31 | >50 |
| 16845-2.22 | C | 11.2 | 22.6 | 0.389 | 1.60 | 2.90 | 12.3 | >50 | 0.172 | >50 |
| 16936-2.21 | C | 0.033 | 0.111 | 0.030 | 0.051 | 0.031 | 0.435 | 0.013 | 1.31 | >50 |
| 25710-2.43 | C | 0.108 | 0.396 | 0.150 | 0.181 | 0.164 | 1.40 | 0.055 | 0.304 | >50 |
| 25711-2.4 | C | 0.081 | 0.242 | 0.160 | 0.113 | 0.124 | 1.44 | 0.041 | 1.69 | >50 |
| 25925-2.22 | C | 0.141 | 0.442 | 0.224 | 0.206 | 0.159 | 1.34 | 0.072 | 1.53 | >50 |
| 26191-2.48 | C | 0.331 | 0.953 | 0.543 | 0.498 | 0.378 | 0.679 | 0.393 | 4.90 | >50 |
| 3168.V4.C10 | C | 1.50 | 2.64 | 2.05 | 1.92 | 0.617 | 0.325 | 1.94 | 8.18 | >50 |
| 3637.V5.C3 | C | 37.1 | >50 | 9.98 | 46.9 | 28.0 | 6.17 | >50 | 6.68 | >50 |
| 3873.V1.C24 | C | 0.664 | 2.03 | 0.069 | 0.151 | 0.230 | 6.97 | 0.106 | 15.7 | >50 |
| 426c | C | 0.967 | 2.48 | 1.20 | 1.39 | 0.831 | 4.41 | >50 | 1.60 | >50 |
| 6322.V4.C1 | C | >50 | 29.0 | 12.0 | 2.11 | 0.261 | >50 | >50 | 3.68 | >50 |
| 6471.V1.C16 | C | >50 | >50 | >50 | >50 | >50 | >50 | >50 | 14.9 | >50 |
| 6631.V3.C10 | C | 6.28 | 9.28 | 8.27 | 6.72 | 4.44 | 0.421 | 0.171 | 3.36 | >50 |
| 6644.V2.C33 | C | 0.075 | 0.448 | 0.100 | 0.156 | 0.090 | 0.686 | 0.072 | 0.124 | >50 |
| 6785.V5.C14 | C | 0.138 | 0.390 | 0.383 | 0.431 | 0.216 | 0.616 | 0.840 | 2.42 | >50 |
| 6838.V1.C35 | C | 0.002 | 0.031 | 0.036 | 0.048 | 0.024 | 2.54 | 0.044 | 1.01 | >50 |
| 962M651.02 | C | 0.099 | 0.200 | 0.087 | 0.118 | 0.123 | 2.37 | 0.012 | 0.177 | >50 |
| BR025.9 | C | 0.047 | 0.091 | 0.061 | 0.094 | 0.050 | 2.37 | 0.007 | 1.11 | 0.020 |

| | | Bi-ScFv | Bi-NAb | Tri-NAb | Tetra-NAb1 | Tetra-NAb2 | Parental mAbs | | | |
|---|---|---|---|---|---|---|---|---|---|---|
| Virus ID | Clade | dVRC01-5X-PGT121 ScFv | 5X-PGT121 Fc | 10E8-5X/dVRC01-5X-PGT121 | 10E8-5X-35O22/dVRC01-5X-PGT121 | 35O22-5X-10E8/dVRC01-5X-PGT121 | VRC01 | PGT121 | 10E8 | 35O22 |
| CAP210.E8 | C | 11.0 | 20.1 | 2.68 | 2.67 | 1.16 | >50 | >50 | 2.01 | >50 |
| CAP244.D3 | C | 1.14 | 3.48 | 0.117 | 0.241 | 0.297 | 3.53 | >50 | 1.48 | >50 |
| CAP256.206.C9 | C | 0.138 | 0.308 | 0.141 | 0.116 | 0.089 | 2.72 | 0.045 | 2.97 | >50 |
| CAP45.G3 | C | 0.386 | 0.963 | 0.483 | 0.377 | 0.251 | >50 | >50 | 3.41 | >50 |
| Ce1176.A3 | C | 0.120 | 0.300 | 0.112 | 0.191 | 0.136 | 4.92 | 0.070 | 1.15 | 2.00 |
| CE703010217.B6 | C | 0.022 | 0.087 | 0.053 | 0.066 | 0.053 | 0.584 | 0.011 | 0.679 | >50 |
| CNE30 | C | 0.688 | 1.44 | 0.466 | 0.668 | 0.584 | 2.15 | 0.249 | 2.29 | >50 |
| CNE31 | C | 2.23 | 7.20 | 2.93 | 3.11 | 1.74 | 2.10 | 2.68 | 3.57 | >50 |
| CNE53 | C | 0.091 | 0.254 | 0.061 | 0.144 | 0.126 | 0.302 | 0.034 | 1.01 | >50 |
| CNE58 | C | 3.09 | 5.78 | 2.46 | 3.36 | 1.74 | 0.582 | >50 | 1.09 | >50 |
| DU123.06 | C | 0.216 | 0.501 | 0.027 | 0.065 | 0.223 | 46.1 | 0.101 | 0.423 | >50 |
| DU151.02 | C | 0.036 | 0.116 | 0.204 | 0.294 | 0.188 | >50 | 0.03 | 1.71 | >50 |
| DU156.12 | C | 0.050 | 0.117 | 0.045 | 0.103 | 0.052 | 0.188 | 0.023 | 0.120 | >50 |
| DU172.17 | C | 0.244 | 0.480 | 0.197 | 0.272 | 0.428 | >50 | 0.846 | 0.238 | >50 |
| DU422.01 | C | 0.231 | 0.757 | 0.719 | 1.36 | 0.843 | >50 | 0.365 | 0.612 | >50 |
| MW965.26 | C | 0.04 | 0.127 | 0.024 | 0.101 | 0.076 | 0.128 | 0.051 | 0.04 | >50 |
| SO18.18 | C | 0.013 | 0.051 | 0.069 | 0.019 | 0.034 | 0.085 | 0.03 | 4.48 | >50 |
| TV1.29 | C | 0.897 | 1.80 | 3.39 | 6.06 | 3.88 | >50 | 0.318 | 0.719 | >50 |
| TZA125.17 | C | 7.29 | 22.1 | 3.14 | 3.21 | 2.81 | 0.147 | 0.060 | 1.19 | >50 |
| TZBD.02 | C | 0.026 | 0.090 | 0.040 | 0.084 | 0.075 | 0.602 | 0.021 | 4.31 | >50 |
| ZA012.29 | C | 0.055 | 0.129 | 0.165 | 0.195 | 0.152 | 0.513 | 0.018 | 4.12 | >50 |
| ZM106.9 | C | 0.059 | 0.161 | 0.155 | 0.233 | 0.143 | 0.414 | >50 | >50 | >50 |
| ZM109.4 | C | 0.312 | 0.926 | 0.368 | 0.329 | 0.281 | 6.10 | 9.25 | 1.07 | >50 |
| ZM135.10a | C | 3.95 | 7.79 | 0.093 | 0.228 | 0.558 | 0.207 | >50 | 0.403 | >50 |
| ZM176.66 | C | 0.232 | 0.727 | 0.171 | 0.324 | 0.239 | 1.64 | >50 | 1.73 | >50 |
| ZM197.7 | C | 3.92 | 15.6 | 0.706 | 2.57 | 2.42 | 3.36 | 2.37 | 0.369 | >50 |
| ZM214.15 | C | 3.40 | 8.45 | 2.68 | 2.94 | 1.30 | 0.937 | 0.057 | 5.98 | >50 |
| ZM215.8 | C | 0.056 | 0.281 | 0.083 | 0.100 | 0.062 | 6.95 | >50 | 0.230 | >50 |
| ZM233.6 | C | 0.199 | 0.628 | 0.322 | 0.335 | 0.161 | 0.442 | >50 | 0.737 | >50 |
| ZM249.1 | C | 1.58 | 3.30 | 0.817 | 0.868 | 0.226 | >50 | >50 | 2.27 | 0.005 |
| ZM53.12 | C | 0.004 | 0.021 | 0.031 | 0.057 | 0.028 | 1.88 | 0.015 | 6.72 | >50 |

| Virus ID | Clade | Bi-ScFv dVRC01-5X-PGT121 ScFv | Bi-NAb 5X-PGT121 Fc | Tri-NAb 10E8/dVRC01-5X-PGT121 | Tetra-NAb1 10E8-5X-35O22/dVRC01-5X-PGT121 | Tetra-NAb2 35O22-5X-10E8/dVRC01-5X-PGT121 | VRC01 | PGT121 | 10E8 | 35O22 |
|---|---|---|---|---|---|---|---|---|---|---|
| ZM55.28a | C | 0.358 | 1.06 | 0.726 | 0.741 | 0.531 | 0.629 | 0.233 | 6.78 | >50 |
| 3326.V4.C3 | CD | 0.035 | 0.042 | 0.075 | 0.067 | 0.057 | 2.98 | >50 | 4.29 | >50 |
| 3337.V2.C6 | CD | 0.119 | 0.241 | 0.178 | 0.159 | 0.103 | 0.211 | >50 | 4.87 | 0.070 |
| 3817.v2.c59 | CD | 35.4 | >50 | 4.56 | 11.2 | 6.02 | >50 | >50 | 1.43 | >50 |
| 191821.E6.1 | D | 1.15 | 3.89 | 3.01 | 2.41 | 1.19 | 1.34 | >50 | 5.89 | >50 |
| 231965.c1 | D | 3.30 | 3.35 | 1.15 | 0.882 | 0.434 | 1.01 | >50 | 20.4 | >50 |
| 247-23 | D | >50 | >50 | 2.06 | 2.59 | 0.443 | 12.3 | >50 | 1.29 | >50 |
| 3016.v5.c45 | D | 0.085 | 0.186 | 0.118 | 0.118 | 0.096 | 0.252 | >50 | 2.17 | >50 |
| 57128.vrc15 | D | 1.37 | 2.73 | 1.03 | 0.897 | 0.473 | >50 | >50 | 1.50 | >50 |
| 6405.v4.c34 | D | 0.255 | 0.645 | 0.357 | 0.383 | 0.151 | 4.24 | 0.080 | 1.80 | >50 |
| A03349M1.vrc4a | D | 0.184 | 0.433 | 0.462 | 0.407 | 0.191 | 13.9 | 0.155 | 0.663 | >50 |
| A07412M1.vrc12 | D | 0.034 | 0.134 | 0.106 | 0.097 | 0.062 | 0.339 | 0.104 | 0.873 | >50 |
| NKU3006.ec1 | D | 10.1 | 26.7 | 6.89 | 11.3 | 2.70 | 1.29 | >50 | 2.46 | 0.022 |
| UG021.16 | D | 0.929 | 1.18 | 0.103 | 0.333 | 0.482 | 1.59 | >50 | 0.362 | >50 |
| UG024.2 | D | 7.55 | 2.13 | 0.204 | 0.528 | 0.509 | 0.667 | >50 | 0.241 | >50 |
| P0402.c2.11 | G | 0.064 | 0.188 | 0.019 | 0.075 | 0.083 | 0.458 | 0.026 | 0.460 | 1.20 |
| P1981.C5.3 | G | 0.018 | 0.054 | 0.072 | 0.093 | 0.092 | 0.691 | 0.613 | 0.124 | 0.004 |
| x1193.c1 | G | 0.332 | 0.709 | 0.021 | 0.093 | 0.154 | 0.350 | 0.0803 | 1.15 | 0.400 |
| X1254.c3 | G | 0.159 | 0.535 | 0.040 | 0.176 | 0.182 | 0.132 | 0.069 | 15.7 | >50 |
| X1632.S2.B10 | G | 0.322 | 0.582 | 0.251 | 0.359 | 0.189 | 0.526 | >50 | 1.76 | >50 |
| X2088.c9 | G | 0.045 | 0.097 | 0.126 | 0.157 | 0.080 | >50 | 0.005 | >50 | 0.175 |
| X2131.C1.B5 | G | 0.080 | 0.197 | 0.026 | 0.137 | 0.136 | 1.41 | 0.043 | >50 | >50 |
| SIVmac251.30.SG3 | NA | >50 | >50 | >50 | >50 | >50 | >50 | >50 | >50 | >50 |
| SVA.MLV | NA | >50 | >50 | >50 | >50 | >50 | >50 | >50 | >50 | >50 |

IC80 (μg/mL): <0.01 / 0.01-0.1 / 0.1-1.00 / 1.00-10.0 / >10.0

Parental mAbs

FIG. 19G

|  | Bi-ScFv | Bi-NAb | Tri-NAb | Tetra-NAb1 | Tetra-NAb2 | Parental mAbs | | | |
|---|---|---|---|---|---|---|---|---|---|
|  | dVRC01-5X-PGT121 ScFv | dVRC01-5X-PGT121 IgG | 10E8/dVRC01-5X-PGT121 | 10E8/dVRC01-35O22/dVRC01-5X-PGT121 | 35O22-5X-10E8/dVRC01-5X-PGT121 | VRC01 | PGT121 | 10E8 | 35O22 |
| # Viruses | 208 | 208 | 208 | 208 | 208 | 208 | 208 | 208 | 208 |
| Total VS Neutralized | | | | | | | | | |
| IC80 <50ug/ml | 196 | 194 | 204 | 200 | 205 | 182 | 112 | 203 | 35 |
| IC80 <10ug/ml | 185 | 176 | 198 | 195 | 201 | 175 | 111 | 193 | 31 |
| IC80 <1.0ug/ml | 144 | 122 | 155 | 149 | 160 | 106 | 99 | 61 | 27 |
| IC80 <0.1ug/ml | 62 | 19 | 55 | 37 | 51 | 13 | 72 | 10 | 24 |
| IC80 <0.01ug/ml | 4 | 0 | 1 | 0 | 0 | 0 | 11 | 5 | 8 |
| % VS Neutralized | | | | | | | | | |
| IC80 <50ug/ml | 94 | 93 | 98.1 | 96 | 98.6 | 88 | 54 | 97.6 | 17 |
| IC80 <10ug/ml | 89 | 85 | 95 | 94 | 97 | 84 | 53 | 93 | 15 |
| IC80 <1.0ug/ml | 69 | 59 | 75 | 72 | 77 | 51 | 48 | 29 | 13 |
| IC80 <0.1ug/ml | 30 | 9 | 26 | 18 | 25 | 6 | 35 | 5 | 12 |
| IC80 <0.01ug/ml | 2 | 0 | 0 | 0 | 0 | 0 | 5 | 2 | 4 |
| Median IC80 | 0.216 | 0.540 | 0.235 | 0.310 | 0.226 | 0.703 | 0.059 | 1.69 | 0.040 |
| Geometric Mean | 0.298 | 0.749 | 0.298 | 0.384 | 0.296 | 0.793 | 0.081 | 1.34 | 0.087 |

Note: Median and Geometric Mean titers are calculated only for samples with IC80 <50ug/ml

FIG. 19H

SEQUENCE LISTING

<160> NUMBER OF SEQ ID NOS: 205

<210> SEQ ID NO 1
<211> LENGTH: 525
<212> TYPE: PRT
<213> ORGANISM: Artificial Sequence
<220> FEATURE:
<223> OTHER INFORMATION: Synthetic peptide

<400> SEQUENCE: 1

| | | | | | | | | | | | | | | |
|---|---|---|---|---|---|---|---|---|---|---|---|---|---|---|
| Glu | Ile | Val | Leu | Thr | Gln | Ser | Pro | Gly | Thr | Leu | Ser | Leu | Ser | Pro | Gly |
| 1 | | | | 5 | | | | | 10 | | | | | 15 | |
| Glu | Thr | Ala | Ile | Ile | Ser | Cys | Arg | Thr | Ser | Gln | Tyr | Gly | Ser | Leu | Ala |
| | | | 20 | | | | | 25 | | | | | 30 | | |
| Trp | Tyr | Gln | Gln | Arg | Pro | Gly | Gln | Ala | Pro | Arg | Leu | Val | Ile | Tyr | Ser |
| | | 35 | | | | | 40 | | | | | 45 | | | |
| Gly | Ser | Thr | Arg | Ala | Ala | Gly | Ile | Pro | Asp | Arg | Phe | Ser | Gly | Ser | Arg |
| | 50 | | | | | 55 | | | | | 60 | | | | |
| Trp | Gly | Pro | Asp | Tyr | Asn | Leu | Thr | Ile | Ser | Asn | Leu | Glu | Ser | Gly | Asp |
| 65 | | | | 70 | | | | | 75 | | | | | 80 | |
| Phe | Gly | Val | Tyr | Tyr | Cys | Gln | Gln | Tyr | Glu | Phe | Phe | Gly | Gln | Gly | Thr |
| | | | | 85 | | | | | 90 | | | | | 95 | |
| Lys | Val | Gln | Val | Asp | Ile | Lys | Gly | Gly | Gly | Ser | Gly | Gly | Gly | Gly | Gly |
| | | | 100 | | | | | 105 | | | | | 110 | | |
| Ser | Gly | Gly | Gly | Gly | Ser | Gln | Val | Gln | Leu | Val | Gln | Ser | Gly | Gly | Gln |
| | | 115 | | | | | 120 | | | | | 125 | | | |
| Met | Lys | Lys | Pro | Gly | Glu | Ser | Met | Arg | Ile | Ser | Cys | Arg | Ala | Ser | Gly |
| | 130 | | | | | 135 | | | | | 140 | | | | |
| Tyr | Glu | Phe | Ile | Asp | Cys | Thr | Leu | Asn | Trp | Ile | Arg | Leu | Ala | Pro | Gly |
| 145 | | | | 150 | | | | | 155 | | | | | 160 | |
| Lys | Arg | Pro | Glu | Trp | Met | Gly | Trp | Leu | Lys | Pro | Arg | Gly | Gly | Ala | Val |
| | | | | 165 | | | | | 170 | | | | | 175 | |
| Asn | Tyr | Ala | Arg | Pro | Leu | Gln | Gly | Arg | Val | Thr | Met | Thr | Arg | Asp | Val |
| | | | 180 | | | | | 185 | | | | | 190 | | |
| Tyr | Ser | Asp | Thr | Ala | Phe | Leu | Glu | Leu | Arg | Ser | Leu | Thr | Val | Asp | Asp |
| | | 195 | | | | | 200 | | | | | 205 | | | |
| Thr | Ala | Val | Tyr | Phe | Cys | Thr | Arg | Gly | Lys | Asn | Cys | Asp | Tyr | Asn | Trp |
| | 210 | | | | | 215 | | | | | 220 | | | | |
| Asp | Phe | Glu | His | Trp | Gly | Arg | Gly | Thr | Pro | Val | Ile | Val | Ser | Ser | Gly |
| 225 | | | | 230 | | | | | 235 | | | | | 240 | |
| Gly | Gly | Gly | Ser | Gly | Gly | Gly | Gly | Ser | Gly | Gly | Gly | Ser | Gly | Gly | |
| | | | 245 | | | | | 250 | | | | | 255 | | |
| Gly | Gly | Ser | Gly | Gly | Gly | Gly | Ser | Ser | Asp | Ile | Ser | Val | Ala | Pro | Gly |
| | | | 260 | | | | | 265 | | | | | 270 | | |
| Glu | Thr | Ala | Arg | Ile | Ser | Cys | Gly | Glu | Lys | Ser | Leu | Gly | Ser | Arg | Ala |
| | | | 275 | | | | | 280 | | | | | 285 | | |
| Val | Gln | Trp | Tyr | Gln | His | Arg | Ala | Gly | Gln | Ala | Pro | Ser | Leu | Ile | Ile |
| | | | 290 | | | | | 295 | | | | | 300 | | |
| Tyr | Asn | Asn | Gln | Asp | Arg | Pro | Ser | Gly | Ile | Pro | Glu | Arg | Phe | Ser | Gly |
| 305 | | | | 310 | | | | | 315 | | | | | 320 | |
| Ser | Pro | Asp | Ser | Pro | Phe | Gly | Thr | Thr | Ala | Thr | Leu | Thr | Ile | Thr | Ser |
| | | | | 325 | | | | | 330 | | | | | 335 | |
| Val | Glu | Ala | Gly | Asp | Glu | Ala | Asp | Tyr | Tyr | Cys | His | Ile | Trp | Asp | Ser |
| | | | 340 | | | | | 345 | | | | | 350 | | |
| Arg | Val | Pro | Thr | Lys | Trp | Val | Phe | Gly | Gly | Gly | Thr | Thr | Leu | Thr | Val |
| | | | 355 | | | | | 360 | | | | | 365 | | |
| Leu | Gly | Gly | Gly | Gly | Ser | Gly | Gly | Gly | Ser | Gly | Gly | Gly | Gly | Ser | |
| | 370 | | | | | 375 | | | | | 380 | | | | |
| Gln | Met | Gln | Leu | Gln | Glu | Ser | Gly | Pro | Gly | Leu | Val | Lys | Pro | Ser | Glu |
| 385 | | | | | 390 | | | | | 395 | | | | | 400 | |
| Thr | Leu | Ser | Leu | Thr | Cys | Ser | Val | Ser | Gly | Ala | Ser | Ile | Ser | Asp | Ser |
| | | | | 405 | | | | | 410 | | | | | 415 | |

```
Tyr Trp Ser Trp Ile Arg Arg Ser Pro Gly Lys Gly Leu Glu Trp Ile
            420                 425                 430

Gly Tyr Val His Lys Ser Gly Asp Thr Asn Tyr Ser Pro Ser Leu Lys
            435                 440                 445

Ser Arg Val Asn Leu Ser Leu Asp Thr Ser Lys Asn Gln Val Ser Leu
450                 455                 460

Ser Leu Val Ala Ala Thr Ala Ala Asp Ser Gly Lys Tyr Tyr Cys Ala
465                 470                 475                 480

Arg Thr Leu His Gly Arg Arg Ile Tyr Gly Ile Val Ala Phe Asn Glu
            485                 490                 495

Trp Phe Thr Tyr Phe Tyr Met Asp Val Trp Gly Asn Gly Thr Gln Val
            500                 505                 510

Thr Val Ser Ser Gly Ser Gly His His His His His
            515                 520                 525

<210> SEQ ID NO 2
<211> LENGTH: 103
<212> TYPE: PRT
<213> ORGANISM: Artificial Sequence
<220> FEATURE:
<223> OTHER INFORMATION: Synthetic peptide

<400> SEQUENCE: 2

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys
            100

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Arg Thr Ser Gln Tyr Gly Ser Leu Ala
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Ser Gly Ser Thr Arg Ala Ala
1               5
```

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

Gln Gln Tyr Glu Phe
1               5

<210> SEQ ID NO 6
<211> LENGTH: 121
<212> TYPE: PRT
<213> ORGANISM: Artificial Sequence
<220> FEATURE:
<223> OTHER INFORMATION: Synthetic peptide

<400> SEQUENCE: 6

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

Thr Arg Gly Lys Asn Cys Asp Tyr Asn Trp Asp Phe Glu His Trp Gly
            100                 105                 110

Arg Gly Thr Pro Val Ile Val Ser Ser
        115                 120

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide

<400> SEQUENCE: 7

Asp Cys Thr Leu Asn
1               5

<210> SEQ ID NO 8
<211> LENGTH: 17
<212> TYPE: PRT
<213> ORGANISM: Artificial Sequence
<220> FEATURE:
<223> OTHER INFORMATION: Synthetic peptide

<400> SEQUENCE: 8

Trp Leu Lys Pro Arg Gly Gly Ala Val Asn Tyr Ala Arg Pro Leu Gln
1               5                   10                  15

Gly

<210> SEQ ID NO 9
<211> LENGTH: 12
<212> TYPE: PRT

```
<213> ORGANISM: Artificial Sequence
<220> FEATURE:
<223> OTHER INFORMATION: Synthetic peptide

<400> SEQUENCE: 9

Gly Lys Asn Cys Asp Tyr Asn Trp Asp Phe Glu His
1               5                   10

<210> SEQ ID NO 10
<211> LENGTH: 105
<212> TYPE: PRT
<213> ORGANISM: Artificial Sequence
<220> FEATURE:
<223> OTHER INFORMATION: Synthetic peptide

<400> SEQUENCE: 10

Ser Asp Ile Ser Val Ala Pro Gly Glu Thr Ala Arg Ile Ser Cys Gly
1               5                   10                  15

Glu Lys Ser Leu Gly Ser Arg Ala Val Gln Trp Tyr Gln His Arg Ala
            20                  25                  30

Gly Gln Ala Pro Ser Leu Ile Ile Tyr Asn Asn Gln Asp Arg Pro Ser
        35                  40                  45

Gly Ile Pro Glu Arg Phe Ser Gly Ser Pro Asp Ser Pro Phe Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Val Pro Thr Lys Trp Val Phe
                85                  90                  95

Gly Gly Gly Thr Thr Leu Thr Val Leu
            100                 105

<210> SEQ ID NO 11
<211> LENGTH: 11
<212> TYPE: PRT
<213> ORGANISM: Artificial Sequence
<220> FEATURE:
<223> OTHER INFORMATION: Synthetic peptide

<400> SEQUENCE: 11

Gly Glu Lys Ser Leu Gly Ser Arg Ala Val Gln
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide

<400> SEQUENCE: 12

Asn Asn Gln Asp Arg Pro Ser
1               5

<210> SEQ ID NO 13
<211> LENGTH: 12
<212> TYPE: PRT
<213> ORGANISM: Artificial Sequence
<220> FEATURE:
<223> OTHER INFORMATION: Synthetic peptide

<400> SEQUENCE: 13

His Ile Trp Asp Ser Arg Val Pro Thr Lys Trp Val
1               5                   10
```

<210> SEQ ID NO 14
<211> LENGTH: 132
<212> TYPE: PRT
<213> ORGANISM: Artificial Sequence
<220> FEATURE:
<223> OTHER INFORMATION: Synthetic peptide

<400> SEQUENCE: 14

```
Gln Met Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Asp Ser
            20                  25                  30

Tyr Trp Ser Trp Ile Arg Arg Ser Pro Gly Lys Gly Leu Glu Trp Ile
        35                  40                  45

Gly Tyr Val His Lys Ser Gly Asp Thr Asn Tyr Ser Pro Ser Leu Lys
    50                  55                  60

Ser Arg Val Asn Leu Ser Leu Asp Thr Ser Lys Asn Gln Val Ser Leu
65                  70                  75                  80

Ser Leu Val Ala Ala Thr Ala Ala Asp Ser Gly Lys Tyr Tyr Cys Ala
                85                  90                  95

Arg Thr Leu His Gly Arg Arg Ile Tyr Gly Ile Val Ala Phe Asn Glu
            100                 105                 110

Trp Phe Thr Tyr Phe Tyr Met Asp Val Trp Gly Asn Gly Thr Gln Val
        115                 120                 125

Thr Val Ser Ser
    130
```

<210> SEQ ID NO 15
<211> LENGTH: 5
<212> TYPE: PRT
<213> ORGANISM: Artificial Sequence
<220> FEATURE:
<223> OTHER INFORMATION: Synthetic peptide

<400> SEQUENCE: 15

```
Asp Ser Tyr Trp Ser
1               5
```

<210> SEQ ID NO 16
<211> LENGTH: 16
<212> TYPE: PRT
<213> ORGANISM: Artificial Sequence
<220> FEATURE:
<223> OTHER INFORMATION: Synthetic peptide

<400> SEQUENCE: 16

```
Tyr Val His Lys Ser Gly Asp Thr Asn Tyr Ser Pro Ser Leu Lys Ser
1               5                   10                  15
```

<210> SEQ ID NO 17
<211> LENGTH: 24
<212> TYPE: PRT
<213> ORGANISM: Artificial Sequence
<220> FEATURE:
<223> OTHER INFORMATION: Synthetic peptide

<400> SEQUENCE: 17

```
Thr Leu His Gly Arg Arg Ile Tyr Gly Ile Val Ala Phe Asn Glu Trp
1               5                   10                  15

Phe Thr Tyr Phe Tyr Met Asp Val
            20
```

```
<210> SEQ ID NO 18
<211> LENGTH: 523
<212> TYPE: PRT
<213> ORGANISM: Artificial Sequence
<220> FEATURE:
<223> OTHER INFORMATION: Synthetic peptide

<400> SEQUENCE: 18

Ser Leu Thr Gln Ser Pro Gly Thr Leu Ser Leu Ser Pro Gly Glu Thr
1               5                   10                  15

Ala Ile Ile Ser Cys Arg Thr Ser Gln Tyr Gly Ser Leu Ala Trp Tyr
            20                  25                  30

Gln Gln Arg Pro Gly Gln Ala Pro Arg Leu Val Ile Tyr Ser Gly Ser
        35                  40                  45

Thr Arg Ala Ala Gly Ile Pro Asp Arg Phe Ser Gly Ser Arg Trp Gly
    50                  55                  60

Pro Asp Tyr Asn Leu Thr Ile Ser Asn Leu Glu Ser Gly Asp Phe Gly
65                  70                  75                  80

Val Tyr Tyr Cys Gln Gln Tyr Glu Phe Phe Gly Gln Gly Thr Lys Val
                85                  90                  95

Gln Val Asp Ile Lys Gly Gly Gly Ser Gly Gly Gly Gly Ser Gly Gly
            100                 105                 110

Gly Gly Ser Gln Val Gln Leu Val Gln Ser Gly Gly Gln Met Lys Lys
        115                 120                 125

Lys Pro Gly Glu Ser Met Arg Ile Ser Cys Arg Ala Ser Gly Tyr Glu
130                 135                 140

Phe Ile Asp Cys Thr Leu Asn Trp Ile Arg Leu Ala Pro Gly Lys Arg
145                 150                 155                 160

Pro Glu Trp Met Gly Trp Leu Lys Pro Arg Gly Gly Ala Val Asn Tyr
                165                 170                 175

Ala Arg Pro Leu Gln Gly Arg Val Thr Met Thr Arg Asp Val Tyr Ser
            180                 185                 190

Asp Thr Ala Phe Leu Glu Leu Arg Ser Leu Thr Val Asp Asp Thr Ala
        195                 200                 205

Val Tyr Phe Cys Thr Arg Gly Lys Asn Cys Asp Tyr Asn Trp Asp Phe
    210                 215                 220

Glu His Trp Gly Arg Gly Thr Pro Val Ile Val Ser Ser Gly Gly Gly
225                 230                 235                 240

Gly Ser Gly Gly Gly Gly Ser Gly Gly Gly Gly Ser Gly Gly Gly Gly
                245                 250                 255

Ser Gly Gly Gly Gly Ser Ser Asp Ile Ser Val Ala Pro Gly Glu Thr
            260                 265                 270

Ala Arg Ile Ser Cys Gly Glu Lys Ser Leu Gly Ser Arg Ala Val Gln
        275                 280                 285

Trp Tyr Gln His Arg Ala Gly Gln Ala Pro Ser Leu Ile Ile Tyr Asn
    290                 295                 300

Asn Gln Asp Arg Pro Ser Gly Ile Pro Glu Arg Phe Ser Gly Ser Pro
305                 310                 315                 320

Asp Ser Pro Phe Gly Thr Thr Ala Thr Leu Thr Ile Thr Ser Val Glu
                325                 330                 335

Ala Gly Asp Glu Ala Asp Tyr Tyr Cys His Ile Trp Asp Ser Arg Val
            340                 345                 350

Pro Thr Lys Trp Val Phe Gly Gly Gly Thr Thr Leu Thr Val Leu Gly
        355                 360                 365
```

```
Gly Gly Gly Ser Gly Gly Gly Ser Gly Gly Gly Ser Gln Met
        370             375             380
Gln Leu Gln Glu Ser Gly Pro Gly Leu Val Lys Pro Ser Glu Thr Leu
385             390             395                 400
Ser Leu Thr Cys Ser Val Ser Gly Ala Ser Ile Ser Asp Ser Tyr Trp
                405             410             415
Ser Trp Ile Arg Arg Ser Pro Gly Lys Gly Leu Glu Trp Ile Gly Tyr
            420             425             430
Val His Lys Ser Gly Asp Thr Asn Tyr Ser Pro Ser Leu Lys Ser Arg
            435             440             445
Val Asn Leu Ser Leu Asp Thr Ser Lys Asn Gln Val Ser Leu Ser Leu
450             455             460
Val Ala Ala Thr Ala Ala Asp Ser Gly Lys Tyr Tyr Cys Ala Arg Thr
465             470             475             480
Leu His Gly Arg Arg Ile Tyr Gly Ile Val Ala Phe Asn Glu Trp Phe
                485             490             495
Thr Tyr Phe Tyr Met Asp Val Trp Gly Asn Gly Thr Gln Val Thr Val
                500             505             510
Ser Ser Gly Ser Gly His His His His His His
            515             520
```

<210> SEQ ID NO 19
<211> LENGTH: 101
<212> TYPE: PRT
<213> ORGANISM: Artificial Sequence
<220> FEATURE:
<223> OTHER INFORMATION: Synthetic peptide

<400> SEQUENCE: 19

```
Ser Leu Thr Gln Ser Pro Gly Thr Leu Ser Leu Ser Pro Gly Glu Thr
1               5                   10                  15
Ala Ile Ile Ser Cys Arg Thr Ser Gln Tyr Gly Ser Leu Ala Trp Tyr
                20                  25                  30
Gln Gln Arg Pro Gly Gln Ala Pro Arg Leu Val Ile Tyr Ser Gly Ser
            35                  40                  45
Thr Arg Ala Ala Gly Ile Pro Asp Arg Phe Ser Gly Ser Arg Trp Gly
        50                  55                  60
Pro Asp Tyr Asn Leu Thr Ile Ser Asn Leu Glu Ser Gly Asp Phe Gly
65                  70                  75                  80
Val Tyr Tyr Cys Gln Gln Tyr Glu Phe Phe Gly Gln Gly Thr Lys Val
                85                  90                  95
Gln Val Asp Ile Lys
            100
```

<210> SEQ ID NO 20
<211> LENGTH: 525
<212> TYPE: PRT
<213> ORGANISM: Artificial Sequence
<220> FEATURE:
<223> OTHER INFORMATION: Synthetic peptide

<400> SEQUENCE: 20

```
Gln Met Gln Leu Gln Glu Ser Gly Pro Gly Leu Val Lys Pro Ser Glu
1               5                   10                  15
Thr Leu Ser Leu Thr Cys Ser Val Ser Gly Ala Ser Ile Ser Asp Ser
                20                  25                  30
Tyr Trp Ser Trp Ile Arg Arg Ser Pro Gly Lys Gly Leu Glu Trp Ile
            35                  40                  45
```

```
Gly Tyr Val His Lys Ser Gly Asp Thr Asn Tyr Ser Pro Ser Leu Lys
 50                  55                  60

Ser Arg Val Asn Leu Ser Leu Asp Thr Ser Lys Asn Gln Val Ser Leu
 65                  70                  75                  80

Ser Leu Val Ala Ala Thr Ala Ala Asp Ser Gly Lys Tyr Tyr Cys Ala
                 85                  90                  95

Arg Thr Leu His Gly Arg Arg Ile Tyr Gly Ile Val Ala Phe Asn Glu
                100                 105                 110

Trp Phe Thr Tyr Phe Tyr Met Asp Val Trp Gly Asn Gly Thr Gln Val
                115                 120                 125

Thr Val Ser Ser Gly Gly Gly Ser Gly Gly Gly Ser Gly Gly Gly Gly
130                 135                 140

Gly Gly Ser Ser Asp Ile Ser Val Ala Pro Gly Glu Thr Ala Arg Ile
145                 150                 155                 160

Ser Cys Gly Glu Lys Ser Leu Gly Ser Arg Ala Val Gln Trp Tyr Gln
                165                 170                 175

His Arg Ala Gly Gln Ala Pro Ser Leu Ile Ile Tyr Asn Asn Gln Asp
                180                 185                 190

Arg Pro Ser Gly Ile Pro Glu Arg Phe Ser Gly Ser Pro Asp Ser Pro
                195                 200                 205

Phe Gly Thr Thr Ala Thr Leu Thr Ile Thr Ser Val Glu Ala Gly Asp
210                 215                 220

Glu Ala Asp Tyr Tyr Cys His Ile Trp Asp Ser Arg Val Pro Thr Lys
225                 230                 235                 240

Trp Val Phe Gly Gly Gly Thr Thr Leu Thr Val Leu Gly Gly Gly Gly
                245                 250                 255

Ser Gly Gly Gly Gly Ser Gly Gly Gly Ser Gly Gly Gly Gly Ser
                260                 265                 270

Gly Gly Gly Gly Ser Gln Val Gln Leu Val Gln Ser Gly Gly Gln Met
                275                 280                 285

Lys Lys Pro Gly Glu Ser Met Arg Ile Ser Cys Arg Ala Ser Gly Tyr
290                 295                 300

Glu Phe Ile Asp Cys Thr Leu Asn Trp Ile Arg Leu Ala Pro Gly Lys
305                 310                 315                 320

Arg Pro Glu Trp Met Gly Trp Leu Lys Pro Arg Gly Gly Ala Val Asn
                325                 330                 335

Tyr Ala Arg Pro Leu Gln Gly Arg Val Thr Met Thr Arg Asp Val Tyr
                340                 345                 350

Ser Asp Thr Ala Phe Leu Glu Leu Arg Ser Leu Thr Val Asp Asp Thr
                355                 360                 365

Ala Val Tyr Phe Cys Thr Arg Gly Lys Asn Cys Asp Tyr Asn Trp Asp
370                 375                 380

Phe Glu His Trp Gly Arg Gly Thr Pro Val Ile Val Ser Ser Gly Gly
385                 390                 395                 400

Gly Gly Ser Gly Gly Gly Ser Gly Gly Gly Ser Glu Ile Val
                405                 410                 415

Leu Thr Gln Ser Pro Gly Thr Leu Ser Leu Ser Pro Gly Glu Thr Ala
                420                 425                 430

Ile Ile Ser Cys Arg Thr Ser Gln Tyr Gly Ser Leu Ala Trp Tyr Gln
                435                 440                 445

Gln Arg Pro Gly Gln Ala Pro Arg Leu Val Ile Tyr Ser Gly Ser Thr
450                 455                 460
```

```
Arg Ala Ala Gly Ile Pro Asp Arg Phe Ser Gly Ser Arg Trp Gly Pro
465                 470                 475                 480

Asp Tyr Asn Leu Thr Ile Ser Asn Leu Glu Ser Gly Asp Phe Gly Val
                485                 490                 495

Tyr Tyr Cys Gln Gln Tyr Glu Phe Phe Gly Gln Gly Thr Lys Val Gln
            500                 505                 510

Val Asp Ile Lys Gly Ser Gly His His His His His His
            515                 520                 525
```

<210> SEQ ID NO 21
<211> LENGTH: 520
<212> TYPE: PRT
<213> ORGANISM: Artificial Sequence
<220> FEATURE:
<223> OTHER INFORMATION: Synthetic peptide

<400> SEQUENCE: 21

```
Gln Met Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Asp Ser
            20                  25                  30

Tyr Trp Ser Trp Ile Arg Arg Ser Pro Gly Lys Gly Leu Glu Trp Ile
        35                  40                  45

Gly Tyr Val His Lys Ser Gly Asp Thr Asn Tyr Ser Pro Ser Leu Lys
50                  55                  60

Ser Arg Val Asn Leu Ser Leu Asp Thr Ser Lys Asn Gln Val Ser Leu
65                  70                  75                  80

Ser Leu Val Ala Ala Thr Ala Ala Asp Ser Gly Lys Tyr Tyr Cys Ala
                85                  90                  95

Arg Thr Leu His Gly Arg Arg Ile Tyr Gly Ile Val Ala Phe Asn Glu
            100                 105                 110

Trp Phe Thr Tyr Phe Tyr Met Asp Val Trp Gly Asn Gly Thr Gln Val
        115                 120                 125

Thr Val Ser Ser Gly Gly Gly Gly Ser Gly Gly Gly Ser Gly Gly
130                 135                 140

Gly Gly Ser Ser Asp Ile Ser Val Ala Pro Gly Glu Thr Ala Arg Ile
145                 150                 155                 160

Ser Cys Gly Glu Lys Ser Leu Gly Ser Arg Ala Val Gln Trp Tyr Gln
                165                 170                 175

His Arg Ala Gly Gln Ala Pro Ser Leu Ile Ile Tyr Asn Asn Gln Asp
            180                 185                 190

Arg Pro Ser Gly Ile Pro Glu Arg Phe Ser Gly Ser Pro Asp Ser Pro
        195                 200                 205

Phe Gly Thr Thr Ala Thr Leu Thr Ile Thr Ser Val Glu Ala Gly Asp
210                 215                 220

Glu Ala Asp Tyr Tyr Cys His Ile Trp Asp Ser Arg Val Pro Thr Lys
225                 230                 235                 240

Trp Val Phe Gly Gly Gly Thr Thr Leu Thr Val Leu Gly Gly Gly Gly
                245                 250                 255

Ser Gly Gly Gly Gly Ser Gly Gly Gly Ser Gly Gly Gly Gly Ser
            260                 265                 270

Gln Val Gln Leu Val Gln Ser Gly Gly Gln Met Lys Lys Pro Gly Glu
        275                 280                 285

Ser Met Arg Ile Ser Cys Arg Ala Ser Gly Tyr Glu Phe Ile Asp Cys
290                 295                 300
```

```
Thr Leu Asn Trp Ile Arg Leu Ala Pro Gly Lys Pro Glu Trp Met
305                 310                 315                 320

Gly Trp Leu Lys Pro Arg Gly Gly Ala Val Asn Tyr Ala Arg Pro Leu
        325                 330                 335

Gln Gly Arg Val Thr Met Thr Arg Asp Val Tyr Ser Asp Thr Ala Phe
            340                 345                 350

Leu Glu Leu Arg Ser Leu Thr Val Asp Asp Thr Ala Val Tyr Phe Cys
        355                 360                 365

Thr Arg Gly Lys Asn Cys Asp Tyr Asn Trp Asp Phe Glu His Trp Gly
370                 375                 380

Arg Gly Thr Pro Val Ile Val Ser Ser Gly Gly Gly Ser Gly Gly
385                 390                 395                 400

Gly Gly Ser Gly Gly Gly Ser Glu Ile Val Leu Thr Gln Ser Pro
            405                 410                 415

Gly Thr Leu Ser Leu Ser Pro Gly Glu Thr Ala Ile Ile Ser Cys Arg
            420                 425                 430

Thr Ser Gln Tyr Gly Ser Leu Ala Trp Tyr Gln Gln Arg Pro Gly Gln
        435                 440                 445

Ala Pro Arg Leu Val Ile Tyr Ser Gly Ser Thr Arg Ala Ala Gly Ile
450                 455                 460

Pro Asp Arg Phe Ser Gly Ser Arg Trp Gly Pro Asp Tyr Asn Leu Thr
465                 470                 475                 480

Ile Ser Asn Leu Glu Ser Gly Asp Phe Gly Val Tyr Tyr Cys Gln Gln
                485                 490                 495

Tyr Glu Phe Phe Gly Gln Gly Thr Lys Val Gln Val Asp Ile Lys Gly
            500                 505                 510

Ser Gly His His His His His His
        515                 520

<210> SEQ ID NO 22
<211> LENGTH: 515
<212> TYPE: PRT
<213> ORGANISM: Artificial Sequence
<220> FEATURE:
<223> OTHER INFORMATION: Synthetic peptide

<400> SEQUENCE: 22

Gln Met Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Asp Ser
            20                  25                  30

Tyr Trp Ser Trp Ile Arg Arg Ser Pro Gly Lys Gly Leu Glu Trp Ile
        35                  40                  45

Gly Tyr Val His Lys Ser Gly Asp Thr Asn Tyr Ser Pro Ser Leu Lys
    50                  55                  60

Ser Arg Val Asn Leu Ser Leu Asp Thr Ser Lys Asn Gln Val Ser Leu
65                  70                  75                  80

Ser Leu Val Ala Ala Thr Ala Ala Asp Ser Gly Lys Tyr Tyr Cys Ala
                85                  90                  95

Arg Thr Leu His Gly Arg Arg Ile Tyr Gly Ile Val Ala Phe Asn Glu
            100                 105                 110

Trp Phe Thr Tyr Phe Tyr Met Asp Val Trp Gly Asn Gly Thr Gln Val
        115                 120                 125

Thr Val Ser Ser Gly Gly Gly Gly Ser Gly Gly Gly Gly Ser Gly Gly
    130                 135                 140
```

Gly Gly Ser Ser Asp Ile Ser Val Ala Pro Gly Glu Thr Ala Arg Ile
145                 150                 155                 160

Ser Cys Gly Glu Lys Ser Leu Gly Ser Arg Ala Val Gln Trp Tyr Gln
                165                 170                 175

His Arg Ala Gly Gln Ala Pro Ser Leu Ile Ile Tyr Asn Asn Gln Asp
            180                 185                 190

Arg Pro Ser Gly Ile Pro Glu Arg Phe Ser Gly Ser Pro Asp Ser Pro
        195                 200                 205

Phe Gly Thr Thr Ala Thr Leu Thr Ile Thr Ser Val Glu Ala Gly Asp
    210                 215                 220

Glu Ala Asp Tyr Tyr Cys His Ile Trp Asp Ser Arg Val Pro Thr Lys
225                 230                 235                 240

Trp Val Phe Gly Gly Gly Thr Thr Leu Thr Val Leu Gly Gly Gly Gly
                245                 250                 255

Ser Gly Gly Gly Gly Ser Gly Gly Gly Ser Gln Val Gln Leu Val
            260                 265                 270

Gln Ser Gly Gly Gln Met Lys Lys Pro Gly Glu Ser Met Arg Ile Ser
        275                 280                 285

Cys Arg Ala Ser Gly Tyr Glu Phe Ile Asp Cys Thr Leu Asn Trp Ile
290                 295                 300

Arg Leu Ala Pro Gly Lys Arg Pro Glu Trp Met Gly Trp Leu Lys Pro
305                 310                 315                 320

Arg Gly Gly Ala Val Asn Tyr Ala Arg Pro Leu Gln Gly Arg Val Thr
                325                 330                 335

Met Thr Arg Asp Val Tyr Ser Asp Thr Ala Phe Leu Glu Leu Arg Ser
            340                 345                 350

Leu Thr Val Asp Asp Thr Ala Val Tyr Phe Cys Thr Arg Gly Lys Asn
        355                 360                 365

Cys Asp Tyr Asn Trp Asp Phe Glu His Trp Gly Arg Gly Thr Pro Val
    370                 375                 380

Ile Val Ser Ser Gly Gly Gly Gly Ser Gly Gly Gly Gly Ser Gly Gly
385                 390                 395                 400

Gly Gly Ser Glu Ile Val Leu Thr Gln Ser Pro Gly Thr Leu Ser Leu
                405                 410                 415

Ser Pro Gly Glu Thr Ala Ile Ile Ser Cys Arg Thr Ser Gln Tyr Gly
            420                 425                 430

Ser Leu Ala Trp Tyr Gln Gln Arg Pro Gly Gln Ala Pro Arg Leu Val
        435                 440                 445

Ile Tyr Ser Gly Ser Thr Arg Ala Ala Gly Ile Pro Asp Arg Phe Ser
    450                 455                 460

Gly Ser Arg Trp Gly Pro Asp Tyr Asn Leu Thr Ile Ser Asn Leu Glu
465                 470                 475                 480

Ser Gly Asp Phe Gly Val Tyr Tyr Cys Gln Gln Tyr Glu Phe Phe Gly
                485                 490                 495

Gln Gly Thr Lys Val Gln Val Asp Ile Lys Gly Ser Gly His His
            500                 505                 510

His His His
        515

<210> SEQ ID NO 23
<211> LENGTH: 750
<212> TYPE: PRT
<213> ORGANISM: Artificial Sequence
<220> FEATURE:
<223> OTHER INFORMATION: Synthetic peptide

<400> SEQUENCE: 23

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys Gly Gly Gly Ser Gly Gly Gly Gly
            100                 105                 110

Ser Gly Gly Gly Ser Gln Val Gln Leu Val Gln Ser Gly Gly Gln
        115                 120                 125

Met Lys Lys Pro Gly Glu Ser Met Arg Ile Ser Cys Arg Ala Ser Gly
130                 135                 140

Tyr Glu Phe Ile Asp Cys Thr Leu Asn Trp Ile Arg Leu Ala Pro Gly
145                 150                 155                 160

Lys Arg Pro Glu Trp Met Gly Trp Leu Lys Pro Arg Gly Gly Ala Val
                165                 170                 175

Asn Tyr Ala Arg Pro Leu Gln Gly Arg Val Thr Met Thr Arg Asp Val
            180                 185                 190

Tyr Ser Asp Thr Ala Phe Leu Glu Leu Arg Ser Leu Thr Val Asp Asp
        195                 200                 205

Thr Ala Val Tyr Phe Cys Thr Arg Gly Lys Asn Cys Asp Tyr Asn Trp
    210                 215                 220

Asp Phe Glu His Trp Gly Arg Gly Thr Pro Val Ile Val Ser Ser Gly
225                 230                 235                 240

Gly Gly Gly Ser Gly Gly Gly Ser Gly Gly Gly Ser Gly Gly
                245                 250                 255

Gly Gly Ser Gly Gly Gly Ser Ser Asp Ile Ser Val Ala Pro Gly
            260                 265                 270

Glu Thr Ala Arg Ile Ser Cys Gly Glu Lys Ser Leu Gly Ser Arg Ala
        275                 280                 285

Val Gln Trp Tyr Gln His Arg Ala Gly Gln Ala Pro Ser Leu Ile Ile
    290                 295                 300

Tyr Asn Asn Gln Asp Arg Pro Ser Gly Ile Pro Glu Arg Phe Ser Gly
305                 310                 315                 320

Ser Pro Asp Ser Pro Phe Gly Thr Thr Ala Thr Leu Thr Ile Thr Ser
                325                 330                 335

Val Glu Ala Gly Asp Glu Ala Asp Tyr Tyr Cys His Ile Trp Asp Ser
            340                 345                 350

Arg Val Pro Thr Lys Trp Val Phe Gly Gly Gly Thr Thr Leu Thr Val
        355                 360                 365

Leu Gly Gly Gly Gly Ser Gly Gly Gly Ser Gly Gly Gly Gly Ser
    370                 375                 380

Gln Met Gln Leu Gln Glu Ser Gly Pro Gly Leu Val Lys Pro Ser Glu
385                 390                 395                 400

Thr Leu Ser Leu Thr Cys Ser Val Ser Gly Ala Ser Ile Ser Asp Ser 405                 410                 415

Tyr Trp Ser Trp Ile Arg Arg Ser Pro Gly Lys Gly Leu Glu Trp Ile
            420                 425                 430

Gly Tyr Val His Lys Ser Gly Asp Thr Asn Tyr Ser Pro Ser Leu Lys
            435                 440                 445

Ser Arg Val Asn Leu Ser Leu Asp Thr Ser Lys Asn Gln Val Ser Leu
450                 455                 460

Ser Leu Val Ala Ala Thr Ala Ala Asp Ser Gly Lys Tyr Tyr Cys Ala
465                 470                 475                 480

Arg Thr Leu His Gly Arg Ile Tyr Gly Ile Val Ala Phe Asn Glu
            485                 490                 495

Trp Phe Thr Tyr Phe Tyr Met Asp Val Trp Gly Asn Gly Thr Gln Val
            500                 505                 510

Thr Val Ser Ser Gly Ser Gly Pro Lys Ser Cys Asp Lys Thr His Thr
            515                 520                 525

Cys Pro Pro Cys Pro Ala Pro Glu Leu Leu Gly Gly Pro Ser Val Phe
530                 535                 540

Leu Phe Pro Pro Lys Pro Lys Asp Thr Leu Met Ile Ser Arg Thr Pro
545                 550                 555                 560

Glu Val Thr Cys Val Val Val Asp Val Ser His Glu Asp Pro Glu Val
                565                 570                 575

Lys Phe Asn Trp Tyr Val Asp Gly Val Glu Val His Asn Ala Lys Thr
            580                 585                 590

Lys Pro Arg Glu Glu Gln Tyr Asn Ser Thr Tyr Arg Val Val Ser Val
            595                 600                 605

Leu Thr Val Leu His Gln Asp Trp Leu Asn Gly Lys Glu Tyr Lys Cys
610                 615                 620

Lys Val Ser Asn Lys Ala Leu Pro Ala Pro Ile Glu Lys Thr Ile Ser
625                 630                 635                 640

Lys Ala Lys Gly Gln Pro Arg Glu Pro Gln Val Tyr Thr Leu Pro Pro
                645                 650                 655

Ser Arg Glu Glu Met Thr Lys Asn Gln Val Ser Leu Thr Cys Leu Val
            660                 665                 670

Lys Gly Phe Tyr Pro Ser Asp Ile Ala Val Glu Trp Glu Ser Asn Gly
            675                 680                 685

Gln Pro Glu Asn Asn Tyr Lys Thr Thr Pro Pro Val Leu Asp Ser Asp
690                 695                 700

Gly Ser Phe Phe Leu Tyr Ser Lys Leu Thr Val Asp Lys Ser Arg Trp
705                 710                 715                 720

Gln Gln Gly Asn Val Phe Ser Cys Ser Val Met His Glu Ala Leu His
                725                 730                 735

Asn His Tyr Thr Gln Lys Ser Leu Ser Leu Ser Pro Gly Lys
            740                 745                 750

<210> SEQ ID NO 24
<211> LENGTH: 748
<212> TYPE: PRT
<213> ORGANISM: Artificial Sequence
<220> FEATURE:
<223> OTHER INFORMATION: Synthetic peptide

<400> SEQUENCE: 24

Ser Leu Thr Gln Ser Pro Gly Thr Leu Ser Leu Ser Pro Gly Glu Thr
1               5                   10                  15

Ala Ile Ile Ser Cys Arg Thr Ser Gln Tyr Gly Ser Leu Ala Trp Tyr

```
                    20                  25                  30
Gln Gln Arg Pro Gly Gln Ala Pro Arg Leu Val Ile Tyr Ser Gly Ser
                35                  40                  45

Thr Arg Ala Ala Gly Ile Pro Asp Arg Phe Ser Gly Ser Arg Trp Gly
            50                  55                  60

Pro Asp Tyr Asn Leu Thr Ile Ser Asn Leu Glu Ser Gly Asp Phe Gly
 65                  70                  75                  80

Val Tyr Tyr Cys Gln Gln Tyr Glu Phe Phe Gly Gln Gly Thr Lys Val
                85                  90                  95

Gln Val Asp Ile Lys Gly Gly Gly Ser Gly Gly Gly Gly Ser Gly
                100                 105                 110

Gly Gly Gly Ser Gln Val Gln Leu Val Gln Ser Gly Gln Met Lys
            115                 120                 125

Lys Pro Gly Glu Ser Met Arg Ile Ser Cys Arg Ala Ser Gly Tyr Glu
                130                 135                 140

Phe Ile Asp Cys Thr Leu Asn Trp Ile Arg Leu Ala Pro Gly Lys Arg
145                 150                 155                 160

Pro Glu Trp Met Gly Trp Leu Lys Pro Arg Gly Gly Ala Val Asn Tyr
                165                 170                 175

Ala Arg Pro Leu Gln Gly Arg Val Thr Met Thr Arg Asp Val Tyr Ser
                180                 185                 190

Asp Thr Ala Phe Leu Glu Leu Arg Ser Leu Thr Val Asp Asp Thr Ala
                195                 200                 205

Val Tyr Phe Cys Thr Arg Gly Lys Asn Cys Asp Tyr Asn Trp Asp Phe
                210                 215                 220

Glu His Trp Gly Arg Gly Thr Pro Val Ile Val Ser Ser Gly Gly Gly
225                 230                 235                 240

Gly Ser Gly Gly Gly Gly Ser Gly Gly Gly Gly Ser Gly Gly Gly Gly
                245                 250                 255

Ser Gly Gly Gly Gly Ser Ser Asp Ile Ser Val Ala Pro Gly Glu Thr
                260                 265                 270

Ala Arg Ile Ser Cys Gly Glu Lys Ser Leu Gly Ser Arg Ala Val Gln
                275                 280                 285

Trp Tyr Gln His Arg Ala Gly Gln Ala Pro Ser Leu Ile Ile Tyr Asn
                290                 295                 300

Asn Gln Asp Arg Pro Ser Gly Ile Pro Glu Arg Phe Ser Gly Ser Pro
305                 310                 315                 320

Asp Ser Pro Phe Gly Thr Thr Ala Thr Leu Thr Ile Thr Ser Val Glu
                325                 330                 335

Ala Gly Asp Glu Ala Asp Tyr Tyr Cys His Ile Trp Asp Ser Arg Val
                340                 345                 350

Pro Thr Lys Trp Val Phe Gly Gly Gly Thr Thr Leu Thr Val Leu Gly
                355                 360                 365

Gly Gly Gly Ser Gly Gly Gly Gly Ser Gly Gly Gly Gly Ser Gln Met
                370                 375                 380

Gln Leu Gln Glu Ser Gly Pro Gly Leu Val Lys Pro Ser Glu Thr Leu
385                 390                 395                 400

Ser Leu Thr Cys Ser Val Ser Gly Ala Ser Ile Ser Asp Ser Tyr Trp
                405                 410                 415

Ser Trp Ile Arg Arg Ser Pro Gly Lys Gly Leu Glu Trp Ile Gly Tyr
                420                 425                 430

Val His Lys Ser Gly Asp Thr Asn Tyr Ser Pro Ser Leu Lys Ser Arg
                435                 440                 445
```

Val Asn Leu Ser Leu Asp Thr Ser Lys Asn Gln Val Ser Leu Ser Leu
        450                 455                 460

Val Ala Ala Thr Ala Ala Asp Ser Gly Lys Tyr Tyr Cys Ala Arg Thr
465                 470                 475                 480

Leu His Gly Arg Arg Ile Tyr Gly Ile Val Ala Phe Asn Glu Trp Phe
                485                 490                 495

Thr Tyr Phe Tyr Met Asp Val Trp Gly Asn Gly Thr Gln Val Thr Val
            500                 505                 510

Ser Ser Gly Ser Gly Pro Lys Ser Cys Asp Lys Thr His Thr Cys Pro
        515                 520                 525

Pro Cys Pro Ala Pro Glu Leu Leu Gly Gly Pro Ser Val Phe Leu Phe
    530                 535                 540

Pro Pro Lys Pro Lys Asp Thr Leu Met Ile Ser Arg Thr Pro Glu Val
545                 550                 555                 560

Thr Cys Val Val Val Asp Val Ser His Glu Asp Pro Glu Val Lys Phe
                565                 570                 575

Asn Trp Tyr Val Asp Gly Val Glu Val His Asn Ala Lys Thr Lys Pro
            580                 585                 590

Arg Glu Glu Gln Tyr Asn Ser Thr Tyr Arg Val Val Ser Val Leu Thr
        595                 600                 605

Val Leu His Gln Asp Trp Leu Asn Gly Lys Glu Tyr Lys Cys Lys Val
    610                 615                 620

Ser Asn Lys Ala Leu Pro Ala Pro Ile Glu Lys Thr Ile Ser Lys Ala
625                 630                 635                 640

Lys Gly Gln Pro Arg Glu Pro Gln Val Tyr Thr Leu Pro Pro Ser Arg
                645                 650                 655

Glu Glu Met Thr Lys Asn Gln Val Ser Leu Thr Cys Leu Val Lys Gly
            660                 665                 670

Phe Tyr Pro Ser Asp Ile Ala Val Glu Trp Glu Ser Asn Gly Gln Pro
        675                 680                 685

Glu Asn Asn Tyr Lys Thr Thr Pro Pro Val Leu Asp Ser Asp Gly Ser
    690                 695                 700

Phe Phe Leu Tyr Ser Lys Leu Thr Val Asp Lys Ser Arg Trp Gln Gln
705                 710                 715                 720

Gly Asn Val Phe Ser Cys Ser Val Met His Glu Ala Leu His Asn His
                725                 730                 735

Tyr Thr Gln Lys Ser Leu Ser Leu Ser Pro Gly Lys
            740                 745

<210> SEQ ID NO 25
<211> LENGTH: 750
<212> TYPE: PRT
<213> ORGANISM: Artificial Sequence
<220> FEATURE:
<223> OTHER INFORMATION: Synthetic peptide

<400> SEQUENCE: 25

Gln Met Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Asp Ser
            20                  25                  30

Tyr Trp Ser Trp Ile Arg Arg Ser Pro Gly Lys Gly Leu Glu Trp Ile
        35                  40                  45

Gly Tyr Val His Lys Ser Gly Asp Thr Asn Tyr Ser Pro Ser Leu Lys
    50                  55                  60

```
Ser Arg Val Asn Leu Ser Leu Asp Thr Ser Lys Asn Gln Val Ser Leu
 65                  70                  75                  80

Ser Leu Val Ala Ala Thr Ala Ala Asp Ser Gly Lys Tyr Tyr Cys Ala
                 85                  90                  95

Arg Thr Leu His Gly Arg Arg Ile Tyr Gly Ile Val Ala Phe Asn Glu
            100                 105                 110

Trp Phe Thr Tyr Phe Tyr Met Asp Val Trp Gly Asn Gly Thr Gln Val
        115                 120                 125

Thr Val Ser Ser Gly Gly Gly Ser Gly Gly Gly Ser Gly Gly
130                 135                 140

Gly Gly Ser Ser Asp Ile Ser Val Ala Pro Gly Glu Thr Ala Arg Ile
145                 150                 155                 160

Ser Cys Gly Glu Lys Ser Leu Gly Ser Arg Ala Val Gln Trp Tyr Gln
                165                 170                 175

His Arg Ala Gly Gln Ala Pro Ser Leu Ile Ile Tyr Asn Asn Gln Asp
            180                 185                 190

Arg Pro Ser Gly Ile Pro Glu Arg Phe Ser Gly Ser Pro Asp Ser Pro
        195                 200                 205

Phe Gly Thr Thr Ala Thr Leu Thr Ile Thr Ser Val Glu Ala Gly Asp
210                 215                 220

Glu Ala Asp Tyr Tyr Cys His Ile Trp Asp Ser Arg Val Pro Thr Lys
225                 230                 235                 240

Trp Val Phe Gly Gly Gly Thr Thr Leu Thr Val Leu Gly Gly Gly Gly
                245                 250                 255

Ser Gly Gly Gly Gly Ser Gly Gly Gly Ser Gly Gly Gly Gly Ser
            260                 265                 270

Gly Gly Gly Gly Ser Gln Val Gln Leu Val Gln Ser Gly Gly Gln Met
275                 280                 285

Lys Lys Pro Gly Glu Ser Met Arg Ile Ser Cys Arg Ala Ser Gly Tyr
290                 295                 300

Glu Phe Ile Asp Cys Thr Leu Asn Trp Ile Arg Leu Ala Pro Gly Lys
305                 310                 315                 320

Arg Pro Glu Trp Met Gly Trp Leu Lys Pro Arg Gly Gly Ala Val Asn
                325                 330                 335

Tyr Ala Arg Pro Leu Gln Gly Arg Val Thr Met Thr Arg Asp Val Tyr
            340                 345                 350

Ser Asp Thr Ala Phe Leu Glu Leu Arg Ser Leu Thr Val Asp Asp Thr
        355                 360                 365

Ala Val Tyr Phe Cys Thr Arg Gly Lys Asn Cys Asp Tyr Asn Trp Asp
370                 375                 380

Phe Glu His Trp Gly Arg Gly Thr Pro Val Ile Val Ser Ser Gly Gly
385                 390                 395                 400

Gly Gly Ser Gly Gly Gly Gly Ser Gly Gly Gly Gly Ser Glu Ile Val
                405                 410                 415

Leu Thr Gln Ser Pro Gly Thr Leu Ser Leu Ser Pro Gly Glu Thr Ala
            420                 425                 430

Ile Ile Ser Cys Arg Thr Ser Gln Tyr Gly Ser Leu Ala Trp Tyr Gln
        435                 440                 445

Gln Arg Pro Gly Gln Ala Pro Arg Leu Val Ile Tyr Ser Gly Ser Thr
450                 455                 460

Arg Ala Ala Gly Ile Pro Asp Arg Phe Ser Gly Ser Arg Trp Gly Pro
465                 470                 475                 480
```

```
Asp Tyr Asn Leu Thr Ile Ser Asn Leu Glu Ser Gly Asp Phe Gly Val
            485                 490                 495

Tyr Tyr Cys Gln Gln Tyr Glu Phe Phe Gly Gln Gly Thr Lys Val Gln
            500                 505                 510

Val Asp Ile Lys Gly Ser Gly Pro Lys Ser Cys Asp Lys Thr His Thr
            515                 520                 525

Cys Pro Pro Cys Pro Ala Pro Glu Leu Leu Gly Gly Pro Ser Val Phe
            530                 535                 540

Leu Phe Pro Pro Lys Pro Lys Asp Thr Leu Met Ile Ser Arg Thr Pro
545                 550                 555                 560

Glu Val Thr Cys Val Val Val Asp Val Ser His Glu Asp Pro Glu Val
                565                 570                 575

Lys Phe Asn Trp Tyr Val Asp Gly Val Glu Val His Asn Ala Lys Thr
            580                 585                 590

Lys Pro Arg Glu Glu Gln Tyr Asn Ser Thr Tyr Arg Val Val Ser Val
            595                 600                 605

Leu Thr Val Leu His Gln Asp Trp Leu Asn Gly Lys Glu Tyr Lys Cys
            610                 615                 620

Lys Val Ser Asn Lys Ala Leu Pro Ala Pro Ile Glu Lys Thr Ile Ser
625                 630                 635                 640

Lys Ala Lys Gly Gln Pro Arg Glu Pro Gln Val Tyr Thr Leu Pro Pro
                645                 650                 655

Ser Arg Glu Glu Met Thr Lys Asn Gln Val Ser Leu Thr Cys Leu Val
            660                 665                 670

Lys Gly Phe Tyr Pro Ser Asp Ile Ala Val Glu Trp Glu Ser Asn Gly
            675                 680                 685

Gln Pro Glu Asn Asn Tyr Lys Thr Thr Pro Pro Val Leu Asp Ser Asp
            690                 695                 700

Gly Ser Phe Phe Leu Tyr Ser Lys Leu Thr Val Asp Lys Ser Arg Trp
705                 710                 715                 720

Gln Gln Gly Asn Val Phe Ser Cys Ser Val Met His Glu Ala Leu His
                725                 730                 735

Asn His Tyr Thr Gln Lys Ser Leu Ser Leu Ser Pro Gly Lys
            740                 745                 750

<210> SEQ ID NO 26
<211> LENGTH: 745
<212> TYPE: PRT
<213> ORGANISM: Artificial Sequence
<220> FEATURE:
<223> OTHER INFORMATION: Synthetic peptide

<400> SEQUENCE: 26

Gln Met Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Asp Ser
            20                  25                  30

Tyr Trp Ser Trp Ile Arg Arg Ser Pro Gly Lys Gly Leu Glu Trp Ile
            35                  40                  45

Gly Tyr Val His Lys Ser Gly Asp Thr Asn Tyr Ser Pro Ser Leu Lys
        50                  55                  60

Ser Arg Val Asn Leu Ser Leu Asp Thr Ser Lys Asn Gln Val Ser Leu
65                  70                  75                  80

Ser Leu Val Ala Ala Thr Ala Ala Asp Ser Gly Lys Tyr Tyr Cys Ala
                85                  90                  95
```

-continued

```
Arg Thr Leu His Gly Arg Arg Ile Tyr Gly Ile Val Ala Phe Asn Glu
             100                 105                 110
Trp Phe Thr Tyr Phe Tyr Met Asp Val Trp Gly Asn Gly Thr Gln Val
        115                 120                 125
Thr Val Ser Ser Gly Gly Gly Ser Gly Gly Gly Ser Gly Gly
130                 135                 140
Gly Gly Ser Ser Asp Ile Ser Val Ala Pro Gly Glu Thr Ala Arg Ile
145                 150                 155                 160
Ser Cys Gly Glu Lys Ser Leu Gly Ser Arg Ala Val Gln Trp Tyr Gln
                165                 170                 175
His Arg Ala Gly Gln Ala Pro Ser Leu Ile Ile Tyr Asn Asn Gln Asp
            180                 185                 190
Arg Pro Ser Gly Ile Pro Glu Arg Phe Ser Gly Ser Pro Asp Ser Pro
        195                 200                 205
Phe Gly Thr Thr Ala Thr Leu Thr Ile Thr Ser Val Glu Ala Gly Asp
    210                 215                 220
Glu Ala Asp Tyr Tyr Cys His Ile Trp Asp Ser Arg Val Pro Thr Lys
225                 230                 235                 240
Trp Val Phe Gly Gly Gly Thr Thr Leu Thr Val Leu Gly Gly Gly Gly
                245                 250                 255
Ser Gly Gly Gly Gly Ser Gly Gly Gly Ser Gly Gly Gly Gly Ser
            260                 265                 270
Gln Val Gln Leu Val Gln Ser Gly Gly Gln Met Lys Lys Pro Gly Glu
        275                 280                 285
Ser Met Arg Ile Ser Cys Arg Ala Ser Gly Tyr Glu Phe Ile Asp Cys
    290                 295                 300
Thr Leu Asn Trp Ile Arg Leu Ala Pro Gly Lys Arg Pro Glu Trp Met
305                 310                 315                 320
Gly Trp Leu Lys Pro Arg Gly Gly Ala Val Asn Tyr Ala Arg Pro Leu
                325                 330                 335
Gln Gly Arg Val Thr Met Thr Arg Asp Val Tyr Ser Asp Thr Ala Phe
            340                 345                 350
Leu Glu Leu Arg Ser Leu Thr Val Asp Asp Thr Ala Val Tyr Phe Cys
        355                 360                 365
Thr Arg Gly Lys Asn Cys Asp Tyr Asn Trp Asp Phe Glu His Trp Gly
    370                 375                 380
Arg Gly Thr Pro Val Ile Val Ser Ser Gly Gly Gly Gly Ser Gly Gly
385                 390                 395                 400
Gly Gly Ser Gly Gly Gly Gly Ser Glu Ile Val Leu Thr Gln Ser Pro
                405                 410                 415
Gly Thr Leu Ser Leu Ser Pro Gly Glu Thr Ala Ile Ile Ser Cys Arg
            420                 425                 430
Thr Ser Gln Tyr Gly Ser Leu Ala Trp Tyr Gln Gln Arg Pro Gly Gln
        435                 440                 445
Ala Pro Arg Leu Val Ile Tyr Ser Gly Ser Thr Arg Ala Ala Gly Ile
    450                 455                 460
Pro Asp Arg Phe Ser Gly Ser Arg Trp Gly Pro Asp Tyr Asn Leu Thr
465                 470                 475                 480
Ile Ser Asn Leu Glu Ser Gly Asp Phe Gly Val Tyr Tyr Cys Gln Gln
                485                 490                 495
Tyr Glu Phe Phe Gly Gln Gly Thr Lys Val Gln Val Asp Ile Lys Gly
            500                 505                 510
Ser Gly Pro Lys Ser Cys Asp Lys Thr His Thr Cys Pro Pro Cys Pro
```

```
                515                 520                 525
Ala Pro Glu Leu Leu Gly Gly Pro Ser Val Phe Leu Phe Pro Pro Lys
        530                 535                 540

Pro Lys Asp Thr Leu Met Ile Ser Arg Thr Pro Glu Val Thr Cys Val
545                 550                 555                 560

Val Val Asp Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
        595                 600                 605

Gln Asp Trp Leu Asn Gly Lys Glu Tyr Lys Cys Lys Val Ser Asn Lys
    610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Thr Leu Pro Pro Ser Arg Glu Glu Met
                645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
        675                 680                 685

Tyr Lys Thr Thr Pro Pro Val Leu Asp Ser Asp Gly Ser Phe Phe Leu
    690                 695                 700

Tyr Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
            740                 745

<210> SEQ ID NO 27
<211> LENGTH: 740
<212> TYPE: PRT
<213> ORGANISM: Artificial Sequence
<220> FEATURE:
<223> OTHER INFORMATION: Synthetic peptide

<400> SEQUENCE: 27

Gln Met Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Asp Ser
            20                  25                  30

Tyr Trp Ser Trp Ile Arg Arg Ser Pro Gly Lys Gly Leu Glu Trp Ile
        35                  40                  45

Gly Tyr Val His Lys Ser Gly Asp Thr Asn Tyr Ser Pro Ser Leu Lys
    50                  55                  60

Ser Arg Val Asn Leu Ser Leu Asp Thr Ser Lys Asn Gln Val Ser Leu
65                  70                  75                  80

Ser Leu Val Ala Ala Thr Ala Ala Asp Ser Gly Lys Tyr Tyr Cys Ala
                85                  90                  95

Arg Thr Leu His Gly Arg Arg Ile Tyr Gly Ile Val Ala Phe Asn Glu
            100                 105                 110

Trp Phe Thr Tyr Phe Tyr Met Asp Val Trp Gly Asn Gly Thr Gln Val
        115                 120                 125

Thr Val Ser Ser Gly Gly Gly Gly Ser Gly Gly Gly Ser Gly Gly
```

```
             130                 135                 140
Gly Gly Ser Ser Asp Ile Ser Val Ala Pro Gly Glu Thr Ala Arg Ile
145                 150                 155                 160

Ser Cys Gly Glu Lys Ser Leu Gly Ser Arg Ala Val Gln Trp Tyr Gln
                165                 170                 175

His Arg Ala Gly Gln Ala Pro Ser Leu Ile Ile Tyr Asn Asn Gln Asp
                180                 185                 190

Arg Pro Ser Gly Ile Pro Glu Arg Phe Ser Gly Ser Pro Asp Ser Pro
                195                 200                 205

Phe Gly Thr Thr Ala Thr Leu Thr Ile Thr Ser Val Glu Ala Gly Asp
                210                 215                 220

Glu Ala Asp Tyr Tyr Cys His Ile Trp Asp Ser Arg Val Pro Thr Lys
225                 230                 235                 240

Trp Val Phe Gly Gly Gly Thr Thr Leu Thr Val Leu Gly Gly Gly Gly
                245                 250                 255

Ser Gly Gly Gly Gly Ser Gly Gly Gly Gly Ser Gln Val Gln Leu Val
                260                 265                 270

Gln Ser Gly Gly Gln Met Lys Lys Pro Gly Glu Ser Met Arg Ile Ser
                275                 280                 285

Cys Arg Ala Ser Gly Tyr Glu Phe Ile Asp Cys Thr Leu Asn Trp Ile
290                 295                 300

Arg Leu Ala Pro Gly Lys Arg Pro Glu Trp Met Gly Trp Leu Lys Pro
305                 310                 315                 320

Arg Gly Gly Ala Val Asn Tyr Ala Arg Pro Leu Gln Gly Arg Val Thr
                325                 330                 335

Met Thr Arg Asp Val Tyr Ser Asp Thr Ala Phe Leu Glu Leu Arg Ser
                340                 345                 350

Leu Thr Val Asp Asp Thr Ala Val Tyr Phe Cys Thr Arg Gly Lys Asn
                355                 360                 365

Cys Asp Tyr Asn Trp Asp Phe Glu His Trp Gly Arg Gly Thr Pro Val
                370                 375                 380

Ile Val Ser Ser Gly Gly Gly Gly Ser Gly Gly Gly Gly Ser Gly Gly
385                 390                 395                 400

Gly Gly Ser Glu Ile Val Leu Thr Gln Ser Pro Gly Thr Leu Ser Leu
                405                 410                 415

Ser Pro Gly Glu Thr Ala Ile Ile Ser Cys Arg Thr Ser Gln Tyr Gly
                420                 425                 430

Ser Leu Ala Trp Tyr Gln Gln Arg Pro Gly Gln Ala Pro Arg Leu Val
                435                 440                 445

Ile Tyr Ser Gly Ser Thr Arg Ala Ala Gly Ile Pro Asp Arg Phe Ser
                450                 455                 460

Gly Ser Arg Trp Gly Pro Asp Tyr Asn Leu Thr Ile Ser Asn Leu Glu
465                 470                 475                 480

Ser Gly Asp Phe Gly Val Tyr Tyr Cys Gln Gln Tyr Glu Phe Phe Gly
                485                 490                 495

Gln Gly Thr Lys Val Gln Val Asp Ile Lys Gly Ser Gly Pro Lys Ser
                500                 505                 510

Cys Asp Lys Thr His Thr Cys Pro Pro Cys Ala Pro Glu Leu Leu
                515                 520                 525

Gly Gly Pro Ser Val Phe Leu Phe Pro Pro Lys Pro Lys Asp Thr Leu
                530                 535                 540

Met Ile Ser Arg Thr Pro Glu Val Thr Cys Val Val Val Asp Val Ser
545                 550                 555                 560
```

```
His Glu Asp Pro Glu Val Lys Phe Asn Trp Tyr Val Asp Gly Val Glu
                565                 570                 575

Val His Asn Ala Lys Thr Lys Pro Arg Glu Glu Gln Tyr Asn Ser Thr
            580                 585                 590

Tyr Arg Val Val Ser Val Leu Thr Val Leu His Gln Asp Trp Leu Asn
        595                 600                 605

Gly Lys Glu Tyr Lys Cys Lys Val Ser Asn Lys Ala Leu Pro Ala Pro
610                 615                 620

Ile Glu Lys Thr Ile Ser Lys Ala Lys Gly Gln Pro Arg Glu Pro Gln
625                 630                 635                 640

Val Tyr Thr Leu Pro Pro Ser Arg Glu Glu Met Thr Lys Asn Gln Val
                645                 650                 655

Ser Leu Thr Cys Leu Val Lys Gly Phe Tyr Pro Ser Asp Ile Ala Val
            660                 665                 670

Glu Trp Glu Ser Asn Gly Gln Pro Glu Asn Asn Tyr Lys Thr Thr Pro
        675                 680                 685

Pro Val Leu Asp Ser Asp Gly Ser Phe Phe Leu Tyr Ser Lys Leu Thr
690                 695                 700

Val Asp Lys Ser Arg Trp Gln Gln Gly Asn Val Phe Ser Cys Ser Val
705                 710                 715                 720

Met His Glu Ala Leu His Asn His Tyr Thr Gln Lys Ser Leu Ser Leu
                725                 730                 735

Ser Pro Gly Lys
            740

<210> SEQ ID NO 28
<211> LENGTH: 231
<212> TYPE: PRT
<213> ORGANISM: Artificial Sequence
<220> FEATURE:
<223> OTHER INFORMATION: Synthetic peptide

<400> SEQUENCE: 28

Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175
```

```
Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 29
<211> LENGTH: 19
<212> TYPE: PRT
<213> ORGANISM: Artificial Sequence
<220> FEATURE:
<223> OTHER INFORMATION: Synthetic peptide

<400> SEQUENCE: 29

Met Gly Trp Ser Cys Ile Ile Leu Phe Leu Val Ala Thr Ala Thr Gly
1               5                   10                  15

Val His Ser

<210> SEQ ID NO 30
<211> LENGTH: 545
<212> TYPE: PRT
<213> ORGANISM: Artificial Sequence
<220> FEATURE:
<223> OTHER INFORMATION: Synthetic peptide

<400> SEQUENCE: 30

Gln Gly Gln Leu Val Gln Ser Gly Ala Glu Leu Lys Lys Pro Gly Ala
1               5                   10                  15

Ser Val Lys Ile Ser Cys Lys Thr Ser Gly Tyr Arg Phe Asn Phe Tyr
            20                  25                  30

His Ile Asn Trp Ile Arg Gln Thr Ala Gly Arg Gly Pro Glu Trp Met
        35                  40                  45

Gly Trp Ile Ser Pro Tyr Ser Gly Asp Lys Asn Leu Ala Pro Ala Phe
    50                  55                  60

Gln Asp Arg Val Ile Met Thr Thr Asp Thr Glu Val Pro Val Thr Ser
65                  70                  75                  80

Phe Thr Ser Thr Gly Ala Ala Tyr Met Glu Ile Arg Asn Leu Lys Phe
                85                  90                  95

Asp Asp Thr Gly Thr Tyr Phe Cys Ala Lys Gly Leu Leu Arg Asp Gly
            100                 105                 110

Ser Ser Thr Trp Leu Pro Tyr Leu Trp Gly Gln Gly Thr Leu Leu Thr
        115                 120                 125

Val Ser Ser Gly Gly Gly Ser Gly Gly Gly Ser Gly Gly Gly Gly Gly
    130                 135                 140

Gly Ser Gln Ser Val Leu Thr Gln Ser Ala Ser Val Ser Gly Ser Leu
145                 150                 155                 160

Gly Gln Ser Val Thr Ile Ser Cys Thr Gly Pro Asn Ser Val Cys Cys
                165                 170                 175

Ser His Lys Ser Ile Ser Trp Tyr Gln Trp Pro Pro Gly Arg Ala Pro
            180                 185                 190

Thr Leu Ile Ile Tyr Glu Asp Asn Glu Arg Ala Pro Gly Ile Ser Pro
        195                 200                 205

Arg Phe Ser Gly Tyr Lys Ser Tyr Trp Ser Ala Tyr Leu Thr Ile Ser
    210                 215                 220
```

-continued

```
Asp Leu Arg Pro Glu Asp Glu Thr Thr Tyr Tyr Cys Cys Ser Tyr Thr
225                 230                 235                 240

His Asn Ser Gly Cys Val Phe Gly Thr Gly Thr Lys Val Ser Val Leu
            245                 250                 255

Gly Gly Gly Gly Ser Gly Gly Gly Ser Gly Gly Gly Gly Ser Gly
        260                 265                 270

Gly Gly Gly Ser Gly Gly Gly Ser Glu Val Gln Leu Val Glu Ser
        275                 280                 285

Gly Gly Gly Leu Val Lys Pro Gly Gly Ser Leu Arg Leu Ser Cys Ser
        290                 295                 300

Ala Ser Gly Phe Asp Phe Asp Asn Ala Trp Met Thr Trp Val Arg Gln
305                 310                 315                 320

Pro Pro Gly Lys Gly Leu Glu Trp Val Gly Arg Ile Thr Gly Pro Gly
            325                 330                 335

Glu Gly Trp Ser Val Asp Tyr Ala Ala Pro Val Glu Gly Arg Phe Thr
            340                 345                 350

Ile Ser Arg Leu Asn Ser Ile Asn Phe Leu Tyr Leu Glu Met Asn Asn
            355                 360                 365

Leu Arg Met Glu Asp Ser Gly Leu Tyr Phe Cys Ala Arg Thr Gly Lys
370                 375                 380

Tyr Tyr Asp Phe Trp Ser Gly Tyr Pro Pro Gly Glu Glu Tyr Phe Gln
385                 390                 395                 400

Asp Trp Gly Arg Gly Thr Leu Val Thr Val Ser Ser Gly Gly Gly Gly
            405                 410                 415

Ser Gly Gly Gly Gly Ser Gly Gly Gly Gly Ser Ser Tyr Glu Leu Thr
            420                 425                 430

Gln Glu Thr Gly Val Ser Val Ala Leu Gly Arg Thr Val Thr Ile Thr
            435                 440                 445

Cys Arg Gly Asp Ser Leu Arg Ser His Tyr Ala Ser Trp Tyr Gln Lys
            450                 455                 460

Lys Pro Gly Gln Ala Pro Ile Leu Leu Phe Tyr Gly Lys Asn Asn Arg
465                 470                 475                 480

Pro Ser Gly Val Pro Asp Arg Phe Ser Gly Ser Ala Ser Gly Asn Arg
            485                 490                 495

Ala Ser Leu Thr Ile Ser Gly Ala Gln Ala Glu Asp Asp Ala Glu Tyr
            500                 505                 510

Tyr Cys Ser Ser Arg Asp Lys Ser Gly Ser Arg Leu Ser Val Phe Gly
            515                 520                 525

Gly Gly Thr Lys Leu Thr Val Leu Gly Ser Gly His His His His His
            530                 535                 540

His
545

<210> SEQ ID NO 31
<211> LENGTH: 110
<212> TYPE: PRT
<213> ORGANISM: Artificial Sequence
<220> FEATURE:
<223> OTHER INFORMATION: Synthetic peptide

<400> SEQUENCE: 31

Gln Ser Val Leu Thr Gln Ser Ala Ser Val Ser Gly Ser Leu Gly Gln
1               5                   10                  15

Ser Val Thr Ile Ser Cys Thr Gly Pro Asn Ser Val Cys Cys Ser His
            20                  25                  30
```

```
Lys Ser Ile Ser Trp Tyr Gln Trp Pro Pro Gly Arg Ala Pro Thr Leu
            35                  40                  45

Ile Ile Tyr Glu Asp Asn Glu Arg Ala Pro Gly Ile Ser Pro Arg Phe
    50                  55                  60

Ser Gly Tyr Lys Ser Tyr Trp Ser Ala Tyr Leu Thr Ile Ser Asp Leu
65                  70                  75                  80

Arg Pro Glu Asp Glu Thr Thr Tyr Tyr Cys Cys Ser Tyr Thr His Asn
                85                  90                  95

Ser Gly Cys Val Phe Gly Thr Gly Thr Lys Val Ser Val Leu
            100                 105                 110

<210> SEQ ID NO 32
<211> LENGTH: 14
<212> TYPE: PRT
<213> ORGANISM: Artificial Sequence
<220> FEATURE:
<223> OTHER INFORMATION: Synthetic peptide

<400> SEQUENCE: 32

Thr Gly Pro Asn Ser Val Cys Cys Ser His Lys Ser Ile Ser
1               5                   10

<210> SEQ ID NO 33
<211> LENGTH: 7
<212> TYPE: PRT
<213> ORGANISM: Artificial Sequence
<220> FEATURE:
<223> OTHER INFORMATION: Synthetic peptide

<400> SEQUENCE: 33

Glu Asp Asn Glu Arg Ala Pro
1               5

<210> SEQ ID NO 34
<211> LENGTH: 10
<212> TYPE: PRT
<213> ORGANISM: Artificial Sequence
<220> FEATURE:
<223> OTHER INFORMATION: Synthetic peptide

<400> SEQUENCE: 34

Cys Ser Tyr Thr His Asn Ser Gly Cys Val
1               5                   10

<210> SEQ ID NO 35
<211> LENGTH: 131
<212> TYPE: PRT
<213> ORGANISM: Artificial Sequence
<220> FEATURE:
<223> OTHER INFORMATION: Synthetic peptide

<400> SEQUENCE: 35

Gln Gly Gln Leu Val Gln Ser Gly Ala Glu Leu Lys Lys Pro Gly Ala
1               5                   10                  15

Ser Val Lys Ile Ser Cys Lys Thr Ser Gly Tyr Arg Phe Asn Phe Tyr
            20                  25                  30

His Ile Asn Trp Ile Arg Gln Thr Ala Gly Arg Gly Pro Glu Trp Met
        35                  40                  45

Gly Trp Ile Ser Pro Tyr Ser Gly Asp Lys Asn Leu Ala Pro Ala Phe
    50                  55                  60

Gln Asp Arg Val Ile Met Thr Thr Asp Thr Glu Val Pro Val Thr Ser
65                  70                  75                  80
```

```
Phe Thr Ser Thr Gly Ala Ala Tyr Met Glu Ile Arg Asn Leu Lys Phe
                85                  90                  95

Asp Asp Thr Gly Thr Tyr Phe Cys Ala Lys Gly Leu Leu Arg Asp Gly
            100                 105                 110

Ser Ser Thr Trp Leu Pro Tyr Leu Trp Gly Gln Gly Thr Leu Leu Thr
        115                 120                 125

Val Ser Ser
    130

<210> SEQ ID NO 36
<211> LENGTH: 5
<212> TYPE: PRT
<213> ORGANISM: Artificial Sequence
<220> FEATURE:
<223> OTHER INFORMATION: Synthetic peptide

<400> SEQUENCE: 36

Phe Tyr His Ile Asn
1               5

<210> SEQ ID NO 37
<211> LENGTH: 17
<212> TYPE: PRT
<213> ORGANISM: Artificial Sequence
<220> FEATURE:
<223> OTHER INFORMATION: Synthetic peptide

<400> SEQUENCE: 37

Trp Ile Ser Pro Tyr Ser Gly Asp Lys Asn Leu Ala Pro Ala Phe Gln
1               5                   10                  15

Asp

<210> SEQ ID NO 38
<211> LENGTH: 14
<212> TYPE: PRT
<213> ORGANISM: Artificial Sequence
<220> FEATURE:
<223> OTHER INFORMATION: Synthetic peptide

<400> SEQUENCE: 38

Gly Leu Leu Arg Asp Gly Ser Ser Thr Trp Leu Pro Tyr Leu
1               5                   10

<210> SEQ ID NO 39
<211> LENGTH: 109
<212> TYPE: PRT
<213> ORGANISM: Artificial Sequence
<220> FEATURE:
<223> OTHER INFORMATION: Synthetic peptide

<400> SEQUENCE: 39

Ser Tyr Glu Leu Thr Gln Glu Thr Gly Val Ser Val Ala Leu Gly Arg
1               5                   10                  15

Thr Val Thr Ile Thr Cys Arg Gly Asp Ser Leu Arg Ser His Tyr Ala
            20                  25                  30

Ser Trp Tyr Gln Lys Lys Pro Gly Gln Ala Pro Ile Leu Leu Phe Tyr
        35                  40                  45

Gly Lys Asn Asn Arg Pro Ser Gly Val Pro Asp Arg Phe Ser Gly Ser
    50                  55                  60

Ala Ser Gly Asn Arg Ala Ser Leu Thr Ile Ser Gly Ala Gln Ala Glu
65                  70                  75                  80
```

```
Asp Asp Ala Glu Tyr Tyr Cys Ser Ser Arg Asp Lys Ser Gly Ser Arg
                85                  90                  95

Leu Ser Val Phe Gly Gly Gly Thr Lys Leu Thr Val Leu
            100                 105

<210> SEQ ID NO 40
<211> LENGTH: 11
<212> TYPE: PRT
<213> ORGANISM: Artificial Sequence
<220> FEATURE:
<223> OTHER INFORMATION: Synthetic peptide

<400> SEQUENCE: 40

Arg Gly Asp Ser Leu Arg Ser His Tyr Ala Ser
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Synthetic peptide

<400> SEQUENCE: 41

Gly Lys Asn Asn Arg Pro Ser
1               5

<210> SEQ ID NO 42
<211> LENGTH: 12
<212> TYPE: PRT
<213> ORGANISM: Artificial Sequence
<220> FEATURE:
<223> OTHER INFORMATION: Synthetic peptide

<400> SEQUENCE: 42

Ser Ser Arg Asp Lys Ser Gly Ser Arg Leu Ser Val
1               5                   10

<210> SEQ ID NO 43
<211> LENGTH: 131
<212> TYPE: PRT
<213> ORGANISM: Artificial Sequence
<220> FEATURE:
<223> OTHER INFORMATION: Synthetic peptide

<400> SEQUENCE: 43

Glu Val Gln Leu Val Glu Ser Gly Gly Leu Val Lys Pro Gly Gly
1               5                   10                  15

Ser Leu Arg Leu Ser Cys Ser Ala Ser Gly Phe Asp Phe Asp Asn Ala
                20                  25                  30

Trp Met Thr Trp Val Arg Gln Pro Pro Gly Lys Gly Leu Glu Trp Val
            35                  40                  45

Gly Arg Ile Thr Gly Pro Gly Glu Gly Trp Ser Val Asp Tyr Ala Ala
        50                  55                  60

Pro Val Glu Gly Arg Phe Thr Ile Ser Arg Leu Asn Ser Ile Asn Phe
65                  70                  75                  80

Leu Tyr Leu Glu Met Asn Asn Leu Arg Met Glu Asp Ser Gly Leu Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Arg Gly Thr Leu Val Thr
        115                 120                 125
```

Val Ser Ser
    130

<210> SEQ ID NO 44
<211> LENGTH: 5
<212> TYPE: PRT
<213> ORGANISM: Artificial Sequence
<220> FEATURE:
<223> OTHER INFORMATION: Synthetic peptide

<400> SEQUENCE: 44

Asn Ala Trp Met Thr
1               5

<210> SEQ ID NO 45
<211> LENGTH: 19
<212> TYPE: PRT
<213> ORGANISM: Artificial Sequence
<220> FEATURE:
<223> OTHER INFORMATION: Synthetic peptide

<400> SEQUENCE: 45

Arg Ile Thr Gly Pro Gly Glu Gly Trp Ser Val Asp Tyr Ala Ala Pro
1               5                   10                  15

Val Glu Gly

<210> SEQ ID NO 46
<211> LENGTH: 20
<212> TYPE: PRT
<213> ORGANISM: Artificial Sequence
<220> FEATURE:
<223> OTHER INFORMATION: Synthetic peptide

<400> SEQUENCE: 46

Thr Gly Lys Tyr Tyr Asp Phe Trp Ser Gly Tyr Pro Pro Gly Glu Glu
1               5                   10                  15

Tyr Phe Gln Asp
            20

<210> SEQ ID NO 47
<211> LENGTH: 555
<212> TYPE: PRT
<213> ORGANISM: Artificial Sequence
<220> FEATURE:
<223> OTHER INFORMATION: Synthetic peptide

<400> SEQUENCE: 47

Gln Gly Gln Leu Val Gln Ser Gly Ala Glu Leu Lys Lys Pro Gly Ala
1               5                   10                  15

Ser Val Lys Ile Ser Cys Lys Thr Ser Gly Tyr Arg Phe Asn Phe Tyr
            20                  25                  30

His Ile Asn Trp Ile Arg Gln Thr Ala Gly Arg Gly Pro Glu Trp Met
        35                  40                  45

Gly Trp Ile Ser Pro Tyr Ser Gly Asp Lys Asn Leu Ala Pro Ala Phe
    50                  55                  60

Gln Asp Arg Val Ile Met Thr Thr Asp Thr Glu Val Pro Val Thr Ser
65                  70                  75                  80

Phe Thr Ser Thr Gly Ala Ala Tyr Met Glu Ile Arg Asn Leu Lys Phe
                85                  90                  95

Asp Asp Thr Gly Thr Tyr Phe Cys Ala Lys Gly Leu Leu Arg Asp Gly
            100                 105                 110

Ser Ser Thr Trp Leu Pro Tyr Leu Trp Gly Gln Gly Thr Leu Leu Thr

```
            115                 120                 125
Val Ser Ser Gly Gly Gly Ser Gly Gly Gly Ser Gly Gly
    130                 135                 140
Gly Ser Gln Ser Val Leu Thr Gln Ser Ala Ser Val Ser Gly Ser Leu
145                 150                 155                 160
Gly Gln Ser Val Thr Ile Ser Cys Thr Gly Pro Asn Ser Val Cys Cys
                    165                 170                 175
Ser His Lys Ser Ile Ser Trp Tyr Gln Trp Pro Pro Gly Arg Ala Pro
                180                 185                 190
Thr Leu Ile Ile Tyr Glu Asp Asn Glu Arg Ala Pro Gly Ile Ser Pro
                195                 200                 205
Arg Phe Ser Gly Tyr Lys Ser Tyr Trp Ser Ala Tyr Leu Thr Ile Ser
            210                 215                 220
Asp Leu Arg Pro Glu Asp Glu Thr Thr Tyr Tyr Cys Cys Ser Tyr Thr
225                 230                 235                 240
His Asn Ser Gly Cys Val Phe Gly Thr Gly Thr Lys Val Ser Val Leu
                    245                 250                 255
Gly Gly Gly Gly Ser Gly Gly Gly Ser Gly Gly Gly Gly Ser Gly
                260                 265                 270
Gly Gly Gly Ser Gly Gly Gly Ser Gly Gly Gly Gly Ser Gly Gly
            275                 280                 285
Gly Gly Ser Glu Val Gln Leu Val Glu Ser Gly Gly Leu Val Lys
            290                 295                 300
Pro Gly Gly Ser Leu Arg Leu Ser Cys Ser Ala Ser Gly Phe Asp Phe
305                 310                 315                 320
Asp Asn Ala Trp Met Thr Trp Val Arg Gln Pro Pro Gly Lys Gly Leu
                325                 330                 335
Glu Trp Val Gly Arg Ile Thr Gly Pro Gly Glu Gly Trp Ser Val Asp
                340                 345                 350
Tyr Ala Ala Pro Val Glu Gly Arg Phe Thr Ile Ser Arg Leu Asn Ser
            355                 360                 365
Ile Asn Phe Leu Tyr Leu Glu Met Asn Asn Leu Arg Met Glu Asp Ser
            370                 375                 380
Gly Leu Tyr Phe Cys Ala Arg Thr Gly Lys Tyr Tyr Asp Phe Trp Ser
385                 390                 395                 400
Gly Tyr Pro Pro Gly Glu Glu Tyr Phe Gln Asp Trp Gly Arg Gly Thr
                405                 410                 415
Leu Val Thr Val Ser Ser Gly Gly Gly Ser Gly Gly Gly Gly Ser
                420                 425                 430
Gly Gly Gly Gly Ser Ser Tyr Glu Leu Thr Gln Glu Thr Gly Val Ser
            435                 440                 445
Val Ala Leu Gly Arg Thr Val Thr Ile Thr Cys Arg Gly Asp Ser Leu
            450                 455                 460
Arg Ser His Tyr Ala Ser Trp Tyr Gln Lys Lys Pro Gly Gln Ala Pro
465                 470                 475                 480
Ile Leu Leu Phe Tyr Gly Lys Asn Asn Arg Pro Ser Gly Val Pro Asp
                    485                 490                 495
Arg Phe Ser Gly Ser Ala Ser Gly Asn Arg Ala Ser Leu Thr Ile Ser
                500                 505                 510
Gly Ala Gln Ala Glu Asp Asp Ala Glu Tyr Tyr Cys Ser Ser Arg Asp
            515                 520                 525
Lys Ser Gly Ser Arg Leu Ser Val Phe Gly Gly Gly Thr Lys Leu Thr
            530                 535                 540
```

```
Val Leu Gly Ser Gly His His His His His
545                 550             555

<210> SEQ ID NO 48
<211> LENGTH: 545
<212> TYPE: PRT
<213> ORGANISM: Artificial Sequence
<220> FEATURE:
<223> OTHER INFORMATION: Synthetic peptide

<400> SEQUENCE: 48

Glu Val Gln Leu Val Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Lys Gly Leu Glu Trp Val
        35                  40                  45

Gly Arg Ile Thr Gly Pro Gly Glu Gly Trp Ser Val Asp Tyr Ala Ala
        50                  55                  60

Pro Val Glu Gly Arg Phe Thr Ile Ser Arg Leu Asn Ser Ile Asn Phe
65              70                  75                  80

Leu Tyr Leu Glu Met Asn Asn Leu Arg Met Glu Asp Ser Gly Leu Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Arg Gly Thr Leu Val Thr
        115                 120                 125

Val Ser Ser Gly Gly Gly Gly Ser Gly Gly Gly Ser Gly Gly Gly
130             135                 140

Gly Ser Ser Tyr Glu Leu Thr Gln Glu Thr Gly Val Ser Val Ala Leu
145             150                 155                 160

Gly Arg Thr Val Thr Ile Thr Cys Arg Gly Asp Ser Leu Arg Ser His
                165                 170                 175

Tyr Ala Ser Trp Tyr Gln Lys Lys Pro Gly Gln Ala Pro Ile Leu Leu
            180                 185                 190

Phe Tyr Gly Lys Asn Asn Arg Pro Ser Gly Val Pro Asp Arg Phe Ser
        195                 200                 205

Gly Ser Ala Ser Gly Asn Arg Ala Ser Leu Thr Ile Ser Gly Ala Gln
    210                 215                 220

Ala Glu Asp Asp Ala Glu Tyr Tyr Cys Ser Ser Arg Asp Lys Ser Gly
225                 230                 235                 240

Ser Arg Leu Ser Val Phe Gly Gly Thr Lys Leu Thr Val Leu Gly
            245                 250                 255

Gly Gly Gly Ser Gly Gly Gly Ser Gly Gly Gly Ser Gly Gly
        260                 265                 270

Gly Gly Ser Gly Gly Gly Ser Gln Gly Gln Leu Val Gln Ser Gly
        275                 280                 285

Ala Glu Leu Lys Lys Pro Gly Ala Ser Val Lys Ile Ser Cys Lys Thr
290                 295                 300

Ser Gly Tyr Arg Phe Asn Phe Tyr His Ile Asn Trp Ile Arg Gln Thr
305                 310                 315                 320

Ala Gly Arg Gly Pro Glu Trp Met Gly Trp Ile Ser Pro Tyr Ser Gly
            325                 330                 335

Asp Lys Asn Leu Ala Pro Ala Phe Gln Asp Arg Val Ile Met Thr Thr
        340                 345                 350
```

-continued

Asp Thr Glu Val Pro Val Thr Ser Phe Thr Ser Thr Gly Ala Ala Tyr
            355                 360                 365

Met Glu Ile Arg Asn Leu Lys Phe Asp Asp Thr Gly Thr Tyr Phe Cys
        370                 375                 380

Ala Lys Gly Leu Leu Arg Asp Gly Ser Ser Thr Trp Leu Pro Tyr Leu
385                 390                 395                 400

Trp Gly Gln Gly Thr Leu Leu Thr Val Ser Ser Gly Gly Gly Gly Ser
                405                 410                 415

Gly Gly Gly Gly Ser Gly Gly Gly Ser Gln Ser Val Leu Thr Gln
                420                 425                 430

Ser Ala Ser Val Ser Gly Ser Leu Gly Gln Ser Val Thr Ile Ser Cys
        435                 440                 445

Thr Gly Pro Asn Ser Val Cys Cys Ser His Lys Ser Ile Ser Trp Tyr
    450                 455                 460

Gln Trp Pro Pro Gly Arg Ala Pro Thr Leu Ile Ile Tyr Glu Asp Asn
465                 470                 475                 480

Glu Arg Ala Pro Gly Ile Ser Pro Arg Phe Ser Gly Tyr Lys Ser Tyr
                485                 490                 495

Trp Ser Ala Tyr Leu Thr Ile Ser Asp Leu Arg Pro Glu Asp Glu Thr
            500                 505                 510

Thr Tyr Tyr Cys Cys Ser Tyr Thr His Asn Ser Gly Cys Val Phe Gly
        515                 520                 525

Thr Gly Thr Lys Val Ser Val Leu Gly Ser Gly His His His His
    530                 535                 540

His
545

<210> SEQ ID NO 49
<211> LENGTH: 555
<212> TYPE: PRT
<213> ORGANISM: Artificial Sequence
<220> FEATURE:
<223> OTHER INFORMATION: Synthetic peptide

<400> SEQUENCE: 49

Glu Val Gln Leu Val Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
                20                  25                  30

Trp Met Thr Trp Val Arg Gln Pro Pro Gly Lys Gly Leu Glu Trp Val
            35                  40                  45

Gly Arg Ile Thr Gly Pro Gly Glu Gly Trp Ser Val Asp Tyr Ala Ala
        50                  55                  60

Pro Val Glu Gly Arg Phe Thr Ile Ser Arg Leu Asn Ser Ile Asn Phe
65                  70                  75                  80

Leu Tyr Leu Glu Met Asn Asn Leu Arg Met Glu Asp Ser Gly Leu Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Arg Gly Thr Leu Val Thr
        115                 120                 125

Val Ser Ser Gly Gly Gly Gly Ser Gly Gly Gly Gly Ser Gly Gly Gly
    130                 135                 140

Gly Ser Ser Tyr Glu Leu Thr Gln Glu Thr Gly Val Ser Val Ala Leu
145                 150                 155                 160

```
Gly Arg Thr Val Thr Ile Thr Cys Arg Gly Asp Ser Leu Arg Ser His
                165                 170                 175

Tyr Ala Ser Trp Tyr Gln Lys Pro Gly Gln Ala Pro Ile Leu Leu
            180                 185                 190

Phe Tyr Gly Lys Asn Asn Arg Pro Ser Gly Val Pro Asp Arg Phe Ser
        195                 200                 205

Gly Ser Ala Ser Gly Asn Arg Ala Ser Leu Thr Ile Ser Gly Ala Gln
    210                 215                 220

Ala Glu Asp Asp Ala Glu Tyr Tyr Cys Ser Ser Arg Asp Lys Ser Gly
225                 230                 235                 240

Ser Arg Leu Ser Val Phe Gly Gly Gly Thr Lys Leu Thr Val Leu Gly
            245                 250                 255

Gly Gly Gly Ser Gly Gly Gly Ser Gly Gly Gly Ser Gly Gly
            260                 265                 270

Gly Gly Ser Gly Gly Gly Ser Gly Gly Gly Ser Gly Gly Gly
            275                 280                 285

Gly Ser Gln Gly Gln Leu Val Gln Ser Gly Ala Glu Leu Lys Lys Pro
    290                 295                 300

Gly Ala Ser Val Lys Ile Ser Cys Lys Thr Ser Gly Tyr Arg Phe Asn
305                 310                 315                 320

Phe Tyr His Ile Asn Trp Ile Arg Gln Thr Ala Gly Arg Gly Pro Glu
            325                 330                 335

Trp Met Gly Trp Ile Ser Pro Tyr Ser Gly Asp Lys Asn Leu Ala Pro
            340                 345                 350

Ala Phe Gln Asp Arg Val Ile Met Thr Thr Asp Thr Glu Val Pro Val
            355                 360                 365

Thr Ser Phe Thr Ser Thr Gly Ala Ala Tyr Met Glu Ile Arg Asn Leu
    370                 375                 380

Lys Phe Asp Asp Thr Gly Thr Tyr Phe Cys Ala Lys Gly Leu Leu Arg
385                 390                 395                 400

Asp Gly Ser Ser Thr Trp Leu Pro Tyr Leu Trp Gly Gln Gly Thr Leu
            405                 410                 415

Leu Thr Val Ser Ser Gly Gly Gly Gly Ser Gly Gly Gly Gly Ser Gly
            420                 425                 430

Gly Gly Gly Ser Gln Ser Val Leu Thr Gln Ser Ala Ser Val Ser Gly
        435                 440                 445

Ser Leu Gly Gln Ser Val Thr Ile Ser Cys Thr Gly Pro Asn Ser Val
    450                 455                 460

Cys Cys Ser His Lys Ser Ile Ser Trp Tyr Gln Trp Pro Pro Gly Arg
465                 470                 475                 480

Ala Pro Thr Leu Ile Ile Tyr Glu Asp Asn Glu Arg Ala Pro Gly Ile
            485                 490                 495

Ser Pro Arg Phe Ser Gly Tyr Lys Ser Tyr Trp Ser Ala Tyr Leu Thr
        500                 505                 510

Ile Ser Asp Leu Arg Pro Glu Asp Glu Thr Thr Tyr Tyr Cys Cys Ser
    515                 520                 525

Tyr Thr His Asn Ser Gly Cys Val Phe Gly Thr Gly Thr Lys Val Ser
    530                 535                 540

Val Leu Gly Ser Gly His His His His His
545                 550                 555

<210> SEQ ID NO 50
<211> LENGTH: 770
```

```
<212> TYPE: PRT
<213> ORGANISM: Artificial Sequence
<220> FEATURE:
<223> OTHER INFORMATION: Synthetic peptide

<400> SEQUENCE: 50
```

Gln Gly Gln Leu Val Gln Ser Gly Ala Glu Leu Lys Lys Pro Gly Ala
1               5                   10                  15

Ser Val Lys Ile Ser Cys Lys Thr Ser Gly Tyr Arg Phe Asn Phe Tyr
            20                  25                  30

His Ile Asn Trp Ile Arg Gln Thr Ala Gly Arg Gly Pro Glu Trp Met
        35                  40                  45

Gly Trp Ile Ser Pro Tyr Ser Gly Asp Lys Asn Leu Ala Pro Ala Phe
    50                  55                  60

Gln Asp Arg Val Ile Met Thr Thr Asp Thr Glu Val Pro Val Thr Ser
65                  70                  75                  80

Phe Thr Ser Thr Gly Ala Ala Tyr Met Glu Ile Arg Asn Leu Lys Phe
                85                  90                  95

Asp Asp Thr Gly Thr Tyr Phe Cys Ala Lys Gly Leu Leu Arg Asp Gly
            100                 105                 110

Ser Ser Thr Trp Leu Pro Tyr Leu Trp Gly Gln Gly Thr Leu Leu Thr
        115                 120                 125

Val Ser Ser Gly Gly Gly Gly Ser Gly Gly Gly Ser Gly Gly Gly Gly
130                 135                 140

Gly Ser Gln Ser Val Leu Thr Gln Ser Ala Ser Val Ser Gly Ser Leu
145                 150                 155                 160

Gly Gln Ser Val Thr Ile Ser Cys Thr Gly Pro Asn Ser Val Cys Cys
                165                 170                 175

Ser His Lys Ser Ile Ser Trp Tyr Gln Trp Pro Pro Gly Arg Ala Pro
            180                 185                 190

Thr Leu Ile Ile Tyr Glu Asp Asn Glu Arg Ala Pro Gly Ile Ser Pro
        195                 200                 205

Arg Phe Ser Gly Tyr Lys Ser Tyr Trp Ser Ala Tyr Leu Thr Ile Ser
    210                 215                 220

Asp Leu Arg Pro Glu Asp Glu Thr Thr Tyr Tyr Cys Cys Ser Tyr Thr
225                 230                 235                 240

His Asn Ser Gly Cys Val Phe Gly Thr Gly Thr Lys Val Ser Val Leu
                245                 250                 255

Gly Gly Gly Gly Ser Gly Gly Gly Ser Gly Gly Gly Gly Ser Gly
                260                 265                 270

Gly Gly Gly Ser Gly Gly Gly Ser Glu Val Gln Leu Val Glu Ser
            275                 280                 285

Gly Gly Gly Leu Val Lys Pro Gly Gly Ser Leu Arg Leu Ser Cys Ser
    290                 295                 300

Ala Ser Gly Phe Asp Phe Asp Asn Ala Trp Met Thr Trp Val Arg Gln
305                 310                 315                 320

Pro Pro Gly Lys Gly Leu Glu Trp Val Gly Arg Ile Thr Gly Pro Gly
                325                 330                 335

Glu Gly Trp Ser Val Asp Tyr Ala Ala Pro Val Glu Gly Arg Phe Thr
            340                 345                 350

Ile Ser Arg Leu Asn Ser Ile Asn Phe Leu Tyr Leu Glu Met Asn Asn
        355                 360                 365

Leu Arg Met Glu Asp Ser Gly Leu Tyr Phe Cys Ala Arg Thr Gly Lys
    370                 375                 380

```
Tyr Tyr Asp Phe Trp Ser Gly Tyr Pro Pro Glu Glu Tyr Phe Gln
385                 390                 395                 400

Asp Trp Gly Arg Gly Thr Leu Val Thr Val Ser Ser Gly Gly Gly
            405                 410                 415

Ser Gly Gly Gly Gly Ser Gly Gly Gly Gly Ser Ser Tyr Glu Leu Thr
        420                 425                 430

Gln Glu Thr Gly Val Ser Val Ala Leu Gly Arg Thr Val Thr Ile Thr
        435                 440                 445

Cys Arg Gly Asp Ser Leu Arg Ser His Tyr Ala Ser Trp Tyr Gln Lys
450                 455                 460

Lys Pro Gly Gln Ala Pro Ile Leu Leu Phe Tyr Gly Lys Asn Asn Arg
465                 470                 475                 480

Pro Ser Gly Val Pro Asp Arg Phe Ser Gly Ser Ala Ser Gly Asn Arg
            485                 490                 495

Ala Ser Leu Thr Ile Ser Gly Ala Gln Ala Glu Asp Ala Glu Tyr
        500                 505                 510

Tyr Cys Ser Ser Arg Asp Lys Ser Gly Ser Arg Leu Ser Val Phe Gly
        515                 520                 525

Gly Gly Thr Lys Leu Thr Val Leu Gly Ser Gly Pro Lys Ser Cys Asp
530                 535                 540

Lys Thr His Thr Cys Pro Pro Cys Pro Ala Pro Glu Leu Leu Gly Gly
545                 550                 555                 560

Pro Ser Val Phe Leu Phe Pro Pro Lys Pro Lys Asp Thr Leu Met Ile
            565                 570                 575

Ser Arg Thr Pro Glu Val Thr Cys Val Val Val Asp Val Ser His Glu
        580                 585                 590

Asp Pro Glu Val Lys Phe Asn Trp Tyr Val Asp Gly Val Glu Val His
        595                 600                 605

Asn Ala Lys Thr Lys Pro Arg Glu Glu Gln Tyr Asn Ser Thr Tyr Arg
610                 615                 620

Val Val Ser Val Leu Thr Val Leu His Gln Asp Trp Leu Asn Gly Lys
625                 630                 635                 640

Glu Tyr Lys Cys Lys Val Ser Asn Lys Ala Leu Pro Ala Pro Ile Glu
            645                 650                 655

Lys Thr Ile Ser Lys Ala Lys Gly Gln Pro Arg Glu Pro Gln Val Tyr
        660                 665                 670

Thr Leu Pro Pro Ser Arg Glu Glu Met Thr Lys Asn Gln Val Ser Leu
        675                 680                 685

Thr Cys Leu Val Lys Gly Phe Tyr Pro Ser Asp Ile Ala Val Glu Trp
        690                 695                 700

Glu Ser Asn Gly Gln Pro Glu Asn Asn Tyr Lys Thr Thr Pro Pro Val
705                 710                 715                 720

Leu Asp Ser Asp Gly Ser Phe Phe Leu Tyr Ser Lys Leu Thr Val Asp
            725                 730                 735

Lys Ser Arg Trp Gln Gln Gly Asn Val Phe Ser Cys Ser Val Met His
            740                 745                 750

Glu Ala Leu His Asn His Tyr Thr Gln Lys Ser Leu Ser Leu Ser Pro
        755                 760                 765

Gly Lys
    770

<210> SEQ ID NO 51
<211> LENGTH: 780
<212> TYPE: PRT
```

<213> ORGANISM: Artificial Sequence
<220> FEATURE:
<223> OTHER INFORMATION: Synthetic peptide

<400> SEQUENCE: 51

```
Gln Gly Gln Leu Val Gln Ser Gly Ala Glu Leu Lys Lys Pro Gly Ala
1               5                   10                  15

Ser Val Lys Ile Ser Cys Lys Thr Ser Gly Tyr Arg Phe Asn Phe Tyr
            20                  25                  30

His Ile Asn Trp Ile Arg Gln Thr Ala Gly Arg Gly Pro Glu Trp Met
        35                  40                  45

Gly Trp Ile Ser Pro Tyr Ser Gly Asp Lys Asn Leu Ala Pro Ala Phe
    50                  55                  60

Gln Asp Arg Val Ile Met Thr Thr Asp Thr Glu Val Pro Val Thr Ser
65                  70                  75                  80

Phe Thr Ser Thr Gly Ala Ala Tyr Met Glu Ile Arg Asn Leu Lys Phe
                85                  90                  95

Asp Asp Thr Gly Thr Tyr Phe Cys Ala Lys Gly Leu Leu Arg Asp Gly
            100                 105                 110

Ser Ser Thr Trp Leu Pro Tyr Leu Trp Gly Gln Gly Thr Leu Leu Thr
        115                 120                 125

Val Ser Ser Gly Gly Gly Gly Ser Gly Gly Gly Gly Ser Gly Gly Gly
130                 135                 140

Gly Ser Gln Ser Val Leu Thr Gln Ser Ala Ser Val Ser Gly Ser Leu
145                 150                 155                 160

Gly Gln Ser Val Thr Ile Ser Cys Thr Gly Pro Asn Ser Val Cys Cys
                165                 170                 175

Ser His Lys Ser Ile Ser Trp Tyr Gln Trp Pro Pro Gly Arg Ala Pro
            180                 185                 190

Thr Leu Ile Ile Tyr Glu Asp Asn Glu Arg Ala Pro Gly Ile Ser Pro
        195                 200                 205

Arg Phe Ser Gly Tyr Lys Ser Tyr Trp Ser Ala Tyr Leu Thr Ile Ser
    210                 215                 220

Asp Leu Arg Pro Glu Asp Glu Thr Thr Tyr Tyr Cys Cys Ser Tyr Thr
225                 230                 235                 240

His Asn Ser Gly Cys Val Phe Gly Thr Gly Thr Lys Val Ser Val Leu
                245                 250                 255

Gly Gly Gly Gly Ser Gly Gly Gly Ser Gly Gly Gly Gly Ser Gly
            260                 265                 270

Gly Gly Gly Ser Gly Gly Gly Gly Ser Gly Gly Gly Gly Ser Gly Gly
        275                 280                 285

Gly Gly Ser Glu Val Gln Leu Val Glu Ser Gly Gly Gly Leu Val Lys
    290                 295                 300

Pro Gly Gly Ser Leu Arg Leu Ser Cys Ser Ala Ser Gly Phe Asp Phe
305                 310                 315                 320

Asp Asn Ala Trp Met Thr Trp Val Arg Gln Pro Pro Gly Lys Gly Leu
                325                 330                 335

Glu Trp Val Gly Arg Ile Thr Gly Pro Gly Glu Gly Trp Ser Val Asp
            340                 345                 350

Tyr Ala Ala Pro Val Glu Gly Arg Phe Thr Ile Ser Arg Leu Asn Ser
        355                 360                 365

Ile Asn Phe Leu Tyr Leu Glu Met Asn Asn Leu Arg Met Glu Asp Ser
    370                 375                 380

Gly Leu Tyr Phe Cys Ala Arg Thr Gly Lys Tyr Tyr Asp Phe Trp Ser
```

```
                385                 390                 395                 400
Gly Tyr Pro Pro Gly Glu Glu Tyr Phe Gln Asp Trp Gly Arg Gly Thr
                    405                 410                 415
Leu Val Thr Val Ser Gly Gly Gly Gly Ser Gly Gly Gly Gly Ser
                420                 425                 430
Gly Gly Gly Gly Ser Ser Tyr Glu Leu Thr Gln Glu Thr Gly Val Ser
            435                 440                 445
Val Ala Leu Gly Arg Thr Val Thr Ile Thr Cys Arg Gly Asp Ser Leu
450                 455                 460
Arg Ser His Tyr Ala Ser Trp Tyr Gln Lys Lys Pro Gly Gln Ala Pro
465                 470                 475                 480
Ile Leu Leu Phe Tyr Gly Lys Asn Asn Arg Pro Ser Gly Val Pro Asp
                485                 490                 495
Arg Phe Ser Gly Ser Ala Ser Gly Asn Arg Ala Ser Leu Thr Ile Ser
            500                 505                 510
Gly Ala Gln Ala Glu Asp Asp Ala Glu Tyr Tyr Cys Ser Ser Arg Asp
        515                 520                 525
Lys Ser Gly Ser Arg Leu Ser Val Phe Gly Gly Gly Thr Lys Leu Thr
530                 535                 540
Val Leu Gly Ser Gly Pro Lys Ser Cys Asp Lys Thr His Thr Cys Pro
545                 550                 555                 560
Pro Cys Pro Ala Pro Glu Leu Leu Gly Gly Pro Ser Val Phe Leu Phe
                565                 570                 575
Pro Pro Lys Pro Lys Asp Thr Leu Met Ile Ser Arg Thr Pro Glu Val
                580                 585                 590
Thr Cys Val Val Val Asp Val Ser His Glu Asp Pro Glu Val Lys Phe
            595                 600                 605
Asn Trp Tyr Val Asp Gly Val Glu Val His Asn Ala Lys Thr Lys Pro
        610                 615                 620
Arg Glu Glu Gln Tyr Asn Ser Thr Tyr Arg Val Val Ser Val Leu Thr
625                 630                 635                 640
Val Leu His Gln Asp Trp Leu Asn Gly Lys Glu Tyr Lys Cys Lys Val
                645                 650                 655
Ser Asn Lys Ala Leu Pro Ala Pro Ile Glu Lys Thr Ile Ser Lys Ala
                660                 665                 670
Lys Gly Gln Pro Arg Glu Pro Gln Val Tyr Thr Leu Pro Pro Ser Arg
            675                 680                 685
Glu Glu Met Thr Lys Asn Gln Val Ser Leu Thr Cys Leu Val Lys Gly
        690                 695                 700
Phe Tyr Pro Ser Asp Ile Ala Val Glu Trp Glu Ser Asn Gly Gln Pro
705                 710                 715                 720
Glu Asn Asn Tyr Lys Thr Thr Pro Pro Val Leu Asp Ser Asp Gly Ser
                725                 730                 735
Phe Phe Leu Tyr Ser Lys Leu Thr Val Asp Lys Ser Arg Trp Gln Gln
            740                 745                 750
Gly Asn Val Phe Ser Cys Ser Val Met His Glu Ala Leu His Asn His
        755                 760                 765
Tyr Thr Gln Lys Ser Leu Ser Leu Ser Pro Gly Lys
770                 775                 780

<210> SEQ ID NO 52
<211> LENGTH: 770
<212> TYPE: PRT
<213> ORGANISM: Artificial Sequence
```

<220> FEATURE:
<223> OTHER INFORMATION: Synthetic peptide

<400> SEQUENCE: 52

Glu Val Gln Leu Val Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Ala
50                  55                  60

Pro Val Glu Gly Arg Phe Thr Ile Ser Arg Leu Asn Ser Ile Asn Phe
65                  70                  75                  80

Leu Tyr Leu Glu Met Asn Asn Leu Arg Met Glu Asp Ser Gly Leu Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Arg Gly Thr Leu Val Thr
        115                 120                 125

Val Ser Ser Gly Gly Gly Gly Ser Gly Gly Gly Gly Ser Gly Gly Gly
130                 135                 140

Gly Ser Ser Tyr Glu Leu Thr Gln Glu Thr Gly Val Ser Val Ala Leu
145                 150                 155                 160

Gly Arg Thr Val Thr Ile Thr Cys Arg Gly Asp Ser Leu Arg Ser His
                165                 170                 175

Tyr Ala Ser Trp Tyr Gln Lys Lys Pro Gly Gln Ala Pro Ile Leu Leu
            180                 185                 190

Phe Tyr Gly Lys Asn Asn Arg Pro Ser Gly Val Pro Asp Arg Phe Ser
        195                 200                 205

Gly Ser Ala Ser Gly Asn Arg Ala Ser Leu Thr Ile Ser Gly Ala Gln
210                 215                 220

Ala Glu Asp Asp Ala Glu Tyr Tyr Cys Ser Ser Arg Asp Lys Ser Gly
225                 230                 235                 240

Ser Arg Leu Ser Val Phe Gly Gly Gly Thr Lys Leu Thr Val Leu Gly
                245                 250                 255

Gly Gly Gly Ser Gly Gly Gly Gly Ser Gly Gly Gly Gly Ser Gly Gly
            260                 265                 270

Gly Gly Ser Gly Gly Gly Gly Ser Gln Gly Gln Leu Val Gln Ser Gly
        275                 280                 285

Ala Glu Leu Lys Lys Pro Gly Ala Ser Val Lys Ile Ser Cys Lys Thr
290                 295                 300

Ser Gly Tyr Arg Phe Asn Phe Tyr His Ile Asn Trp Ile Arg Gln Thr
305                 310                 315                 320

Ala Gly Arg Gly Pro Glu Trp Met Gly Trp Ile Ser Pro Tyr Ser Gly
                325                 330                 335

Asp Lys Asn Leu Ala Pro Ala Phe Gln Asp Arg Val Ile Met Thr Thr
            340                 345                 350

Asp Thr Glu Val Pro Val Thr Ser Phe Thr Ser Thr Gly Ala Ala Tyr
        355                 360                 365

Met Glu Ile Arg Asn Leu Lys Phe Asp Asp Thr Gly Thr Tyr Phe Cys
370                 375                 380

Ala Lys Gly Leu Leu Arg Asp Gly Ser Ser Thr Trp Leu Pro Tyr Leu
385                 390                 395                 400

-continued

```
Trp Gly Gln Gly Thr Leu Leu Thr Val Ser Ser Gly Gly Gly Ser
                405                 410                 415
Gly Gly Gly Gly Ser Gly Gly Gly Ser Gln Ser Val Leu Thr Gln
            420                 425                 430
Ser Ala Ser Val Ser Gly Ser Leu Gly Gln Ser Val Thr Ile Ser Cys
        435                 440                 445
Thr Gly Pro Asn Ser Val Cys Cys Ser His Lys Ser Ile Ser Trp Tyr
    450                 455                 460
Gln Trp Pro Pro Gly Arg Ala Pro Thr Leu Ile Ile Tyr Glu Asp Asn
465                 470                 475                 480
Glu Arg Ala Pro Gly Ile Ser Pro Arg Phe Ser Gly Tyr Lys Ser Tyr
                485                 490                 495
Trp Ser Ala Tyr Leu Thr Ile Ser Asp Leu Arg Pro Glu Asp Glu Thr
                500                 505                 510
Thr Tyr Tyr Cys Cys Ser Tyr Thr His Asn Ser Gly Cys Val Phe Gly
            515                 520                 525
Thr Gly Thr Lys Val Ser Val Leu Gly Ser Gly Pro Lys Ser Cys Asp
    530                 535                 540
Lys Thr His Thr Cys Pro Pro Cys Pro Ala Pro Glu Leu Leu Gly Gly
545                 550                 555                 560
Pro Ser Val Phe Leu Phe Pro Pro Lys Pro Lys Asp Thr Leu Met Ile
                565                 570                 575
Ser Arg Thr Pro Glu Val Thr Cys Val Val Val Asp Val Ser His Glu
                580                 585                 590
Asp Pro Glu Val Lys Phe Asn Trp Tyr Val Asp Gly Val Glu Val His
            595                 600                 605
Asn Ala Lys Thr Lys Pro Arg Glu Glu Gln Tyr Asn Ser Thr Tyr Arg
    610                 615                 620
Val Val Ser Val Leu Thr Val Leu His Gln Asp Trp Leu Asn Gly Lys
625                 630                 635                 640
Glu Tyr Lys Cys Lys Val Ser Asn Lys Ala Leu Pro Ala Pro Ile Glu
                645                 650                 655
Lys Thr Ile Ser Lys Ala Lys Gly Gln Pro Arg Glu Pro Gln Val Tyr
                660                 665                 670
Thr Leu Pro Pro Ser Arg Glu Glu Met Thr Lys Asn Gln Val Ser Leu
            675                 680                 685
Thr Cys Leu Val Lys Gly Phe Tyr Pro Ser Asp Ile Ala Val Glu Trp
    690                 695                 700
Glu Ser Asn Gly Gln Pro Glu Asn Asn Tyr Lys Thr Thr Pro Pro Val
705                 710                 715                 720
Leu Asp Ser Asp Gly Ser Phe Phe Leu Tyr Ser Lys Leu Thr Val Asp
                725                 730                 735
Lys Ser Arg Trp Gln Gln Gly Asn Val Phe Ser Cys Ser Val Met His
                740                 745                 750
Glu Ala Leu His Asn His Tyr Thr Gln Lys Ser Leu Ser Leu Ser Pro
            755                 760                 765
Gly Lys
    770

<210> SEQ ID NO 53
<211> LENGTH: 780
<212> TYPE: PRT
<213> ORGANISM: Artificial Sequence
<220> FEATURE:
```

<223> OTHER INFORMATION: Synthetic peptide

<400> SEQUENCE: 53

```
Glu Val Gln Leu Val Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Ala
    50                  55                  60

Pro Val Glu Gly Arg Phe Thr Ile Ser Arg Leu Asn Ser Ile Asn Phe
65                  70                  75                  80

Leu Tyr Leu Glu Met Asn Asn Leu Arg Met Glu Asp Ser Gly Leu Tyr
            85                  90                  95

Phe Cys Ala Arg Thr Gly Lys Tyr Tyr Asp Phe Trp Ser Gly Tyr Pro
        100                 105                 110

Pro Gly Glu Glu Tyr Phe Gln Asp Trp Gly Arg Gly Thr Leu Val Thr
    115                 120                 125

Val Ser Gly Gly Gly Gly Ser Gly Gly Gly Ser Gly Gly Gly Gly Gly
130                 135                 140

Gly Ser Ser Tyr Glu Leu Thr Gln Glu Thr Gly Val Ser Val Ala Leu
145                 150                 155                 160

Gly Arg Thr Val Thr Ile Thr Cys Arg Gly Asp Ser Leu Arg Ser His
            165                 170                 175

Tyr Ala Ser Trp Tyr Gln Lys Lys Pro Gly Gln Ala Pro Ile Leu Leu
        180                 185                 190

Phe Tyr Gly Lys Asn Asn Arg Pro Ser Gly Val Pro Asp Arg Phe Ser
    195                 200                 205

Gly Ser Ala Ser Gly Asn Arg Ala Ser Leu Thr Ile Ser Gly Ala Gln
    210                 215                 220

Ala Glu Asp Asp Ala Glu Tyr Tyr Cys Ser Ser Arg Asp Lys Ser Gly
225                 230                 235                 240

Ser Arg Leu Ser Val Phe Gly Gly Gly Thr Lys Leu Thr Val Leu Gly
            245                 250                 255

Gly Gly Gly Ser Gly Gly Gly Gly Ser Gly Gly Gly Ser Gly Gly
        260                 265                 270

Gly Gly Ser Gly Gly Gly Gly Ser Gly Gly Gly Gly Ser Gly Gly Gly
    275                 280                 285

Gly Ser Gln Gly Gln Leu Val Gln Ser Gly Ala Glu Leu Lys Lys Pro
    290                 295                 300

Gly Ala Ser Val Lys Ile Ser Cys Lys Thr Ser Gly Tyr Arg Phe Asn
305                 310                 315                 320

Phe Tyr His Ile Asn Trp Ile Arg Gln Thr Ala Gly Arg Gly Pro Glu
            325                 330                 335

Trp Met Gly Trp Ile Ser Pro Tyr Ser Gly Asp Lys Asn Leu Ala Pro
        340                 345                 350

Ala Phe Gln Asp Arg Val Ile Met Thr Thr Asp Thr Glu Val Pro Val
    355                 360                 365

Thr Ser Phe Thr Ser Thr Gly Ala Ala Tyr Met Glu Ile Arg Asn Leu
    370                 375                 380

Lys Phe Asp Asp Thr Gly Thr Tyr Phe Cys Ala Lys Gly Leu Leu Arg
385                 390                 395                 400
```

```
Asp Gly Ser Ser Thr Trp Leu Pro Tyr Leu Trp Gln Gly Thr Leu
                405                 410                 415
Leu Thr Val Ser Ser Gly Gly Gly Gly Ser Gly Gly Gly Gly Ser Gly
            420                 425                 430
Gly Gly Gly Ser Gln Ser Val Leu Thr Gln Ser Ala Ser Val Ser Gly
            435                 440                 445
Ser Leu Gly Gln Ser Val Thr Ile Ser Cys Thr Gly Pro Asn Ser Val
        450                 455                 460
Cys Cys Ser His Lys Ser Ile Ser Trp Tyr Gln Trp Pro Pro Gly Arg
465                 470                 475                 480
Ala Pro Thr Leu Ile Ile Tyr Glu Asp Asn Glu Arg Ala Pro Gly Ile
                485                 490                 495
Ser Pro Arg Phe Ser Gly Tyr Lys Ser Tyr Trp Ser Ala Tyr Leu Thr
            500                 505                 510
Ile Ser Asp Leu Arg Pro Glu Asp Glu Thr Thr Tyr Tyr Cys Cys Ser
            515                 520                 525
Tyr Thr His Asn Ser Gly Cys Val Phe Gly Thr Gly Thr Lys Val Ser
        530                 535                 540
Val Leu Gly Ser Gly Pro Lys Ser Cys Asp Lys Thr His Thr Cys Pro
545                 550                 555                 560
Pro Cys Pro Ala Pro Glu Leu Leu Gly Gly Pro Ser Val Phe Leu Phe
                565                 570                 575
Pro Pro Lys Pro Lys Asp Thr Leu Met Ile Ser Arg Thr Pro Glu Val
            580                 585                 590
Thr Cys Val Val Val Asp Val Ser His Glu Asp Pro Glu Val Lys Phe
            595                 600                 605
Asn Trp Tyr Val Asp Gly Val Glu Val His Asn Ala Lys Thr Lys Pro
        610                 615                 620
Arg Glu Glu Gln Tyr Asn Ser Thr Tyr Arg Val Val Ser Val Leu Thr
625                 630                 635                 640
Val Leu His Gln Asp Trp Leu Asn Gly Lys Glu Tyr Lys Cys Lys Val
                645                 650                 655
Ser Asn Lys Ala Leu Pro Ala Pro Ile Glu Lys Thr Ile Ser Lys Ala
            660                 665                 670
Lys Gly Gln Pro Arg Glu Pro Gln Val Tyr Thr Leu Pro Pro Ser Arg
            675                 680                 685
Glu Glu Met Thr Lys Asn Gln Val Ser Leu Thr Cys Leu Val Lys Gly
        690                 695                 700
Phe Tyr Pro Ser Asp Ile Ala Val Glu Trp Glu Ser Asn Gly Gln Pro
705                 710                 715                 720
Glu Asn Asn Tyr Lys Thr Thr Pro Pro Val Leu Asp Ser Asp Gly Ser
                725                 730                 735
Phe Phe Leu Tyr Ser Lys Leu Thr Val Asp Lys Ser Arg Trp Gln Gln
            740                 745                 750
Gly Asn Val Phe Ser Cys Ser Val Met His Glu Ala Leu His Asn His
            755                 760                 765
Tyr Thr Gln Lys Ser Leu Ser Leu Ser Pro Gly Lys
        770                 775                 780

<210> SEQ ID NO 54
<211> LENGTH: 108
<212> TYPE: PRT
<213> ORGANISM: Artificial Sequence
<220> FEATURE:
<223> OTHER INFORMATION: Synthetic peptide
```

```
<400> SEQUENCE: 54

Ser Tyr Val Arg Pro Leu Ser Val Ala Leu Gly Glu Thr Ala Arg Ile
1               5                   10                  15

Ser Cys Gly Arg Gln Ala Leu Gly Ser Arg Ala Val Gln Trp Tyr Gln
            20                  25                  30

His Arg Pro Gly Gln Ala Pro Ile Leu Leu Ile Tyr Asn Asn Gln Asp
        35                  40                  45

Arg Pro Ser Gly Ile Pro Glu Arg Phe Ser Gly Thr Pro Asp Ile Asn
    50                  55                  60

Phe Gly Thr Arg Ala Thr Leu Thr Ile Ser Val Glu Ala Gly Asp
65                  70                  75                  80

Glu Ala Asp Tyr Tyr Cys His Met Trp Asp Ser Arg Ser Gly Phe Ser
                85                  90                  95

Trp Ser Phe Gly Gly Ala Thr Arg Leu Thr Val Leu
            100                 105

<210> SEQ ID NO 55
<211> LENGTH: 11
<212> TYPE: PRT
<213> ORGANISM: Artificial Sequence
<220> FEATURE:
<223> OTHER INFORMATION: Synthetic peptide

<400> SEQUENCE: 55

Gly Arg Gln Ala Leu Gly Ser Arg Ala Val Gln
1               5                   10

<210> SEQ ID NO 56
<211> LENGTH: 7
<212> TYPE: PRT
<213> ORGANISM: Artificial Sequence
<220> FEATURE:
<223> OTHER INFORMATION: Synthetic peptide

<400> SEQUENCE: 56

Asn Asn Gln Asp Arg Pro Ser
1               5

<210> SEQ ID NO 57
<211> LENGTH: 12
<212> TYPE: PRT
<213> ORGANISM: Artificial Sequence
<220> FEATURE:
<223> OTHER INFORMATION: Synthetic peptide

<400> SEQUENCE: 57

His Met Trp Asp Ser Arg Ser Gly Phe Ser Trp Ser
1               5                   10

<210> SEQ ID NO 58
<211> LENGTH: 132
<212> TYPE: PRT
<213> ORGANISM: Artificial Sequence
<220> FEATURE:
<223> OTHER INFORMATION: Synthetic peptide

<400> SEQUENCE: 58

Gln Val Gln Leu Gln Glu Ser Gly Pro Gly Leu Val Lys Pro Ser Glu
1               5                   10                  15

Thr Leu Ser Val Thr Cys Ser Val Ser Gly Asp Ser Met Asn Asn Tyr
            20                  25                  30
```

Tyr Trp Thr Trp Ile Arg Gln Ser Pro Gly Lys Gly Leu Glu Trp Ile
            35                  40                  45

Gly Tyr Ile Ser Asp Arg Glu Ser Ala Thr Tyr Asn Pro Ser Leu Asn
 50                  55                  60

Ser Arg Val Val Ile Ser Arg Asp Thr Ser Lys Asn Gln Leu Ser Leu
 65                  70                  75                  80

Lys Leu Asn Ser Val Thr Pro Ala Asp Thr Ala Val Tyr Tyr Cys Ala
                 85                  90                  95

Thr Ala Arg Arg Gly Gln Arg Ile Tyr Gly Val Val Ser Phe Gly Glu
            100                 105                 110

Phe Phe Tyr Tyr Tyr Ser Met Asp Val Trp Gly Lys Gly Thr Thr Val
            115                 120                 125

Thr Val Ser Ser
    130

<210> SEQ ID NO 59
<211> LENGTH: 5
<212> TYPE: PRT
<213> ORGANISM: Artificial Sequence
<220> FEATURE:
<223> OTHER INFORMATION: Synthetic peptide

<400> SEQUENCE: 59

Asn Tyr Tyr Trp Thr
1               5

<210> SEQ ID NO 60
<211> LENGTH: 16
<212> TYPE: PRT
<213> ORGANISM: Artificial Sequence
<220> FEATURE:
<223> OTHER INFORMATION: Synthetic peptide

<400> SEQUENCE: 60

Tyr Ile Ser Asp Arg Glu Ser Ala Thr Tyr Asn Pro Ser Leu Asn Ser
1               5                   10                  15

<210> SEQ ID NO 61
<211> LENGTH: 24
<212> TYPE: PRT
<213> ORGANISM: Artificial Sequence
<220> FEATURE:
<223> OTHER INFORMATION: Synthetic peptide

<400> SEQUENCE: 61

Ala Arg Arg Gly Gln Arg Ile Tyr Gly Val Val Ser Phe Gly Glu Phe
1               5                   10                  15

Phe Tyr Tyr Tyr Ser Met Asp Val
            20

<210> SEQ ID NO 62
<211> LENGTH: 110
<212> TYPE: PRT
<213> ORGANISM: Artificial Sequence
<220> FEATURE:
<223> OTHER INFORMATION: Synthetic peptide

<400> SEQUENCE: 62

Trp Ala Ser Ser Glu Leu Thr Gln Pro Pro Ser Val Ser Val Ser Pro
1               5                   10                  15

Gly Gln Thr Ala Arg Ile Thr Cys Ser Gly Ala Pro Leu Thr Ser Arg
            20                  25                  30

```
Phe Thr Tyr Trp Tyr Arg Gln Lys Pro Gly Gln Ala Pro Val Leu Ile
         35                  40                  45

Ile Ser Arg Ser Ser Gln Arg Ser Ser Gly Ser Gly Arg Phe Ser
 50                  55                  60

Ala Ser Trp Ser Gly Thr Thr Val Thr Leu Thr Ile Arg Gly Val Gln
 65                  70                  75                  80

Ala Asp Asp Glu Ala Asp Tyr Tyr Cys Gln Ser Ser Asp Thr Ser Asp
                 85                  90                  95

Ser Tyr Lys Met Phe Gly Gly Gly Thr Lys Leu Thr Val Leu
            100                 105                 110

<210> SEQ ID NO 63
<211> LENGTH: 11
<212> TYPE: PRT
<213> ORGANISM: Artificial Sequence
<220> FEATURE:
<223> OTHER INFORMATION: Synthetic peptide

<400> SEQUENCE: 63

Ser Gly Ala Pro Leu Thr Ser Arg Phe Thr Tyr
1               5                   10

<210> SEQ ID NO 64
<211> LENGTH: 7
<212> TYPE: PRT
<213> ORGANISM: Artificial Sequence
<220> FEATURE:
<223> OTHER INFORMATION: Synthetic peptide

<400> SEQUENCE: 64

Ser Arg Ser Ser Gln Arg Ser
1               5

<210> SEQ ID NO 65
<211> LENGTH: 11
<212> TYPE: PRT
<213> ORGANISM: Artificial Sequence
<220> FEATURE:
<223> OTHER INFORMATION: Synthetic peptide

<400> SEQUENCE: 65

Gln Ser Ser Asp Thr Ser Asp Ser Tyr Lys Met
1               5                   10

<210> SEQ ID NO 66
<211> LENGTH: 131
<212> TYPE: PRT
<213> ORGANISM: Artificial Sequence
<220> FEATURE:
<223> OTHER INFORMATION: Synthetic peptide

<400> SEQUENCE: 66

Glu Gln Val Gln Leu Arg Glu Ser Gly Pro Gly Leu Val Lys Pro Ser
1               5                   10                  15

Glu Thr Leu Ser Leu Ser Cys Thr Val Ser Gln Asp Ser Arg Pro Ser
            20                  25                  30

Asp His Ser Trp Thr Trp Val Arg Gln Ser Pro Gly Lys Ala Leu Glu
         35                  40                  45

Trp Ile Gly Asp Ile His Tyr Asn Gly Ala Thr Thr Tyr Asn Pro Ser
 50                  55                  60

Leu Arg Ser Arg Val Arg Ile Glu Leu Asp Gln Ser Ile Pro Arg Phe
 65                  70                  75                  80
```

```
                                            -continued

Ser Leu Lys Met Thr Ser Met Thr Ala Ala Asp Thr Gly Met Tyr Tyr
                85                  90                  95

Cys Ala Arg Asn Ala Ile Arg Ile Tyr Gly Val Val Ala Leu Gly Glu
            100                 105                 110

Trp Phe His Tyr Gly Met Asp Val Trp Gly Gln Gly Thr Ala Val Thr
        115                 120                 125

Val Ser Ser
    130

<210> SEQ ID NO 67
<211> LENGTH: 6
<212> TYPE: PRT
<213> ORGANISM: Artificial Sequence
<220> FEATURE:
<223> OTHER INFORMATION: Synthetic peptide

<400> SEQUENCE: 67

Ser Asp His Ser Trp Thr
1               5

<210> SEQ ID NO 68
<211> LENGTH: 16
<212> TYPE: PRT
<213> ORGANISM: Artificial Sequence
<220> FEATURE:
<223> OTHER INFORMATION: Synthetic peptide

<400> SEQUENCE: 68

Asp Ile His Tyr Asn Gly Ala Thr Thr Tyr Asn Pro Ser Leu Arg Ser
1               5                   10                  15

<210> SEQ ID NO 69
<211> LENGTH: 21
<212> TYPE: PRT
<213> ORGANISM: Artificial Sequence
<220> FEATURE:
<223> OTHER INFORMATION: Synthetic peptide

<400> SEQUENCE: 69

Asn Ala Ile Arg Ile Tyr Gly Val Val Ala Leu Gly Glu Trp Phe His
1               5                   10                  15

Tyr Gly Met Asp Val
            20

<210> SEQ ID NO 70
<211> LENGTH: 107
<212> TYPE: PRT
<213> ORGANISM: Artificial Sequence
<220> FEATURE:
<223> OTHER INFORMATION: Synthetic peptide

<400> SEQUENCE: 70

Glu Ile Val Met Thr Gln Ser Pro Asp Thr Leu Ser Val Ser Pro Gly
1               5                   10                  15

Glu Thr Val Thr Leu Ser Cys Arg Ala Ser Gln Asn Ile Asn Lys Asn
            20                  25                  30

Leu Ala Trp Tyr Gln Tyr Lys Pro Gly Gln Ser Pro Arg Leu Val Ile
        35                  40                  45

Phe Glu Thr Tyr Ser Lys Ile Ala Ala Phe Pro Ala Arg Phe Val Ala
    50                  55                  60

Ser Gly Ser Gly Thr Glu Phe Thr Leu Thr Ile Asn Asn Met Gln Ser
65                  70                  75                  80
```

Glu Asp Val Ala Val Tyr Tyr Cys Gln Gln Tyr Glu Glu Trp Pro Arg
            85                  90                  95

Thr Phe Gly Gln Gly Thr Lys Val Asp Ile Lys
            100                 105

<210> SEQ ID NO 71
<211> LENGTH: 11
<212> TYPE: PRT
<213> ORGANISM: Artificial Sequence
<220> FEATURE:
<223> OTHER INFORMATION: Synthetic peptide

<400> SEQUENCE: 71

Arg Ala Ser Gln Asn Ile Asn Lys Asn Leu Ala
1               5                   10

<210> SEQ ID NO 72
<211> LENGTH: 7
<212> TYPE: PRT
<213> ORGANISM: Artificial Sequence
<220> FEATURE:
<223> OTHER INFORMATION: Synthetic peptide

<400> SEQUENCE: 72

Glu Thr Tyr Ser Lys Ile Ala
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic peptide

<400> SEQUENCE: 73

Gln Gln Tyr Glu Glu Trp Pro Arg Thr
1               5

<210> SEQ ID NO 74
<211> LENGTH: 132
<212> TYPE: PRT
<213> ORGANISM: Artificial Sequence
<220> FEATURE:
<223> OTHER INFORMATION: Synthetic peptide

<400> SEQUENCE: 74

Gln Leu Gln Met Gln Glu Ser Gly Pro Gly Leu Val Lys Pro Ser Glu
1               5                   10                  15

Thr Leu Ser Leu Ser Cys Thr Val Ser Gly Asp Ser Ile Arg Gly Gly
            20                  25                  30

Glu Trp Gly Asp Lys Asp Tyr His Trp Gly Trp Val Arg His Ser Ala
        35                  40                  45

Gly Lys Gly Leu Glu Trp Ile Gly Ser Ile His Trp Arg Gly Thr Thr
    50                  55                  60

His Tyr Lys Glu Ser Leu Arg Arg Arg Val Ser Met Ser Ile Asp Thr
65                  70                  75                  80

Ser Arg Asn Trp Phe Ser Leu Arg Leu Ala Ser Val Thr Ala Ala Asp
                85                  90                  95

Thr Ala Val Tyr Phe Cys Ala Arg His Arg His His Asp Val Phe Met
            100                 105                 110

Val Pro Ile Ala Gly Trp Phe Asp Val Trp Gly Pro Gly Val Gln Val
        115                 120                 125

Thr Val Ser Ser
    130

<210> SEQ ID NO 75
<211> LENGTH: 12
<212> TYPE: PRT
<213> ORGANISM: Artificial Sequence
<220> FEATURE:
<223> OTHER INFORMATION: Synthetic peptide

<400> SEQUENCE: 75

Gly Gly Glu Trp Gly Asp Lys Asp Tyr His Trp Gly
1               5                   10

<210> SEQ ID NO 76
<211> LENGTH: 16
<212> TYPE: PRT
<213> ORGANISM: Artificial Sequence
<220> FEATURE:
<223> OTHER INFORMATION: Synthetic peptide

<400> SEQUENCE: 76

Ser Ile His Trp Arg Gly Thr Thr His Tyr Lys Glu Ser Leu Arg Arg
1               5                   10                  15

<210> SEQ ID NO 77
<211> LENGTH: 17
<212> TYPE: PRT
<213> ORGANISM: Artificial Sequence
<220> FEATURE:
<223> OTHER INFORMATION: Synthetic peptide

<400> SEQUENCE: 77

His Arg His His Asp Val Phe Met Val Pro Ile Ala Gly Trp Phe Asp
1               5                   10                  15

Val

<210> SEQ ID NO 78
<211> LENGTH: 105
<212> TYPE: PRT
<213> ORGANISM: Artificial Sequence
<220> FEATURE:
<223> OTHER INFORMATION: Synthetic peptide

<400> SEQUENCE: 78

Thr Phe Val Ser Val Ala Pro Gly Gln Thr Ala Arg Ile Thr Cys Gly
1               5                   10                  15

Glu Glu Ser Leu Gly Ser Arg Ser Val Ile Trp Tyr Gln Gln Arg Pro
            20                  25                  30

Gly Gln Ala Pro Ser Leu Ile Ile Tyr Asn Asn Asn Asp Arg Pro Ser
        35                  40                  45

Gly Ile Pro Asp Arg Phe Ser Gly Ser Pro Gly Ser Thr Phe Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Arg Pro Thr Asn Trp Val Phe
                85                  90                  95

Gly Glu Gly Thr Thr Leu Ile Val Leu
            100                 105

<210> SEQ ID NO 79
<211> LENGTH: 11
<212> TYPE: PRT

<213> ORGANISM: Artificial Sequence
<220> FEATURE:
<223> OTHER INFORMATION: Synthetic peptide

<400> SEQUENCE: 79

Gly Glu Glu Ser Leu Gly Ser Arg Ser Val Ile
1               5                   10

<210> SEQ ID NO 80
<211> LENGTH: 7
<212> TYPE: PRT
<213> ORGANISM: Artificial Sequence
<220> FEATURE:
<223> OTHER INFORMATION: Synthetic peptide

<400> SEQUENCE: 80

Asn Asn Asn Asp Arg Pro Ser
1               5

<210> SEQ ID NO 81
<211> LENGTH: 12
<212> TYPE: PRT
<213> ORGANISM: Artificial Sequence
<220> FEATURE:
<223> OTHER INFORMATION: Synthetic peptide

<400> SEQUENCE: 81

His Ile Trp Asp Ser Arg Arg Pro Thr Asn Trp Val
1               5                   10

<210> SEQ ID NO 82
<211> LENGTH: 132
<212> TYPE: PRT
<213> ORGANISM: Artificial Sequence
<220> FEATURE:
<223> OTHER INFORMATION: Synthetic peptide

<400> SEQUENCE: 82

Gln Val His Leu Gln Glu Ser Gly Pro Gly Leu Val Lys Pro Ser Glu
1               5                   10                  15

Thr Leu Ser Leu Thr Cys Asn Val Ser Gly Thr Leu Val Arg Asp Asn
            20                  25                  30

Tyr Trp Ser Trp Ile Arg Gln Pro Leu Gly Lys Gln Pro Glu Trp Ile
        35                  40                  45

Gly Tyr Val His Asp Ser Gly Asp Thr Asn Tyr Asn Pro Ser Leu Lys
    50                  55                  60

Ser Arg Val His Leu Ser Leu Asp Lys Ser Lys Asn Leu Val Ser Leu
65                  70                  75                  80

Arg Leu Thr Gly Val Thr Ala Ala Asp Ser Ala Ile Tyr Tyr Cys Ala
                85                  90                  95

Thr Thr Lys His Gly Arg Arg Ile Tyr Gly Val Val Ala Phe Lys Glu
            100                 105                 110

Trp Phe Thr Tyr Phe Tyr Met Asp Val Trp Gly Lys Gly Thr Ser Val
        115                 120                 125

Thr Val Ser Ser
    130

<210> SEQ ID NO 83
<211> LENGTH: 5
<212> TYPE: PRT
<213> ORGANISM: Artificial Sequence
<220> FEATURE:
<223> OTHER INFORMATION: Synthetic peptide

<400> SEQUENCE: 83

Asp Asn Tyr Trp Ser
1               5

<210> SEQ ID NO 84
<211> LENGTH: 16
<212> TYPE: PRT
<213> ORGANISM: Artificial Sequence
<220> FEATURE:
<223> OTHER INFORMATION: Synthetic peptide

<400> SEQUENCE: 84

Tyr Val His Asp Ser Gly Asp Thr Asn Tyr Asn Pro Ser Leu Lys Ser
1               5                   10                  15

<210> SEQ ID NO 85
<211> LENGTH: 24
<212> TYPE: PRT
<213> ORGANISM: Artificial Sequence
<220> FEATURE:
<223> OTHER INFORMATION: Synthetic peptide

<400> SEQUENCE: 85

Thr Lys His Gly Arg Arg Ile Tyr Gly Val Val Ala Phe Lys Glu Trp
1               5                   10                  15

Phe Thr Tyr Phe Tyr Met Asp Val
            20

<210> SEQ ID NO 86
<211> LENGTH: 105
<212> TYPE: PRT
<213> ORGANISM: Artificial Sequence
<220> FEATURE:
<223> OTHER INFORMATION: Synthetic peptide

<400> SEQUENCE: 86

Thr Phe Val Ser Val Ala Pro Gly Gln Thr Ala Arg Ile Thr Cys Gly
1               5                   10                  15

Glu Glu Ser Leu Gly Ser Arg Ser Val Ile Trp Tyr Gln Gln Arg Pro
            20                  25                  30

Gly Gln Ala Pro Ser Leu Ile Ile Tyr Asn Asn Asn Asp Arg Pro Ser
        35                  40                  45

Gly Ile Pro Asp Arg Phe Ser Gly Ser Pro Gly Ser Thr Phe Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Arg Pro Thr Asn Trp Val Phe
                85                  90                  95

Gly Glu Gly Thr Thr Leu Ile Val Leu
            100                 105

<210> SEQ ID NO 87
<211> LENGTH: 11
<212> TYPE: PRT
<213> ORGANISM: Artificial Sequence
<220> FEATURE:
<223> OTHER INFORMATION: Synthetic peptide

<400> SEQUENCE: 87

Gly Glu Glu Ser Leu Gly Ser Arg Ser Val Ile
1               5                   10

<210> SEQ ID NO 88
<211> LENGTH: 7
<212> TYPE: PRT
<213> ORGANISM: Artificial Sequence
<220> FEATURE:
<223> OTHER INFORMATION: Synthetic peptide

<400> SEQUENCE: 88

Asn Asn Asn Asp Arg Pro Ser
1               5

<210> SEQ ID NO 89
<211> LENGTH: 12
<212> TYPE: PRT
<213> ORGANISM: Artificial Sequence
<220> FEATURE:
<223> OTHER INFORMATION: Synthetic peptide

<400> SEQUENCE: 89

His Ile Trp Asp Ser Arg Arg Pro Thr Asn Trp Val
1               5                   10

<210> SEQ ID NO 90
<211> LENGTH: 135
<212> TYPE: PRT
<213> ORGANISM: Artificial Sequence
<220> FEATURE:
<223> OTHER INFORMATION: Synthetic peptide

<400> SEQUENCE: 90

Glu Pro Gln Leu Gln Glu Ser Gly Pro Thr Leu Val Glu Ala Ser Glu
1               5                   10                  15

Thr Leu Ser Leu Thr Cys Ala Val Ser Gly Asp Ser Thr Ala Ala Cys
            20                  25                  30

Asn Ser Phe Trp Gly Trp Val Arg Gln Pro Pro Gly Lys Gly Leu Glu
        35                  40                  45

Trp Val Gly Ser Leu Ser His Cys Ala Ser Tyr Trp Asn Arg Gly Trp
    50                  55                  60

Thr Tyr His Asn Pro Ser Leu Lys Ser Arg Leu Thr Leu Ala Leu Asp
65                  70                  75                  80

Thr Pro Lys Asn Leu Val Phe Leu Lys Leu Asn Ser Val Thr Ala Ala
                85                  90                  95

Asp Thr Ala Thr Tyr Tyr Cys Ala Arg Phe Gly Gly Glu Val Leu Arg
            100                 105                 110

Tyr Thr Asp Trp Pro Lys Pro Ala Trp Val Asp Leu Trp Gly Arg Gly
        115                 120                 125

Thr Leu Val Thr Val Ser Ser
    130                 135

<210> SEQ ID NO 91
<211> LENGTH: 7
<212> TYPE: PRT
<213> ORGANISM: Artificial Sequence
<220> FEATURE:
<223> OTHER INFORMATION: Synthetic peptide

<400> SEQUENCE: 91

Ala Cys Asn Ser Phe Trp Gly
1               5

<210> SEQ ID NO 92
<211> LENGTH: 22

```
<212> TYPE: PRT
<213> ORGANISM: Artificial Sequence
<220> FEATURE:
<223> OTHER INFORMATION: Synthetic peptide

<400> SEQUENCE: 92

Ser Leu Ser His Cys Ala Ser Tyr Trp Asn Arg Gly Trp Thr Tyr His
1               5                   10                  15

Asn Pro Ser Leu Lys Ser
            20

<210> SEQ ID NO 93
<211> LENGTH: 19
<212> TYPE: PRT
<213> ORGANISM: Artificial Sequence
<220> FEATURE:
<223> OTHER INFORMATION: Synthetic peptide

<400> SEQUENCE: 93

Phe Gly Gly Glu Val Leu Arg Tyr Thr Asp Trp Pro Lys Pro Ala Trp
1               5                   10                  15

Val Asp Leu

<210> SEQ ID NO 94
<211> LENGTH: 108
<212> TYPE: PRT
<213> ORGANISM: Artificial Sequence
<220> FEATURE:
<223> OTHER INFORMATION: Synthetic peptide

<400> SEQUENCE: 94

Ser Glu Leu Thr Gln Asp Pro Ala Val Ser Val Ala Leu Lys Gln Thr
1               5                   10                  15

Val Thr Ile Thr Cys Arg Gly Asp Ser Leu Arg Ser His Tyr Ala Ser
            20                  25                  30

Trp Tyr Gln Lys Lys Pro Gly Gln Ala Pro Val Leu Leu Phe Tyr Gly
        35                  40                  45

Lys Asn Asn Arg Pro Ser Gly Ile Pro Asp Arg Phe Ser Gly Ser Ala
    50                  55                  60

Ser Gly Asn Arg Ala Ser Leu Thr Ile Thr Gly Ala Gln Ala Glu Asp
65                  70                  75                  80

Glu Ala Asp Tyr Tyr Cys Ser Ser Arg Asp Lys Ser Gly Ser Arg Leu
                85                  90                  95

Ser Val Phe Gly Gly Gly Thr Lys Leu Thr Val Leu
            100                 105

<210> SEQ ID NO 95
<211> LENGTH: 11
<212> TYPE: PRT
<213> ORGANISM: Artificial Sequence
<220> FEATURE:
<223> OTHER INFORMATION: Synthetic peptide

<400> SEQUENCE: 95

Arg Gly Asp Ser Leu Arg Ser His Tyr Ala Ser
1               5                   10

<210> SEQ ID NO 96
<211> LENGTH: 7
<212> TYPE: PRT
<213> ORGANISM: Artificial Sequence
<220> FEATURE:
<223> OTHER INFORMATION: Synthetic peptide
```

<400> SEQUENCE: 96

Gly Lys Asn Asn Arg Pro Ser
1               5

<210> SEQ ID NO 97
<211> LENGTH: 12
<212> TYPE: PRT
<213> ORGANISM: Artificial Sequence
<220> FEATURE:
<223> OTHER INFORMATION: Synthetic peptide

<400> SEQUENCE: 97

Ser Ser Arg Asp Lys Ser Gly Ser Arg Leu Ser Val
1               5                   10

<210> SEQ ID NO 98
<211> LENGTH: 131
<212> TYPE: PRT
<213> ORGANISM: Artificial Sequence
<220> FEATURE:
<223> OTHER INFORMATION: Synthetic peptide

<400> SEQUENCE: 98

Glu Val Arg Leu Val Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Glu
    50                  55                  60

Ser Val Lys Gly Arg Phe Thr Ile Ser Arg Asp Asn Thr Lys Asn Thr
65                  70                  75                  80

Leu Tyr Leu Glu Met Asn Asn Val Arg Thr Glu Asp Thr Gly Tyr Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Gln Gly Thr Leu Val Ile
        115                 120                 125

Val Ser Ser
    130

<210> SEQ ID NO 99
<211> LENGTH: 5
<212> TYPE: PRT
<213> ORGANISM: Artificial Sequence
<220> FEATURE:
<223> OTHER INFORMATION: Synthetic peptide

<400> SEQUENCE: 99

Asn Ala Trp Met Thr
1               5

<210> SEQ ID NO 100
<211> LENGTH: 19
<212> TYPE: PRT
<213> ORGANISM: Artificial Sequence
<220> FEATURE:
<223> OTHER INFORMATION: Synthetic peptide

<400> SEQUENCE: 100

```
Arg Ile Thr Gly Pro Gly Glu Gly Trp Ser Val Asp Tyr Ala Glu Ser
 1               5                  10                  15

Val Lys Gly
```

<210> SEQ ID NO 101
<211> LENGTH: 20
<212> TYPE: PRT
<213> ORGANISM: Artificial Sequence
<220> FEATURE:
<223> OTHER INFORMATION: Synthetic peptide

<400> SEQUENCE: 101

```
Thr Gly Lys Tyr Tyr Asp Phe Trp Ser Gly Tyr Pro Pro Gly Glu Glu
 1               5                  10                  15

Tyr Phe Gln Asp
            20
```

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106
<211> LENGTH: 131
<212> TYPE: PRT
<213> ORGANISM: Artificial Sequence
<220> FEATURE:
<223> OTHER INFORMATION: Synthetic peptide

<400> SEQUENCE: 106

```
Glu Val Arg Leu Val Glu Ser Gly Gly Gly Leu Val Lys Pro Gly Gly
 1               5                  10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Glu
    50                  55                  60

Ser Val Lys Gly Arg Phe Thr Ile Ser Arg Asp Asn Thr Lys Asn Thr
65                  70                  75                  80

Leu Tyr Leu Glu Met Asn Asn Val Arg Thr Glu Asp Thr Gly Tyr Tyr
                85                  90                  95

Phe Cys Ala Arg Thr Gly Lys Tyr Tyr Asp Phe Trp Phe Gly Tyr Pro
            100                 105                 110
```

Pro Gly Glu Glu Tyr Phe Gln Asp Trp Gly Gln Gly Thr Leu Val Ile
            115                 120                 125

Val Ser Ser
    130

<210> SEQ ID NO 107
<211> LENGTH: 5
<212> TYPE: PRT
<213> ORGANISM: Artificial Sequence
<220> FEATURE:
<223> OTHER INFORMATION: Synthetic peptide

<400> SEQUENCE: 107

Asn Ala Trp Met Thr
1               5

<210> SEQ ID NO 108
<211> LENGTH: 19
<212> TYPE: PRT
<213> ORGANISM: Artificial Sequence
<220> FEATURE:
<223> OTHER INFORMATION: Synthetic peptide

<400> SEQUENCE: 108

Arg Ile Thr Gly Pro Gly Glu Gly Trp Ser Val Asp Tyr Ala Glu Ser
1               5                   10                  15

Val Lys Gly

<210> SEQ ID NO 109
<211> LENGTH: 20
<212> TYPE: PRT
<213> ORGANISM: Artificial Sequence
<220> FEATURE:
<223> OTHER INFORMATION: Synthetic peptide

<400> SEQUENCE: 109

Thr Gly Lys Tyr Tyr Asp Phe Trp Phe Gly Tyr Pro Pro Gly Glu Glu
1               5                   10                  15

Tyr Phe Gln Asp
            20

<210> SEQ ID NO 110
<211> LENGTH: 108
<212> TYPE: PRT
<213> ORGANISM: Artificial Sequence
<220> FEATURE:
<223> OTHER INFORMATION: Synthetic peptide

<400> SEQUENCE: 110

Asp Ile Gln Met Thr Gln Ser Pro Ser Phe Leu Tyr Gly Ser Val Gly
1               5                   10                  15

Asp Arg Val Thr Ile Thr Cys Arg Ala Ser Gln Asn Ile Lys Asp Tyr
            20                  25                  30

Leu Asn Trp Tyr Gln Gln Arg Pro Gly Arg Ala Pro Arg Leu Leu Ile
        35                  40                  45

Tyr Ala Ala Ser Asn Leu Gln Ser Gly Val Pro Ser Arg Phe Ser Gly
    50                  55                  60

Ser Gly Tyr Gly Thr Asp Phe Thr Leu Ile Ile Ser Ser Leu Gln Pro
65                  70                  75                  80

Glu Asp Phe Ala Thr Tyr Phe Cys Gln Glu Ser Tyr Ser Ser Thr Pro
                85                  90                  95

Thr His Ile Phe Gly Leu Gly Thr Lys Leu Glu Lys
            100                 105

<210> SEQ ID NO 111
<211> LENGTH: 11
<212> TYPE: PRT
<213> ORGANISM: Artificial Sequence
<220> FEATURE:
<223> OTHER INFORMATION: Synthetic peptide

<400> SEQUENCE: 111

Arg Ala Ser Gln Asn Ile Lys Asp Tyr Leu Asn
1               5                   10

<210> SEQ ID NO 112
<211> LENGTH: 7
<212> TYPE: PRT
<213> ORGANISM: Artificial Sequence
<220> FEATURE:
<223> OTHER INFORMATION: Synthetic peptide

<400> SEQUENCE: 112

Ala Ala Ser Asn Leu Gln Ser
1               5

<210> SEQ ID NO 113
<211> LENGTH: 11
<212> TYPE: PRT
<213> ORGANISM: Artificial Sequence
<220> FEATURE:
<223> OTHER INFORMATION: Synthetic peptide

<400> SEQUENCE: 113

Gln Glu Ser Tyr Ser Ser Thr Pro Thr His Ile
1               5                   10

<210> SEQ ID NO 114
<211> LENGTH: 132
<212> TYPE: PRT
<213> ORGANISM: Artificial Sequence
<220> FEATURE:
<223> OTHER INFORMATION: Synthetic peptide

<400> SEQUENCE: 114

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Asp Asn Ser
                20                  25                  30

Trp Met Gly Trp Val Arg Gln Ala Pro Gly Lys Gly Leu Glu Trp Val
            35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
    130

<210> SEQ ID NO 115
<211> LENGTH: 5
<212> TYPE: PRT
<213> ORGANISM: Artificial Sequence
<220> FEATURE:
<223> OTHER INFORMATION: Synthetic peptide

<400> SEQUENCE: 115

Asn Ser Trp Met Gly
1               5

<210> SEQ ID NO 116
<211> LENGTH: 19
<212> TYPE: PRT
<213> ORGANISM: Artificial Sequence
<220> FEATURE:
<223> OTHER INFORMATION: Synthetic peptide

<400> SEQUENCE: 116

Arg Ile Arg Arg Leu Lys Asp Gly Ala Thr Gly Glu Tyr Gly Ala Ala
1               5                   10                  15

Val Lys Asp

<210> SEQ ID NO 117
<211> LENGTH: 21
<212> TYPE: PRT
<213> ORGANISM: Artificial Sequence
<220> FEATURE:
<223> OTHER INFORMATION: Synthetic peptide

<400> SEQUENCE: 117

Asp Glu Gly Thr Pro Val Thr Arg Phe Leu Glu Trp Gly Tyr Phe Tyr
1               5                   10                  15

Tyr Tyr Met Ala Val
            20

<210> SEQ ID NO 118
<211> LENGTH: 108
<212> TYPE: PRT
<213> ORGANISM: Artificial Sequence
<220> FEATURE:
<223> OTHER INFORMATION: Synthetic peptide

<400> SEQUENCE: 118

Glu Ile Val Leu Thr Gln Ser Pro Gly Thr Gln Ser Leu Ser Pro Gly
1               5                   10                  15

Glu Arg Ala Thr Leu Ser Cys Arg Ala Ser Gln Ser Val Gly Asn Asn
            20                  25                  30

Lys Leu Ala Trp Tyr Gln Gln Arg Pro Gly Gln Ala Pro Arg Leu Leu
        35                  40                  45

Ile Tyr Gly Ala Ser Ser Arg Pro Ser Gly Val Ala Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Gln Ser Leu
                85                  90                  95

Ser Thr Phe Gly Gln Gly Thr Lys Val Glu Val Lys
            100                 105

<210> SEQ ID NO 119
<211> LENGTH: 12
<212> TYPE: PRT

```
<213> ORGANISM: Artificial Sequence
<220> FEATURE:
<223> OTHER INFORMATION: Synthetic peptide

<400> SEQUENCE: 119

Arg Ala Ser Gln Ser Val Gly Asn Asn Lys Leu Ala
1               5                   10

<210> SEQ ID NO 120
<211> LENGTH: 7
<212> TYPE: PRT
<213> ORGANISM: Artificial Sequence
<220> FEATURE:
<223> OTHER INFORMATION: Synthetic peptide

<400> SEQUENCE: 120

Gly Ala Ser Ser Arg Pro Ser
1               5

<210> SEQ ID NO 121
<211> LENGTH: 9
<212> TYPE: PRT
<213> ORGANISM: Artificial Sequence
<220> FEATURE:
<223> OTHER INFORMATION: Synthetic peptide

<400> SEQUENCE: 121

Gln Gln Tyr Gly Gln Ser Leu Ser Thr
1               5

<210> SEQ ID NO 122
<211> LENGTH: 126
<212> TYPE: PRT
<213> ORGANISM: Artificial Sequence
<220> FEATURE:
<223> OTHER INFORMATION: Synthetic peptide

<400> SEQUENCE: 122

Val Gln Leu Val Gln Ser Gly Ala Glu Val Lys Arg Pro Gly Ser Ser
1               5                   10                  15

Val Thr Val Ser Cys Lys Ala Ser Gly Gly Ser Phe Ser Thr Tyr Ala
            20                  25                  30

Leu Ser Trp Val Arg Gln Ala Pro Gly Arg Gly Leu Glu Trp Met Gly
        35                  40                  45

Gly Val Ile Pro Leu Leu Thr Ile Thr Asn Tyr Ala Pro Arg Phe Gln
    50                  55                  60

Gly Arg Ile Thr Ile Thr Ala Asp Arg Ser Thr Ser Thr Ala Tyr Leu
65                  70                  75                  80

Glu Leu Asn Ser Leu Arg Pro Glu Asp Thr Ala Val Tyr Tyr Cys Ala
                85                  90                  95

Arg Glu Gly Thr Thr Gly Trp Gly Trp Leu Gly Lys Pro Ile Gly Ala
            100                 105                 110

Phe Ala His Trp Gly Gln Gly Thr Leu Val Thr Val Ser Ser
        115                 120                 125

<210> SEQ ID NO 123
<211> LENGTH: 5
<212> TYPE: PRT
<213> ORGANISM: Artificial Sequence
<220> FEATURE:
<223> OTHER INFORMATION: Synthetic peptide

<400> SEQUENCE: 123
```

Thr Tyr Ala Leu Ser
1               5

<210> SEQ ID NO 124
<211> LENGTH: 17
<212> TYPE: PRT
<213> ORGANISM: Artificial Sequence
<220> FEATURE:
<223> OTHER INFORMATION: Synthetic peptide

<400> SEQUENCE: 124

Gly Val Ile Pro Leu Leu Thr Ile Thr Asn Tyr Ala Pro Arg Phe Gln
1               5                   10                  15

Gly

<210> SEQ ID NO 125
<211> LENGTH: 18
<212> TYPE: PRT
<213> ORGANISM: Artificial Sequence
<220> FEATURE:
<223> OTHER INFORMATION: Synthetic peptide

<400> SEQUENCE: 125

Glu Gly Thr Thr Gly Trp Gly Trp Leu Gly Lys Pro Ile Gly Ala Phe
1               5                   10                  15

Ala His

<210> SEQ ID NO 126
<211> LENGTH: 107
<212> TYPE: PRT
<213> ORGANISM: Artificial Sequence
<220> FEATURE:
<223> OTHER INFORMATION: Synthetic peptide

<400> SEQUENCE: 126

Ala Leu Gln Leu Thr Gln Ser Pro Ser Leu Ser Ala Ser Val Gly
1               5                   10                  15

Asp Arg Ile Thr Ile Thr Cys Arg Ala Ser Gln Gly Val Thr Ser Ala
            20                  25                  30

Leu Ala Trp Tyr Arg Gln Lys Pro Gly Ser Pro Gln Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Thr Leu Arg Pro
65                  70                  75                  80

Glu Asp Phe Ala Thr Tyr Tyr Cys Gln Gln Leu His Phe Tyr Pro His
                85                  90                  95

Thr Phe Gly Gly Gly Thr Arg Val Asp Val Arg
            100                 105

<210> SEQ ID NO 127
<211> LENGTH: 11
<212> TYPE: PRT
<213> ORGANISM: Artificial Sequence
<220> FEATURE:
<223> OTHER INFORMATION: Synthetic peptide

<400> SEQUENCE: 127

Arg Ala Ser Gln Gly Val Thr Ser Ala Leu Ala
1               5                   10

<210> SEQ ID NO 128

```
<211> LENGTH: 7
<212> TYPE: PRT
<213> ORGANISM: Artificial Sequence
<220> FEATURE:
<223> OTHER INFORMATION: Synthetic peptide

<400> SEQUENCE: 128

Asp Ala Ser Ser Leu Glu Ser
1               5

<210> SEQ ID NO 129
<211> LENGTH: 9
<212> TYPE: PRT
<213> ORGANISM: Artificial Sequence
<220> FEATURE:
<223> OTHER INFORMATION: Synthetic peptide

<400> SEQUENCE: 129

Gln Gln Leu His Phe Tyr Pro His Thr
1               5

<210> SEQ ID NO 130
<211> LENGTH: 132
<212> TYPE: PRT
<213> ORGANISM: Artificial Sequence
<220> FEATURE:
<223> OTHER INFORMATION: Synthetic peptide

<400> SEQUENCE: 130

Arg Ile Thr Leu Lys Glu Ser Gly Pro Pro Leu Val Lys Pro Thr Gln
1               5                   10                  15

Thr Leu Thr Leu Thr Cys Ser Phe Ser Gly Phe Ser Leu Ser Asp Phe
            20                  25                  30

Gly Val Gly Val Gly Trp Ile Arg Gln Pro Pro Gly Lys Ala Leu Glu
        35                  40                  45

Trp Leu Ala Ile Ile Tyr Ser Asp Asp Lys Arg Tyr Ser Pro Ser
    50                  55                  60

Leu Asn Thr Arg Leu Thr Ile Thr Lys Asp Thr Ser Lys Asn Gln Val
65                  70                  75                  80

Val Leu Val Met Thr Arg Val Ser Pro Val Asp Thr Ala Thr Tyr Phe
                85                  90                  95

Cys Ala His Arg Arg Gly Pro Thr Thr Leu Phe Gly Val Pro Ile Ala
            100                 105                 110

Arg Gly Pro Val Asn Ala Met Asp Val Trp Gly Gln Gly Ile Thr Val
        115                 120                 125

Thr Ile Ser Ser
    130

<210> SEQ ID NO 131
<211> LENGTH: 7
<212> TYPE: PRT
<213> ORGANISM: Artificial Sequence
<220> FEATURE:
<223> OTHER INFORMATION: Synthetic peptide

<400> SEQUENCE: 131

Asp Phe Gly Val Gly Val Gly
1               5

<210> SEQ ID NO 132
<211> LENGTH: 16
<212> TYPE: PRT
<213> ORGANISM: Artificial Sequence
```

<220> FEATURE:
<223> OTHER INFORMATION: Synthetic peptide

<400> SEQUENCE: 132

Ile Ile Tyr Ser Asp Asp Lys Arg Tyr Ser Pro Ser Leu Asn Thr
1               5                   10                  15

<210> SEQ ID NO 133
<211> LENGTH: 22
<212> TYPE: PRT
<213> ORGANISM: Artificial Sequence
<220> FEATURE:
<223> OTHER INFORMATION: Synthetic peptide

<400> SEQUENCE: 133

Arg Arg Gly Pro Thr Thr Leu Phe Gly Val Pro Ile Ala Arg Gly Pro
1               5                   10                  15

Val Asn Ala Met Asp Val
            20

<210> SEQ ID NO 134
<211> LENGTH: 107
<212> TYPE: PRT
<213> ORGANISM: Artificial Sequence
<220> FEATURE:
<223> OTHER INFORMATION: Synthetic peptide

<400> SEQUENCE: 134

Asp Ile Gln Leu Thr Gln Ser Pro Ser Phe Leu Ser Ala Ser Val Gly
1               5                   10                  15

Asp Lys Val Thr Ile Thr Cys Arg Ala Ser Gln Gly Val Arg Asn Glu
            20                  25                  30

Leu Ala Trp Tyr Gln Gln Lys Pro Gly Lys Ala Pro Asn Leu Leu Ile
        35                  40                  45

Tyr Tyr Ala Ser Thr Leu Gln Ser Gly Val Pro Ser Arg Phe Ser Ala
    50                  55                  60

Thr Gly Ser Gly Thr His Phe Thr Leu Thr Val Ser Ser Leu Gln Pro
65                  70                  75                  80

Glu Asp Phe Ala Thr Tyr Phe Cys Gln His Met Ser Ser Tyr Pro Leu
                85                  90                  95

Thr Phe Gly Gly Gly Thr Lys Val Glu Ile Lys
            100                 105

<210> SEQ ID NO 135
<211> LENGTH: 11
<212> TYPE: PRT
<213> ORGANISM: Artificial Sequence
<220> FEATURE:
<223> OTHER INFORMATION: Synthetic peptide

<400> SEQUENCE: 135

Arg Ala Ser Gln Gly Val Arg Asn Glu Leu Ala
1               5                   10

<210> SEQ ID NO 136
<211> LENGTH: 7
<212> TYPE: PRT
<213> ORGANISM: Artificial Sequence
<220> FEATURE:
<223> OTHER INFORMATION: Synthetic peptide

<400> SEQUENCE: 136

Tyr Ala Ser Thr Leu Gln Ser

```
1               5
```

<210> SEQ ID NO 137
<211> LENGTH: 9
<212> TYPE: PRT
<213> ORGANISM: Artificial Sequence
<220> FEATURE:
<223> OTHER INFORMATION: Synthetic peptide

<400> SEQUENCE: 137

```
Gln His Met Ser Ser Tyr Pro Leu Thr
1               5
```

<210> SEQ ID NO 138
<211> LENGTH: 122
<212> TYPE: PRT
<213> ORGANISM: Artificial Sequence
<220> FEATURE:
<223> OTHER INFORMATION: Synthetic peptide

<400> SEQUENCE: 138

```
Gln Glu Val Leu Val Gln Ser Gly Ala Glu Val Lys Lys Pro Gly Ala
1               5                   10                  15

Ser Val Lys Val Ser Cys Arg Ala Phe Gly Tyr Thr Phe Thr Gly Asn
            20                  25                  30

Ala Leu His Trp Val Arg Gln Ala Pro Gly Gln Gly Leu Glu Trp Leu
        35                  40                  45

Gly Trp Ile Asn Pro His Ser Gly Asp Thr Thr Thr Ser Gln Lys Phe
    50                  55                  60

Gln Gly Arg Val Tyr Met Thr Arg Asp Lys Ser Ile Asn Thr Ala Phe
65                  70                  75                  80

Leu Asp Val Thr Arg Leu Thr Ser Asp Thr Gly Ile Tyr Tyr Cys
                85                  90                  95

Ala Arg Asp Lys Tyr Tyr Gly Asn Glu Ala Val Gly Met Asp Val Trp
            100                 105                 110

Gly Gln Gly Thr Ser Val Thr Val Ser Ser
        115                 120
```

<210> SEQ ID NO 139
<211> LENGTH: 5
<212> TYPE: PRT
<213> ORGANISM: Artificial Sequence
<220> FEATURE:
<223> OTHER INFORMATION: Synthetic peptide

<400> SEQUENCE: 139

```
Gly Asn Ala Leu His
1               5
```

<210> SEQ ID NO 140
<211> LENGTH: 17
<212> TYPE: PRT
<213> ORGANISM: Artificial Sequence
<220> FEATURE:
<223> OTHER INFORMATION: Synthetic peptide

<400> SEQUENCE: 140

```
Trp Ile Asn Pro His Ser Gly Asp Thr Thr Thr Ser Gln Lys Phe Gln
1               5                   10                  15

Gly
```

<210> SEQ ID NO 141

```
<211> LENGTH: 13
<212> TYPE: PRT
<213> ORGANISM: Artificial Sequence
<220> FEATURE:
<223> OTHER INFORMATION: Synthetic peptide

<400> SEQUENCE: 141

Asp Lys Tyr Tyr Gly Asn Glu Ala Val Gly Met Asp Val
1               5                   10

<210> SEQ ID NO 142
<211> LENGTH: 110
<212> TYPE: PRT
<213> ORGANISM: Artificial Sequence
<220> FEATURE:
<223> OTHER INFORMATION: Synthetic peptide

<400> SEQUENCE: 142

Gln Ser Ala Leu Thr Gln Pro Ala Ser Val Ser Ala Ser Pro Gly Gln
1               5                   10                  15

Ser Ile Thr Ile Ser Cys Ser Gly Thr Arg Ser Asp Val Gly Gly Tyr
            20                  25                  30

Asp Phe Val Ser Trp Tyr Gln Gln His Pro Gly Lys Val Pro Lys Leu
        35                  40                  45

Ile Ile Tyr Glu Val Thr Lys Arg Pro Ser Gly Ile Pro Gln Arg Phe
    50                  55                  60

Ser Gly Ser Lys Ser Gly Asn Thr Ala Ser Leu Thr Ile Ser Gly Leu
65                  70                  75                  80

Gln Ala Asp Asp Glu Ala Asp Tyr Tyr Cys Cys Ser Tyr Ala Asn Tyr
                85                  90                  95

Asp Lys Leu Ile Leu Gly Gly Gly Thr Lys Leu Thr Val Leu
            100                 105                 110

<210> SEQ ID NO 143
<211> LENGTH: 14
<212> TYPE: PRT
<213> ORGANISM: Artificial Sequence
<220> FEATURE:
<223> OTHER INFORMATION: Synthetic peptide

<400> SEQUENCE: 143

Ser Gly Thr Arg Ser Asp Val Gly Gly Tyr Asp Phe Val Ser
1               5                   10

<210> SEQ ID NO 144
<211> LENGTH: 7
<212> TYPE: PRT
<213> ORGANISM: Artificial Sequence
<220> FEATURE:
<223> OTHER INFORMATION: Synthetic peptide

<400> SEQUENCE: 144

Glu Val Thr Lys Arg Pro Ser
1               5

<210> SEQ ID NO 145
<211> LENGTH: 10
<212> TYPE: PRT
<213> ORGANISM: Artificial Sequence
<220> FEATURE:
<223> OTHER INFORMATION: Synthetic peptide

<400> SEQUENCE: 145

Cys Ser Tyr Ala Asn Tyr Asp Lys Leu Ile
```

<210> SEQ ID NO 146
<211> LENGTH: 128
<212> TYPE: PRT
<213> ORGANISM: Artificial Sequence
<220> FEATURE:
<223> OTHER INFORMATION: Synthetic peptide

<400> SEQUENCE: 146

Gln Val Gln Leu Val Gln Ser Gly Ala Glu Met Lys Asp Pro Gly Ala
1               5                   10                  15

Ser Val Lys Val Ser Cys Arg Ala Ser Gly Tyr Lys Phe Thr Asp Tyr
            20                  25                  30

Tyr Met His Trp Val Arg Gln Ala Pro Gly Gln Gly Leu Glu Trp Val
        35                  40                  45

Gly Trp Val Asn Thr Asn Gly Gly Phe Thr Lys Tyr Gly Ala Lys Phe
    50                  55                  60

Gln Gly Arg Val Thr Val Thr Arg Asp Thr Ser Thr Asn Thr Val Phe
65                  70                  75                  80

Leu Glu Leu Ser Arg Leu Thr Phe Gly Asp Thr Ala Met Tyr Phe Cys
                85                  90                  95

Ala Arg Pro Met Arg Pro Val Ser His Gly Ile Asp Tyr Ser Gly Leu
            100                 105                 110

Phe Val Phe Gln Phe Trp Gly Arg Gly Thr Met Val Thr Val Ser Ser
        115                 120                 125

<210> SEQ ID NO 147
<211> LENGTH: 5
<212> TYPE: PRT
<213> ORGANISM: Artificial Sequence
<220> FEATURE:
<223> OTHER INFORMATION: Synthetic peptide

<400> SEQUENCE: 147

Asp Tyr Tyr Met His
1               5

<210> SEQ ID NO 148
<211> LENGTH: 17
<212> TYPE: PRT
<213> ORGANISM: Artificial Sequence
<220> FEATURE:
<223> OTHER INFORMATION: Synthetic peptide

<400> SEQUENCE: 148

Trp Val Asn Thr Asn Gly Gly Phe Thr Lys Tyr Gly Ala Lys Phe Gln
1               5                   10                  15

Gly

<210> SEQ ID NO 149
<211> LENGTH: 19
<212> TYPE: PRT
<213> ORGANISM: Artificial Sequence
<220> FEATURE:
<223> OTHER INFORMATION: Synthetic peptide

<400> SEQUENCE: 149

Pro Met Arg Pro Val Ser His Gly Ile Asp Tyr Ser Gly Leu Phe Val
1               5                   10                  15

Phe Gln Phe

<210> SEQ ID NO 150
<211> LENGTH: 112
<212> TYPE: PRT
<213> ORGANISM: Artificial Sequence
<220> FEATURE:
<223> OTHER INFORMATION: Synthetic peptide

<400> SEQUENCE: 150

Asp Ile Val Met Thr Gln Thr Pro Leu Ser Leu Ser Val Thr Pro Gly
1               5                   10                  15

Gln Pro Ala Ser Ile Ser Cys Lys Ser Ser Glu Ser Leu Arg Gln Ser
            20                  25                  30

Asn Gly Lys Thr Ser Leu Tyr Trp Tyr Arg Gln Lys Pro Gly Gln Ser
        35                  40                  45

Pro Gln Leu Leu Val Phe Glu Val Ser Asn Arg Phe Ser Gly Val Ser
    50                  55                  60

Asp Arg Phe Val Gly Ser Gly Ser Gly Thr Asp Phe Thr Leu Arg Ile
65                  70                  75                  80

Ser Arg Val Glu Ala Glu Asp Val Gly Phe Tyr Tyr Cys Met Gln Ser
                85                  90                  95

Lys Asp Phe Pro Leu Thr Phe Gly Gly Gly Thr Lys Val Asp Leu Lys
            100                 105                 110

<210> SEQ ID NO 151
<211> LENGTH: 16
<212> TYPE: PRT
<213> ORGANISM: Artificial Sequence
<220> FEATURE:
<223> OTHER INFORMATION: Synthetic peptide

<400> SEQUENCE: 151

Lys Ser Ser Glu Ser Leu Arg Gln Ser Asn Gly Lys Thr Ser Leu Tyr
1               5                   10                  15

<210> SEQ ID NO 152
<211> LENGTH: 7
<212> TYPE: PRT
<213> ORGANISM: Artificial Sequence
<220> FEATURE:
<223> OTHER INFORMATION: Synthetic peptide

<400> SEQUENCE: 152

Glu Val Ser Asn Arg Phe Ser
1               5

<210> SEQ ID NO 153
<211> LENGTH: 9
<212> TYPE: PRT
<213> ORGANISM: Artificial Sequence
<220> FEATURE:
<223> OTHER INFORMATION: Synthetic peptide

<400> SEQUENCE: 153

Met Gln Ser Lys Asp Phe Pro Leu Thr
1               5

<210> SEQ ID NO 154
<211> LENGTH: 135
<212> TYPE: PRT
<213> ORGANISM: Artificial Sequence
<220> FEATURE:
<223> OTHER INFORMATION: Synthetic peptide

<400> SEQUENCE: 154

```
Arg Val Gln Leu Val Glu Ser Gly Gly Gly Val Val Gln Pro Gly Lys
1               5                   10                  15

Ser Val Arg Leu Ser Cys Val Val Ser Asp Phe Pro Phe Ser Lys Tyr
            20                  25                  30

Pro Met Tyr Trp Val Arg Gln Ala Pro Gly Lys Gly Leu Glu Trp Val
        35                  40                  45

Ala Ala Ile Ser Gly Asp Ala Trp His Val Val Tyr Ser Asn Ser Val
    50                  55                  60

Gln Gly Arg Phe Leu Val Ser Arg Asp Asn Val Lys Asn Thr Leu Tyr
65                  70                  75                  80

Leu Glu Met Asn Ser Leu Lys Ile Glu Asp Thr Ala Val Tyr Arg Cys
                85                  90                  95

Ala Arg Met Phe Gln Glu Ser Gly Pro Pro Arg Leu Asp Arg Trp Ser
            100                 105                 110

Gly Arg Asn Tyr Tyr Tyr Tyr Ser Gly Met Asp Val Trp Gly Gln Gly
        115                 120                 125

Thr Thr Val Thr Val Ser Ser
        130                 135

<210> SEQ ID NO 155
<211> LENGTH: 5
<212> TYPE: PRT
<213> ORGANISM: Artificial Sequence
<220> FEATURE:
<223> OTHER INFORMATION: Synthetic peptide

<400> SEQUENCE: 155

Lys Tyr Pro Met Tyr
1               5

<210> SEQ ID NO 156
<211> LENGTH: 17
<212> TYPE: PRT
<213> ORGANISM: Artificial Sequence
<220> FEATURE:
<223> OTHER INFORMATION: Synthetic peptide

<400> SEQUENCE: 156

Ala Ile Ser Gly Asp Ala Trp His Val Val Tyr Ser Asn Ser Val Gln
1               5                   10                  15

Gly

<210> SEQ ID NO 157
<211> LENGTH: 26
<212> TYPE: PRT
<213> ORGANISM: Artificial Sequence
<220> FEATURE:
<223> OTHER INFORMATION: Synthetic peptide

<400> SEQUENCE: 157

Met Phe Gln Glu Ser Gly Pro Pro Arg Leu Asp Arg Trp Ser Gly Arg
1               5                   10                  15

Asn Tyr Tyr Tyr Tyr Ser Gly Met Asp Val
            20                  25

<210> SEQ ID NO 158
<211> LENGTH: 103
<212> TYPE: PRT
<213> ORGANISM: Artificial Sequence
<220> FEATURE:
<223> OTHER INFORMATION: Synthetic peptide
```

<400> SEQUENCE: 158

Glu Ile Val Leu Thr Gln Ser Pro Gly Ile Leu Ser Leu Ser Pro Gly
1               5                   10                  15

Glu Thr Ala Thr Leu Phe Cys Lys Ala Ser Gln Gly Gly Asn Ala Met
            20                  25                  30

Thr Trp Tyr Gln Lys Arg Arg Gly Gln Val Pro Arg Leu Leu Ile Tyr
        35                  40                  45

Asp Thr Ser Arg Arg Ala Ser Gly Val Pro Asp Arg Phe Val Gly Ser
    50                  55                  60

Gly Ser Gly Thr Asp Phe Phe Leu Thr Ile Asn Lys Leu Asp Arg Glu
65                  70                  75                  80

Asp Phe Ala Val Tyr Tyr Cys Gln Gln Phe Glu Phe Phe Gly Leu Gly
                85                  90                  95

Ser Glu Leu Glu Val His Arg
            100

<210> SEQ ID NO 159
<211> LENGTH: 10
<212> TYPE: PRT
<213> ORGANISM: Artificial Sequence
<220> FEATURE:
<223> OTHER INFORMATION: Synthetic peptide

<400> SEQUENCE: 159

Lys Ala Ser Gln Gly Gly Asn Ala Met Thr
1               5                   10

<210> SEQ ID NO 160
<211> LENGTH: 7
<212> TYPE: PRT
<213> ORGANISM: Artificial Sequence
<220> FEATURE:
<223> OTHER INFORMATION: Synthetic peptide

<400> SEQUENCE: 160

Asp Thr Ser Arg Arg Ala Ser
1               5

<210> SEQ ID NO 161
<211> LENGTH: 5
<212> TYPE: PRT
<213> ORGANISM: Artificial Sequence
<220> FEATURE:
<223> OTHER INFORMATION: Synthetic peptide

<400> SEQUENCE: 161

Gln Gln Phe Glu Phe
1               5

<210> SEQ ID NO 162
<211> LENGTH: 130
<212> TYPE: PRT
<213> ORGANISM: Artificial Sequence
<220> FEATURE:
<223> OTHER INFORMATION: Synthetic peptide

<400> SEQUENCE: 162

Gln Val Gln Leu Val Gln Ser Gly Ala Val Ile Lys Thr Pro Gly Ser
1               5                   10                  15

Ser Val Lys Ile Ser Cys Arg Ala Ser Gly Tyr Asn Phe Arg Asp Tyr
            20                  25                  30

```
Ser Ile His Trp Val Arg Leu Ile Pro Asp Lys Gly Phe Glu Trp Ile
        35                  40                  45

Gly Trp Ile Lys Pro Leu Trp Gly Ala Val Ser Tyr Ala Arg Gln Leu
 50                  55                  60

Gln Gly Arg Val Ser Met Thr Arg Gln Leu Ser Gln Asp Pro Asp Asp
 65                  70                  75                  80

Pro Asp Trp Gly Val Ala Tyr Met Glu Phe Ser Gly Leu Thr Pro Ala
                 85                  90                  95

Asp Thr Ala Glu Tyr Phe Cys Val Arg Arg Gly Ser Cys Asp Tyr Cys
            100                 105                 110

Gly Asp Phe Pro Trp Gln Tyr Trp Gly Gln Gly Thr Val Val Val Val
        115                 120                 125

Ser Ser
    130

<210> SEQ ID NO 163
<211> LENGTH: 5
<212> TYPE: PRT
<213> ORGANISM: Artificial Sequence
<220> FEATURE:
<223> OTHER INFORMATION: Synthetic peptide

<400> SEQUENCE: 163

Asp Tyr Ser Ile His
1               5

<210> SEQ ID NO 164
<211> LENGTH: 17
<212> TYPE: PRT
<213> ORGANISM: Artificial Sequence
<220> FEATURE:
<223> OTHER INFORMATION: Synthetic peptide

<400> SEQUENCE: 164

Trp Ile Lys Pro Leu Trp Gly Ala Val Ser Tyr Ala Arg Gln Leu Gln
1               5                   10                  15

Gly

<210> SEQ ID NO 165
<211> LENGTH: 16
<212> TYPE: PRT
<213> ORGANISM: Artificial Sequence
<220> FEATURE:
<223> OTHER INFORMATION: Synthetic peptide

<400> SEQUENCE: 165

Val Arg Arg Gly Ser Cys Asp Tyr Cys Gly Asp Phe Pro Trp Gln Tyr
1               5                   10                  15

<210> SEQ ID NO 166
<211> LENGTH: 102
<212> TYPE: PRT
<213> ORGANISM: Artificial Sequence
<220> FEATURE:
<223> OTHER INFORMATION: Synthetic peptide

<400> SEQUENCE: 166

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Gly Asn Ser Leu
            20                  25                  30

Asn Trp Tyr Gln Lys Arg Arg Gly Gln Thr Pro Arg Leu Leu Ile Tyr
```

```
            35                  40                  45
Asp Thr Ser Arg Arg Ala Ser Asp Ile Pro Glu Lys Phe Val Gly Ser
     50                  55                  60
Gly Ser Gly Thr Asp Phe Ser Leu Thr Ile Thr Lys Val Gly Pro Glu
 65                  70                  75                  80
Asp Phe Ala Val Tyr Tyr Cys Gln Gln Phe Glu Phe Phe Gly Leu Gly
                 85                  90                  95
Thr Thr Leu Glu Ile Asn
            100

<210> SEQ ID NO 167
<211> LENGTH: 10
<212> TYPE: PRT
<213> ORGANISM: Artificial Sequence
<220> FEATURE:
<223> OTHER INFORMATION: Synthetic peptide

<400> SEQUENCE: 167

Arg Ala Ser Gln Gly Gly Asn Ser Leu Asn
 1               5                  10

<210> SEQ ID NO 168
<211> LENGTH: 7
<212> TYPE: PRT
<213> ORGANISM: Artificial Sequence
<220> FEATURE:
<223> OTHER INFORMATION: Synthetic peptide

<400> SEQUENCE: 168

Asp Thr Ser Arg Arg Ala Ser
 1               5

<210> SEQ ID NO 169
<211> LENGTH: 5
<212> TYPE: PRT
<213> ORGANISM: Artificial Sequence
<220> FEATURE:
<223> OTHER INFORMATION: Synthetic peptide

<400> SEQUENCE: 169

Gln Gln Phe Glu Phe
 1               5

<210> SEQ ID NO 170
<211> LENGTH: 131
<212> TYPE: PRT
<213> ORGANISM: Artificial Sequence
<220> FEATURE:
<223> OTHER INFORMATION: Synthetic peptide

<400> SEQUENCE: 170

Glu Val Gln Leu Val Glu Ser Gly Pro Val Met Arg Lys Pro Gly Ser
 1               5                  10                  15
Ser Met Lys Ile Ser Cys Ala Thr Ser Gly Tyr Asn Phe Arg Asp Phe
             20                  25                  30
Ser Ile His Trp Val Arg Phe Asn Arg Arg Tyr Gly Phe Glu Trp Ile
         35                  40                  45
Gly Trp Ile Lys Pro Met Trp Gly Ala Val Asn Tyr Ala Arg Gln Leu
     50                  55                  60
Gln Gly Arg Val Ser Met Ser Arg Leu Phe Ser Gln Asp Leu Tyr Tyr
 65                  70                  75                  80
Pro Asp Arg Gly Thr Ala Tyr Leu Glu Phe Ser Gly Leu Thr Ser Ala
```

85                  90                  95
Asp Thr Ala Asp Tyr Phe Cys Val Arg Arg Gly Ser Ser Cys Pro His
            100                 105                 110
Cys Gly Asp Phe His Phe Glu His Trp Gly Gln Gly Thr Ala Val Val
            115                 120                 125
Val Ser Ala
    130

<210> SEQ ID NO 171
<211> LENGTH: 5
<212> TYPE: PRT
<213> ORGANISM: Artificial Sequence
<220> FEATURE:
<223> OTHER INFORMATION: Synthetic peptide

<400> SEQUENCE: 171

Asp Phe Ser Ile His
1               5

<210> SEQ ID NO 172
<211> LENGTH: 17
<212> TYPE: PRT
<213> ORGANISM: Artificial Sequence
<220> FEATURE:
<223> OTHER INFORMATION: Synthetic peptide

<400> SEQUENCE: 172

Trp Ile Lys Pro Met Trp Gly Ala Val Asn Tyr Ala Arg Gln Leu Gln
1               5                   10                  15
Gly

<210> SEQ ID NO 173
<211> LENGTH: 15
<212> TYPE: PRT
<213> ORGANISM: Artificial Sequence
<220> FEATURE:
<223> OTHER INFORMATION: Synthetic peptide

<400> SEQUENCE: 173

Arg Gly Ser Ser Cys Pro His Cys Gly Asp Phe His Phe Glu His
1               5                   10                  15

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

```
<210> SEQ ID NO 178
<211> LENGTH: 125
<212> TYPE: PRT
<213> ORGANISM: Artificial Sequence
<220> FEATURE:
<223> OTHER INFORMATION: Synthetic peptide

<400> SEQUENCE: 178
```

Gln Val Gln Leu Val Gln Ser Gly Ala Gln Val Lys Lys Pro Gly Ser
1               5                   10                  15

Ser Val Lys Val Ser Cys Lys Ala Ser Gly Tyr Glu Phe Ile Asn Cys
            20                  25                  30

Pro Ile Asn Trp Val Arg Gln Ala Pro Arg Gln Arg Pro Glu Trp Met
        35                  40                  45

Gly Trp Met Lys Pro Arg Gly Gly Ala Val Ser Tyr Ala Arg Gln Leu
    50                  55                  60

Gln Gly Arg Val Thr Met Thr Arg Asp Met Tyr Thr Ser Thr Ala Tyr
65                  70                  75                  80

Leu Glu Leu Arg Ser Leu Thr Ser Glu Asp Thr Ala Val Tyr Tyr Cys
                85                  90                  95

Ala Arg Gly Lys Tyr Cys Thr Ala Arg Asp Tyr Tyr Asn Trp Asp Phe
            100                 105                 110

Glu His Trp Gly Pro Gly Thr Pro Ile Thr Val Ser Ser
        115                 120                 125

```
<210> SEQ ID NO 179
<211> LENGTH: 5
<212> TYPE: PRT
<213> ORGANISM: Artificial Sequence
<220> FEATURE:
<223> OTHER INFORMATION: Synthetic peptide

<400> SEQUENCE: 179
```

Asn Cys Pro Ile Asn
1               5

```
<210> SEQ ID NO 180
<211> LENGTH: 17
<212> TYPE: PRT
<213> ORGANISM: Artificial Sequence
<220> FEATURE:
<223> OTHER INFORMATION: Synthetic peptide

<400> SEQUENCE: 180
```

Trp Met Lys Pro Arg Gly Gly Ala Val Ser Tyr Ala Arg Gln Leu Gln
1               5                   10                  15

Gly

```
<210> SEQ ID NO 181
<211> LENGTH: 16
<212> TYPE: PRT
<213> ORGANISM: Artificial Sequence
<220> FEATURE:
<223> OTHER INFORMATION: Synthetic peptide

<400> SEQUENCE: 181
```

Gly Lys Tyr Cys Thr Ala Arg Asp Tyr Tyr Asn Trp Asp Phe Glu His
1               5                   10                  15

```
<210> SEQ ID NO 182
<211> LENGTH: 99
```

```
<212> TYPE: PRT
<213> ORGANISM: Artificial Sequence
<220> FEATURE:
<223> OTHER INFORMATION: Synthetic peptide

<400> SEQUENCE: 182

Asp Ile Gln Met Thr Gln Ser Pro Ser Ser Leu Ser Ala Ser Val Gly
1               5                   10                  15

Asp Thr Val Thr Ile Thr Cys Gln Ala Asn Gly Tyr Leu Asn Trp Tyr
            20                  25                  30

Gln Gln Arg Arg Gly Lys Ala Pro Lys Leu Leu Ile Tyr Asp Gly Ser
        35                  40                  45

Lys Leu Glu Arg Gly Val Pro Ser Arg Phe Ser Gly Arg Trp Gly
50                  55                  60

Gln Glu Tyr Asn Leu Thr Ile Asn Asn Leu Gln Pro Glu Asp Ile Ala
65                  70                  75                  80

Thr Tyr Phe Cys Gln Val Tyr Glu Phe Val Val Pro Gly Thr Arg Leu
                85                  90                  95

Asp Leu Lys

<210> SEQ ID NO 183
<211> LENGTH: 7
<212> TYPE: PRT
<213> ORGANISM: Artificial Sequence
<220> FEATURE:
<223> OTHER INFORMATION: Synthetic peptide

<400> SEQUENCE: 183

Gln Ala Asn Gly Tyr Leu Asn
1               5

<210> SEQ ID NO 184
<211> LENGTH: 7
<212> TYPE: PRT
<213> ORGANISM: Artificial Sequence
<220> FEATURE:
<223> OTHER INFORMATION: Synthetic peptide

<400> SEQUENCE: 184

Asp Gly Ser Lys Leu Glu Arg
1               5

<210> SEQ ID NO 185
<211> LENGTH: 5
<212> TYPE: PRT
<213> ORGANISM: Artificial Sequence
<220> FEATURE:
<223> OTHER INFORMATION: Synthetic peptide

<400> SEQUENCE: 185

Gln Val Tyr Glu Phe
1               5

<210> SEQ ID NO 186
<211> LENGTH: 123
<212> TYPE: PRT
<213> ORGANISM: Artificial Sequence
<220> FEATURE:
<223> OTHER INFORMATION: Synthetic peptide

<400> SEQUENCE: 186

Gln Val Gln Leu Leu Gln Ser Gly Ala Ala Val Thr Lys Pro Gly Ala
1               5                   10                  15
```

```
Ser Val Arg Val Ser Cys Glu Ala Ser Gly Tyr Asn Ile Arg Asp Tyr
            20                  25                  30

Phe Ile His Trp Trp Arg Gln Ala Pro Gly Gln Gly Leu Gln Trp Val
        35                  40                  45

Gly Trp Ile Asn Pro Lys Thr Gly Gln Pro Asn Asn Pro Arg Gln Phe
50                      55                  60

Gln Gly Arg Val Ser Leu Thr Arg His Ala Ser Trp Asp Phe Asp Thr
65                  70                  75                  80

Phe Ser Phe Tyr Met Asp Leu Lys Ala Leu Arg Ser Asp Thr Ala
                85                  90                  95

Val Tyr Phe Cys Ala Arg Gln Arg Ser Asp Tyr Trp Asp Phe Asp Val
                100                 105                 110

Trp Gly Ser Gly Thr Gln Val Thr Val Ser Ser
            115                 120

<210> SEQ ID NO 187
<211> LENGTH: 5
<212> TYPE: PRT
<213> ORGANISM: Artificial Sequence
<220> FEATURE:
<223> OTHER INFORMATION: Synthetic peptide

<400> SEQUENCE: 187

Asp Tyr Phe Ile His
1               5

<210> SEQ ID NO 188
<211> LENGTH: 17
<212> TYPE: PRT
<213> ORGANISM: Artificial Sequence
<220> FEATURE:
<223> OTHER INFORMATION: Synthetic peptide

<400> SEQUENCE: 188

Trp Ile Asn Pro Lys Thr Gly Gln Pro Asn Asn Pro Arg Gln Phe Gln
1               5                   10                  15

Gly

<210> SEQ ID NO 189
<211> LENGTH: 10
<212> TYPE: PRT
<213> ORGANISM: Artificial Sequence
<220> FEATURE:
<223> OTHER INFORMATION: Synthetic peptide

<400> SEQUENCE: 189

Gln Arg Ser Asp Tyr Trp Asp Phe Asp Val
1               5                   10

<210> SEQ ID NO 190
<211> LENGTH: 103
<212> TYPE: PRT
<213> ORGANISM: Artificial Sequence
<220> FEATURE:
<223> OTHER INFORMATION: Synthetic peptide

<400> SEQUENCE: 190

Tyr Ile His Val Thr Gln Ser Pro Ser Ser Leu Ser Val Ser Ile Gly
1               5                   10                  15

Asp Arg Val Thr Ile Asn Cys Gln Thr Ser Gln Gly Val Gly Ser Asp
            20                  25                  30

Leu His Trp Tyr Gln His Lys Pro Gly Arg Ala Pro Lys Leu Leu Ile
```

```
                35                  40                  45
His His Thr Ser Ser Val Glu Asp Gly Val Pro Ser Arg Phe Ser Gly
    50                  55                  60

Ser Gly Phe His Thr Ser Phe Asn Leu Thr Ile Ser Asp Leu Gln Ala
65                  70                  75                  80

Asp Asp Ile Ala Thr Tyr Tyr Cys Gln Val Leu Gln Phe Phe Gly Arg
                85                  90                  95

Gly Ser Arg Leu His Ile Lys
            100

<210> SEQ ID NO 191
<211> LENGTH: 11
<212> TYPE: PRT
<213> ORGANISM: Artificial Sequence
<220> FEATURE:
<223> OTHER INFORMATION: Synthetic peptide

<400> SEQUENCE: 191

Gln Thr Ser Gln Gly Val Gly Ser Asp Leu His
1               5                   10

<210> SEQ ID NO 192
<211> LENGTH: 7
<212> TYPE: PRT
<213> ORGANISM: Artificial Sequence
<220> FEATURE:
<223> OTHER INFORMATION: Synthetic peptide

<400> SEQUENCE: 192

His Thr Ser Ser Val Glu Asp
1               5

<210> SEQ ID NO 193
<211> LENGTH: 5
<212> TYPE: PRT
<213> ORGANISM: Artificial Sequence
<220> FEATURE:
<223> OTHER INFORMATION: Synthetic peptide

<400> SEQUENCE: 193

Gln Val Leu Gln Phe
1               5

<210> SEQ ID NO 194
<211> LENGTH: 122
<212> TYPE: PRT
<213> ORGANISM: Artificial Sequence
<220> FEATURE:
<223> OTHER INFORMATION: Synthetic peptide

<400> SEQUENCE: 194

Arg Ala His Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
                20                  25                  30

Ile Leu Phe Trp Phe Arg Gln Ala Pro Gly Arg Gly Leu Glu Trp Val
            35                  40                  45

Gly Trp Ile Lys Pro Gln Tyr Gly Ala Val Asn Phe Gly Gly Gly Phe
        50                  55                  60

Arg Asp Arg Val Thr Leu Thr Arg Asp Val Tyr Arg Glu Ile Ala Tyr
65                  70                  75                  80

Met Asp Ile Arg Gly Leu Lys Pro Asp Asp Thr Ala Val Tyr Tyr Cys
```

```
                     85                  90                  95

Ala Arg Asp Arg Ser Tyr Gly Asp Ser Ser Trp Ala Leu Asp Ala Trp
            100                 105                 110

Gly Gln Gly Thr Thr Val Val Val Ser Ala
        115                 120

<210> SEQ ID NO 195
<211> LENGTH: 5
<212> TYPE: PRT
<213> ORGANISM: Artificial Sequence
<220> FEATURE:
<223> OTHER INFORMATION: Synthetic peptide

<400> SEQUENCE: 195

Ala His Ile Leu Phe
1               5

<210> SEQ ID NO 196
<211> LENGTH: 17
<212> TYPE: PRT
<213> ORGANISM: Artificial Sequence
<220> FEATURE:
<223> OTHER INFORMATION: Synthetic peptide

<400> SEQUENCE: 196

Trp Ile Lys Pro Gln Tyr Gly Ala Val Asn Phe Gly Gly Gly Phe Arg
1               5                   10                  15

Asp

<210> SEQ ID NO 197
<211> LENGTH: 13
<212> TYPE: PRT
<213> ORGANISM: Artificial Sequence
<220> FEATURE:
<223> OTHER INFORMATION: Synthetic peptide

<400> SEQUENCE: 197

Asp Arg Ser Tyr Gly Asp Ser Ser Trp Ala Leu Asp Ala
1               5                   10

<210> SEQ ID NO 198
<211> LENGTH: 108
<212> TYPE: PRT
<213> ORGANISM: Artificial Sequence
<220> FEATURE:
<223> OTHER INFORMATION: Synthetic peptide

<400> SEQUENCE: 198

Gln Ser Ala Leu Thr Gln Pro Ala Ser Val Ser Gly Ser Pro Gly Gln
1               5                   10                  15

Ser Ile Thr Ile Ser Cys Ala Gly Ser Ser Arg Asp Val Gly Gly Phe
            20                  25                  30

Asp Leu Val Ser Trp Tyr Gln Gln His Pro Gly Lys Ala Pro Lys Leu
        35                  40                  45

Ile Ile Tyr Glu Val Asn Lys Arg Pro Ser Gly Ile Ser Ser Arg Phe
    50                  55                  60

Ser Ala Ser Lys Ser Gly Asn Thr Ala Ser Leu Thr Ile Ser Gly Leu
65                  70                  75                  80

Gln Glu Glu Asp Glu Ala His Tyr Tyr Cys Tyr Ser Tyr Ala Asp Gly
                85                  90                  95

Val Ala Phe Gly Gly Gly Thr Lys Leu Thr Val Leu
            100                 105
```

<210> SEQ ID NO 199
<211> LENGTH: 14
<212> TYPE: PRT
<213> ORGANISM: Artificial Sequence
<220> FEATURE:
<223> OTHER INFORMATION: Synthetic peptide

<400> SEQUENCE: 199

Ala Gly Ser Ser Arg Asp Val Gly Gly Phe Asp Leu Val Ser
1               5                   10

<210> SEQ ID NO 200
<211> LENGTH: 7
<212> TYPE: PRT
<213> ORGANISM: Artificial Sequence
<220> FEATURE:
<223> OTHER INFORMATION: Synthetic peptide

<400> SEQUENCE: 200

Glu Val Asn Lys Arg Pro Ser
1               5

<210> SEQ ID NO 201
<211> LENGTH: 8
<212> TYPE: PRT
<213> ORGANISM: Artificial Sequence
<220> FEATURE:
<223> OTHER INFORMATION: Synthetic peptide

<400> SEQUENCE: 201

Tyr Ser Tyr Ala Asp Gly Val Ala
1               5

<210> SEQ ID NO 202
<211> LENGTH: 126
<212> TYPE: PRT
<213> ORGANISM: Artificial Sequence
<220> FEATURE:
<223> OTHER INFORMATION: Synthetic peptide

<400> SEQUENCE: 202

Glu Val Gln Leu Val Glu Ser Gly Ala Gln Val Lys Lys Pro Gly Ala
1               5                   10                  15

Ser Val Thr Val Ser Cys Thr Ala Ser Gly Tyr Lys Phe Thr Gly Tyr
                20                  25                  30

His Met His Trp Val Arg Gln Ala Pro Gly Arg Gly Leu Glu Trp Met
            35                  40                  45

Gly Trp Ile Asn Pro Phe Arg Gly Ala Val Lys Tyr Pro Gln Asn Phe
    50                  55                  60

Arg Gly Arg Val Ser Met Thr Arg Asp Thr Ser Met Glu Ile Phe Tyr
65                  70                  75                  80

Met Glu Leu Ser Arg Leu Thr Ser Asp Asp Thr Ala Val Tyr Tyr Cys
                85                  90                  95

Ala Arg Glu Met Phe Asp Ser Ser Ala Asp Trp Ser Pro Trp Arg Gly
            100                 105                 110

Met Val Ala Trp Gly Gln Gly Thr Leu Val Thr Val Ser Ser
        115                 120                 125

<210> SEQ ID NO 203
<211> LENGTH: 5
<212> TYPE: PRT
<213> ORGANISM: Artificial Sequence

```
<220> FEATURE:
<223> OTHER INFORMATION: Synthetic peptide

<400> SEQUENCE: 203

Gly Tyr His Met His
1               5

<210> SEQ ID NO 204
<211> LENGTH: 17
<212> TYPE: PRT
<213> ORGANISM: Artificial Sequence
<220> FEATURE:
<223> OTHER INFORMATION: Synthetic peptide

<400> SEQUENCE: 204

Trp Ile Asn Pro Phe Arg Gly Ala Val Lys Tyr Pro Gln Asn Phe Arg
1               5                   10                  15

Gly

<210> SEQ ID NO 205
<211> LENGTH: 17
<212> TYPE: PRT
<213> ORGANISM: Artificial Sequence
<220> FEATURE:
<223> OTHER INFORMATION: Synthetic peptide

<400> SEQUENCE: 205

Glu Met Phe Asp Ser Ser Ala Asp Trp Ser Pro Trp Arg Gly Met Val
1               5                   10                  15

Ala
```

MULTISPECIFIC ANTIBODIES TARGETING HUMAN IMMUNODEFICIENCY VIRUS AND METHODS OF USING THE SAME

RELATED APPLICATIONS

The present application is a U.S. National Phase application filed under 35 U.S.C. § 371 from and claiming priority to International Patent Application No. PCT/US2017/057053, filed Oct. 17, 2017, which claims priority to and the benefit of U.S. Provisional Application Ser. No. 62/409,097, filed on Oct. 17, 2016, the contents of which are incorporated herein by reference in their entireties.

FIELD OF THE DISCLOSURE

The present disclosure relates to multispecific antibodies targeting the human immunodeficiency virus-1 (HIV-1) envelope, methods for their production, pharmaceutical compositions containing said antibodies and uses thereof in treatment and prevention of HIV infection.

BACKGROUND

The human immunodeficiency viruses type 1 (HIV-1) infects and causes the destruction of human CD4+ lymphocytes, resulting in the development of acquired immunodeficiency syndrome (AIDS). The entry of HIV-1 into host cells is mediated by the viral envelope glycoproteins (Env), which are displayed as trimeric spokes on the surface of the HIV virion. The trimeric Env complex, consisting of three of each of exterior envelope glycoprotein, gp120, and the gp41 transmembrane envelope glycoprotein, are associated in the viral membrane. Besides mediating virus entry, HIV-1 Env complex is also the sole target of neutralizing antibody responses.

Recent advances in the discovery of broadly neutralizing antibodies (bNAbs) targeting the HIV-1 envelope glycoproteins (Env) have awakened great interest in their use as pre-exposure prophylaxis for prevention and as therapeutic agents, particularly in combination with antiretroviral treatment (ART) for HIV remission and eradication. bNAb isolation and characterization has been accelerated via the integration of emerging functional and structural information and new technologies of single B cell sorting and cloning. bNAbs are therapeutically beneficial as they possess high capacity for viral neutralization. Additionally, bNAbs can facilitate fragment crystallizable (Fc)-mediated effector functions that promote cell lysis and/or clearance of infected cells that express HIV-1 Env on the cell surface via antibody-dependent cell-mediated cytotoxicity and complement-dependent cytotoxicity.

The characterization of HIV-1 bNAbs and their cognate epitopes on the Env spikes has identified five conserved Env sites of vulnerability including the CD4-binding site (CD4bs), the V1/V2-glycan region, the V3-glycan region, the gp41 membrane proximal external region (MPER), and the gp120-gp41 interface. Passive immunization with bNAbs is being explored as a means for prevention in healthy individuals and as treatment for HIV infected patients. Passive immunization in humans has proven highly effective in treating many infections such as hepatitis A, hepatitis B, rabies, and respiratory syncytial viruses.

However, these viruses have relatively low genetic diversity compared to the extreme antigenic diversity observed for circulating HIV-1 isolates which leads to greatly confounded outcome. Administration of a single bNAb as a therapeutic agent has successfully cleared phase I safety clinical trials, demonstrating temporary HIV-1 viremia suppression in the majority of patients. However, the HIV virus rapidly develops resistance mutations under a single bNAb pressure, which suggests that passive treatment with a single bNAb is unlikely to result in long-term viremia suppression. Some of the Env mutations associated with bNAb resistance can significantly reduce viral fitness. Therefore, simultaneously targeting different Env epitopes may completely compromise viral replication, as mutations that confer resistance to each bNAb often accumulate to severely reduce viral fitness. Additionally, treatment of simian/human immunodeficiency virus infection in non-human primate models demonstrated that passive immunotherapy with bNAb cocktails prevent mother to child transmission, suppress viremia and, in contrast to combinatorial antiviral therapy (cART) treatments, as well as facilitate CD8+ T-cell immunity for durable suppression of virus replication. Compared to both cART and single bNAb treatments, preliminary data on bNAb cocktails suggest significant advantages for the treatment and management of HIV-1 infection.

While antibody cocktails demonstrated improved efficacy in preclinical studies, multispecific "single agents" are desirable for manufacturing purposes as well as for improved avidity that may result in enhanced neutralization breadth and potency. Bi-NAbs with two Env-epitope binding sites have been generated using CrossMab formats with up to 97% virus coverage. However, their neutralization breadth could be further improved and truly bivalent binding has yet to be experimentally demonstrated. Most recently, one study showed that swapping the IgG1 hinge for a more flexibly IgG3 hinge lacking disulfide bonds (denoted IgG3C-) greatly improved the potency of anti-HIV CrossMabs. While both the CrossMab and IgG3C-designs have significantly improved the potency and breadth of antibodies against HIV, they only target two epitopes, one corresponding to each antigen-binding Fragment (Fab) arm. This limits the potential increase of avidity that would result from simultaneous engagement of multiple functional moieties. Furthermore, the traditional CrossMab format imposes steric constraints that may impede true bivalent engagement of the Fab arms due to the rigidity of the dimeric IgG Fc fragment where the Fabs are placed.

One study has demonstrated the use of DNA-linkers as "molecular rulers" to connect Fab moieties of two bNAbs resulting in molecules capable of intra-spike crosslinking to enhance the avidity and potency of bNAbs. However, the chemical conjugation process required for connecting Fabs with DNA-linker in this method limits its feasibility and application scale.

SUMMARY OF THE DISCLOSURE

In one aspect, the disclosure features a multispecific antibody, or an antigen-binding fragment thereof, comprising a) a first light chain comprising a first light chain variable region (VL) and a first heavy chain comprising a first heavy chain variable region (VH), wherein the first light chain and the first heavy chain are derived from a first antibody or an antigen-binding fragment thereof; and b) a second light chain comprising a second light chain variable region (VL) and a second heavy chain comprising a second heavy chain variable region (VH), wherein the second light chain and the second heavy chain are derived from a second antibody or an antigen-binding fragment thereof, wherein the first antibody and the second antibody bind non-overlapping epitopes of the envelope protein of human immunodeficiency virus-1 (HIV-1), and wherein the VH from the first light chain and the VL from the second light chain are connected by one or more linkers or wherein the VL from the first light chain and the VH from the second light chain are connected by one or more linkers. In one embodiment, the VH from the first light chain and the VL from the second light chain are connected by a two or more tetra-glycine serine (G4S) protein linkers or wherein the VL from the first light chain and the VH from the second light chain are connected by two or more tetra-glycine serine (G4S) protein linkers. In one embodiment, the linker is not a single glycine (Gly) residue; a diglycine peptide (Gly-Gly); a tripeptide (Gly-Gly-Gly); a peptide with four glycine residues (Gly-Gly-Gly-Gly); a peptide with five glycine residues (Gly-Gly-Gly-Gly-Gly); a peptide with six glycine residues (Gly-Gly-Gly-Gly-Gly-Gly); a peptide with seven glycine residues (Gly-Gly-Gly-Gly-Gly-Gly-Gly); a peptide with eight glycine residues (Gly-Gly-Gly-Gly-Gly-Gly-Gly-Gly), the peptide Gly-Gly-Gly-Gly-Ser, the peptide Gly-Gly-Gly-Gly-Ser-Gly-Gly-Gly-Gly-Ser, the peptide Gly-Gly-Gly-Gly-Ser-Gly-Gly-Gly-Gly-Ser-Gly-Gly-Gly-Gly-Ser (SEQ ID NO: 292), a single Ser, a single Va, the dipeptide Arg-Thr, Gln-Pro, Ser-Ser, Thr-Lys, and Ser-Leu; Thr-Lys-Gly-Pro-Ser, Thr-Val-Ala-Ala-Pro, Gln-Pro-Lys-Ala-Ala, Gln-Arg-Ile-Glu-Gly, Ala-Ser-Thr-Lys-Gly-Pro-Ser, Arg-Thr-Val-Ala-Ala-Pro-Ser, Gly-Gln-Pro-Lys-Ala-Ala-Pro, and His-Ile-Asp-Ser-Pro-Asn-Lys. In one embodiment, the non-overlapping epitopes are located in the CD4-binding site, the V1/V2-glycan region, the V3-glycan region, the gp41 membrane proximal external region (MPER), or the gp120/gp41 interface of the envelope protein. In one embodiment, the VH from the first light chain and the VL from the second light chain are connected by three tetra-glycine serine (G4S) protein linkers or wherein the VL from the first light chain and the VH from the second light chain are connected by three tetra-glycine serine (G4S) protein linkers. In one embodiment, the VH from the first light chain and the VL from the second light chain are connected by five tetra-glycine serine (G4S) protein linkers or wherein the VL from the first light chain and the VH from the second light chain are connected by five tetra-glycine serine (G4S) protein linkers. In one embodiment, the VH from the first light chain and the VL from the second light chain are connected by seven tetra-glycine serine (G4S) protein linkers or wherein the VL from the first light chain and the VH from the second light chain are connected by seven tetra-glycine serine (G4S) protein linkers. In one embodiment, the multispecific antibody of any of the above aspects or embodiments further comprises a third antibody which specifically binds to a third epitope. In one embodiment, the multispecific antibody of any of the above aspects or embodiments further comprises a fourth antibody which specifically binds to a third epitope. In one embodiment, the third epitope is located in the CD4-binding site (CD4bs), the V1/V2-glycan region, the V3-glycan region, the gp41 membrane proximal external region (MPER), or the gp120-gp41 interface of the envelope protein of HIV. In one embodiment, the third epitope is different from the first epitope and the second epitope. In one embodiment, the first antibody binds to an epitope in the CD4-binding site of the of the envelope protein of HIV-1 and the second antibody binds to an epitope in the V3-glycan region of the of the envelope protein of HIV-1. In one embodiment, the first antibody binds to an epitope in the V3-glycan region of the of the envelope protein of HIV-1 and the second antibody binds to an epitope in the CD4-binding site of the of the envelope protein of HIV-1. In one embodiment, the antibody that binds to an epitope in the CD4-binding site of the of the envelope protein of HIV-1 is selected from the group consisting of: VRC03, VRC06, VRC07, 3BNC117, IOMA, and N6. In one embodiment, the antibody that binds to an epitope in the V3-glycan region of the of the envelope protein of HIV-1 is selected from the group consisting of: PGT121, PGT122, PGT128, PGT135, 10-1074, and BG18. In one embodiment, the first antibody binds to an epitope in the gp120/gp41 interface of the of the envelope protein of HIV-1 and the second antibody binds to an epitope in the MPER of the of the envelope protein of HIV-1. In one embodiment, the first antibody binds to an epitope in the MPER of the of the envelope protein of HIV-1 and the second antibody binds to an epitope in the gp120/gp41 interface of the of the envelope protein of HIV-1. In one embodiment, the antibody that binds to an epitope in the gp120/gp41 interface of the of the envelope protein of HIV-1 is selected from the group consisting of: 35022, N123-VRC34.01, 3BC315, and PGT151. In one embodiment, the antibody that binds to an epitope in the MPER of the of the envelope protein of HIV-1 is selected from the group consisting of: 10E8, 10E8v4, 10E8v4 S100cF, Dh511.2_k3, Z13, 4E10, and 2F5. In one embodiment, the variable domain of the first light chain comprises a light chain variable domain comprising a CDR set (CDR1, CDR2, and CDR3) as set forth in SEQ ID NOs 3, 4, 5 and the variable domain of the first heavy chain comprises a heavy chain variable domain comprising a CDR set (CDR1, CDR2, and CDR3) as set forth in SEQ ID NOs 7, 8, 9. In one embodiment, the variable domain of the second light chain comprises a light chain variable domain comprising a CDR set (CDR1, CDR2, and CDR3) as set forth in SEQ ID NOs 11, 12, 13 and the variable domain of the second heavy chain comprises a heavy chain variable domain comprising a CDR set (CDR1, CDR2, and CDR3) as set forth in SEQ ID NOs 15, 16, 17. In one embodiment, the variable domain of the first light chain comprises a light chain variable domain comprising a CDR set (CDR1, CDR2, and CDR3) as set forth in SEQ ID NOs 32, 33, 34 and the variable domain of the first heavy chain comprises a heavy chain variable domain comprising a CDR set (CDR1, CDR2, and CDR3) as set forth in SEQ ID NOs 36, 37, 38. In one embodiment, the variable domain of the second light chain comprises a light chain variable domain comprising a CDR set (CDR1, CDR2, and CDR3) as set forth in SEQ ID NOs 40, 41, 42 and the variable domain of the second heavy chain comprises a heavy chain variable domain comprising a CDR set (CDR1, CDR2, and CDR3) as set forth in SEQ ID NOs 44, 45, 46. In one embodiment, the variable domain of the first light chain comprises an amino acid sequence that is 95% identical to an amino acid sequence selected from the group consisting of: SEQ ID NO. 2, SEQ ID NO. 10, SEQ ID NO. 19, SEQ ID NO. 31 and SEQ ID NO. 39 and the variable domain of the first heavy chain comprises an amino acid sequence that is 95% identical to an amino acid sequence selected from the group consisting of: SEQ ID NO. 6, SEQ ID NO. 14, SEQ ID NO. 35 and SEQ ID NO. 43. In one embodiment, the variable domain of the second light chain comprises an amino acid sequence that is 95% identical to an amino acid sequence selected from the group consisting of: SEQ ID NO. 2, SEQ ID NO. 10, SEQ ID NO. 19, SEQ ID NO. 31 and SEQ ID NO. 39 and the variable domain of the second heavy chain comprises an amino acid sequence that is 95% identical to an amino acid sequence selected from the group consisting of: SEQ ID NO. 6, SEQ ID NO. 14, SEQ ID NO. 35 and SEQ ID NO. 43. In one embodiment, the variable domain of the first light chain comprises an amino acid sequence that is 95% identical to SEQ ID NO. 2, and the variable domain of the first heavy chain comprises an amino acid sequence that is 95% identical to SEQ ID NO. 6, and the variable domain of the second light chain comprises an amino acid sequence that is 95% identical to SEQ ID NO. 10, and the variable domain of the second heavy chain comprises an amino acid sequence that is 95% identical to SEQ ID NO. 14. In one embodiment, the variable domain of the first light chain comprises an amino acid sequence that is 95% identical to SEQ ID NO. 19, and the variable domain of the first heavy chain comprises an amino acid sequence that is 95% identical to SEQ ID NO. 6, and the variable domain of the second light chain comprises an amino acid sequence that is 95% identical to SEQ ID NO. 10, and the variable domain of the second heavy chain comprises an amino acid sequence that is 95% identical to SEQ ID NO. 14. In one embodiment, the variable domain of the first light chain comprises an amino acid sequence that is 95% identical to SEQ ID NO. 10, and the variable domain of the first heavy chain comprises an amino acid sequence that is 95% identical to SEQ ID NO. 14, and the variable domain of the second light chain comprises an amino acid sequence that is 95% identical to SEQ ID NO. 2, and the variable domain of the second heavy chain comprises an amino acid sequence that is 95% identical to SEQ ID NO. 6. In one embodiment, the variable domain of the first light chain comprises an amino acid sequence that is 95% identical to SEQ ID NO. 10, and the variable domain of the first heavy chain comprises an amino acid sequence that is 95% identical to SEQ ID NO. 14, and the variable domain of the second light chain comprises an amino acid sequence that is 95% identical to SEQ ID NO. 19, and the variable domain of the second heavy chain comprises an amino acid sequence that is 95% identical to SEQ ID NO. 6. In one embodiment, the variable domain of the first light chain comprises an amino acid sequence that is 95% identical to SEQ ID NO. 31, and the variable domain of the first heavy chain comprises an amino acid sequence that is 95% identical to SEQ ID NO. 35, and the variable domain of the second light chain comprises an amino acid sequence that is 95% identical to SEQ ID NO. 39, and the variable domain of the second heavy chain comprises an amino acid sequence that is 95% identical to SEQ ID NO. 43. In one embodiment, the variable domain of the first light chain comprises an amino acid sequence that is 95% identical to SEQ ID NO. 39, and the variable domain of the first heavy chain comprises an amino acid sequence that is 95% identical to SEQ ID NO. 43, and the variable domain of the second light chain comprises an amino acid sequence that is 95% identical to SEQ ID NO. 31, and the variable domain of the second heavy chain comprises an amino acid sequence that is 95% identical to SEQ ID NO. 35. In one embodiment, the multispecific antibody comprises an amino acid sequence that is 95% identical to an amino acid sequence selected from the group consisting of: SEQ ID NO. 1, SEQ ID NO. 18, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 30, SEQ ID NO. 47, SEQ ID NO. 48, SEQ ID NO. 49, SEQ ID NO. 50, SEQ ID NO. 51, SEQ ID NO. 52 and SEQ ID NO. 53.

In another aspect, the disclosure features a multispecific antibody comprising a) a first light chain comprising a first light chain variable region (VL) and a first heavy chain comprising a first heavy chain variable region (VH), wherein the first light chain and the first heavy chain are derived from a first antibody or an antigen-binding fragment thereof; b) a second light chain comprising a second light chain variable region (VL) and a second heavy chain comprising a second heavy chain variable region (VH), wherein the second light chain and the second heavy chain are derived from a second antibody or an antigen-binding fragment thereof; and c) a third light chain comprising a first light chain variable region (VL) and a third heavy chain comprising a first heavy chain variable region (VH), wherein the third light chain and the third heavy chain are derived from a third antibody or an antigen-binding fragment thereof, wherein the first antibody, the second antibody and the third antibody bind non-overlapping epitopes of the envelope protein of human immunodeficiency virus-1 (HIV-1), and wherein the VH from the first light chain and the VL from the second light chain are connected by two or more tetra-glycine serine (G4S) protein linkers or wherein the VL from the first light chain and the VH from the second light chain are connected by two or more tetra-glycine serine (G4S) protein linkers. In one embodiment, the multispecific antibody further includes a modification in the Fc region. In one embodiment the first antibody, the second antibody or the third antibody is an ScFv. In one embodiment, the multispecific antibody has an $IC_{50}$ less than 0.1 µg/ml. In one embodiment, the multispecific antibody has an $IC_{50}$ less than 0.01 µg/ml. In one embodiment, the multispecific antibody has an $IC_{80}$ less than 0.3 µg/ml. In one embodiment, the multispecific antibody has an $IC_{80}$ less than 0.1 µg/ml.

In another aspect, the disclosure features a method of treating or preventing an HIV infection, comprising administering to a subject in need thereof an effective amount of the multispecific antibody of any of the above aspects and embodiments.

In another aspect, the disclosure features a pharmaceutical composition comprising the multispecific antibody of any one of the above aspects and embodiments and a pharmaceutically acceptable carrier.

In another aspect, the disclosure features a nucleic acid encoding the multispecific antibody of any of the above aspects and embodiments. In one embodiment, the disclosure features a vector that comprises the nucleic acid. In another embodiment, the disclosure features a host cell that comprises the vector.

In another aspect, the disclosure features a method for the preparation of a multispecific antibody, comprising the step of culturing the host cell under conditions that allow synthesis of said multispecific antibody. In one embodiment, the method further comprises the step of recovering the multispecific antibody from the host cell culture.

In another aspect, the disclosure features an immunoconjugate comprising the multispecific antibody of any of the above aspects or embodiments, coupled to a cytotoxic agent.

In another aspect, the disclosure features a multispecific antibody, or an antigen-binding fragment thereof or salt thereof, comprising a) a first light chain comprising a first light chain variable region (VL) and/or a first heavy chain comprising a first heavy chain variable region (VH), wherein the first light chain and the first heavy chain; b) a second light chain comprising a second light chain variable region (VL) and/or a second heavy chain comprising a second heavy chain variable region (VH), wherein the first light chain and/or first heavy chain binds an epitope on CD4s of HIV-1 and the second light and/or heavy chain binds an epitope of a V1, V2, and/or V3 glycan of HIV-1; wherein the VH from the first light chain and the VH or VL from the second light chain are connected by three or more linkers or wherein the VL from the first light chain and the VH or VL from the second light chain are connected by three or more linkers. In one embodiment, the VH from the first light chain and the VL from the second light chain are connected by a two or more tetra-glycine serine (G4S) protein linkers or wherein the VL from the first light chain and the VH from the second light chain are connected by two or more tetra-glycine serine (G4S) protein linkers. In another embodiment, the linker is not a single glycine (Gly) residue; a diglycine peptide (Gly-Gly); a tripeptide (Gly-Gly-Gly); a peptide with four glycine residues (Gly-Gly-Gly-Gly); a peptide with five glycine residues (Gly-Gly-Gly-Gly-Gly); a peptide with six glycine residues (Gly-Gly-Gly-Gly-Gly-Gly); a peptide with seven glycine residues (Gly-Gly-Gly-Gly-Gly-Gly-Gly); a peptide with eight glycine residues (Gly-Gly-Gly-Gly-Gly-Gly-Gly-Gly), the peptide Gly-Gly-Gly-Gly-Ser, the peptide Gly-Gly-Gly-Gly-Ser-Gly-Gly-Gly-Gly-Ser, the peptide Gly-Gly-Gly-Gly-Ser-Gly-Gly-Gly-Gly-Ser-Gly-Gly-Gly-Gly-Ser (SEQ ID NO: 292), a single Ser, a single Va, the dipeptide Arg-Thr, Gln-Pro, Ser-Ser, Thr-Lys, and Ser-Leu; Thr-Lys-Gly-Pro-Ser, Thr-Val-Ala-Ala-Pro, Gln-Pro-Lys-Ala-Ala, Gln-Arg-Ile-Glu-Gly, Ala-Ser-Thr-Lys-Gly-Pro-Ser, Arg-Thr-Val-Ala-Ala-Pro-Ser, Gly-Gln-Pro-Lys-Ala-Ala-Pro, and His-Ile-Asp-Ser-Pro-Asn-Lys. In another embodiment, the non-overlapping epitopes are located in the CD4-binding site, the V1/V2-glycan region, the V3-glycan region, the gp41 membrane proximal external region (MPER), or the gp120/gp41 interface of the envelope protein. In another embodiment, the multispecific antibody, salt or antigen binding fragment further comprises a IgG-1 like domain covalently linked to the first and/or second light chain. In another further embodiment, the multispecific antibody, salt or antigen binding fragment the VH from the first light chain and the VL from the second light chain are connected by five tetra-glycine serine (G4S) protein linkers or wherein the VL from the first light chain and the VH from the second light chain are connected by five tetra-glycine serine (G4S) protein linkers. In another embodiment, the VH from the first light chain and the VL from the second light chain are connected by seven tetra-glycine serine (G4S) protein linkers or wherein the VL from the first light chain and the VH from the second light chain are connected by seven tetra-glycine serine (G4S) protein linkers. In another embodiment, the multispecific antibody, salt or antigen binding fragment further comprises a third antibody light chain that binds to a third epitope. In one embodiment, the third epitope is located in the CD4-binding site (CD4bs), the V1/V2-glycan region, the V3-glycan region, the gp41 membrane proximal external region (MPER), or the gp120-gp41 interface of the envelope protein of HIV. In another embodiment, the third epitope is different from the first epitope and the second epitope.

In another aspect, the disclosure features a multispecific antibody, or an antigen-binding fragment thereof or salt thereof, comprising a variable domain and a constant domain; the variable domain comprising a) a first light chain comprising a first light chain variable region (VL) and/or a first heavy chain comprising a first heavy chain variable region (VH) b) a second light chain comprising a second light chain variable region (VL) and/or a second heavy chain comprising a second heavy chain variable region (VH); the constant domain comprising an IgG-like amino acid sequence; wherein the first light chain and the second light chain bind non-overlapping epitopes of the envelope protein of human immunodeficiency virus-1 (HIV-1); and wherein the first light chain and the second light chain are connected by from about 3 to about 5 or linkers. In one embodiment, the first and second light chains bind an epitope that is located in the CD4-binding site (CD4bs), the V1/V2-glycan region, the V3-glycan region, the gp41 membrane proximal external region (MPER), or the gp120-gp41 interface of the envelope protein of HIV.

BRIEF DESCRIPTION OF THE DRAWINGS

FIG. 3A (right) shows strategies of engineering VRC01-PGT bi-ScFv by joining the termini of VHs and VLs by 3-5 GGGGS (G4S) linkers in dash lines (magenta) based on the atomic distance of VRC01 and PGT121 functional domains (39 and 54 Å) estimated by the modeling.

FIG. 5C is a table that shows a summary of the virus neutralization parameters of the bispecific antibody molecules. FIG. 5D-FIG. 5E is a table that shows virus neutralization potency displayed with $IC_{50}$ (µg/ml) values.

FIG. 6B is a table that shows a summary of the virus neutralization parameters of the bispecific antibody molecules. FIG. 6C is a table that shows the potency and breadth curve tested with 200 virus panel.

FIG. 7A-FIG. 7G is a table that shows neutralization potency and breadth ($IC_{50}$ value, in µg/ml) of $_d$VRC01-PGT bi-ScFv and IgG assessed against a 200-isolate virus panel.

FIG. 9C is a table that shows possible synergistic effect of 35022-10E8 bispecific IgG on virus neutralization potency. $IC_{50}$ (μg/ml) of bispecific IgG, 10E8 and 35022 against selected virus isolates from the tested virus panel were displayed. Note that the neutralization potency (1/IC 50) of the bispecific IgG is substantially higher than the parental.

FIG. 10A shows the structure of HIV-1 JR-FL SOSIP.664 Env trimer (PDB: 5FYK) showing the footprints of bNAbs VRC01 and PGT121 and their proximity in both intra-protomer (left) and inter-protomer (right) binding configurations. PGT122 serves as a surrogate for PGT121. FIG. 10B shows distances between VRC01 and PGT121 VH/VL termini and two Bi-ScFv molecules of different topology. FIG. 10C shows a schematic presentation of the Bi-ScFv and Bi-NAb antibody constructs. FIG. 10D shows a schematic diagram of the molecular configurations of the Bi-ScFv and Bi-NAb antibodies.

FIG. 11A shows reduced SDS-PAGE analysis of bispecific antibodies. FIG. 11B shows analytical size exclusion profiles of bispecific antibodies.

FIG. 12A is a schematic diagram of the bispecific binding assay via biolayer interferometry (BLI). FIG. 12B shows BLI response curves of bispecific binding assay. OCTET biosensors were loaded with biotinylated RSC3 (ligand 1) presenting the CD4bs epitope, and then probed sequentially with the bispecific antibody and BG505.SOSIP.664_D368R trimer (ligand 2) presenting the V3 glycan epitope. As controls, parental IgGs were used in place of the bispecific antibody. FIG. 12C, depicts representative images of negative stain EM of Bi-ScFv dVRC01-5X-PGT121, in complex with BG505 SOSIP.664 Env at a molar ratio of 0.5:1 and 6:1. BG505 SOSIP trimer and Bi-ScFv dVRC01-5X-PGT121 is denoted with arrow, respectively.

FIG. 13A shows bi-ScFv, dVRC01-5X-PGT121, in complex with BG505.SOSIP.664 at a ratio of 0.5:1. Left, Raw micrograph; Right, 2D classes of complex. FIG. 13B left, Raw micrograph; FIG. 13B right, 2D classes of complex.

FIGS. 14A-1, FIGS. 14A-2 and B shows the neutralization profile of bispecific antibodies tested with a 20-virus panel. FIG. 14A-1, FIG. 14A-2 is a summary of $IC_{50}$ (μg/ml) for bispecific antibodies tested in 20 virus panel.

FIG. 15A shows neutralization breadth of the parental and bispecific antibodies was tested against an HIV-1 pseudovirus panel consisting of Envs of 20 viral strains. Heat maps of IC50 titers were generated in Excel. In the heatmaps, each row represents a virus strain while columns represent antibodies. Warmer colors indicate more potent neutralization and blue indicates at 50 μg/ml, antibody virus neutralization is below detection threshold (see legend). Breadths based on $IC_{50}$s are also summarized. Potency is shown as $IC_{50}$ geometric mean values calculated against sensitive viruses. FIG. 15B shows neutralization breadth of the parental and bispecific antibodies was tested against a panel of 208 viral strains. Heat maps of $IC_{50}$, breadth and potency are shown as in (A). FIG. 15C shows potency-breadth curves comparing the bispecific antibodies to their parental IgGs (left panel) and summary of $IC_{50}$ titers (μg/ml) against VRC01- and dual-resistant viruses that are sensitive to the bispecific antibodies (right panel). († indicates that the IC50 was adjusted by a factor of 3 to account for the molarity difference between the lower molecular weight Bi-ScFv and the IgG or Bi-NAb).

FIG. 16A shows tri-NAb constructs scheme.

FIGS. 17A through 17E depict neutralization breadth and potency of trispecific antibodies. FIG. 17A shows neutralization breadth of the parental, bispecific and trispecific antibodies was tested against a panel of 208 viral strains. Heat maps of IC50, breadth and potency are shown as in FIG. 3A. FIG. 17B shows scatter plots of IC50 titers in which each virus is represented by an individual dot. Statistical differences in neutralization were evaluated using non-parametric t test (Wilcoxon matched-pairs signed rank test) with *p<0.05, p<0.01, *p<0.001, ****p<0.0001. FIG. 17C shows potency-breadth curves comparing the Tri-NAb to the Bi-NAb as well as the parental IgGs (left panel) and summary of IC50 (μm/ml) against viruses that are resistant to Bi-NAb but sensitive to the Tri-NAb (right panel). FIG. 17D shows comparison of Tri-NAb potency to parental IgGs potencies. Each dot on the graph represents a virus plotted in decreasing order of sensitivity to the parental IgG (black). The potency of the Tri-NAb (green) and the second parental IgG (gray) against the same virus is overlaid with data points below the parental IgG indicating increased potency. FIG. 17E shows neutralization potency of Bi-NAb (upper panel) and Tri-NAb (lower panel) compared to the parental antibodies. Viruses were grouped by parental antibody sensitivity, with S indicating sensitive and R, resistant. IC50 titer fold change reflecting potency compared to the respective antibodies is indicated in the parentheses next to the multispecific antibody potency. Fold changes in red indicating improved potency. († indicates that the IC50 was adjusted by a factor of 3 to account for the molarity difference between the lower molecular weight Bi-ScFv and the IgG, Bi-NAb or Tri-NAb).

FIG. 18A-FIG. 18H is a summary of IC50 (μg/ml) for trispecific and bispecific antibodies tested in a 208 virus panel.

FIG. 19A-FIG. 19H is a summary of IC80 (μg/ml) for trispecific and bispecific antibodies tested in a 208 virus panel.

DETAILED DESCRIPTION

Figure 1:
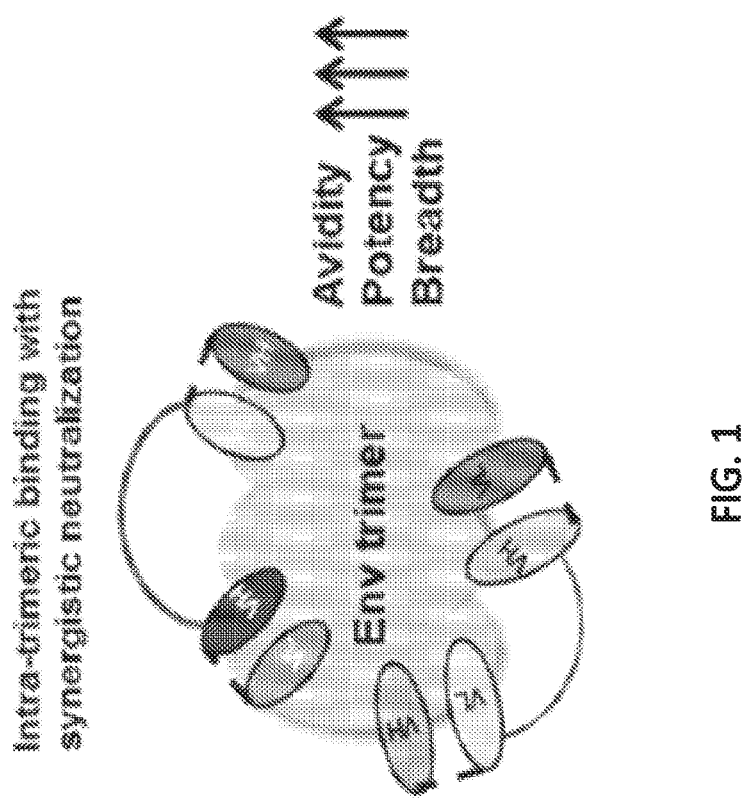
FIG. 1 is a schematic that shows the construction of a single agent to target multiple independent epitopes by structure-based rational design with superior avidity, potency and breadth, resulting from the crosslinking of protomers of each functional Env trimer due to the additive and potential synergistic effect of individual protomer engagement.

The present disclosure is based, at least in part, on the concept of joining single-chain variable fragment (ScFv) domains of two bNAbs, specific for the Env receptor binding site and a conserved Env glycan patch, respectively, to form bispecific ScFvs (Bi-ScFvs). The optimal Bi-ScFv cross-links adjacent protomers within one HIV-1 Env spike and demonstrates superior neutralization breadth over its parental bNAbs. Furthermore, the present disclosure shows that the combination of this Bi-ScFv with a third bNAb recognizing the Env membrane proximal external region (MPER) resulted in a trispecific bNAb, which displays near-pan neutralization breadth potently. Thus, multispecific antibodies combining functional moieties of Env bNAbs could achieve exceptional neutralization capacity with profoundly augmented avidity. The multispecific antibodies described herein can be used in studies aimed at preventing HIV disease progression or mother to child transmission, and curing HIV. Furthermore, the approach described herein, that combines multi-functional moieties of individual bNAbs with profoundly elevated avidity and cooperative effect of multivalence interactions, may be applied to generate superior antibody-based anti-viral therapeutics against other infectious agents.

Definitions

Unless otherwise defined herein, scientific and technical terms used in connection with the present disclosure shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to" or "including, without limitation."

The term "or" is used herein to mean, and is used interchangeably with, the term "and/or," unless context clearly indicates otherwise. For example, an amino acid sequence with a modified amino acid is understood to include the options of an amino acid with a modified sidechain, a an amino acid with a modified backbone, and an amino acid with a modified sidechain and a modified backbone.

The term "about" is used herein to mean within the typical ranges of tolerances in the art. For example, "about" can be understood as about 2 standard deviations from the mean. According to certain embodiments, about means ±10%, ±9%, ±8%, ±7%, ±6%, ±5%, ±4%, ±3%, ±2%, ±1%, ±0.9%, ±0.8%, ±0.7%, ±0.6%, ±0.5%, 0.4%, 0.3%, ±0.2%, +0.1% or +0.05%. According to certain embodiments, about means +5%. When "about" is present before a series of numbers or a range, it is understood that "about" can modify each of the numbers in the series or range.

The term "at least" prior to a number or series of numbers (e.g. "at least two") is understood to include the number adjacent to the term "at least", and all subsequent numbers or integers that could logically be included, as clear from context. When at least is present before a series of numbers or a range, it is understood that "at least" can modify each of the numbers in the series or range.

As used herein, "up to" as in "up to 10" is understood as up to and including 10, i.e., 0, 1, 2, 3, 4, 5, 6, 7, 8, 9, or 10.

Ranges provided herein are understood to include all individual integer values and all subranges within the ranges.

The term "broad neutralizing antibody" refers to an antibody which inhibits HIV-1 infection, as defined by at least about 50% inhibition of infection in vitro, in more than 50%, 60%, 70%, 80%, 90%, 95%), 99% or greater, of a large panel of (greater than 100) HIV-1 envelope pseudotyped viruses and/or viral isolates. In some embodiments, the borad neutralizing antibody is an anitbod that inhibits HIV-1 infection as defined by at least about 70%, 80%, 90%, 91%, 92%, 93%, 94%, 95%, 96%, 97%, 98%, 99% or 100% inhibition of infection in vitro in more than about 50%, 60%, 70%, 80%, 90%, 95%), 99% or greater, of a large panel of (greater than 100) HIV-1 envelope pseudotyped viruses and/or viral isolates. In some embodiments, the disclosure relates to a composition or pharmaceutical composition comprising one ore a plurality of broad neutralizing antibodies.

As used herein, the term "in combination with," is not intended to imply that the therapy or the therapeutic agents must be administered at the same time and/or formulated for delivery together, although these methods of delivery are within the scope described herein. The therapeutic agents can be administered concurrently with, prior to, or subsequent to, one or more other additional therapies or therapeutic agents.

The term "antibody", as used herein, broadly refers to any immunoglobulin (Ig) molecule comprised of four polypeptide chains, two heavy (H) chains and two light (L) chains, or any functional fragment, mutant, variant, or derivative thereof, which retains the essential epitope binding features of an Ig molecule. Such mutant, variant, or derivative antibody formats are known in the art. Non-limiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

As used herein, "conservative" amino acid substitutions may be defined as set out in Tables A, B, or C below. Antibodies, antibody-like molecules and derivative, mutants, variants and salts thereof include those amino acid sequence wherein conservative substitutions have been introduced by solid state chemistry and/or recombinant modification of nucleic acids that encode amino acid sequences disclosed herein. In some embodiments, the compositions and pharmaceutical compositions of the disclosure comprise, 1, 2, 3, 4, 5 or more conservative amino acid substitutions. Amino acids can be classified according to physical properties and contribution to secondary and tertiary protein structure. A conservative substitution is recognized in the art as a substitution of one amino acid for another amino acid that has similar properties. Exemplary conservative substitutions are set out in Table A.

TABLE A

Conservative Substitutions I

| Side Chain Characteristics | Amino Acid |
|---|---|
| Aliphatic | |
| Non-polar | G A P I L V F |
| Polar - uncharged | C S T M N Q |
| Polar - charged | D E K R |
| Aromatic | H F W Y |
| Other | N Q D E |

Alternately, conservative amino acids can be grouped as described in Lehninger, (Biochemistry, Second Edition; Worth Publishers, Inc. NY, N.Y. (1975), pp. 71-77) as set forth in Table B.

TABLE B

Conservative Substitutions II

| Side Chain Characteristic | Amino Acid |
|---|---|
| Non-polar (hydrophobic) | |
| Aliphatic: | A L I V P |
| Aromatic: | F W Y |
| Sulfur-containing: | M |
| Borderline: | G Y |
| Uncharged-polar | |
| Hydroxyl: | S T Y |
| Amides: | N Q |
| Sulfhydryl: | C |
| Borderline: | G Y |
| Positively Charged (Basic): | K R H |
| Negatively Charged (Acidic): | D E |

Alternately, exemplary conservative substitutions are set out in Table C.

TABLE C

Conservative Substitutions III

| Original Residue | Exemplary Substitution |
|---|---|
| Ala (A) | Val Leu Ile Met |
| Arg (R) | Lys His |
| Asn (N) | Gln |
| Asp (D) | Glu |
| Cys (C) | Ser Thr |
| Gln (Q) | Asn |
| Glu (E) | Asp |
| Gly (G) | Ala Val Leu Pro |
| His (H) | Lys Arg |
| Ile (I) | Leu Val Met Ala Phe |
| Leu (L) | Ile Val Met Ala Phe |
| Lys (K) | Arg His |
| Met (M) | Leu Ile Val Ala |
| Phe (F) | Trp Tyr Ile |
| Pro (P) | Gly Ala Val Leu Ile |
| Ser (S) | Thr |
| Thr (T) | Ser |
| Trp (W) | Tyr Phe Ile |

TABLE C-continued

Conservative Substitutions III

| Original Residue | Exemplary Substitution |
|---|---|
| Tyr (Y) | Trp Phe Thr Ser |
| Val (V) | Ile Leu Met Ala |

It should be understood that the polypeptides comprising polypeptide sequences associated with the extracellular matrix described herein are intended to include polypeptides bearing one or more insertions, deletions, or substitutions, or any combination thereof, of amino acid residues as well as modifications other than insertions, deletions, or substitutions of amino acid residues.

As used herein, the term "CDR" refers to the complementarity determining region within antibody variable sequences. In some embodiments, there are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia et al., J. Mol. Biol. 196:901-917 (1987) and Chothia et al., Nature 342: 877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "fragment" is defined as a physically contiguous portion of the primary structure of a biomolecule. In the case of polypeptides, a fragment may be defined by a contiguous portion of the amino acid sequence of a protein and may be at least 3-5 amino acids, at least 6-10 amino acids, at least 11-15 amino acids, at least 16-24 amino acids, at least 25-30 amino acids, at least 30-45 amino acids and up to the full length of the protein minus a few amino acids. In the case of polynucleotides, a fragment is defined by a contiguous portion of the nucleic acid sequence of a polynucleotide and may be at least 9-15 nucleotides, at least 15-30 nucleotides, at least 31-45 nucleotides, at least 46-74 nucleotides, at least 75-90 nucleotides, and at least 90-130 nucleotides. In some embodiments, fragments of biomolecules are immunogenic fragments.

In some embodiments, the term "functional fragment" means any portion of a polypeptide or amino acid sequence that is of a sufficient length to retain at least partial biological function that is similar to or substantially similar to the wild-type polypeptide or amino acid sequence upon which the fragment is based. If the fragment is a functional fragment of an antibody or antibody-like molecule, the fragment can be immunogenic and therefore possess a binding avidity for one or a plurality of antigens. In some embodiments, a functional fragment of a polypeptide associated with the extracellular matrix is a polypeptide that comprises 80, 85, 90, 95, 96, 97, 98, or 99% sequence identity of any polypeptide disclosed in Table 1 and has sufficient length to retain at least partial binding affinity to one or a plurality of ligands that bind to the amino acid sequence in Table 1. In some embodiments, the fragment is a fragment of any amino acid sequence disclosed in Table 1 and has a length of at least about 10, about 20, about 30, about 40, about 50, about 60, about 70, about 80, about 90, or about 100 contiguous amino acids. In some embodiments, the fragment is a fragment of any amino acid sequence disclosed in Table I and has a length of at least about 50 amino acids. In some embodiments, the fragment is a fragment of any amino acid sequence disclosed in Table I and has a length of at least about 100 amino acids. In some embodiments, the fragment is a fragment of any amino acid sequence disclosed in Table I and has a length of at least about 150 amino acids. In some embodiments, the fragment is a fragment of any amino acid sequence disclosed in Table I and has a length of at least about 200 amino acids. In some embodiments, the fragment is a fragment of any amino acid sequence disclosed in Table I and has a length of at least about 250 amino acids. In some embodiments, the fragment is a fragment of any amino acid sequence disclosed in Table I and has a length of at least about 300 amino acids. In some embodiments, the fragment is a fragment of any amino acid sequence disclosed in Table I and has a length of at least about 350 amino acids. In some embodiments, the fragment is a fragment of any amino acid sequence disclosed in Table I and has a length of at least about 400 amino acids. In some embodiments, the fragment is a fragment of any amino acid sequence disclosed in Table I and has a length of at least about 450 amino acids. In some embodiments, the fragment is a fragment of any amino acid sequence disclosed in Table I and has a length of at least about 500 amino acids. In some embodiments, the fragment is a fragment of any amino acid sequence disclosed in Table I and has a length of at least about 550 amino acids. In some embodiments, the fragment is a fragment of any amino acid sequence disclosed in Table I and has a length of at least about 600 amino acids. In some embodiments, the fragment is a fragment of any amino acid sequence disclosed in Table I and has a length of at least about 650 amino acids. In some embodiments, the fragment is a fragment of any amino acid sequence disclosed in Table I and has a length of at least about 700 amino acids. In some embodiments, the fragment is a fragment of any polypeptide disclosed in Table I and has a length of at least about 750 amino acids. In some embodiments, the fragment is a fragment of any amino acid sequence disclosed in Table I and has a length of at least about 800 amino acids. In some embodiments, the fragment is a fragment of any amino acid sequence disclosed in Table I and has a length of at least about 850 amino acids. In some embodiments, the fragment is a fragment of any amino acid sequence disclosed in Table I and has a length of at least about 900 amino acids. In some embodiments, the fragment is a fragment of any amino acid sequence disclosed in Table I and has a length of at least about 950 amino acids. In some embodiments, the fragment is a fragment of any amino acid sequence disclosed in Table I and has a length of at least about 1000 amino acids. In some embodiments, the fragment is a fragment of any amino acid sequence disclosed in Table I and has a length of at least about 1050 amino acids. In some embodiments, the fragment is a fragment of any amino acid sequence disclosed in Table I and has a length of no more than the aforementioned alternative number of amino acids in this paragraph.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

The "variable domain" (variable domain of a light chain (VL), variable domain of a heavy chain (VH)) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a beta-sheet conformation and the CDRs may form loops connecting the beta-sheet structure. The CDRs in each chain are held in their three-dimensional structure by the framework regions and form together with the CDRs from the other chain an antigen binding site. References to "VH" refer to the variable domain of an immunoglobulin heavy chain, including that of an antibody fragment, such as Fv, scFv, dsFv or Fab. References to "VL" refer to the variable domain of an immunoglobulin light chain, including that of an Fv, scFv, dsFv or Fab.

The term "antigen binding portion" or "antigen binding fragment" of an antibody (or simply "antibody portion" or "antibody fragment"), as used herein, refers to one or more fragments of an antibody that retain the ability to specifically bind to an antigen (e.g., hCD40). It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen-binding portion" or "antigen binding fragment" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" or "antigen binding fragment" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). Such antibody binding portions are known in the art (Kontermann and Dubel eds., *Antibody Engineering* (2001) Springer-Verlag. New York. 790 pp. (ISBN 3-540-41354-5).

Full length antibodies comprise immunoglobulin constant regions of one or more immunoglobulin classes. Immunoglobulin classes include IgG, IgM, IgA, IgD, and IgE isotypes and, in the case of IgG and IgA, their subtypes. In a preferred embodiment, an full length antibody of the disclosure has a constant domain structure of an IgG type antibody.

The terms "Kabat numbering", "Kabat definitions and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen-binding portion thereof (Kabat et al. (1971) *Ann. NY Acad. Sci.* 190:382-391 and, Kabat, E. A., et al. (1991) *Sequences of Proteins of Immunological Interest, Fifth Edition*, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

The term "multispecific antibody" refers to an antibody or antibody-like molecule, or fragment thereof, capable of binding two or more related or unrelated targets, or antigens. Antibody specificity refers to selective recognition of the antibody for a particular epitope, or amino acid sequence, of an antigen. Natural antibodies, for example, are monospecific. Bispecific antibodies are antibodies which have two different antigen-binding specificities. Trispecific antibodies accordingly are antibodies of the disclosure which have three different antigen-binding specificities. Tetraspecific antibodies according to the disclosure are antibodies which have four different antigen-binding specificities.

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

The term "antigen" refers to a polypeptide that can stimulate the production of antibodies or a T cell response in an animal, including polypeptides that are injected or absorbed into an animal. An antigen reacts with the products of specific humoral or cellular immunity.

The term "HIV Envelope protein (Env)" refers to the glycoprotein that is found on the surface of HIV. The HIV envelope protein is initially synthesized as a longer precursor protein of 845-870 amino acids in size, designated gp160. gp160 forms a homotrimer and undergoes glycosylation within the Golgi apparatus. In vivo, it is then cleaved by a cellular protease into gp120 and gp41. gp120 contains most of the external, surface-exposed, domains of the HIV envelope glycoprotein complex, and it is gp120 which binds both to cellular CD4 receptors and to cellular chemokine receptors (such as CCR5). gp41 contains a transmembrane domain and remains in a trimeric configuration within the membrane of the virus or the membrane of a host cell; it interacts with gp120 in a noncovalent manner.

The term "CD4" includes polypeptide molecules that are derived from CD4 include fragments of CD4, generated either by chemical (for example enzymatic) digestion or genetic engineering means. Such a fragment may be one or more entire CD4 protein domains. The extracellular domain of CD4 consists of four contiguous immunoglobulin-like regions (D1, D2, D3, and D4, see Sakihama et al., Proc. Natl. Acad. Sci. 92:6444, 1995; U.S. Pat. No. 6,117,655), and amino acids 1 to 183 have been shown to be involved in gp120 binding. For instance, a binding molecule or binding domain derived from CD4 would include a sufficient portion of the CD4 protein to mediate specific and functional interaction between the binding fragment and a native or viral binding site of CD4. One such binding fragment includes both the D1 and D2 extracellular domains of CD4 (D1D2 is also a fragment of soluble CD4 or sCD4 which is comprised of D1 D2 D3 and D4), although smaller fragments may also provide specific and functional CD4-like binding. The gp120-binding site has been mapped to D1 of CD4. CD4 polypeptides also include "CD4-derived molecules" which encompasses analogs (non-protein organic molecules), derivatives (chemically functionalized protein molecules obtained starting with the disclosed protein sequences) or mimetics (three-dimensionally similar chemicals) of the native CD4 structure, as well as proteins sequence variants or genetic alleles that maintain the ability to functionally bind to a target molecule.

The term "CD4 binding site (CD4BS) antibodies" refers to antibodies that bind to the CD4 binding surface of a gp120 polypeptide. The antibodies interfere with or prevent CD4 from binding to a gp120 polypeptide.

The term "gp120" refers to an envelope protein from Human Immunodeficiency Virus (HIV). This envelope protein is initially synthesized as a longer precursor protein of 845-870 amino acids in size, designated gp160. gp160 is cleaved by a cellular protease into gp120 and gp41. gp120 contains most of the external, surface-exposed, domains of the HIV envelope glycoprotein complex, and it is gp120 which binds both to cellular CD4 receptors and to cellular chemokine receptors (such as CCR5). The mature gp120 wildtype polypeptides have about 500 amino acids in the primary sequence. gp120 is heavily N-glycosylated giving rise to an apparent molecular weight of 120 kD. The polypeptide is comprised of five conserved regions (C1-05) and five regions of high variability (V1-V5). Exemplary sequence of wt gp120 polypeptides are shown on GEN-BANK, for example accession numbers AAB05604 and AAD12142 (as available on Oct. 16, 2009), incorporated by reference herein. It is understood that there are numerous variation in the sequence of gp120 from what is given in GENBANK, for example accession numbers AAB05604 and AAD12142, and that these variants are skill recognized in the art as gp120. The gp120 core has a molecular structure, which includes two domains: an "inner" domain (which faces gp41) and an "outer" domain (which is mostly exposed on the surface of the oligomeric envelope glycoprotein complex). The two gp120 domains are separated by a "bridging sheet" that is not part of either domain. The gp120 core includes 25 beta strands, 5 alpha helices, and 10 defined loop segments.

The term "V3 loops" refers to a loop of about 35 amino acids critical for the binding of the co-receptor and determination of which of the co-receptors will bind. In certain examples the V3 loop includes residues 296-331.

The term "membrane-proximal external region or MPER" refers to a highly conserved region of the gp41 envelope protein. The MPER comprises the last 24 C-terminal amino acids of the gp41 ectodomain, LLELDKWASLWNWF(N/D)ITNWLWYIK (aa 660 to 683) (Zwick et al. J Virol. 2005 January; 79(2):1252-61).

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

"Polynucleotide" or "nucleic acid" as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. A sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, .alpha.-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO, or CH2 ("formacetal"), in which each R or R' is independently H or substituted or unsubstituted alkyl (1-20C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "host cell" as used herein is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic and eukaryotic cells selected from any of the Kingdoms of life. Preferred eukaryotic cells include protist, fungal, plant and animal cells. Most preferably host cells include but are not limited to the prokaryotic cell line *E. coli*; mammalian cell lines CHO, HEK 293 and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

The term "inhibit" and its various grammatical forms is used to refer to a restraining, blocking, or limiting of the range or extent of a certain biological event or effect.

The term "effective amount," is used herein to include the amount of an agent (e.g. a multispecific antibody) that, when administered to a patient for treating a subject infection, is sufficient to effect treatment of the disease (e.g., by diminishing, ameliorating or maintaining the existing disease or one or more symptoms of disease or its related comorbidities). The "effective amount" may vary depending on the agent, how it is administered, the disease and its severity and the history, age, weight, family history, genetic makeup, stage of pathological processes, the types of preceding or concomitant treatments, if any, and other individual characteristics of the patient to be treated. An effective amount includes an amount that results in a clinically relevant change or stabilization, as appropriate, of an indicator of a disease or condition. "Effective amount" refers to an amount of a compound, material, or composition, as described herein effective to achieve a particular biological result such as, but not limited to, biological results disclosed, described, or exemplified herein. Such results may include, but are not limited to, the effective reduction of symptoms associated with any of the disease states mentioned herein, as determined by any means suitable in the art. The effective amount of the composition may be dependent on any number of variables, including without limitation, the species, breed, size, height, weight, age, overall health of the subject, the type of formulation, the mode or manner or administration, the type and/or severity of the particular condition being treated, or the need to modulate the activity of the molecular pathway induced by association of the analog to its receptor. The appropriate effective amount can be routinely determined by those of skill in the art using routine optimization techniques and the skilled and informed judgment of the practitioner and other factors evident to those skilled in the art. An effective dose of the antibodies or mutants or variants described herein may provide partial or complete biological activity as compared to the biological activity induced by the wild-type or naturally occurring polypeptides upon which the antibodies or mutants or variants are derived. A therapeutically effective dose of the antibodies or mutants or variants described herein may provide a sustained biochemical or biological affect and/or an increased resistance to degradation when placed in solution as compared with the normal affect observed when the naturally occurring and fully processed tranlated protein is administered to the same subject.

An "immunoconjugate" is an antibody or multispecific antibody conjugated to one or more heterologous molecule (s), including but not limited to a cytotoxic agent.

The term "cytotoxic agent" as used herein refers to a substance that inhibits or prevents a cellular function and/or causes cell death or destruction. Cytotoxic agents include, but are not limited to, radioactive isotopes; growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof.

The term "administer" as used herein means to give or to apply. The term "administering" as used herein includes in vivo administration.

The term "linker" refers to a chemical moiety that connects one peptide to another, e.g., one antibody to another. Linkers can also be used to attach antibodies to labels or solid substrates. A linker can include amino acids. Linkers can be straight or branched, saturated or unsaturated carbon chains. They can also include one or more heteroatoms within the chain.

The term "pharmaceutical composition" refers to a preparation which is in such form as to permit the biological activity of an active ingredient contained therein to be effective, and which contains no additional components which are unacceptably toxic to a subject to which the composition would be administered. A pharmaceutical composition of the present disclosure can be administered by a variety of methods known in the art. As will be appreciated by the skilled artisan, the route and/or mode of administration will vary depending upon the desired results. To administer an antibody according to the disclosure by certain routes of administration, it may be necessary to coat the antibody with, or co-administer the antibody with, a material to prevent its inactivation. For example, the antibody may be administered to a subject in an appropriate carrier, for example, liposomes, or a diluent. Pharmaceutically acceptable diluents include saline and aqueous buffer solutions.

A "pharmaceutically acceptable carrier" refers to an ingredient in a pharmaceutical formulation, other than an active ingredient, which is nontoxic to a subject. Pharmaceutically acceptable carriers includes any and all solvents, dispersion media, coatings, antibacterial and antifungal agents, isotonic and absorption delaying agents, and the like that are physiologically compatible. In one preferred embodiment, the carrier is suitable for intravenous, intramuscular, subcutaneous, parenteral, spinal or epidermal administration (e.g. by injection or infusion).

The pharmaceutical compositions according to the disclosure may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The term "subject" is used throughout the specification to describe an animal to which one or more compositions comprising the antibody or antibodies disclosed herein. In some embodiment, the animal is a human. For diagnosis of those conditions which are specific for a specific subject, such as a human being, the term "patient" may be interchangeably used. In some instances in the description of the present disclosure, the term "patient" will refer to human patients suffering from a particular disease or disorder. In some embodiments, the subject may be a human suspected of having or being identified as at risk to develop HIV infection. In some embodiments, the subject is suspected of having or has been diagnosed with HIV or HIV-1 infection or AIDS. In some embodiments, the subject may be a human suspected of having or being identified as at risk to develop AIDS or an AIDS-associated disorder. In some embodiments, the subject may be a mammal. In some embodiments, the subject may be a non-human animal. The term "mammal" encompasses both humans and non-humans and includes but is not limited to humans, non-human primates, canines, felines, murines, bovines, equines, and porcines. is used herein to refer to an animal, such as a mammal, including a primate (such as a human, a non-human primate, e.g., a monkey, and a chimpanzee), a non-primate (such as a cow, a pig, a camel, a llama, a horse, a goat, a rabbit, a sheep, a hamster, a guinea pig, a cat, a dog, a rat, a mouse, a horse, and a whale), or a bird (e.g., a duck or a goose). In an embodiment, the subject is a human, such as a human being treated or assessed for an HIV infection; or a human having an HIV infection that would benefit from a multi-specific antibody as described herein. In some embodiments, the subject is a subject in need thereof, meaning that the subject is need of the treatment being administered.

The term "salt" refers to acidic salts formed with inorganic and/or organic acids, as well as basic salts formed with inorganic and/or organic bases. Examples of these acids and bases are well known to those of ordinary skill in the art. Such acid addition salts will normally be pharmaceutically acceptable although salts of non-pharmaceutically acceptable acids may be of utility in the preparation and purification of the compound in question. Salts include those formed from hydrochloric, hydrobromic, sulphuric, phosphoric, citric, tartaric, lactic, pyruvic, acetic, succinic, fumaric, maleic, methanesulphonic and benzenesulphonic acids. In some embodiments, salts of the compositions comprising either an antibody or antibody-like molecule may be formed by reacting the free base, or a salt, enantiomer or racemate thereof, with one or more equivalents of the appropriate acid. In some embodiments, pharmaceutical acceptable salts of the present disclosure refer to derivatives or amino acid sequences comprising at least one basic group or at least one basic radical. In some embodiments, pharmaceutical acceptable salts of the disclosed compositions comprise a free amino group, a free guanidino group, a pyrazinyl radical, or a pyridyl radical that forms acid addition salts. In some embodiments, the pharmaceutical acceptable salts of the present disclosure refer to modified amino acids that are acid addition salts of the subject compounds with (for example) inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxybenzoic acid, 2-acetoxybenzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxy-ethane-sulfonic acid, or aromatic sulfonic acids, for example benzene-, p-toluene- or naphthalene-2-sulfonic acid. When several basic groups are present mono- or poly-acid addition salts may be formed. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuo or by freeze drying. The reaction may also be a metathetical process or it may be carried out on an ion exchange resin. In some embodiments, the salts may be those that are physiologically tolerated by a patient. Salts according to the present disclosure may be found in their anhydrous form or as in hydrated crystalline form (i.e., complexed or crystallized with one or more molecules of water). In some embodiments, the compositions or pharmaceutical compositions comprise crystalline forms or lyophilized forms of the antibodies, antibody-like molecules or salts thereof.

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. The term "treat" or "treating" as used herein further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously symptomatic for the disorder(s).

The term "potency" as used herein refers to the neutralization capacity, i.e. the $IC_{50}$ or $IC_{80}$ of the antibody, or fragment thereof.

Humanization and primatization refer to in cases where the tri-specific fusion antibody or the three antibodies forming the tri-specific fusion antibody are non-human antibodies, the antibody can be "humanized" to reduce immunogenicity to a human recipient. Methods for humanizing non-human antibodies have been described in the art. See, e.g., Jones et al., Nature 321:522-525 (1986); Riechmann et al, Nature 332:323-327 (1988); Verhoeyen et al., Science 239: 1534-1536 (1988), and U.S. Pat. No. 4,816,567. Generally, residues from the variable domain of a non-human antibody are "imported" into a human immunoglobulin molecule, resulting in antibodies in which some hypervariable region residues and possibly some FR residues of a human antibody are substituted by residues from analogous sites of non-human antibodies. It is important to humanize a non-human antibody while retaining high affinity for the antigen. To this end, three dimensional immunoglobulin models are commonly available and suitable for use in analyzing proposed humanized sequences in comparison to the parental non-human antibodies. Such analysis permits identification of residues likely involved in recognition and binding of the antigen, and therefore rational design of humanized sequences that retain the specificity and affinity for the antigen.

In specific embodiments, tri-specific fusion antibodies are formed from anti-HIV human or humanized antibodies.

Similarly, a tri-specific fusion antibody or the three antibodies forming the fusion can be "primatized" to reduce immunogenicity to another primate, non-human recipient, e.g., a rhesus recipient. Residues from the variable domain of a donor antibody (such as a non-primate antibody or an antibody of a primate species different from the recipient primate) are "imported" into a nonhuman primate recipient immunoglobulin molecule, resulting in antibodies in which some hypervariable region residues and possibly some FR residues of a nonhuman primate antibody are substituted by residues from analogous sites of donor antibodies. Alternatively, primatized antibodies can be made for use in a desirable primate species by using a recipient immunoglobulin having non-primate sequences or sequences from a different primate species by introducing the Fc fragment, and/or residues, including particularly framework region residues, from the desirable primate, into the recipient immunoglobulin.

By "affinity maturation" is meant when one or more hypervariable region residues of an antibody can be substituted to select for variants that have improved biological properties relative to the parent antibody by employing, e.g., affinity maturation using phage or yeast display. For example, the Fab region of an anti-HIV antibody can be mutated at several sites selected based on available structural information to generate all possible amino substitutions at each site. The antibody variants thus generated are displayed in a monovalent fashion from phage particles or on the surface of yeast cells. The displayed variants are then screened for their biological activity (e.g. binding affinity).

The term "$IC_{50}$" as used herein refers to the concentration of an inhibitor, such as a multispecific antibody, where the response or biological activity is reduced by half.

The term "$IC_{80}$" as used herein refers to the concentration of an inhibitor (e.g. a multispecific antibody) where the response or biological activity is reduced by eighty percent.

Compositions Comprising Anti-HIV-1 Broadly Neutralizing Antibodies (bNAbs)

In some embodiments, the present disclosure involves multimeric anti-HIV-1 broad neutralizing antibodies (or "bNAbs"). In some embodiments, bNAbs target conserved sites of vulnerability on the HIV-1 envelope (env). In some embodiments, the disclosure relates to pharmaceutical compositions or compositions comprising one or a plurality of bNAbs disclosed herein. In some embodiments, if a composition comprises two or more bNAbs, the mixture may be hetergeneous, meaning that there are two different species of bNAbs in the same composition. In some embodiments, if a composition comprises two or more bNAbs, the mixture may be homogeneous, meaning that there is a single species of bNAb in the same composition. All embodiments of combinations of bNAbs are contemplated by this disclosure. In some embodiments, the pharmaceutical compositions disclosed herein comprises a combination of two, three, four, five, or six or more different species of antibodies disclosed herein.

The disclosure relates to the identification of a sequence orientation of antibody fragments that are capable of neutralizing HIV ENV protein on the surface of a cell, in vitro or in vivo, or in culture. In some embodiments, The disclosure relates to the identification of a sequence orientation of antibody fragments that are sufficient to neutralize or bind up to or at least about 50%, 60%, 70%, 80%, 85%, 86%, 87%, 88%, 89%, 90%, 91%, 92%, 93%, 94%, 95%, 96%, 97%, 98%, 99% or up to 100% of viral isolates in culture or in a subject. In some embodiments, the antibody or antibody-like molecule comprises an orientation set forth in FIG. 20. In some embodiments, the antibody or antibody-like molecule comprises an orientation in which, beginning on the amino terminius of an arm of the antibody or antibody-like molecule and following to the carboxy terminus of the molecule, 1, 2, or 3 CDR sequences from the variable light and/or heavy chain of VCOR1 or VCOR7 are fused to 1, 2, or 3 CDR sequences from the variable light and/or heavy chain of PT121 by a linker comprising 3, 4, 5 or more amino acid sequences (GGGGS) or a linker equivalent in angstrom length of 3, 4, or 5 or more amino acid sequences (GGGGS). In some embodiments, the antibody comprises amino acid sequences that are at least 88%, 89%, 90%, 91%, 92%, 93%, 94%, 95%, 96%, 97%, 98%, 99% homologous to 1, 2, and/or 3 CDR sequences from the variable light and/or heavy chain of VCOR1 and/or PT12. In some embodiments, the antibody comprises amino acid sequences that are at least 88%, 89%, 90%, 91%, 92%, 93%, 94%, 95%, 96%, 97%, 98%, 99% homologous to 1, 2, or 3 CDR sequences from the variable light and/or heavy chain of PT121. In some embodiments, the antibody comprises amino acid sequences that are at least 88%, 89%, 90%, 91%, 92%, 93%, 94%, 95%, 96%, 97%, 98%, 99% homologous to 1, 2, or 3 CDR sequences from the variable light and/or heavy chain of VCOR1. In some embodiments, the antibody comprises an antibody fragment of $Fv_{sc}$ of VCOR1 fused to an antibody fragment of $Fv_{sc}$ of PT121 by a linker GGGGS that is repeated 3, 4, or 5 times. In some embodiments, the antibody comprises a linker comprising GGGGS repeated no less than 4 times, 5 times, or 6 times between each set of variable light chains specific a for a different epitope. In some embodiments, the antibody comprises a linker comprising GGGGS repeated no less than 4 times, 5 times, or 6 times between each set of variable heavy chains specific for a different epitope. In some embodiments, the antibody comprises a linker comprising GGGGS repeated no less than 4 times, 5 times, or 6 times between each set of CDR amino acid sequences specific for a different epitope. In some embodiments, the antibody comprises amino acid sequences that are at least 80%, 81%, 82%, 83%, 84%, 85%, 86%, 87%, 88%, 89%, 90%, 91%, 92%, 93%, 94%, 95%, 96%, 97%, 98%, 99% homologous to any one or combination of sequences of Table 1.

In some embodiments, the disclosure relates to an antibody with at least one antibody fragment specific for an CD4s epitope fused to at least one antibody fragment specific for an V1/V2-glycan region epitope by a linker GGGGS that is repeated 3, 4, or 5 times or a linker equivalent in length to an amino acid sequence GGGGS repeated 3, 4, or 5 times. In some embodiments, the antibody has at least three valencies, wherein the first valency comprises or consists of antibody fragment specific for an CD4s epitope; wherein the second valency comprises or consists of antibody fragment specific for a V1/V2-glycan region epitope; and wherein the third valency comprises or consists of an antibody fragment specific for an epitope that is located in the gp41 membrane proximal external region (MPER). In some embodiments, if any one antibody fragment comprises both heavy and light variable chains specific for one of the epiptopes disclosed herein, the heavy and light variable chains of such antibody are separated by a linker that comprises the amino acid sequence GGGGS repeated 1, 2, 3, 4 or more times. n some embodiments, if any one antibody fragment comprises both heavy and light variable chains specific for one of the epiptopes disclosed herein, the heavy and light variable chains of such antibody are separated by a linker that comprises the amino acid sequence GGGGS repeated 3 times. In some embodiments, the linker GGGGS is replaced with a linker of equivalent length such that orientation of and distance between the various variable heavy and light chain antibody fragments remains substantially comparable or identical to the orientation and distance between the various variable heavy and light chain antibody fragments separated by one or more amino acid sequences GGGGS.

In some embodiments, the disclosure relates to an antibody comprising a variable portion and a constant portion, the variable portion comprising any one or plurality of variable heavy and/or light antibody fragments (such as a scFv fragment) capable of binding to one or more of the epiptopes disclosed herein, and the constant portion comprising an IgG-like domain. The IgG domain can comprise SEQ ID NO:28 or any amino acid sequence from about 50% to about 99% homolgous to SEQ ID NO:28. In some embodiments, the variable portion of the antibody comprising 1, 2, 3, 4 or more amino acid sequences capable of binding any 1, 2, 3, or 4 or more epitopes disclosed herein, wherein each amino acid sequence capable of binding an epitope is separated by at least 3, 4, or 5 contiguous amino acid linkers (such as GGGGS). In some embodiments, the variable portion comprises one or more CDR sequences specific for an epitope disclosed herein. In some embodiments, the variable portion comprises at least three or at least four amino acid domains comprising from 1 to about 3 CDR sequences specific for an epitope disclosed herein. In some embodiments, the order in which the CDR sequences are placed or oriented within the antibody correlates to its efficacy in neutralizing various isolates of HIV. Any permutation or order of CDR sequences disclosed in Table 1 is contemplated.

Various bNAbs are known in the art and can be used according to this disclosure. In some embodiments, the present disclosure comprises a composition or cell comprising bispecific, trispecific or tetraspecific anti-HIV bNAbs. Examples include but are not limited to those described in U.S. Pat. No. 8,673,307, WO2014063059, WO2012158948, WO2015/117008, and PCT/US2015/41272, including antibodies 3BNC117, 3BNC60, 12A12, 12A21, NIH45-46, bANC131, 8ANC134, D32530, INC9, 8ANC195. 8ANC196, 10-259, 10-303, 10-410, 10-847, 10-996, 10-1074, 10-1121, 10-1130, 10-1146, 10-1341, 10-1369, and 10-1074GM. Additional examples include those described in Klein et al, Nature, 2012. 492(7427): p. 118-22, Horwitz et al, Proc Natl Acad Sci USA, 2013. 110(41): p. 16538-43, Scheid, et al. 2011. Science, 333: 1633-1637, Scheid, et al. 2009. Nature, 458:636-640, Eroshkin et al, Nucleic Acids Res. 2014 January; 42 (Database issue):D1 133-9, Mascola et al. Immunol Rev. 2013 July; 254(1):225-44.

Certain bNAbs target conserved sites of vulnerability on the HIV-1 envelope (ENV) such as the CD4 binding site (CD4bs). The b12 monoclonal antibody was for many years considered the prototype and optimal CD4bs bNAb, although it was only able to neutralize about 40% of HIV-1 strains. In 2010, a new group of CD4bs antibodies named VRC01, VRC02, and VRC03 was disclosed. Of these, VRC01 was the most potent and broad. In a large neutralization panel (190 viruses), VRC01 neutralized 91% of viruses with an $IC_{50}$ less than 50 µg/ml and 72% of viruses with an IC50 less than 1 µg/ml (Wu et al., Science, 329 (5993):856-861, 2010). Structural analyses have explained VRC01's high potency and breadth: VRC01 partially mimics the CD4 interaction with gp120. Specifically, the majority of the gp120 area targeted by VRC01 is the highly conserved site of initial CD4 attachment in the outer domain of gp120, which allows VRC01 to bypass conformational and glycan masking that impaired previously identified CD4bs bNAbs. Both the heavy and light chain of VRC01 contribute to the binding of gp120, with the CDRH2 providing the primary interaction, and CDRL1, CDRL3, CDRH1, and CDRH3 providing additional contact points. It has been shown that passive transfer of VRC01 protects against intrarectal or intravaginal simian-HIV (SHIV) challenge in non-human primates.

VRC01 is a monoclonal antibody that specifically binds to gp120 and is neutralizes a broad range of HIV viruses. The amino acid sequences of the variable heavy (VH) chain and variable light (VL) chain of VRC01 are shown in SEQ ID NOs 6 and 2, respectively and have been described in Wu et al., Science, 329(5993):856-861, 2010, and PCT publication WO2012/154312, incorporated by reference herein in its entirety. The heavy chain CDRs (CDR1, CDR2, CDR3) are shown in SEQ ID NOs 7, 8, 9, respectively. The light chain CDRs are shown in SEQ ID NOs 3, 4, 5, respectively.

VRC01-like antibodies are described, for example in US20170267748, incorporated by reference herein in its entirety. Generally, these antibodies bind to the CD4 binding surface of gp120 in substantially the same orientation as VRC01, and are broadly neutralizing VRC01-like antibodies, with several of the important contacts between CD4 and gp120 mimicked by the VRC01-like antibodies. Several VRC01-like antibodies are available, including VRC01-like antibodies, heavy chains and light chains disclosed in PCT International Application No. PCT/US2010/050295, filed Sep. 24, 2010, which is incorporated by reference herein and Wu et al., "Rational design of envelope identifies broadly neutralizing human monoclonal antibodies to HIV-1," Science, 329(5993):856-861, 2010, which is incorporated by reference herein. These include heavy and light chains of the VRC01, VRC02, VRC03, VRC06, VRC07, 3BNC117, IOMA and N6. In one embodiment, the antibody that binds to an epitope in the CD4-binding site of the of the envelope protein of HIV-1 is selected from the group consisting of VRC03, VRC06, VRC07, 3BNC117, IOMA, and N6. The amino acid sequences of the heavy and light variable regions of VRC03 are shown in SEQ ID NOs 162 and 158, respectively and have been described in Wu et al., (Science. 2010 Aug. 13; 329(5993):856-61; PMID 20616233). The heavy chain CDRs (CDR1, CDR2, CDR3) are shown in SEQ ID NOs 163, 164, 165, respectively. The light chain CDRs (CDR1, CDR2, CDR3) are shown in SEQ ID NOs 159, 160, 161, respectively. The amino acid sequences of the heavy and light variable regions of VRC06 are shown in SEQ ID NOs 170 and 166, respectively and have been described in Li et al., (J Virol. 2012 October; 86(20):11231-41; PMID 22875963). The heavy chain CDRs (CDR1, CDR2, CDR3) are shown in SEQ ID NOs 171, 172, 173, respectively. The light chain CDRs (CDR1, CDR2, CDR3) are shown in SEQ ID NOs 167, 168, 169, respectively. The amino acid sequences of the heavy and light variable regions of VRC07 are shown in SEQ ID NOs 178 and 2, respectively and have been described in Rudicell et al., (J Virol. 2014 November; 88(21):12669-82; PMID 25142607). The heavy chain CDRs (CDR1, CDR2, CDR3) are shown in SEQ ID NOs 179, 180, 181, respectively. The light chain CDRs (CDR1, CDR2, CDR3) are shown in SEQ ID NOs 3, 4, 5, respectively. The amino acid sequences of the heavy and light variable regions of 3BNC117 are shown in SEQ ID NOs 186 and 182, respectively and have been described in Scheid et al., (Science. 2011 Sep. 16; 333(6049):1633-7; PMID 21764753). The heavy chain CDRs (CDR1, CDR2, CDR3) are shown in SEQ ID NOs 187, 188, 189, respectively. The light chain CDRs (CDR1, CDR2, CDR3) are shown in SEQ ID NOs 183, 184, 185, respectively. The amino acid sequences of the heavy and light variable regions of IOMA are shown in SEQ ID NOs 202 and 198, respectively and have been described in Gristick et al., (Nat Struct Mol Biol. 2016 October; 23(10):906-915; PMID 27617431). The heavy chain CDRs (CDR1, CDR2, CDR3) are shown in SEQ ID NOs 203, 204, 205, respectively. The light chain CDRs (CDR1, CDR2, CDR3) are shown in SEQ ID NOs 199, 200, 201, respectively. The amino acid sequences of the heavy and light variable regions of N6 are shown in SEQ ID NOs 194 and 190, respectively and have been described in Huang et al., (Immunity. 2016 Nov. 15; 45(5):1108-1121; PMID 27851912). The heavy chain CDRs (CDR1, CDR2, CDR3) are shown in SEQ ID NOs 195, 196, 197, respectively. The light chain CDRs (CDR1, CDR2, CDR3) are shown in SEQ ID NOs 191, 192, 193, respectively.

PGT121, PGT122, PGT123, PGT127, PGT128, PGT135, 10-1074 and BG18 are a family of neutralizing monoclonal antibodies that specifically bind to the V1/V2 and V3 regions of HIV-1 Env and can inhibit HIV-1 infection of target cells. PGT121, PGT122, and PGT123 mAbs and methods of producing them are described in, for example, Walker et al., Nature, 477:466-470, 2011, and Int. Pub. No. WO 2012/030904, each of which is incorporated by reference herein. PGT127 and PGT128 are described in, for example Pejchal et al. (Science, 2011 Nov. 25, 334 (6059): 1097-103). PGT135 is described, for example, in Kong et al. (Nature Structural and Molecular Biology, 2013 July, 20:796-803). In one embodiment, the antibody that binds to an epitope in the V3-glycan region of the of the envelope protein of HIV-1 is selected from the group consisting of PGT121, PGT122, PGT128, PGT135, 10-1074, and BG18. The amino acid sequences of the heavy and light variable regions of PGT121 are shown in SEQ ID NOs 14 and 10, respectively. The heavy chain CDRs (CDR1, CDR2, CDR3) are shown in SEQ ID NOs 15, 16, 17, respectively. The light chain CDRs are shown in SEQ ID NOs 11, 12, 13, respectively. The amino acid sequences of the heavy and light variable regions of 10-1074 are shown in SEQ ID NOs 58 and 54, respectively and have been described in Mouquet et al. ((2012) Proc. Natl. Acad. Sci. USA 109: E3268-E3277). The heavy chain CDRs (CDR1, CDR2, CDR3) are shown in SEQ ID NOs 59, 60, 61, respectively. The light chain CDRs (CDR1, CDR2, CDR3) are shown in SEQ ID NOs 55, 56, 57, respectively. The amino acid sequences of the heavy and light variable regions of BG18 are shown in SEQ ID NOs 66 and 62, respectively and have been described in Freund et al. ((2012) Sci Transl Med. 2017 Jan. 18; 9(373); PMID 28100831). The heavy chain CDRs (CDR1, CDR2, CDR3) are shown in SEQ ID NOs 67, 68, 69, respectively. The light chain CDRs (CDR1, CDR2, CDR3) are shown in SEQ ID NOs 63, 64, 65, respectively. The amino acid sequences of the heavy and light variable regions of PGT135 are shown in SEQ ID NOs 74 and 70, respectively and have been described in Kong et al. (Nat Struct Mol Biol. 2013 July; 20(7):796-80; PMID 23708606). The heavy chain CDRs (CDR1, CDR2, CDR3) are shown in SEQ ID NOs 75, 76, 77, respectively. The light chain CDRs (CDR1, CDR2, CDR3) are shown in SEQ ID NOs 71, 72, 73, respectively. The amino acid sequences of the heavy and light variable regions of PGT122 are shown in SEQ ID NOs 82 and 78, respectively and have been described in Julien et al. (PLoS Pathog. 2013; 9(5):e1003342; PMID 23658524). The heavy chain CDRs (CDR1, CDR2, CDR3) are shown in SEQ ID NOs 83, 84, 85, respectively. The light chain CDRs (CDR1, CDR2, CDR3) are shown in SEQ ID NOs 79, 80, 81, respectively. The amino acid sequences of the heavy and light variable regions of PGT128 are shown in SEQ ID NOs 90 and 86, respectively and have been described in Lee et al. (Structure. 2015 Oct. 6; 23(10):1943-51; PMID 26388028). The heavy chain CDRs (CDR1, CDR2, CDR3) are shown in SEQ ID NOs 91, 92, 93, respectively. The light chain CDRs (CDR1, CDR2, CDR3) are shown in SEQ ID NOs 87, 88, 89, respectively.

35022, N123-VRC34.01, 3BC315, and PGT151 are broadly neutralizing monoclonal antibody that specifically bind to the gp120/gp41 interface of HIV-1 Env in its prefusion mature (cleaved) conformation, and which can inhibit HIV-1 infection of target cells. PGT151 antibody and methods of producing this antibody are described in, for example, Blattner et al., Immunity, 40, 669-680, 2014, and Falkowska et al., Immunity, 40, 657-668, 2014, each of which is incorporated by reference herein in its entirety). The amino acid sequences of the heavy and light variable regions of the PGT151 mAb are known and have been deposited in GenBank as Nos. KJ700282.1 (PGT151 VH) and KJ700290.1 (PGT151 VL), each of which is incorporated by reference herein in its entirety). In one embodiment, the antibody that binds to an epitope in the gp120/gp41 interface of the of the envelope protein of HIV-1 is selected from the group consisting of 35022, N123-VRC34.01, 3BC315, and PGT151. The amino acid sequences of the heavy and light variable regions of N123-VRC34.01 are shown in SEQ ID NOs 138 and 134, respectively and have been described in Kong et al., (Science 352 (6287), 828-833 (2016)). The heavy chain CDRs (CDR1, CDR2, CDR3) are shown in SEQ ID NOs 139, 140, 141, respectively. The light chain CDRs (CDR1, CDR2, CDR3) are shown in SEQ ID NOs 135, 136, 137, respectively. The amino acid sequences of the heavy and light variable regions of 3BC315 are shown in SEQ ID NOs 146 and 142, respectively and have been described in Lee et al. (Nat Commun. 2015 Sep. 25; 6:8167; PMID 26404402). The heavy chain CDRs (CDR1, CDR2, CDR3) are shown in SEQ ID NOs 147, 148, 149, respectively. The light chain CDRs (CDR1, CDR2, CDR3) are shown in SEQ ID NOs 143, 144, 145, respectively. The amino acid sequences of the heavy and light variable regions of PGT151 are shown in SEQ ID NOs 154 and 150, respectively and have been described in Blattner et al. (Immunity. 2014 May 15; 40(5):669-80; PMID 24768348). The heavy chain CDRs (CDR1, CDR2, CDR3) are shown in SEQ ID NOs 155, 156, 157, respectively. The light chain CDRs (CDR1, CDR2, CDR3) are shown in SEQ ID NOs 151, 152, 153, respectively.

10E8, 10E8v4, 10E8v4 S100cF, Dh511.2 k3, Z13, 4E10, and 2F5 are broadly neutralizing monoclonal antibody that primarily targets a HIV Env membrane proximal external region (MPER) helix spanning residues 671-683. In one embodiment, the antibody that binds to an epitope in the MPER of the of the envelope protein of HIV-1 is selected from the group consisting of: 10E8, 10E8v4, 10E8v4 S100cF, Dh511.2_k3, Z13, 4E10, and 2F5. The amino acid sequences of the heavy and light variable regions of 10E8v4 are shown in SEQ ID NOs 98 and 94, respectively and have been described in Kwon et al. (J Virol. 2016 Jun. 10; 90(13):5899-914; PMID PMC4907239). The heavy chain CDRs (CDR1, CDR2, CDR3) are shown in SEQ ID NOs 99, 100, 101, respectively. The light chain CDRs (CDR1, CDR2, CDR3) are shown in SEQ ID NOs 95, 96, 97, respectively. The amino acid sequences of the heavy and light variable regions of 10E8v4 S100cF are shown in SEQ ID NOs 106 and 94, respectively and have been described in PCT/US2016/060390 and WO2017079479. The heavy chain CDRs (CDR1, CDR2, CDR3) are shown in SEQ ID NOs 107, 108, 109, respectively. The light chain CDRs (CDR1, CDR2, CDR3) are shown in SEQ ID NOs 95, 96, 97, respectively. The amino acid sequences of the heavy and light variable regions of DH511.2_k3 are shown in SEQ ID NOs 114 and 110, respectively and have been described in Williams et al. (Sci Immunol. 2017 Jan. 27; 2(7); PMID 28783671). The heavy chain CDRs (CDR1, CDR2, CDR3) are shown in SEQ ID NOs 115, 116, 117, respectively. The light chain CDRs (CDR1, CDR2, CDR3) are shown in SEQ ID NOs 111, 112, 113, respectively. The amino acid sequences of the heavy and light variable regions of 4E10 are shown in SEQ ID NOs 122 and 118, respectively and have been described in Rujas et al. (J Virol. 2015 December; 89(23):11975-89; PMID 26378169). The heavy chain CDRs (CDR1, CDR2, CDR3) are shown in SEQ ID NOs 123, 124, 125, respectively. The light chain CDRs (CDR1, CDR2, CDR3) are shown in SEQ ID NOs 119, 120, 121, respectively. The amino acid sequences of the heavy and light variable regions of 2F5 are shown in SEQ ID NOs 130 and 126, respectively and have been described in Julien et al. J Mol Biol. 2008 Dec. 12; 384(2):377-92; PMID 18824005). The heavy chain CDRs (CDR1, CDR2, CDR3) are shown in SEQ ID NOs 131, 132, 133, respectively. The light chain CDRs (CDR1, CDR2, CDR3) are shown in SEQ ID NOs 126, 127, 128, respectively.

PGT141, PGT142, PGT143, and PGT145 are family of broadly neutralizing monoclonal antibodies that specifically bind to the V1/V2 domain of the HIV-1 Env ectodomain trimer in its prefusion mature closed conformation, and which can inhibit HIV-1 infection of target cells. PGT141, PGT142, PGT143, and PGT145 mAbs and methods of producing them are described in, for example, Walker et al., Nature, 477:466-470, 2011, and Int. Pub. No. WO2012/030904, each of which is incorporated by reference herein). The amino acid sequences of the heavy and light variable regions of the PGT141, PGT142, PGT143, PGT144, and PGT145 mAbs are known and have been deposited in GenBank as Nos. JN201906.1 (PGT141 VH), JN201923.1 (PGT141 VL), JN201907.1 (PGT142 VH), JN201924.1 (PGT142 VL), JN201908.1 (PGT143 VH), JN201925.1 (PGT143 VL), JN201909.1 (PGT144 VH), JN201926.1 (PGT144 VL), JN201910.1 (PGT145 VH), and JN201927.1 (PGT145 VL), each of which is incorporated by reference herein in its entirety).

In one embodiment, the disclosure features an antibody, or a fragment thereof, or a salt thereof that binds to an epitope that is located in the CD4-binding site (CD4bs). In one embodiment, the disclosure features an antibody, or a fragment thereof, that binds to an epitope that is located in the V1/V2-glycan region. In one embodiment, the disclosure features an antibody, or a fragment thereof, that binds to an epitope that is located in the V3-glycan region. In one embodiment, the disclosure features an antibody, or a fragment thereof, that binds to an epitope that is located in the gp41 membrane proximal external region (MPER). In one embodiment, the disclosure features an antibody, or a fragment thereof, that binds to an epitope that is located the gp120-gp41 interface of the envelope protein of HIV.

In one embodiment, the present disclosure is directed to an antibody, or an antigen binding fragment thereof, or a salt thereof, comprising any one or combination of the antigen binding regions of any of the antibodies described in Table 1.

TABLE 1

| SEQ ID NO | Description | Sequence |
|---|---|---|
| 1 | VRC01 (VL-3x-VH)-(5X)-PGT121 (VL-3x-VH) ScEv amino acid sequence | EIVLTQSPGTLSLSPGETAIISCRTSQYGSLAWYQQRPGQAPRLVIYS GSTRAAGIPDRFSGSRWGPDYNLTISNLESGDFGVYYCQQYEFFGQGT KVQVDIKGGGGSGGGGSGGGGSQVQLVQSGGQMKKPGESMRISCRASG YEFIDCTLNWIRLAPGKRPEWMGWLKPRGGAVNYARPLQGRVTMTRDV YSDTAFLELRSLTVDDTAVYFCTRGKNCDYNWDFEHWGRGTPVIVSSG GGGSGGGGSGGGGSGGGGSGGGGSSDISVAPGETARISCGEKSLGSRA VQWYQHRAGQAPSLIIYNNQDRPSGIPERFSGSPDSPFGTTATLTITS VEAGDEADYYCHIWDSRVPTKWVFGGGTTLTVLGGGGSGGGGSGGGGS QMQLQESGPGLVKPSETLSLTCSVSGASISDSYWSWIRRSPGKGLEWI GYVHKSGDTNYSPSLKSRVNLSLDTSKNQVSLSLVAATAADSGKYYCA RTLHGRRIYGIVAFNEWFTYFYMDVWGNGTQVTVSSGSGHHHHHH |
| 2 | VRC01 variable light (VL) chain amino acid sequence | EIVLTQSPGTLSLSPGETAIISCRTSQYGSLAWYQQRPGQAPRLVIYS GSTRAAGIPDRFSGSRWGPDYNLTISNLESGDFGVYYCQQYEFFGQGT KVQVDIK |
| 3 | VL-CDR1 | RTSQYGSLA |
| 4 | VL-CDR2 | SGSTRAA |
| 5 | VL-CDR3 | QQYEF |
| 6 | VRC01 variable heavy (VH) chain amino acid sequence | QVQLVQSGGQMKKPGESMRISCRASGYEFIDCTLNWIRLAPGKRPEWM GWLKPRGGAVNYARPLQGRVTMTRDVYSDTAFLELRSLTVDDTAVYFC TRGKNCDYNWDFEHWGRGTPVIVSS |
| 7 | VH-CDR1 | DCTLN |
| 8 | VH-CDR2 | WLKPRGGAVNYARPLQG |
| 9 | VH-CDR3 | GKNCDYNWDFEH |
| 10 | PGT121 variable light (VL) chain amino acid sequence | SDISVAPGETARISCGEKSLGSRAVQWYQHRAGQAPSLIIYNNQDRPS GIPERFSGSPDSPFGTTATLTITSVEAGDEADYYCHIWDSRVPTKWVF GGGTTLTVL |
| 11 | VL-CDR1 | GEKSLGSRAVQ |
| 12 | VL-CDR2 | NNQDRPS |
| 13 | VL-CDR3 | HIWDSRVPTKWV |

TABLE 1-continued

| SEQ ID NO | Description | Sequence |
|---|---|---|
| 14 | PGT121 variable heavy (VH) chain amino acid sequence | QMQLQESGPGLVKPSETLSLTCSVSGASISDSYWSWIRRSPGKGLEWI GYVHKSGDTNYSPSLKSRVNLSLDTSKNQVSLSLVAATAADSGKYYCA RTLHGRRIYGIVAFNEWFTYFYMDVWGNGTQVTVSS |
| 15 | VH-CDR1 | DSYWS |
| 16 | VH-CDR2 | YVHKSGDTNYSPSLKS |
| 17 | VH-CDR3 | TLHGRRIYGIVAFNEWFTYFYMDV |
| 18 | dVRC01 (VL(Δ1,2-V3S)-3x-VH)-(VL-(5X)-PGT121 3x-VH) ScFv amino acid sequence | SLTQSPGTLSLSPGETAIISCRTSQYGSLAWYQQRPGQAPRLVIYSGS TRAAGIPDRFSGSRWGPDYNLTISNLESGDFGVYYCQQYEFFGQGTKV QVDIKGGGGSGGGGSGGGGSQVQLVQSGGQMKKPGESMRISCRASGYE FIDCTLNWIRLAPGKRPEWMGWLKPRGGAVNYARPLQGRVTMTRDVYS DTAFLELRSLTVDDTAVYFCTRGKNCDYNWDFEHWGRGTPVIVSSGGG GSGGGGSGGGGSGGGGSSDISVAPGETARISCGEKSLGSRAVQ WYQHRAGQAPSLIIYNNQDRPSGIPERFSGSPDSPFGTTATLTITSVE AGDEADYYCHIWDSRVPTKWVFGGGTTLTVLGGGGSGGGGSGGGGSQM QLQESGPGLVKPSETLSLTCSVSGASISDSYWSWIRRSPGKGLEWIGY VHKSGDTNYSPSLKSRVNLSLDTSKNQVSLSLVAATAADSGKYYCART LHGRRIYGIVAFNEWFTYFYMDVWGNGTQVTVSSGGHHHHHH |
| 19 | dVRC01 variable light (VL) chain amino acid sequence | SLTQSPGTLSLSPGETAIISCRTSQYGSLAWYQQRPGQAPRLVIYSGS TRAAGIPDRFSGSRWGPDYNLTISNLESGDFGVYYCQQYEFFGQGTKV QVDIK |
| 20 | PGT121 (VH-3x-VL)-(5X)-VRC01 (VH-3x-VL) ScFv amino acid sequence | QMQLQESGPGLVKPSETLSLTCSVSGASISDSYWSWIRRSPGKGLEWI GYVHKSGDTNYSPSLKSRVNLSLDTSKNQVSLSLVAATAADSGKYYCA RTLHGRRIYGIVAFNEWFTYFYMDVWGNGTQVTVSSGGGGSGGGGSGG GGSSDISVAPGETARISCGEKSLGSRAVQWYQHRAGQAPSLIIYNNQD RPSGIPERFSGSPDSPFGTTATLTITSVEAGDEADYYCHIWDSRVPTK WVFGGGTTLTVLGGGGSGGGGSGGGGSGGGGSQVQLVQSGGQM KKPGESMRISCRASGYEFIDCTLNWIRLAPGKRPEWMGWLKPRGGAYN YARPLQGRVTMTRDVYSDTAFLELRSLTVDDTAVYFCTRGKNCDYNWD FEHWGRGTPVIVSSGGGGSGGGGSGGGGSEIVLTQSPGTLSLSPGETA IISCRTSQYGSLAWYQQRPGQAPRLVIYSGSTRAAGIPDRFSGSRWGP DYNLTISNLESGDFGVYYCQQYEFFGQGTKVQVDIKGSGHHHHHH |
| 21 | PGT121 (VH-3x-VL)-(4X)-VRC01 (VH-3x-VL) ScFv amino acid sequence | QMQLQESGPGLVKPSETLSLTCSVSGASISDSYWSWIRRSPGKGLEWI GYVHKSGDTNYSPSLKSRVNLSLDTSKNQVSLSLVAATAADSGKYYCA RTLHGRRIYGIVAFNEWFTYFYMDVWGNGTQVTVSSGGGGSGGGGSGG GGSSDISVAPGETARISCGEKSLGSRAVQWYQHRAGQAPSLIIYNNQD RPSGIPERFSGSPDSPFGTTATLTITSVEAGDEADYYCHIWDSRVPTK WVFGGGTTLTVLGGGGSGGGGSGGGGSGGGGSQVQLVQSGGQMKKPGE SMRISCRASGYEFIDCTLNWIRLAPGKRPEWMGWLKPRGGAVNYARPL QGRVTMTRDVYSDTAFLELRSLTVDDTAVYFCTRGKNCDYNWDFEHWG RGTPVIVSSGGGGSGGGGSGGGGSEIVLTQSPGTLSLSPGETAIISCR TSQYGSLAWYQQRPGQAPRLVIYSGSTRAAGIPDRFSGSRWGPDYNLT ISNLESGDFGVYYCQQYEFFGQGTKVQVDIKGSGHHHHHH |
| 22 | PGT121 (VH-3x-VL)-(3X)-VRC01 (VH-3x-VL) ScFv amino acid sequence | QMQLQESGPGLVKPSETLSLTCSVSGASISDSYWSWIRRSPGKGLEWI GYVHKSGDTNYSPSLKSRVNLSLDTSKNQVSLSLVAATAADSGKYYCA RTLHGRRIYGIVAFNEWFTYFYMDVWGNGTQVTVSSGGGGSGGGGSGG GGSSDISVAPGETARISCGEKSLGSRAVQWYQHRAGQAPSLIIYNNQD RPSGIPERFSGSPDSPFGTTATLTITSVEAGDEADYYCHIWDSRVPTK WVFGGGTTLTVLGGGGSGGGGSGGGGSQVQLVQSGGQMKKPGESMRIS CRASGYEFIDCTLNWIRLAPGKRPEWMGWLKPRGGAVNYARPLQGRVT MTRDVYSDTAFLELRSLTVDDTAVYFCTRGKNCDYNWDFEHWGRGTPV IVSSGGGGSGGGGSGGGGSEIVLTQSPGTLSLSPGETAIISCRTSQYG SLAWYQQRPGQAPRLVIYSGSTRAAGIPDRFSGSRWGPDYNLTISNLE SGDFGVYYCQQYEFFGQGTKVQVDIKGSGHHHHHH |
| 23 | VRC01 (VL-3x-VH)-(5X)-PGT121 (VL-3x-VH) IgG1 amino acid sequence | EIVLTQSPGTLSLSPGETAIISCRTSQYGSLAWYQQRPGQAPRLVIYS GSTRAAGIPDRFSGSRWGPDYNLTISNLESGDFGVYYCQQYEFFGQGT KVQVDIKGSGGGGSGGGGSGGGGSQVQLVQSGGQMKKPGESMRISCRASG YEFIDCTLNWIRLAPGKRPEWMGWLKPRGGAVNYARPLQGRVTMTRDV YSDTAFLELRSLTVDDTAVYFCTRGKNCDYNWDFEHWGRGTPVIVSSG GGGSGGGGSGGGGSGGGGSGGGGSSDISVAPGETARISCGEKSLGSRA VQWYQHRAGQAPSLIIYNNQDRPSGIPERFSGSPDSPFGTTATLTITS VEAGDEADYYCHIWDSRVPTKWVFGGGTTLTVLGGGGSGGGGSGGGGS QMQLQESGPGLVKPSETLSLTCSVSGASISDSYWSWIRRSPGKGLEWI GYVHKSGDTNYSPSLKSRVNLSLDTSKNQVSLSLVAATAADSGKYYCA RTLHGRRIYGIVAFNEWFTYFYMDVWGNGTQVTVSSGGGPKSCDKTHT CPPCPAPELLGGPSVFLFPPKPKDTLMISRTPEVTCVVVDVSHEDPEV |

TABLE 1 -continued

| SEQ ID NO | Description | Sequence |
|---|---|---|
| | | KFNWYVDGVEVHNAKTKPREEQYNSTYRVVSVLTVLHQDWLNGKEYKC KVSNKALPAPIEKTISKAKGQPREPQVYTLPPSREEMTKNQVSLTCLV KGFYPSDIAVEWESNGQPENNYKTTPPVLDSDGSFFLYSKLTVDKSRW QQGNVFSCSVMHEALHNHYTQKSLSLSPGK |
| 24 | dVRC01 (VL(Δ1,2-V3S)-3x-VH)-(5X)-PGT121 (VL-3x-VH) IgG1 amino acid sequence | SLTQSPGTLSLSPGETAIISCRTSQYGSLAWYQQRPGQAPRLVIYSGS TRAAGIPDRFSGSRWGPDYNLTISNLESGDFGVYYCQQYEFFGQGTKV QVDIKGGGGSGGGGSGGGGSQVQLVQSGGQMKKPGESMRISCRASGYE FIDCTLNWIRLAPGKRPEWMGWLKPRGGAVNYARPLQGRVTMTRDVYS DTAFLELRSLTVDDTAVYFCTRGKNCDYNWDFEHWGRGTPVIVSSGGG GSGGGGSGGGGSGGGGSGGGGSSDISVAPGETARISCGEKSLGSRAVQ WYQHRAGQAPSLIIYNNQDRPSGIPERFSGSPDSPFGTTATLTITSVE AGDEADYYCHIWDSRVPTKWVFGGGTTLTVLGGGGSGGGGSGGGGSQM QLQESGPGLVKPSETLSLTCSVSGASISDSYWSWIRRSPGKGLEWIGY VHKSGDTNYSPSLKSRVNLSLDTSKNQVSLSLVAATAADSGKYYCART LHGRRIYGIVAFNEWFTYFYMDVWGNGTQVTVSSGSGPKSCDKTHTCP PCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKV SNKALPAPIEKTISKAKGQPREPQVYTLPPSREEMTKNQVSLTCLVKG FYPSDIAVEWESNGQPENNYKTTPPVLDSDGSFFLYSKLTVDKSRWQQ GNVFSCSVMHEALHNHYTQKSLSLSPGK |
| 25 | PGT121 (VH-3x-VL)-(5X)-VRC01 (VH-3x-VL) IgG1 amino acid sequence | QMQLQESGPGLVKPSETLSLTCSVSGASISDSYWSWIRRSPGKGLEWI GYVHKSGDTNYSPSLKSRVNLSLDTSKNQVSLSLVAATAADSGKYYCA RTLHGRRIYGIVAFNEWFTYFYMDVWGNGTQVTVSSGGGGSGGGGSGG GGSSDISVAPGETARISCGEKSLGSRAVQWYQHRAGQAPSLIIYNNQD RPSGIPERFSGSPDSPFGTTATLTITSVEAGDEADYYCHIWDSRVPTK WVFGGGTTLTVLGGGGSGGGGSGGGGSGGGGSQVQLVQSGGQMKKPGESMRISCRASGYEFIDCTLNWIRLAPGKRPEWMGWLKPRGGAYN YARPLQGRVTMTRDVYSDTAFLELRSLTVDDTAVYFCTRGKNCDYNWD FEHWGRGTPVIVSSGGGGSGGGGSGGGGSEIVLTQSPGTLSLSPGETA IISCRTSQYGSLAWYQQRPGQAPRLVIYSGSTRAAGIPDRFSGSRWGP DYNLTISNLESGDFGVYYCQQYEFFGQGTKVQVDIKGSGPKSCDKTHT CPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKC KVSNKALPAPIEKTISKAKGQPREPQVYTLPPSREEMTKNQVSLTCLV KGFYPSDIAVEWESNGQPENNYKTTPPVLDSDGSFFLYSKLTVDKSRW QQGNVFSCSVMHEALHNHYTQKSLSLSPGK |
| 26 | PGT121 (VH-3x-VL)-(4X)-VRC01 (VH-3x-VL) IgG1 amino acid sequence | QMQLQESGPGLVKPSETLSLTCSVSGASISDSYWSWIRRSPGKGLEWI GYVHKSGDTNYSPSLKSRVNLSLDTSKNQVSLSLVAATAADSGKYYCA RTLHGRRIYGIVAFNEWFTYFYMDVWGNGTQVTVSSGGGGSGGGGSGG GGSSDISVAPGETARISCGEKSLGSRAVQWYQHRAGQAPSLIIYNNQD RPSGIPERFSGSPDSPFGTTATLTITSVEAGDEADYYCHIWDSRVPTK WVFGGGTTLTVLGGGGSGGGGSGGGGSGGGGSQVQLVQSGGQMKKPGE SMRISCRASGYEFIDCTLNWIRLAPGKRPEWMGWLKPRGGAVNYARPL QGRVTMTRDVYSDTAFLELRSLTVDDTAVYFCTRGKNCDYNWDFEHWG RGTPVIVSSGGGGSGGGGSGGGGSEIVLTQSPGTLSLSPGETAIISCR TSQYGSLAWYQQRPGQAPRLVIYSGSTRAAGIPDRFSGSRWGPDYNLT ISNLESGDFGVYYCQQYEFFGQGTKVQVDIKGSGPKSCDKTHTCPPCP APELLGGPSVFLFPPKPKDTLMISRTPEVTCVVVDVSHEDPEVKFNWY VDGVEVHNAKTKPREEQYNSTYRVVSVLTVLHQDWLNGKEYKCKVSNK ALPAPIEKTISKAKGQPREPQVYTLPPSREEMTKNQVSLTCLVKGFYP SDIAVEWESNGQPENNYKTTPPVLDSDGSFFLYSKLTVDKSRWQQGNV FSCSVMHEALHNHYTQKSLSLSPGK |
| 27 | PGT121 (VH-3x-VL)-(3X)-VRC01 (VH-3x-VL) IgG1 amino acid sequence | QMQLQESGPGLVKPSETLSLTCSVSGASISDSYWSWIRRSPGKGLEWI GYVHKSGDTNYSPSLKSRVNLSLDTSKNQVSLSLVAATAADSGKYYCA RTLHGRRIYGIVAFNEWFTYFYMDVWGNGTQVTVSSGGGGSGGGGSGG GGSSDISVAPGETARISCGEKSLGSRAVQWYQHRAGQAPSLIIYNNQD RPSGIPERFSGSPDSPFGTTATLTITSVEAGDEADYYCHIWDSRVPTK WVFGGGTTLTVLGGGGSGGGGSGGGGSQVQLVQSGGQMKKPGESMRIS CRASGYEFIDCTLNWIRLAPGKRPEWMGWLKPRGGAVNYARPLQGRVT MTRDVYSDTAFLELRSLTVDDTAVYFCTRGKNCDYNWDFEHWGRGTPV IVSSGGGGSGGGGSGGGGSEIVLTQSPGTLSLSPGETAIISCRTSQYG SLAWYQQRPGQAPRLVIYSGSTRAAGIPDRFSGSRWGPDYNLTISNLE SGDFGVYYCQQYEFFGQGTKVQVDIKGSGPKSCDKTHTCPPCPAPELL GGPSVFLFPPKPKDTLMISRTPEVTCVVVDVSHEDPEVKFNWYVDGVE VHNAKTKPREEQYNSTYRVVSVLTVLHQDWLNGKEYKCKVSNKALPAP IEKTISKAKGQPREPQVYTLPPSREEMTKNQVSLTCLVKGFYPSDIAV EWESNGQPENNYKTTPPVLDSDGSFFLYSKLTVDKSRWQQGNVFSCSV MHEALHNHYTQKSLSLSPGK |

TABLE 1 -continued

| SEQ ID NO | Description | Sequence |
|---|---|---|
| 28 | IgG1 Fc (hinge-CH2-CH3) amino acid sequence | PKSCDKTHTCPPCPAPELLGGPSVFLFPPKPKDTLMISRTPEVTCVVV DVSHEDPEVKFNWYVDGVEVHNAKTKPREEQYNSTYRVVSVLTVLHQD WLNGKEYKCKVSNKALPAPIEKTISKAKGQPREPQVYTLPPSREEMTK NQVSLTCLVKGFYPSDIAVEWESNGQPENNYKTTPPVLDSDGSFFLYS KLTVDKSRWQQGNVFSCSVMHEALHNHYTQKSLSLSPGK |
| 29 | signal sequence | MGWSCIILFLVATATGVHS |
| 30 | 35022(VH-3x-VL)-(5X)-10E8(VH-3x-VL) ScEv amino acid sequence | QGQLVQSGAELKKPGASVKISCKTSGYRFNFYHINWIRQTAGRGPEWM GWISPYSGDKNLAPAFQDRVIMTTDTEVPVTSFTSTGAAYMEIRNLKF DDTGTYFCAKGLLRDGSSTWLPYLWGQGTLLTVSSGGGGSGGGGSGGG GSQSVLTQSASVSGSLGQSVTISCTGPNSVCCSHKSISWYQWPPGRAP TLIIYEDNERAPGISPRFSGYKSYWSAYLTISDLRPEDETTYYCCSYT HNSGCVFGTGTKVSVLGGGGSGGGGSGGGGSGGGGSGGGGSEVQLVES GGGLVKPGGSLRLSCSASGFDFDNAWMTWVRQPPGKGLEWVGRITGPG EGWSVDYAAPVEGRFTISRLNSINFLYLEMNNLRMEDSGLYFCARTGK YYDFWSGYPPGEEYFQDWGRGTLVTVSSGGGGSGGGGSGGGGSSYELT QETGVSVALGRTVTITCRGDSLRSHYASWYQKKPGQAPILLFYGKNNR PSGVPDRFSGSASGNRASLTISGAQAEDDAEYYCSSRDKSGSRLSVFG GGTKLTVLGSGHHHHHH |
| 31 | 35022 variable light (VL) chain amino acid sequence | QSVLTQSASVSGSLGQSVTISCTGPNSVCCSHKSISWYQWPPGRAPTL IIYEDNERAPGISPRFSGYKSYWSAYLTISDLRPEDETTYYCCSYTHN SGCVFGTGTKVSVL |
| 32 | VL-CDR1 | TGPNSVCCSHKSIS |
| 33 | VL-CDR2 | EDNERAP |
| 34 | VL-CDR3 | CSYTHNSGCV |
| 35 | 35022 variable heavy (VH) chain amino acid sequence | QGQLVQSGAELKKPGASVKISCKTSGYRFNFYHINWIRQTAGRGPEWM GWISPYSGDKNLAPAFQDRVIMTTDTEVPVTSFTSTGAAYMEIRNLKF DDTGTYFCAKGLLRDGSSTWLPYLWGQGTLLTVSS |
| 36 | VH-CDR1 | FYHIN |
| 37 | VH-CDR2 | WISPYSGDKNLAPAFQD |
| 38 | VH-CDR3 | GLLRDGSSTWLPYL |
| 39 | 10E8 variable light (VL) chain amino acid sequence | SYELTQETGVSVALGRTVTITCRGDSLRSHYASWYQKKPGQAPILLFY GKNNRPSGVPDRFSGSASGNRASLTISGAQAEDDAEYYCSSRDKSGSR LSVFGGGTKLTVL |
| 40 | VL-CDR1 | RGDSLRSHYAS |
| 41 | VL-CDR2 | GKNNRPS |
| 42 | VL-CDR3 | SSRDKSGSRLSV |
| 43 | 10E8 variable heavy (VH) chain amino acid sequence | EVQLVESGGGLVKPGGSLRLSCSASGFDFDNAWMTWVRQPPGKGLEWV GRITGPGEGWSVDYAAPVEGRFTISRLNSINFLYLEMNNLRMEDSGLY FCARTGKYYDFWSGYPPGEEYFQDWGRGTLVTVSS |
| 44 | VH-CDR1 | NAWMT |
| 45 | VH-CDR2 | RITGPGEGWSVDYAAPVEG |
| 46 | VH-CDR3 | TGKYYDFWSGYPPGEEYFQD |
| 47 | 35022(VH-3x-VL)-(7X)-10E8(VH-3x-VL) ScEv amino acid sequence | QGQLVQSGAELKKPGASVKISCKTSGYRFNFYHINWIRQTAGRGPEWM GWISPYSGDKNLAPAFQDRVIMTTDTEVPVTSFTSTGAAYMEIRNLKF DDTGTYFCAKGLLRDGSSTWLPYLWGQGTLLTVSSGGGGSGGGGSGGG GSQSVLTQSASVSGSLGQSVTISCTGPNSVCCSHKSISWYQWPPGRAP TLIIYEDNERAPGISPRFSGYKSYWSAYLTISDLRPEDETTYYCCSYT HNSGCVFGTGTKVSVLGGGGSGGGGSGGGGSGGGGSGGGGSGGGGSGG GGSEVQLVESGGGLVKPGGSLRLSCSASGFDFDNAWMTWVRQPPGKGL EWVGRITGPGEGWSVDYAAPVEGRFTISRLNSINFLYLEMNNLRMEDS |

TABLE 1 -continued

| SEQ ID NO | Description | Sequence |
|---|---|---|
| | | GLYFCARTGKYYDFWSGYPPGEEYFQDWGRGTLVTVSSGGGGSGGGGS GGGGSSYELTQETGVSVALGRTVTITCRGDSLRSHYASWYQKKPGQAP ILLFYGKNNRPSGVPDRFSGSASGNRASLTISGAQAEDDAEYYCSSRD KSGSRLSVFGGGTKLTVLGSGHHHHHH |
| 48 | 10E8(VH-3x-VL)- (5X)-35022(VH- 3x-VL) ScFv amino acid sequence | EVQLVESGGGLVKPGGSLRLSCSASGFDFDNAWMTWVRQPPGKGLEWV GRITGPGEGWSVDYAAPVEGRFTISRLNSINFLYLEMNNLRMEDSGLY FCARTGKYYDFWSGYPPGEEYFQDWGRGTLVTVSSGGGGSGGGGSGGG GSSYELTQETGVSVALGRTVTITCRGDSLRSHYASWYQKKPGQAPILL FYGKNNRPSGVPDRFSGSASGNRASLTISGAQAEDDAEYYCSSRDKSG SRLSVFGGGTKLTVLGGGGSGGGGSGGGGSGGGGSGGGGSQGQLVQSG AELKKPGASVKISCKTSGYRFNFYHINWIRQTAGRGPEWMGWISPYSG DKNLAPAFQDRVIMTTDTEVPVTSFTSTGAAYMEIRNLKFDDTGTYFC AKGLLRDGSSTWLPYLWGQGTLLTVSSGGGGSGGGGSGGGGSQSVLTQ SASVSGSLGQSVTISCTGPNSVCCSHKSISWYQWPPGRAPTLIIYEDN ERAPGISPRFSGYKSYWSAYLTISDLRPEDETTYYCCSYTHNSGCVFG TGTKVSVLGSGHHHHHH |
| 49 | 10E8(VH-3x-VL)- (7X)-35022(VH- 3x-VL) ScFv amino acid sequence | EVQLVESGGGLVKPGGSLRLSCSASGFDFDNAWMTWVRQPPGKGLEWV GRITGPGEGWSVDYAAPVEGRFTISRLNSINFLYLEMNNLRMEDSGLY FCARTGKYYDFWSGYPPGEEYFQDWGRGTLVTVSSGGGGSGGGGSGGG GSSYELTQETGVSVALGRTVTITCRGDSLRSHYASWYQKKPGQAPILL FYGKNNRPSGVPDRFSGSASGNRASLTISGAQAEDDAEYYCSSRDKSG SRLSVFGGGTKLTVLGGGGSGGGGSGGGGSGGGGSGGGGSGGGGSGGG GSQGQLVQSGAELKKPGASVKISCKTSGYRFNFYHINWIRQTAGRGPE WMGWISPYSGDKNLAPAFQDRVIMTTDTEVPVTSFTSTGAAYMEIRNL KFDDTGTYFCAKGLLRDGSSTWLPYLWGQGTLLTVSSGGGGSGGGGSG GGGSQSVLTQSASVSGSLGQSVTISCTGPNSVCCSHKSISWYQWPPGR APTLIIYEDNERAPGISPRFSGYKSYWSAYLTISDLRPEDETTYYCCS YTHNSGCVFGTGTKVSVLGSGHHHHHH |
| 50 | 35022(VH-3x-VL)- (5X)-10E8(VH-3x- VL) IgG1 amino acid sequence | QGQLVQSGAELKKPGASVKISCKTSGYRFNFYHINWIRQTAGRGPEWM GWISPYSGDKNLAPAFQDRVIMTTDTEVPVTSFTSTGAAYMEIRNLKF DDTGTYFCAKGLLRDGSSTWLPYLWGQGTLLTVSSGGGGSGGGGSGGG GSQSVLTQSASVSGSLGQSVTISCTGPNSVCCSHKSISWYQWPPGRAP TLIIYEDNERAPGISPRFSGYKSYWSAYLTISDLRPEDETTYYCCSYT HNSGCVFGTGTKVSVLGGGGSGGGGSGGGGSGGGGSGGGGSEVQLVES GGGLVKPGGSLRLSCSASGFDFDNAWMTWVRQPPGKGLEWVGRITGPG EGWSVDYAAPVEGRFTISRLNSINFLYLEMNNLRMEDSGLYFCARTGK YYDFWSGYPPGEEYFQDWGRGTLVTVSSGGGGSGGGGSGGGGSSYELT QETGVSVALGRTVTITCRGDSLRSHYASWYQKKPGQAPILLFYGKNNR PSGVPDRFSGSASGNRASLTISGAQAEDDAEYYCSSRDKSGSRLSVFG GGTKLTVLGSGPKSCDKTHTCPPCPAPELLGGPSVFLFPPKPKDTLMI SRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVY TLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSP GK |
| 51 | 35022(VH-3x-VL)- (7X)-10E8(VH-3x- VL) IgG1 amino acid sequence | QGQLVQSGAELKKPGASVKISCKTSGYRFNFYHINWIRQTAGRGPEWM GWISPYSGDKNLAPAFQDRVIMTTDTEVPVTSFTSTGAAYMEIRNLKF DDTGTYFCAKGLLRDGSSTWLPYLWGQGTLLTVSSGGGGSGGGGSGGG GSQSVLTQSASVSGSLGQSVTISCTGPNSVCCSHKSISWYQWPPGRAP TLIIYEDNERAPGISPRFSGYKSYWSAYLTISDLRPEDETTYYCCSYT HNSGCVFGTGTKVSVLGGGGSGGGGSGGGGSGGGGSGGGGSGGGGSGG GGSEVQLVESGGGLVKPGGSLRLSCSASGFDFDNAWMTWVRQPPGKGL EWVGRITGPGEGWSVDYAAPVEGRFTISRLNSINFLYLEMNNLRMEDS GLYFCARTGKYYDFWSGYPPGEEYFQDWGRGTLVTVSSGGGGSGGGGS GGGGSSYELTQETGVSVALGRTVTITCRGDSLRSHYASWYQKKPGQAP ILLFYGKNNRPSGVPDRFSGSASGNRASLTISGAQAEDDAEYYCSSRD KSGSRLSVFGGGTKLTVLGSGPKSCDKTHTCPPCPAPELLGGPSVFLF PPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKA KGQPREPQVYTLPPSREEMTKNQVSLTCLVKGFYPSDIAVEWESNGQP ENNYKTTPPVLDSDGSFFLYSKLTVDKSRWQQGNVFSCSVMHEALHNH YTQKSLSLSPGK |
| 52 | 10E8(VH-3x-VL)- (5X)-35022(VH- 3x-VL) IgG1 amino acid sequence | EVQLVESGGGLVKPGGSLRLSCSASGFDFDNAWMTWVRQPPGKGLEWV GRITGPGEGWSVDYAAPVEGRFTISRLNSINFLYLEMNNLRMEDSGLY FCARTGKYYDFWSGYPPGEEYFQDWGRGTLVTVSSGGGGSGGGGSGGG GSSYELTQETGVSVALGRTVTITCRGDSLRSHYASWYQKKPGQAPILL FYGKNNRPSGVPDRFSGSASGNRASLTISGAQAEDDAEYYCSSRDKSG SRLSVFGGGTKLTVLGGGGSGGGGSGGGGSGGGGSGGGGSQGQLVQSG AELKKPGASVKISCKTSGYRFNFYHINWIRQTAGRGPEWMGWISPYSG DKNLAPAFQDRVIMTTDTEVPVTSFTSTGAAYMEIRNLKFDDTGTYFC AKGLLRDGSSTWLPYLWGQGTLLTVSSGGGGSGGGGSGGGGSQSVLTQ SASVSGSLGQSVTISCTGPNSVCCSHKSISWYQWPPGRAPTLIIYEDN |

TABLE 1 -continued

| SEQ ID NO | Description | Sequence |
|---|---|---|
|  |  | ERAPGISPRFSGYKSYWSAYLTISDLRPEDETTYYCCSYTHNSGCVFG TGTKVSVLGSGPKSCDKTHTCPPCPAPELLGGPSVFLFPPKPKDTLMI SRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVY TLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSP GK |
| 53 | 10E8(VH-3x-VL)-(7X)-35022(VH-3x-VL) IgG1 amino acid sequence | EVQLVESGGGLVKPGGSLRLSCSASGFDFDNAWMTWVRQPPGKGLEWV GRITGPGEGWSVDYAAPVEGRFTISRLNSINFLYLEMNNLRMEDSGLY FCARTGKYYDFWSGYPPGEEYFQDWGRGTLVTVSSGGGGSGGGGSGGG GSSYELTQETGVSVALGRTVTITCRGDSLRSHYASWYQKKPGQAPILL FYGKNNRPSGVPDRFSGSASGNRASLTISGAQAEDDAEYYCSSRDKSG SRLSVFGGGTKLTVLGGGGSGGGGSGGGGSGGGGSGGGGSGGGGSGGG GSQGQLVQSGAELKKPGASVKISCKTSGYRFNFYHINWIRQTAGRGPE WMGWISPYSGDKNLAPAFQDRVIMTTDTEVPVTSFTSTGAAYMEIRNL KFDDTGTYFCAKGLLRDGSSTWLPYLWGQGTLLTVSSGGGGSGGGGSG GGGSQSVLTQSASVSGSLGQSVTISCTGPNSVCCSHKSISWYQWPPGR APTLIIYEDNERAPGISPRFSGYKSYWSAYLTISDLRPEDETTYYCCS YTHNSGCVFGTGTKVSVLGSGPKSCDKTHTCPPCPAPELLGGPSVFLF PPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKA KGQPREPQVYTLPPSREEMTKNQVSLTCLVKGFYPSDIAVEWESNGQP ENNYKTTPPVLDSDGSFFLYSKLTVDKSRWQQGNVFSCSVMHEALHNH YTQKSLSLSPGK |

In one embodiment, the disclosure provides an antibody, or an antigen-binding fragment thereof, that binds to comprises a heavy chain having a variable domain comprising an amino acid sequence as set forth in SEQ ID NO. 6. In one embodiment, the disclosure provides an antibody, or an antigen-binding fragment thereof, that comprises a light chain having a variable domain comprising an amino acid sequence as set forth in SEQ ID NO. 2. In one embodiment, the disclosure provides an antibody, or an antigen-binding fragment thereof, that comprises a light chain having a variable domain comprising an amino acid sequence as set forth in SEQ ID NO. 2, and a heavy chain having a variable domain comprising an amino acid sequence as set forth in SEQ ID NO. 6. In one embodiment, the antibody, or a fragment thereof, binds to an epitope that is located in the CD4-binding site (CD4bs).

In one embodiment, the disclosure provides an antibody, or an antigen-binding fragment thereof, that binds to comprises a heavy chain having a variable domain comprising an amino acid sequence as set forth in SEQ ID NO. 14. In one embodiment, the disclosure provides an antibody, or an antigen-binding fragment thereof, that comprises a light chain having a variable domain comprising an amino acid sequence as set forth in SEQ ID NO. 10. In one embodiment, the disclosure provides an antibody, or an antigen-binding fragment thereof, that comprises a light chain having a variable domain comprising an amino acid sequence as set forth in SEQ ID NO. 10, and a heavy chain having a variable domain comprising an amino acid sequence as set forth in SEQ ID NO. 14. In one embodiment, the antibody, or a fragment thereof, binds to an epitope that is located in the V3-glycan region.

In one embodiment, the disclosure provides an antibody, or an antigen-binding fragment thereof, that binds to comprises a heavy chain having a variable domain comprising an amino acid sequence as set forth in SEQ ID NO. 6. In one embodiment, the disclosure provides an antibody, or an antigen-binding fragment thereof, that comprises a light chain having a variable domain comprising an amino acid sequence as set forth in SEQ ID NO. 19. In one embodiment, the disclosure provides an antibody, or an antigen-binding fragment thereof, that comprises a light chain having a variable domain comprising an amino acid sequence as set forth in SEQ ID NO. 19, and a heavy chain having a variable domain comprising an amino acid sequence as set forth in SEQ ID NO. 6. In one embodiment, the antibody, or a fragment thereof, binds to an epitope that is located in the CD4-binding site (CD4bs).

In one embodiment, the disclosure provides an antibody, or an antigen-binding fragment thereof, that binds to comprises a heavy chain having a variable domain comprising an amino acid sequence as set forth in SEQ ID NO. 35. In one embodiment, the disclosure provides an antibody, or an antigen-binding fragment thereof, that comprises a light chain having a variable domain comprising an amino acid sequence as set forth in SEQ ID NO. 31. In one embodiment, the disclosure provides an antibody, or an antigen-binding fragment thereof, that comprises a light chain having a variable domain comprising an amino acid sequence as set forth in SEQ ID NO. 31, and a heavy chain having a variable domain comprising an amino acid sequence as set forth in SEQ ID NO. 35. In one embodiment, the antibody, or a fragment thereof, binds to an epitope that is located in the gp120-gp41 interface.

In one embodiment, the disclosure provides an antibody, or an antigen-binding fragment thereof, that binds to comprises a heavy chain having a variable domain comprising an amino acid sequence as set forth in SEQ ID NO. 43. In one embodiment, the disclosure provides an antibody, or an antigen-binding fragment thereof, that comprises a light chain having a variable domain comprising an amino acid sequence as set forth in SEQ ID NO. 39. In one embodiment, the disclosure provides an antibody, or an antigen-binding fragment thereof, that comprises a light chain having a variable domain comprising an amino acid sequence as set forth in SEQ ID NO. 39, and a heavy chain having a variable domain comprising an amino acid sequence as set forth in SEQ ID NO. 43. In one embodiment, the antibody, or a fragment thereof, binds to an epitope that is located in the gp41 membrane proximal external region (MPER).

In one embodiment, the present disclosure provides a human antibody or antigen-binding fragment, has a heavy chain variable domain sequence which is at least 95% identical, at least 96% identical, at least 97% identical, at least 98% identical, or at least 99% identical, or identical, to an amino acid sequence selected from the group consisting of SEQ ID NO. 6, SEQ ID NO. 14, SEQ ID NO. 35, and SEQ ID NO. 43, and has a light chain variable domain sequence that is at least 95% identical, at least 96% identical, at least 97% identical, at least 98% identical, or at least 99% identical, or identical to an amino acid sequence selected from the group consisting of SEQ ID NO. 2, SEQ ID NO. 10, SEQ ID NO. 19, SEQ ID NO. 31, and SEQ ID NO. 39.

In one embodiment, the disclosure features an isolated antibody comprising a heavy chain/light chain variable domain amino acid sequence selected from the group consisting of SEQ ID NO. 6/SEQ ID NO. 2, SEQ ID NO. 14/SEQ ID NO. 10, SEQ ID NO. 6/SEQ ID NO. 19, SEQ ID NO. 35/SEQ ID NO. 31, and SEQ ID NO. 43/SEQ ID NO. 39.

Complementarity determining regions (CDRs) are known as hypervariable regions both in the light chain and the heavy chain variable domains of an antibody. The more highly conserved portions of variable domains are called the framework (FR). Complementarity determining regions (CDRs) and framework regions (FR) of a given antibody may be identified using systems known in the art, such as those described by Kabat et al. supra; Lefranc et al., supra and/or Honegger and Pluckthun, supra. For example, the numbering system described in Kabat et al. (1991, NIH Publication 91-3242, National Technical Information Service, Springfield, Va.) is well known to those in the art. Kabat et al. defined a numbering system for variable domain sequences that is applicable to any antibody. One of ordinary skill in the art can unambiguously assign this system of "Kabat numbering" to any variable domain amino acid sequence, without reliance on any experimental data beyond the sequence itself.

In certain embodiments, the present disclosure provides an antibody comprising the CDRs of the heavy and light chain variable domains described in Table 1. For example, the disclosure provides an antibody, or antigen-binding fragment thereof, comprising a heavy chain variable region having the CDRs described in an amino acid sequence as set forth in any one of SEQ ID NO. 6, SEQ ID NO. 14, SEQ ID NO. 35, and SEQ ID NO. 43. In one embodiment, the disclosure provides an antibody, or antigen-binding fragment thereof, comprising a light chain variable region having the CDRs described in an amino acid sequence as set forth in any one of SEQ ID NO. 2, SEQ ID NO. 10, SEQ ID NO. 19, SEQ ID NO. 31, and SEQ ID NO. 39. In one embodiment, the disclosure provides an antibody, or antigen-binding fragment thereof, comprising a light chain variable region having the CDRs described in an amino acid sequence as set forth in any one of SEQ ID NO. 2, SEQ ID NO. 10, SEQ ID NO. 19, SEQ ID NO. 31, and SEQ ID NO. 39; and a heavy chain variable region having the CDRs described in an amino acid sequence as set forth in any one of SEQ ID NO. 6, SEQ ID NO. 14, SEQ ID NO. 35, and SEQ ID NO. 43.

In one embodiment, the present disclosure features an antibody, or an antigen-binding fragment thereof, comprising a heavy chain variable domain comprising a heavy chain CDR set (CDR1, CDR2, and CDR3) selected from the group consisting of SEQ ID NO. 7, SEQ ID NO. 8 and SEQ ID NO. 9; SEQ ID NO. 15, SEQ ID NO. 16 and SEQ ID NO. 17; SEQ ID NO. 36, SEQ ID NO. 37 and SEQ ID NO. 38; and SEQ ID NO. 44, SEQ ID NO. 45 and SEQ ID NO. 46, and a light chain variable domain comprising a light chain CDR set (CDR1, CDR2, and CDR3) selected from the group consisting of SEQ ID NO. 3, SEQ ID NO. 4 and SEQ ID NO. 5; SEQ ID NO. 11, SEQ ID NO. 12 and SEQ ID NO. 13; SEQ ID NO. 32, SEQ ID NO. 33 and SEQ ID NO. 34; and SEQ ID NO. 40, SEQ ID NO. 41 and SEQ ID NO. 42.

In one embodiment, the antibody of the disclosure comprises a heavy chain CDR set/light chain CDR set selected from the group consisting of the heavy chain variable domain CDR set of SEQ ID NO. 7, SEQ ID NO. 8 and SEQ ID NO. 9/the light chain variable domain CDR set of SEQ ID NO. 3, SEQ ID NO. 4 and SEQ ID NO. 5; the heavy chain variable domain CDR set of SEQ ID NO. 15, SEQ ID NO. 16 and SEQ ID NO. 17/the light chain variable domain CDR set of SEQ ID NO. 11, SEQ ID NO. 12 and SEQ ID NO. 13; the heavy chain variable domain CDR set of SEQ ID NO. 36, SEQ ID NO. 37 and SEQ ID NO. 38/the light chain variable domain CDR set of SEQ ID NO. 32, SEQ ID NO. 33 and SEQ ID NO. 34; and the heavy chain variable domain CDR set of SEQ ID NO. 44, SEQ ID NO. 45 and SEQ ID NO. 46/the light chain variable domain CDR set of SEQ ID NO. 40, SEQ ID NO. 41 and SEQ ID NO. 42.

One or more CDRs may be incorporated into a molecule either covalently or noncovalently to make it an antigen binding protein.

An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

In one embodiment, the present disclosure is directed to an antibody, or an antigen binding fragment thereof, having the antigen binding regions of any of the antibodies described in Table 1.

In one embodiment, the present disclosure is directed to an antibody, or an antigen binding fragment thereof, having antigen binding regions of antibody VRC01. In one embodiment, the disclosure provides an antibody, or antigen-binding fragment thereof, comprising a heavy chain variable domain sequence as set forth in SEQ ID NO. 6, and a light chain variable domain sequence as set forth in SEQ ID NO. 2. In one embodiment, the disclosure is directed to an antibody having a heavy chain variable domain comprising the CDRs of SEQ ID NO. 6, and a light chain variable domain comprising the CDRs of SEQ ID NO. 2. In one embodiment, the disclosure features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 6, and comprises a light chain variable region having an amino acid sequence that is at least 95% identical, at least 96% identical, at least 97% identical, at least 98% identical, or at least 99% identical to the sequence set forth in SEQ ID NO. 2. In one embodiment, the disclosure features an antibody, or an antigen-binding portion thereof, having antigen binding regions of antibody VRC01, comprising a heavy chain variable region comprising a CDR3 domain comprising the amino acid as set forth in SEQ ID NO. 9, a CDR2 domain comprising the amino acid sequence as set forth in SEQ ID NO. 8, and a CDR1 domain comprising the amino acid sequence as set forth in SEQ ID NO. 7; and comprising a light chain variable region comprising a CDR3 domain comprising the amino acid as set forth in SEQ ID NO. 5, a CDR2 domain comprising the amino acid sequence as set forth in SEQ ID NO. 4, and a CDR1 domain comprising the amino acid sequence as set forth in SEQ ID NO. 3.

In one embodiment, the present disclosure is directed to an antibody, or an antigen binding fragment thereof, having antigen binding regions of antibody PGT121. In one embodiment, the disclosure provides an antibody, or antigen-binding fragment thereof, comprising a heavy chain variable domain sequence as set forth in SEQ ID NO. 14, and a light chain variable domain sequence as set forth in SEQ ID NO. 10. In one embodiment, the disclosure is directed to an antibody having a heavy chain variable domain comprising the CDRs of SEQ ID NO. 14, and a light chain variable domain comprising the CDRs of SEQ ID NO. 10. In one embodiment, the disclosure features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 14, and comprises a light chain variable region having an amino acid sequence that is at least 95% identical, at least 96% identical, at least 97% identical, at least 98% identical, or at least 99% identical to the sequence set forth in SEQ ID NO. 10. In one embodiment, the disclosure features an antibody, or an antigen-binding portion thereof, having antigen binding regions of antibody PGT121, comprising a heavy chain variable region comprising a CDR3 domain comprising the amino acid as set forth in SEQ ID NO. 17, a CDR2 domain comprising the amino acid sequence as set forth in SEQ ID NO. 16, and a CDR1 domain comprising the amino acid sequence as set forth in SEQ ID NO. 15; and comprising a light chain variable region comprising a CDR3 domain comprising the amino acid as set forth in SEQ ID NO. 13, a CDR2 domain comprising the amino acid sequence as set forth in SEQ ID NO. 12, and a CDR1 domain comprising the amino acid sequence as set forth in SEQ ID NO. 11.

In one embodiment, the present disclosure is directed to an antibody, or an antigen binding fragment thereof, having antigen binding regions of antibody 35022. In one embodiment, the disclosure provides an antibody, or antigen-binding fragment thereof, comprising a heavy chain variable domain sequence as set forth in SEQ ID NO. 35, and a light chain variable domain sequence as set forth in SEQ ID NO. 31. In one embodiment, the disclosure is directed to an antibody having a heavy chain variable domain comprising the CDRs of SEQ ID NO. 35, and a light chain variable domain comprising the CDRs of SEQ ID NO. 31. In one embodiment, the disclosure features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 35, and comprises a light chain variable region having an amino acid sequence that is at least 95% identical, at least 96% identical, at least 97% identical, at least 98% identical, or at least 99% identical to the sequence set forth in SEQ ID NO. 31. In one embodiment, the disclosure features an antibody, or an antigen-binding portion thereof, having antigen binding regions of antibody 35022, comprising a heavy chain variable region comprising a CDR3 domain comprising the amino acid as set forth in SEQ ID NO. 38, a CDR2 domain comprising the amino acid sequence as set forth in SEQ ID NO. 37, and a CDR1 domain comprising the amino acid sequence as set forth in SEQ ID NO. 36; and comprising a light chain variable region comprising a CDR3 domain comprising the amino acid as set forth in SEQ ID NO. 34, a CDR2 domain comprising the amino acid sequence as set forth in SEQ ID NO. 33, and a CDR1 domain comprising the amino acid sequence as set forth in SEQ ID NO. 32.

In one embodiment, the present disclosure is directed to an antibody, or an antigen binding fragment thereof, having antigen binding regions of antibody 10E8. In one embodiment, the disclosure provides an antibody, or antigen-binding fragment thereof, comprising a heavy chain variable domain sequence as set forth in SEQ ID NO. 43, and a light chain variable domain sequence as set forth in SEQ ID NO. 39. In one embodiment, the disclosure is directed to an antibody having a heavy chain variable domain comprising the CDRs of SEQ ID NO. 43, and a light chain variable domain comprising the CDRs of SEQ ID NO. 39. In one embodiment, the disclosure features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 43, and comprises a light chain variable region having an amino acid sequence that is at least 95% identical, at least 96% identical, at least 97% identical, at least 98% identical, or at least 99% identical to the sequence set forth in SEQ ID NO. 39. In one embodiment, the disclosure features an antibody, or an antigen-binding portion thereof, having antigen binding regions of antibody 10E8, comprising a heavy chain variable region comprising a CDR3 domain comprising the amino acid as set forth in SEQ ID NO. 46, a CDR2 domain comprising the amino acid sequence as set forth in SEQ ID NO. 45, and a CDR1 domain comprising the amino acid sequence as set forth in SEQ ID NO. 44; and comprising a light chain variable region comprising a CDR3 domain comprising the amino acid as set forth in SEQ ID NO. 42, a CDR2 domain comprising the amino acid sequence as set forth in SEQ ID NO. 41, and a CDR1 domain comprising the amino acid sequence as set forth in SEQ ID NO. 40.

In one embodiment, the present disclosure is directed to an antibody, or an antigen binding fragment thereof, having antigen binding regions of antibody VRC01 VL(Δ1,2-V3S). In one embodiment, the disclosure provides an antibody, or antigen-binding fragment thereof, comprising a heavy chain variable domain sequence as set forth in SEQ ID NO. 43, and a light chain variable domain sequence as set forth in SEQ ID NO. 39. In one embodiment, the disclosure is directed to an antibody having a heavy chain variable domain comprising the CDRs of SEQ ID NO. 43, and a light chain variable domain comprising the CDRs of SEQ ID NO. 39. In one embodiment, the disclosure features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 43, and comprises a light chain variable region having an amino acid sequence that is at least 95% identical, at least 96% identical, at least 97% identical, at least 98% identical, or at least 99% identical to the sequence set forth in SEQ ID NO. 39. In one embodiment, the disclosure features an antibody, or an antigen-binding portion thereof, having antigen binding regions of antibody VRC01 VL(Δ1,2-V3S), comprising a heavy chain variable region comprising a CDR3 domain comprising the amino acid as set forth in SEQ ID NO. 46, a CDR2 domain comprising the amino acid sequence as set forth in SEQ ID NO. 45, and a CDR1 domain comprising the amino acid sequence as set forth in SEQ ID NO. 44; and comprising a light chain variable region comprising a CDR3 domain comprising the amino acid as set forth in SEQ ID NO. 42, a CDR2 domain comprising the amino acid sequence as set forth in SEQ ID NO. 41, and a CDR1 domain comprising the amino acid sequence as set forth in SEQ ID NO. 40.

The antibody of the disclosure may be of an IgG class. The antibody of the disclosure may further be an IgG1 isotype.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides (VL and VH). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different VL and VH-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol. Biol. 178:379-87.

In one embodiment, the present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical, at least 96% identical, at least 97% identical, at least 98% identical, at least 99% identical, or 100% identical to the amino acid sequences selected from the group consisting of SEQ ID NO. 6, SEQ ID NO. 14, SEQ ID NO. 35, and SEQ ID NO. 43; and that has a light chain variable domain sequence that is at least 95% identical, at least 96% identical, at least 97% identical, at least 98% identical, at least 99%, or 100% identical to the amino acid sequence consisting of SEQ ID NO. 2, SEQ ID NO. 10, SEQ ID NO. 19, SEQ ID NO. 31, and SEQ ID NO. 39. Preferably, the single chain antibody has both a heavy chain variable domain region and a light chain variable domain region, wherein the single chain human antibody has a heavy chain/light chain variable domain sequence selected from the group consisting of SEQ ID NO. 6/SEQ ID NO. 2, SEQ ID NO. 14/SEQ ID NO. 10, SEQ ID NO. 6/SEQ ID NO. 19, SEQ ID NO. 35/SEQ ID NO. 31, and SEQ ID NO. 43/SEQ ID NO. 39.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype (Lantto et al., 2002, Methods Mol. Biol. 178:303-16).

The present disclosure provides a number of antibodies structurally characterized by the amino acid sequences of their variable domain regions. However, the amino acid sequences can undergo some changes while retaining their high degree of binding to their specific targets. More specifically, many amino acids in the variable domain region can be changed with conservative substitutions and it is predictable that the binding characteristics of the resulting antibody will not differ from the binding characteristics of the wild type antibody sequence. There are many amino acids in an antibody variable domain that do not directly interact with the antigen or impact antigen binding and are not critical for determining antibody structure. For example, a predicted nonessential amino acid residue in any of the disclosed antibodies is preferably replaced with another amino acid residue from the same class. Methods of identifying amino acid conservative substitutions which do not eliminate antigen binding are well-known in the art (see, e.g., Brummell et al., Biochem. 32: 1180-1187 (1993); Kobayashi et al. Protein Eng. 12(10):879-884 (1999); and Burks et al. Proc. Natl. Acad. Sci. USA 94:412-417 (1997), all of which are incorporated by reference in their entireties herein). Near et al. Mol. Immunol. 30:369-377, 1993 explains how to impact or not impact binding through site-directed mutagenesis. Near et al. only mutated residues that they thought had a high probability of changing antigen binding. Most had a modest or negative effect on binding affinity (Near et al. Table 3) and binding to different forms of digoxin (Near et al. Table 2).

A conservative modification or functional equivalent of a peptide, polypeptide, or protein disclosed in this disclosure (e.g., the hinge region or a heavy chain having the hinge region) refers to a polypeptide derivative of the peptide, polypeptide, or protein, e.g., a protein having one or more point mutations, insertions, deletions, truncations, a fusion protein, or a combination thereof. It retains substantially the activity to of the parent peptide, polypeptide, or protein (such as those disclosed in this disclosure). In general, a conservative modification or functional equivalent is at least 60% (e.g., any number between 60% and 100%, inclusive, e.g., 60%, 70%, 75%, 80%, 85%, 90%, 95%, 96%, 97%, 98%, and 99%) identical to a parent (e.g., one of SEQ ID NOs: 1-53).

In one embodiment, the substitutions made within a heavy or light chain that is at least 95% identical (or at least 96% identical, or at least 97% identical, or at least 98% identical, or at least 99% identical) are conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3)

amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4: 11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present disclosure can further be used as a "query sequence" to perform a search against public databases to, for example, identify related sequences. Such searches can be performed using the XBLAST program (version 2.0) of Altschul, et al. (1990) J. Mol. Biol. 215:403-10. BLAST protein searches can be performed with the XBLAST program, score=50, wordlength=3 to obtain amino acid sequences homologous to the molecules of the disclosure. To obtain gapped alignments for comparison purposes, Gapped BLAST can be utilized as described in Altschul et al, (1997) Nucleic Acids Res. 25(17):3389-3402. When utilizing BLAST and Gapped BLAST programs, the default parameters of the respective programs {e.g., XBLAST and NBLAST) can be used. (See www.ncbi.nlm.nih.gov).

Other modifications of the antibody are contemplated herein. For example, the antibody can be linked to one of a variety of nonproteinaceous polymers, for example, polyethylene glycol, polypropylene glycol, polyoxyalkylenes, or copolymers of polyethylene glycol and polypropylene glycol. The antibody also can be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in, for example, Remington's Pharmaceutical Sciences, 16th edition, Oslo, A., Ed., (1980).

Variant antibodies and salts thereof also are included within the scope of the disclosure. Variants of the sequences recited in the application also are included within the scope of the disclosure. Further variants of the antibody sequences having improved affinity can be obtained using methods known in the art and are included within the scope of the disclosure. For example, amino acid substitutions can be used to obtain antibodies with further improved affinity. Alternatively, codon optimization of the nucleotide sequence can be used to improve the efficiency of translation in expression systems for the production of the antibody. Variants may include non-natural amino acids up to a certain percentage. In some embodiments, the antibody comprises a variant amino acid sequence comprising about 1, 2, 3, 4, 5, 6, 7, 8, 9, 10, 11, 12, 13, 14, 15, 16, 17, 18, 19, 20 or more percent of non-natural amino acids.

Antibody Modifications

Humanization and Primatization

In cases where the multispecific antibody or the antibodies forming the multispecific antibody are non-human antibodies, the antibody can be "humanized" to reduce immunogenicity to a human recipient. Methods for humanizing non-human antibodies have been described in the art. See, e.g., Jones et al., Nature 321:522-525 (1986); Riechmann et al, Nature 332:323-327 (1988); Verhoeyen et al., Science 239: 1534-1536 (1988), and U.S. Pat. No. 4,816,567. Generally, residues from the variable domain of a non-human antibody are "imported" into a human immunoglobulin molecule, resulting in antibodies in which some hypervariable region residues and possibly some FR residues of a human antibody are substituted by residues from analogous sites of non-human antibodies. It is important to humanize a non-human antibody while retaining high affinity for the antigen. To this end, three dimensional immunoglobulin models are commonly available and suitable for use in analyzing proposed humanized sequences in comparison to the parental non-human antibodies. Such analysis permits identification of residues likely involved in recognition and binding of the antigen, and therefore rational design of humanized sequences that retain the specificity and affinity for the antigen.

In specific embodiments, multispecific antibodies are formed from anti-HIV human or humanized antibodies.

Similarly, a tri-specific fusion antibody or the three antibodies forming the fusion can be "primatized" to reduce immunogenicity to another primate, non-human recipient, e.g., a rhesus recipient. Residues from the variable domain of a donor antibody (such as a non-primate antibody or an antibody of a primate species different from the recipient primate) are "imported" into a nonhuman primate recipient immunoglobulin molecule, resulting in antibodies in which some hypervariable region residues and possibly some FR residues of a nonhuman primate antibody are substituted by residues from analogous sites of donor antibodies. Alternatively, primatized antibodies can be made for use in a desirable primate species by using a recipient immunoglobulin having non-primate sequences or sequences from a different primate species by introducing the Fc fragment, and/or residues, including particularly framework region residues, from the desirable primate, into the recipient immunoglobulin.

Affinity Maturation

One or more hypervariable region residues of an antibody can be substituted to select for variants that have improved biological properties relative to the parent antibody by employing, e.g., affinity maturation using phage or yeast display. For example, the Fab region of an anti-HIV antibody can be mutated at several sites selected based on available structural information to generate all possible amino substitutions at each site. The antibody variants thus generated are displayed in a monovalent fashion from phage particles or on the surface of yeast cells. The displayed variants are then screened for their biological activity (e.g. binding affinity).

Modifications to the Fc Region

The antibody can be modified to improve certain biological properties of the antibody, e.g., to improve stability, to enhance or reduce effector functions such as antigen-dependent cell-mediated cyotoxicity (ADCC) and/or complement dependent cytotoxicity (CDC) of the antibody, improved or decreased internalization and/or recycling, among others.

For example, the Fc fragment of some antibodies (derived from human Ig4) can be replaced with human IgG1 that increases effector function mediated through FcRs (except FcRn). Such modification may improve the stability of the resulting antibody by about 5 fold. In another example, the IgG1 Fc fragment can be modified to improve the recycling of the antibody via the antibody salvage pathway.

Still another type of modification involves alteration of the glycosylation pattern of a parent antibody, including deletions of one or more carbohydrate moieties found in the parent antibody, or addition of one or more carbohydrates (via addition of one or more glycosylation sites) that are not present in the parent antibody.

Multispecific bNAbs Comprising Tetra-Glycine-Serine (G4S) Peptide Linkers

As discussed herein, a variety of broadly neutralizing antibodies (bnAbs) have been isolated from HIV-1-infected individuals, but their potential to treat or prevent infection in humans may be limited by the potency or breadth of viruses neutralized. The present disclosure describes combinations of bnAbs that optimize potency and breadth of protection, thus reducing the likelihood of resistance and viral escape. Because multiple antibodies may help to reduce the viral replication that sustains chronic HIV-1 infection, the present disclosure reports the generation of multispecific antibodies designed to increase the potential efficacy of HIV-1 antibodies for prevention or therapy.

In one embodiment, the multispecific antibody is capable of binding two different antigen targets. In one embodiment, the multispecific antibody is capable of binding three different antigen targets. In one embodiment, the multispecific antibody is capable of binding four different antigen targets. In one embodiment, the multispecific antibody is capable of binding five different antigen targets.

In one embodiment, the disclosure features a multispecific antibody that binds two or more non-overlapping epitopes, wherein the non-overlapping epitopes are located in the CD4-binding site, the V1/V2-glycan region, the V3-glycan region, the gp41 membrane proximal external region (MPER), or the gp120/gp41 interface of the HIV envelope protein, wherein the multispecific antibody has an $IC_{50}$ less than 0.1 μg/ml, an $IC_{50}$ less than 0.09 μg/ml, an $IC_{50}$ less than 0.08 μg/ml, an $IC_{50}$ less than 0.07 μg/ml, an $IC_{50}$ less than 0.06 μg/ml, an $IC_{50}$ less than 0.05 μg/ml, an $IC_{50}$ less than 0.04 μg/ml, an $IC_{50}$ less than 0.03 μg/ml, an $IC_{50}$ less than 0.02 μg/ml, and $IC_{50}$ less than 0.01 μg/ml.

In one embodiment, the disclosure features a multispecific antibody that binds two or more non-overlapping epitopes, wherein the non-overlapping epitopes are located in the CD4-binding site, the V1/V2-glycan region, the V3-glycan region, the gp41 membrane proximal external region (MPER), or the gp120/gp41 interface of the HIV envelope protein, wherein the multispecific antibody has an $IC_{80}$ less than 0.3 μg/ml, an $IC_{80}$ less than 0.2 μg/ml, an $IC_{80}$ less than 0.1 μg/ml.

In one embodiment, the disclosure features a multispecific antibody that binds two or more non-overlapping epitopes, wherein a first antibody binds an epitope in the CD4-binding site of the HIV envelope protein, and the second antibody binds an epitope in the V3-glycan region of the HIV envelope protein, wherein the multispecific antibody has an $IC_{50}$ less than 0.1 μg/ml, an $IC_{50}$ less than 0.09 μg/ml, an $IC_{50}$ less than 0.08 μg/ml, an $IC_{50}$ less than 0.07 μg/ml, an $IC_{50}$ less than 0.06 μg/ml, an $IC_{50}$ less than 0.05 μg/ml, an $IC_{50}$ less than 0.04 μg/ml, an $IC_{50}$ less than 0.03 μg/ml, an $IC_{50}$ less than 0.02 μg/ml, and $IC_{50}$ less than 0.01 μg/ml.

In one embodiment, the disclosure features a multispecific antibody that binds two or more non-overlapping epitopes, wherein a first antibody binds an epitope in the gp120/gp41 interface of the HIV envelope protein, and the second antibody binds an epitope in the MPER of the envelope protein, wherein the multispecific antibody has an $IC_{50}$ less than 0.1 μg/ml, an $IC_{50}$ less than 0.09 μg/ml, an $IC_{50}$ less than 0.08 μg/ml, an $IC_{50}$ less than 0.07 μg/ml, an $IC_{50}$ less than 0.06 μg/ml, an $IC_{50}$ less than 0.05 μg/ml, an $IC_{50}$ less than 0.04 μg/ml, an $IC_{50}$ less than 0.03 μg/ml, an $IC_{50}$ less than 0.02 μg/ml, and $IC_{50}$ less than 0.01 μg/ml.

In one aspect, the disclosure features a multispecific antibody, or an antigen-binding fragment thereof, comprising a) a first light chain comprising a first light chain variable region (VL) and a first heavy chain comprising a first heavy chain variable region (VH), wherein the first light chain and the first heavy chain are derived from a first antibody or an antigen-binding fragment thereof; and b) a second light chain comprising a second light chain variable region (VL) and a second heavy chain comprising a second heavy chain variable region (VH), wherein the second light chain and the second heavy chain are derived from a second antibody or an antigen-binding fragment thereof, wherein the first antibody and the second antibody bind non-overlapping epitopes of the envelope protein of human immunodeficiency virus-1 (HIV-1), and wherein the VH from the first light chain and the VL from the second light chain are connected by two or more tetra-glycine serine (G4S) protein linkers or wherein the VL from the first light chain and the VH from the second light chain are connected by two or more tetra-glycine serine (G4S) proteinone or more linkers.

In one embodiment, the multispecific antibody has an $IC_{50}$ less than 0.1 μg/ml. In one embodiment, the multispecific antibody has an $IC_{50}$ less than 0.09 μg/ml. In one embodiment, the multispecific antibody has an $IC_{50}$ less than 0.08 μg/ml. In one embodiment, the multispecific antibody has an $IC_{50}$ less than 0.07 μg/ml. In one embodiment, the multispecific antibody has an $IC_{50}$ less than 0.06 μg/ml. In one embodiment, the multispecific antibody has an $IC_{50}$ less than 0.05 μg/ml. In one embodiment, the multispecific antibody has an $IC_{50}$ less than 0.04 μg/ml. In one embodiment, the multispecific antibody has an $IC_{50}$ less than 0.03 μg/ml. In one embodiment, the multispecific antibody has an $IC_{50}$ less than 0.02 μg/ml. In one embodiment, the multispecific antibody has an $IC_{50}$ less than 0.01 μg/ml. In one embodiment, the multispecific antibody has an $IC_{50}$ between 0.01 and 0.1 μg/ml.

In one embodiment, the multispecific antibody has an $IC_{80}$ less than 0.3 μg/ml. In one embodiment, the multispecific antibody has an $IC_{80}$ less than 0.2 μg/ml. In one embodiment, the multispecific antibody has an $IC_{80}$ less than 0.1 μg/ml. In one embodiment, the multispecific antibody has an $IC_{80}$ between 0.1 and 0.3 μg/ml.

In one embodiment, the linker is a tetra-glycerine-serine (G4S) linker. In some embodiments, linker comprises 1, 2, 3, 4, 5, 6, 7 or more G4S linkers.

In one embodiment, the VH from the first light chain and the VL from the second light chain are connected by two tetra-glycine serine (G4S) protein linkers. In another embodiment, the VL from the first light chain and the VH from the second light chain are connected by two tetra-glycine serine (G4S) protein linkers.

In one embodiment, the VH from the first light chain and the VL from the second light chain are connected by three tetra-glycine serine (G4S) protein linkers. In another embodiment, the VL from the first light chain and the VH from the second light chain are connected by three tetra-glycine serine (G4S) protein linkers.

In one embodiment, the VH from the first light chain and the VL from the second light chain are connected by four tetra-glycine serine (G4S) protein linkers. In another embodiment, the VL from the first light chain and the VH from the second light chain are connected by four tetra-glycine serine (G4S) protein linkers.

In one embodiment, the VH from the first light chain and the VL from the second light chain are connected by five tetra-glycine serine (G4S) protein linkers. In another embodiment, the VL from the first light chain and the VH from the second light chain are connected by five tetra-glycine serine (G4S) protein linkers.

In one embodiment, the VH from the first light chain and the VL from the second light chain are connected by six tetra-glycine serine (G4S) protein linkers. In another embodiment, the VL from the first light chain and the VH from the second light chain are connected by six tetra-glycine serine (G4S) protein linkers.

In one embodiment, the VH from the first light chain and the VL from the second light chain are connected by seven tetra-glycine serine (G4S) protein linkers. In another embodiment, the VL from the first light chain and the VH from the second light chain are connected by seven tetra-glycine serine (G4S) protein linkers.

In one embodiment, the linker is not a single glycine (Gly) residue; a diglycine peptide (Gly-Gly); a tripeptide (Gly-Gly-Gly); a peptide with four glycine residues (Gly-Gly-Gly-Gly); a peptide with five glycine residues (Gly-Gly-Gly-Gly-Gly); a peptide with six glycine residues (Gly-Gly-Gly-Gly-Gly-Gly); a peptide with seven glycine residues (Gly-Gly-Gly-Gly-Gly-Gly-Gly); a peptide with eight glycine residues (Gly-Gly-Gly-Gly-Gly-Gly-Gly-Gly), the peptide Gly-Gly-Gly-Gly-Ser, the peptide Gly-Gly-Gly-Gly-Ser-Gly-Gly-Gly-Gly-Ser, the peptide Gly-Gly-Gly-Gly-Ser-Gly-Gly-Gly-Gly-Ser-Gly-Gly-Gly-Gly-Ser (SEQ ID NO: 292), a single Ser, a single Va, the dipeptide Arg-Thr, Gln-Pro, Ser-Ser, Thr-Lys, and Ser-Leu; Thr-Lys-Gly-Pro-Ser, Thr-Val-Ala-Ala-Pro, Gln-Pro-Lys-Ala-Ala, Gln-Arg-Ile-Glu-Gly, Ala-Ser-Thr-Lys-Gly-Pro-Ser, Arg-Thr-Val-Ala-Ala-Pro-Ser, Gly-Gln-Pro-Lys-Ala-Ala-Pro, and His-Ile-Asp-Ser-Pro-Asn-Lys.

In one embodiment, the non-overlapping epitopes are located in the CD4-binding site, the V1/V2-glycan region, the V3-glycan region, the gp41 membrane proximal external region (MPER), or the gp120/gp41 interface of the envelope protein.

In one embodiment, the multispecific antibody, further comprises a third antibody which specifically binds to a third epitope.

The third antibody may be added using knob-in-hole dimerization, as described for example in Merchant et al. (Nat. Biotechnol. 16, 677-681 (1998)).

In one embodiment, the third epitope is located in the CD4-binding site (CD4bs), the V1/V2-glycan region, the V3-glycan region, the gp41 membrane proximal external region (MPER), or the gp120-gp41 interface of the envelope protein of HIV. In one embodiment, the third epitope is different from the first epitope and the second epitope.

In one embodiment, the first antibody binds to an epitope in the CD4-binding site of the of the envelope protein of HIV-1 and the second antibody binds to an epitope in the V3-glycan region of the of the envelope protein of HIV-1.

In one embodiment, the first antibody binds to an epitope in the V3-glycan region of the of the envelope protein of HIV-1 and the second antibody binds to an epitope in the CD4-binding site of the of the envelope protein of HIV-1.

In one embodiment, the antibody that binds to an epitope in the CD4-binding site of the of the envelope protein of HIV-1 is selected from the group consisting of VRC03, VRC06, VRC07, 3BNC117, IOMA, and N6.

In one embodiment, the antibody that binds to an epitope in the V3-glycan region of the of the envelope protein of HIV-1 is selected from the group consisting of PGT121, PGT122, PGT128, PGT135, 10-1074, and BG18.

In one embodiment, the first antibody binds to an epitope in the gp120/gp41 interface of the of the envelope protein of HIV-1 and the second antibody binds to an epitope in the MPER of the of the envelope protein of HIV-1.

In one embodiment, the first antibody binds to an epitope in the MPER of the of the envelope protein of HIV-1 and the second antibody binds to an epitope in the gp120/gp41 interface of the of the envelope protein of HIV-1.

In one embodiment, the antibody that binds to an epitope in the gp120/gp41 interface of the of the envelope protein of HIV-1 is selected from the group consisting of 35022, N123-VRC34.01, 3BC315, and PGT151.

In one embodiment, the antibody that binds to an epitope in the MPER of the of the envelope protein of HIV-1 is selected from the group consisting of 10E8, 10E8v4, 10E8v4 S100cF, Dh511.2_k3, Z13, 4E10, and 2F5.

In one aspect, the disclosure features a multispecific antibody, or antigen binding fragment thereof, wherein the variable domain of the first light chain comprises a light chain variable domain comprising a CDR set (CDR1, CDR2, and CDR3) as set forth in SEQ ID NOs 3, 4, 5 and the variable domain of the first heavy chain comprises a heavy chain variable domain comprising a CDR set (CDR1, CDR2, and CDR3) as set forth in SEQ ID NOs 7, 8, 9; and the variable domain of the second light chain comprises a light chain variable domain comprising a CDR set (CDR1, CDR2, and CDR3) as set forth in SEQ ID NOs 11, 12, 13 and the variable domain of the second heavy chain comprises a heavy chain variable domain comprising a CDR set (CDR1, CDR2, and CDR3) as set forth in SEQ ID NOs 15, 16, 17.

In one aspect, the disclosure features a multispecific antibody, or antigen binding fragment thereof, wherein the variable domain of the first light chain comprises a light chain variable domain comprising a CDR set (CDR1, CDR2, and CDR3) as set forth in SEQ ID NOs 32, 33, 34 and the variable domain of the first heavy chain comprises a heavy chain variable domain comprising a CDR set (CDR1, CDR2, and CDR3) as set forth in SEQ ID NOs 36, 37, 38; and the variable domain of the second light chain comprises a light chain variable domain comprising a CDR set (CDR1, CDR2, and CDR3) as set forth in SEQ ID NOs 40, 41, 42 and the variable domain of the second heavy chain comprises a heavy chain variable domain comprising a CDR set (CDR1, CDR2, and CDR3) as set forth in SEQ ID NOs 44, 45, 46.

In one embodiment, the variable domain of the first light chain comprises an amino acid sequence that is 95% identical to an amino acid sequence selected from the group consisting of SEQ ID NO. 2, SEQ ID NO. 10, SEQ ID NO. 19, SEQ ID NO. 31 and SEQ ID NO. 39 and the variable domain of the first heavy chain comprises an amino acid sequence that is 95% identical to an amino acid sequence selected from the group consisting of SEQ ID NO. 6, SEQ ID NO. 14, SEQ ID NO. 35 and SEQ ID NO. 43.

In one embodiment, the variable domain of the first light chain comprises an amino acid sequence that is 96% identical to an amino acid sequence selected from the group consisting of SEQ ID NO. 2, SEQ ID NO. 10, SEQ ID NO. 19, SEQ ID NO. 31 and SEQ ID NO. 39 and the variable domain of the first heavy chain comprises an amino acid sequence that is 96% identical to an amino acid sequence selected from the group consisting of SEQ ID NO. 6, SEQ ID NO. 14, SEQ ID NO. 35 and SEQ ID NO. 43.

In one embodiment, the variable domain of the first light chain comprises an amino acid sequence that is 97% identical to an amino acid sequence selected from the group consisting of SEQ ID NO. 2, SEQ ID NO. 10, SEQ ID NO. 19, SEQ ID NO. 31 and SEQ ID NO. 39 and the variable domain of the first heavy chain comprises an amino acid sequence that is 97% identical to an amino acid sequence selected from the group consisting of SEQ ID NO. 6, SEQ ID NO. 14, SEQ ID NO. 35 and SEQ ID NO. 43.

In one embodiment, the variable domain of the first light chain comprises an amino acid sequence that is 98% identical to an amino acid sequence selected from the group consisting of SEQ ID NO. 2, SEQ ID NO. 10, SEQ ID NO. 19, SEQ ID NO. 31 and SEQ ID NO. 39 and the variable domain of the first heavy chain comprises an amino acid sequence that is 98% identical to an amino acid sequence selected from the group consisting of SEQ ID NO. 6, SEQ ID NO. 14, SEQ ID NO. 35 and SEQ ID NO. 43.

In one embodiment, the variable domain of the first light chain comprises an amino acid sequence that is 99% identical to an amino acid sequence selected from the group consisting of SEQ ID NO. 2, SEQ ID NO. 10, SEQ ID NO. 19, SEQ ID NO. 31 and SEQ ID NO. 39 and the variable domain of the first heavy chain comprises an amino acid sequence that is 99% identical to an amino acid sequence selected from the group consisting of SEQ ID NO. 6, SEQ ID NO. 14, SEQ ID NO. 35 and SEQ ID NO. 43.

In one embodiment, the variable domain of the second light chain comprises an amino acid sequence that is 95% identical to an amino acid sequence selected from the group consisting of SEQ ID NO. 2, SEQ ID NO. 10, SEQ ID NO. 19, SEQ ID NO. 31 and SEQ ID NO. 39 and the variable domain of the second heavy chain comprises an amino acid sequence that is 95% identical to an amino acid sequence selected from the group consisting of SEQ ID NO. 6, SEQ ID NO. 14, SEQ ID NO. 35 and SEQ ID NO. 43.

In one embodiment, the variable domain of the second light chain comprises an amino acid sequence that is 96% identical to an amino acid sequence selected from the group consisting of SEQ ID NO. 2, SEQ ID NO. 10, SEQ ID NO. 19, SEQ ID NO. 31 and SEQ ID NO. 39 and the variable domain of the second heavy chain comprises an amino acid sequence that is 96% identical to an amino acid sequence selected from the group consisting of SEQ ID NO. 6, SEQ ID NO. 14, SEQ ID NO. 35 and SEQ ID NO. 43.

In one embodiment, the variable domain of the second light chain comprises an amino acid sequence that is 97% identical to an amino acid sequence selected from the group consisting of SEQ ID NO. 2, SEQ ID NO. 10, SEQ ID NO. 19, SEQ ID NO. 31 and SEQ ID NO. 39 and the variable domain of the second heavy chain comprises an amino acid sequence that is 97% identical to an amino acid sequence selected from the group consisting of SEQ ID NO. 6, SEQ ID NO. 14, SEQ ID NO. 35 and SEQ ID NO. 43.

In one embodiment, the variable domain of the second light chain comprises an amino acid sequence that is 98% identical to an amino acid sequence selected from the group consisting of SEQ ID NO. 2, SEQ ID NO. 10, SEQ ID NO. 19, SEQ ID NO. 31 and SEQ ID NO. 39 and the variable domain of the second heavy chain comprises an amino acid sequence that is 98% identical to an amino acid sequence selected from the group consisting of SEQ ID NO. 6, SEQ ID NO. 14, SEQ ID NO. 35 and SEQ ID NO. 43.

In one embodiment, the variable domain of the second light chain comprises an amino acid sequence that is 99% identical to an amino acid sequence selected from the group consisting of SEQ ID NO. 2, SEQ ID NO. 10, SEQ ID NO. 19, SEQ ID NO. 31 and SEQ ID NO. 39 and the variable domain of the second heavy chain comprises an amino acid sequence that is 99% identical to an amino acid sequence selected from the group consisting of SEQ ID NO. 6, SEQ ID NO. 14, SEQ ID NO. 35 and SEQ ID NO. 43.

In one embodiment, the variable domain of the first light chain comprises an amino acid sequence that is 95% identical to SEQ ID NO. 2, and the variable domain of the first heavy chain comprises an amino acid sequence that is 95% identical to SEQ ID NO. 6, and the variable domain of the second light chain comprises an amino acid sequence that is 95% identical to SEQ ID NO. 10, and the variable domain of the second heavy chain comprises an amino acid sequence that is 95% identical to SEQ ID NO. 14.

In one embodiment, the variable domain of the first light chain comprises an amino acid sequence that is 95% identical to SEQ ID NO. 19, and the variable domain of the first heavy chain comprises an amino acid sequence that is 95% identical to SEQ ID NO. 6, and the variable domain of the second light chain comprises an amino acid sequence that is 95% identical to SEQ ID NO. 10, and the variable domain of the second heavy chain comprises an amino acid sequence that is 95% identical to SEQ ID NO. 14.

In one embodiment, the variable domain of the first light chain comprises an amino acid sequence that is 95% identical to SEQ ID NO. 10, and the variable domain of the first heavy chain comprises an amino acid sequence that is 95% identical to SEQ ID NO. 14, and the variable domain of the second light chain comprises an amino acid sequence that is 95% identical to SEQ ID NO. 2, and the variable domain of the second heavy chain comprises an amino acid sequence that is 95% identical to SEQ ID NO. 6.

In one embodiment, the variable domain of the first light chain comprises an amino acid sequence that is 95% identical to SEQ ID NO. 10, and the variable domain of the first heavy chain comprises an amino acid sequence that is 95% identical to SEQ ID NO. 14, and the variable domain of the second light chain comprises an amino acid sequence that is 95% identical to SEQ ID NO. 19, and the variable domain of the second heavy chain comprises an amino acid sequence that is 95% identical to SEQ ID NO. 6.

In one embodiment, the variable domain of the first light chain comprises an amino acid sequence that is 95% identical to SEQ ID NO. 31, and the variable domain of the first heavy chain comprises an amino acid sequence that is 95% identical to SEQ ID NO. 35, and the variable domain of the second light chain comprises an amino acid sequence that is 95% identical to SEQ ID NO. 39, and the variable domain of the second heavy chain comprises an amino acid sequence that is 95% identical to SEQ ID NO. 43.

In one embodiment, the variable domain of the first light chain comprises an amino acid sequence that is 95% identical to SEQ ID NO. 39, and the variable domain of the first heavy chain comprises an amino acid sequence that is 95% identical to SEQ ID NO. 43, and the variable domain of the second light chain comprises an amino acid sequence that is 95% identical to SEQ ID NO. 31, and the variable domain of the second heavy chain comprises an amino acid sequence that is 95% identical to SEQ ID NO. 35.

In one embodiment, the multispecific antibody comprises an amino acid sequence that is 95% identical to an amino acid sequence selected from the group consisting of SEQ ID NO. 1, SEQ ID NO. 18, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 30, SEQ ID NO. 47, SEQ ID NO. 48, SEQ ID NO. 49, SEQ ID NO. 50, SEQ ID NO. 51, SEQ ID NO. 52 and SEQ ID NO. 53.

In one embodiment, the multispecific antibody comprises an amino acid sequence that is 96% identical to an amino acid sequence selected from the group consisting of SEQ ID NO. 1, SEQ ID NO. 18, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 30, SEQ ID NO. 47, SEQ ID NO. 48, SEQ ID NO. 49, SEQ ID NO. 50, SEQ ID NO. 51, SEQ ID NO. 52 and SEQ ID NO. 53.

In one embodiment, the multispecific antibody comprises an amino acid sequence that is 97% identical to an amino acid sequence selected from the group consisting of SEQ ID NO. 1, SEQ ID NO. 18, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 30, SEQ ID NO. 47, SEQ ID NO. 48, SEQ ID NO. 49, SEQ ID NO. 50, SEQ ID NO. 51, SEQ ID NO. 52 and SEQ ID NO. 53.

In one embodiment, the multispecific antibody comprises an amino acid sequence that is 98% identical to an amino acid sequence selected from the group consisting of SEQ ID NO. 1, SEQ ID NO. 18, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 30, SEQ ID NO. 47, SEQ ID NO. 48, SEQ ID NO. 49, SEQ ID NO. 50, SEQ ID NO. 51, SEQ ID NO. 52 and SEQ ID NO. 53.

In one embodiment, the multispecific antibody comprises an amino acid sequence that is 99% identical to an amino acid sequence selected from the group consisting of SEQ ID NO. 1, SEQ ID NO. 18, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 30, SEQ ID NO. 47, SEQ ID NO. 48, SEQ ID NO. 49, SEQ ID NO. 50, SEQ ID NO. 51, SEQ ID NO. 52 and SEQ ID NO. 53.

In one embodiment, the multispecific antibody comprises an amino acid sequence set forth in an amino acid sequence selected from the group consisting of SEQ ID NO. 1, SEQ ID NO. 18, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 30, SEQ ID NO. 47, SEQ ID NO. 48, SEQ ID NO. 49, SEQ ID NO. 50, SEQ ID NO. 51, SEQ ID NO. 52 and SEQ ID NO. 53.

Trispecific

In another aspect, the disclosure features a multispecific antibody comprising a) a first light chain comprising a first light chain variable region (VL) and a first heavy chain comprising a first heavy chain variable region (VH), wherein the first light chain and the first heavy chain are derived from a first antibody or an antigen-binding fragment thereof; b) a second light chain comprising a second light chain variable region (VL) and a second heavy chain comprising a second heavy chain variable region (VH), wherein the second light chain and the second heavy chain are derived from a second antibody or an antigen-binding fragment thereof; and c) a third light chain comprising a first light chain variable region (VL) and a third heavy chain comprising a first heavy chain variable region (VH), wherein the third light chain and the third heavy chain are derived from a third antibody or an antigen-binding fragment thereof, wherein the first antibody, the second antibody and the third antibody bind non-overlapping epitopes of the envelope protein of human immunodeficiency virus-1 (HIV-1), and wherein the VH from the first light chain and the VL from the second light chain are connected by two or more tetra-glycine serine (G4S) protein linkers or wherein the VL from the first light chain and the VH from the second light chain are connected by two or more tetra-glycine serine (G4S) protein linkers.

Tetraspecific

In certain embodiments, the disclosure features a multispecific antibody with four binding sites. In one embodiment, the four binding sites can be arranged by joining two bispecific antibody arms using complementary "Knob-into-holes" Fc fragments. In another embodiment, the four binding sites can be arranged by joining variable VH and VL of four different antibodies by G4S linkers of various length based on structural information, for example 3, 4, 5, 6, 7, or more G4S linkers.

Pentaspecific

In certain embodiments, the disclosure features a multispecific antibody with five binding sites. Antibodies with five binding sites can be arranged in the similar manner as antibodies with four binding sites. In one embodiment, the five binding sites can be arranged by joining one bispecific and one trispecific (VH/VL of three antibodies connected by G4S linkers in tandem) antibody arms using complementary "Knobs-into-holes" Fc fragments; or join variable VH and VL of five different antibodies by G4S linkers of various length based on structural information.

In certain embodiments, the first antibody, the second antibody, the third antibody, the fourth antibody or the fifth antibody is an ScFv.

In certain embodiments, the multispecific antibody as described herein further includes a modification in the Fc region. In certain embodiments, the multispecific antibodies of the disclosure include mutations that increase binding to the neonatal Fc receptor (FcRn), which recycles IgG in intestinal epithelial cells and increases levels in the serum, extended half-life, enhanced mucosal localization, and conferred more efficient protection against lentivirus infection relative to the wild-type antibody. Enhanced neonatal Fc receptor function improves protection against primate SHIV infection. Such mutations are described, for example in Ko et al. (Nature 514, 642-645 (2014)).

Pharmaceutical Formulations

Pharmaceutical formulations of the multispecific antibodies disclosed can be prepared by mixing the antibody with optional pharmaceutically acceptable carriers. Pharmaceutically acceptable carriers include solvents, dispersion media, isotonic agents and the like. The carrier can be liquid, semi-solid, e.g. pastes, or solid carriers. Examples of carriers include water, saline solutions or other buffers (such as phosphate, citrate buffers), oil, alcohol, proteins (such as serum albumin, gelatin), carbohydrates (such as monosaccharides, di saccharides, and other carbohydrates including glucose, sucrose, trehalose, mannose, mannitol, sorbitol or dextrins), gel, lipids, liposomes, resins, porous matrices, binders, fillers, coatings, stabilizers, preservatives, antioxidants including ascorbic acid and methionine, chelating agents such as EDTA; salt forming counter-ions such as sodium; non-ionic surfactants such as TWEEN, PLURONICS or polyethylene glycol (PEG), or combinations thereof.

The formulation can contain more than one active compound, e.g., one or more multispecifc antibodies, in combination with one or more additional beneficial compound for preventing and treating HIV infections.

The above-described antibodies can be used in combination with one or more anti-retroviral agents for the treatment of HIV latency and/or infection. See, e.g., US 2010/0166806, US 2010/0324034, and US 2012/0203014, which are hereby incorporated in their entirety.

Compositions according to the present disclosure may also be administered in combination with other agents to enhance the biological activity of such agents. Such agents may include any one or more of the standard anti-HIV agents which are known in the art, including, but not limited to, azidothymidine (AZT), dideoxycytidine (ddC), and dideoxyinosine (ddI). Additional agents which have shown anti-HIV effects and may be combined with compositions in accordance to the disclosure include, for example, raltegravir, maraviroc, bestatin, human chorionic gonadotropin (hCG), levamisole, estrogen, efavirenz, etravirine, indomethacin, emtricitabine, tenofovir disoproxil fumarate, amprenavir, tipranavir, indinavir, ritonavir, darunavir, enfuvirtide, and gramicidin.

The active ingredients can be combined with the carrier in any convenient and practical manner, e.g., by admixture, solution, suspension, emulsification, encapsulation, absorption and the like, and can be made in formulations such as tablets, capsules, powder (including lyophilized powder), syrup, suspensions that are suitable for injections, ingestions, infusion, or the like. Sustained-release preparations can also be prepared.

The instant disclosure is related to pharmaceutical compositions of the instant disclosure or the pharmaceutical acceptable salts derived therefrom that comprise analogs that comprise isotopes. In some embodiments, the compositions of the claimed disclosure may contain any isotope described in Cyr and Pearson (Stabilization of radiopharmaceutical compositions using hydrophilic thioethers and hydrophilic 6-hydroxy chromans. Cyr, John E.; Pearson, Daniel A. (Diatide, Inc., USA). PCT Int. Appl. (2002), WO 200260491 A2 20020808), which is herein incorporated by reference. In some embodiments the compositions of the disclosure comprise analog that comprise one or more of the following isotopes: $^{125}$I, $^{131}$I, $^{211}$At, $^{47}$Sc, $^{67}$Cu, $^{72}$Ga, $^{90}$Y, $^{153}$Sm, $^{159}$Gd, $^{165}$Dy, $^{166}$Ho, $^{175}$Yb, $^{177}$Lu, $^{212}$Bi, $^{213}$Bi, $^{68}$Ga, $^{99}$Tc, $^{111}$In, $^{123}$I and $^3$H.

The pharmaceutical compositions of the instant disclosure or the pharmaceutical acceptable salts derived therefrom may be in a liquid or solid dosage form. Such compositions may include any type of dosage form such as tablets, capsules, powders, liquid formulations, delayed or sustained release, patches, snuffs, nasal sprays and the like. The formulations may additionally include other ingredients such as dyes, preservatives, buffers and anti-oxidants, for example. The physical form and content of the pharmaceutical formulations contemplated are conventional preparations that can be formulated by those skilled in the pharmaceutical formulation field and are based on well established principles and compositions described in, for example, Remington: The Science and Practice of Pharmacy, 19th Edition, 1995; British Pharmacopoeia 2000, each of which is incorporated herein by reference. The compositions of the present disclosure may also include other active agents useful in the treatment of cardiovascular conditions. Solid forms can be prepared according to any means suitable in the art. For example, capsules are prepared by mixing the analog composition with a suitable diluent and filling the proper amount of the mixture in capsules. Tablets are prepared by direct compression, by wet granulation, or by dry granulation. Their formulations usually incorporate diluents, binders, lubricants and disintegrators as well as the compound. Diluents, but are not limited to, include various types of starch, cellulose, crystalline cellulose, microcrystalline cellulose, lactose, fructose, sucrose, mannitol or other sugar alcohols, kaolin, calcium phosphate or sulfate, inorganic salts such as sodium chloride and powdered sugar. Powdered cellulose derivatives are also useful. Non-limiting examples of tablet binders include, but are not limited to, starches, gelatin and sugars such as lactose, fructose, glucose and the like. Natural and synthetic gums are also convenient, including, but not limited to, acacia, alginates, methylcellulose, polyvinylpyrrolidone and the like. Polyethylene glycol, ethylcellulose and waxes can also serve as binders. A lubricant can be used in a tablet formulation to prevent the tablet and punches from sticking in the die. The lubricant include, but are not limited to, such slippery solids as talc, magnesium and calcium stearate, stearic acid and hydrogenated vegetable oils. Tablets can be coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established in the art. Also contemplated are liquid formulations and solid form preparations which are intended to be converted, shortly before use, to liquid form preparations. Such liquid forms include, but are not limited to, solutions, suspensions, syrups, slurries, and emulsions. Liquid preparations may be prepared by conventional means with pharmaceutically acceptable additives such as suspending agents (e.g., sorbitol syrup, cellulose derivatives or hydrogenated edible fats or oils); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorboc acid). These preparations may contain, in addition to the active agent, colorants, flavors, stabilizers, buffers, artificial and natural sweeteners, dispersants, thickeners, solubilizing agents, and the like. The compositions may be in powder form for constitution with a suitable vehicle such as sterile water, saline solution, or alcohol, before use.

The pharmaceutical compositions of the instant disclosure or the pharmaceutical acceptable salts derived therefrom may be in a dosage amount in an effective amount for inducing or increasing the naturally occurring biological activity of the wild-type amino acid sequence upon which the antibody is derived. The pharmaceutical compositions of the instant disclosure or the pharmaceutical acceptable salts derived therefrom may be in a dosage amount in an effective amount for inducing or increasing the naturally occurring biological activity of the wild-type VIP polypeptide upon which the analog is derived.

In some embodiments, a subject in need thereof is administered from about 0.0001 to about 3000 milligrams of antibody, antibody binding fragment or pharmaceutically salt thereof per day, per week or per month. In some embodiments, a subject is administered up to about 2000 milligrams of antibody, antibody binding fragment or pharmaceutically salt thereof day. In some embodiments, a subject is administered up to about 1800 milligrams of antibody, antibody binding fragment or pharmaceutically salt thereof per day, per week or per month. In some embodiments, a subject is administered up to about 1600 milligrams of Antibody, antibody binding fragment or pharmaceutically salt thereof per day, per week or per month. In some embodiments, a subject is administered up to about 1400 milligrams of Antibody, antibody binding fragment or pharmaceutically salt thereof per day, per week or per month. In some embodiments, a subject is administered up to about 1200 milligrams of Antibody, antibody binding fragment or pharmaceutically salt thereof per day, per week or per month. In some embodiments, a subject is administered up to about 1000 milligrams of Antibody, antibody binding fragment or pharmaceutically salt thereof per day, per week or per month. In some embodiments, a subject is administered up to about 800 milligrams of Antibody, antibody binding fragment or pharmaceutically salt thereof per day, per week or per month. In some embodiments, a subject is administered from about 0.0001 milligrams to about 700 milligrams of Antibody, antibody binding fragment or pharmaceutically salt thereof per dose. In some embodiments, a subject is administered up to about 700 milligrams of Antibody, antibody binding fragment or pharmaceutically salt thereof per dose. In some embodiments, a subject is administered up to about 600 milligrams of Antibody, antibody binding fragment or pharmaceutically salt thereof per dose. In some embodiments, a subject is administered up to about 500 milligrams of Antibody, antibody binding fragment or pharmaceutically salt thereof per dose. In some embodiments, a subject is administered up to about 400 milligrams of Antibody, antibody binding fragment or pharmaceutically salt thereof per dose. In some embodiments, a subject is administered up to about 300 milligrams of Antibody, antibody binding fragment or pharmaceutically salt thereof per dose. In some embodiments, a subject is administered up to about 200 milligrams of Antibody, antibody binding fragment or pharmaceutically salt thereof per dose. In some embodiments, a subject is administered up to about 100 milligrams of Antibody, antibody binding fragment or pharmaceutically salt thereof per dose. In some embodiments, a subject is administered up to about 50 milligrams of Antibody, antibody binding fragment or pharmaceutically salt thereof per dose. In some embodiments, a subject is administered up to about 25 milligrams of Antibody, antibody binding fragment or pharmaceutically salt thereof per dose. In some embodiments, a subject is administered up to about 15 milligrams of Antibody, antibody binding fragment or pharmaceutically salt thereof per dose.

Methods of Treatment and Prevention

In one embodiment, the present disclosure provides a composition comprising a multispecific antibody, or an antigen-binding fragment thereof, as described herein, and a pharmaceutically acceptable carrier. The composition may include a plurality of the antibodies having the characteristics described herein in any combination and can further include antibodies neutralizing to HIV as are known in the art.

It is to be understood that compositions can be a single or a combination of antibodies disclosed herein, which can be the same or different, in order to prophylactically or therapeutically treat the progression of various subtypes of HIV infection. When an antibody or active agent is administered to an animal or a human, it can be combined with one or more pharmaceutically acceptable carriers, excipients or adjuvants as are known to one of ordinary skilled in the art.

Further, with respect to determining the effective level in a patient for treatment of HIV, in particular, suitable animal models are available and have been widely implemented for evaluating the in vivo efficacy against HIV of various therapy protocols. These models include mice, monkeys and cats. Even though these animals are not naturally susceptible to HIV disease, chimeric mice models (for example, SCID, bg/nu/xid, NOD/SCID, SCID-hu, immunocompetent SCID-hu, bone marrow-ablated BALB/c) reconstituted with human peripheral blood mononuclear cells (PBMCs), lymph nodes, fetal liver/thymus or other tissues can be infected with lentiviral vector or HIV, and employed as models for HIV pathogenesis. Similarly, the simian immune deficiency virus (SrV)/monkey model can be employed, as can the feline immune deficiency virus (FIV)/cat model. The pharmaceutical composition can contain other pharmaceuticals, in conjunction with a vector according to the disclosure, when used to therapeutically treat AIDS. These other pharmaceuticals can be used in their traditional fashion (i.e., as agents to treat HIV infection).

According to another embodiment, the present disclosure provides a pharmaceutical composition comprising a multispecific antibody, or an antigen-binding fragment thereof, as described herein, which provides a prophylactic or therapeutic treatment choice to reduce the latent reservoir and infection of the HIV virus. The pharmaceutical compositions of the present disclosure may be formulated by any number of strategies known in the art (e.g., see McGoff and Scher, 2000, Solution Formulation of Proteins/Peptides: In McNally, E. J., ed. Protein Formulation and Delivery. New York, N.Y.: Marcel Dekker; pp. 139-158; Akers and Defilippis, 2000, Peptides and Proteins as Parenteral Solutions. In: Pharmaceutical Formulation Development of Peptides and Proteins. Philadelphia, Pa.: Talyor and Francis; pp. 145-177; Akers, et al., 2002, Pharm. Biotechnol. 14:47-127). A pharmaceutically acceptable composition suitable for patient administration will contain an effective amount of the multispecific in a formulation which both retains biological activity while also promoting maximal stability during storage within an acceptable temperature range. The pharmaceutical compositions can also include, depending on the formulation desired, pharmaceutically acceptable diluents, pharmaceutically acceptable carriers and/or pharmaceutically acceptable excipients, or any such vehicle commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. The amount of an excipient that is useful in the pharmaceutical composition or formulation of this disclosure is an amount that serves to uniformly distribute the antibody throughout the composition so that it can be uniformly dispersed when it is to be delivered to a subject in need thereof. It may serve to dilute the antibody or other active agent to a concentration which provides the desired beneficial palliative or curative results while at the same time minimizing any adverse side effects that might occur from too high a concentration. It may also have a preservative effect. Thus, for an active ingredient having a high physiological activity, more of the excipient will be employed. On the other hand, for any active ingredient(s) that exhibit a lower physiological activity, a lesser quantity of the excipient will be employed.

The above described multispecific antibodies and antibody compositions, comprising at least one or a combination of the antibodies described herein, can be administered for the prophylactic and therapeutic treatment of HIV viral infection.

The composition can be a pharmaceutical composition that contains a pharmaceutically acceptable carrier.

According to another embodiment, the present disclosure provides a method of reducing or preventing the establishment of a latent reservoir of HIV infected cells in a subject in need thereof (e.g., a subject infected with HIV or at risk of infection with HIV), thereby treating infection with a HIV infection, comprising administering to the subject a pharmaceutical composition comprising the multispecific antibodies disclosed herein. The compositions of the disclosure can include more than one antibody having the characteristics disclosed (for example, a plurality or pool of antibodies). It also can include other HIV neutralizing antibodies and/or active agent known in the art.

Subjects at risk for HIV-related diseases or disorders include patients who have come into contact with an infected person or who have been exposed to HIV in some other way.

Administration of a prophylactic agent can occur prior to the manifestation of symptoms characteristic of HIV-related disease or disorder, such that a disease or disorder is prevented or, alternatively, delayed in its progression.

For in vivo treatment of human and non-human patients, the patient is administered or provided a pharmaceutical formulation including an HIV antibody of the disclosure. When used for in vivo therapy, the antibodies of the disclosure are administered to the patient in therapeutically effective amounts (i.e., amounts that eliminate or reduce the patient's latent viral reservoir). The antibodies are administered to a human patient, in accord with known methods, such as intravenous administration, for example, as a bolus or by continuous infusion over a period of time, by intramuscular, intraperitoneal, intracerobrospinal, subcutaneous, intra-articular, intrasynovial, intrathecal, oral, topical, or inhalation routes. The antibodies can be administered parenterally, when possible, at the target cell site, or intravenously. In some embodiments, antibody is administered by intravenous or subcutaneous administration. Therapeutic compositions of the disclosure may be administered to a patient or subject systemically, parenterally, or locally. The above parameters for assessing successful treatment and improvement in the disease are readily measurable by routine procedures familiar to a physician.

For parenteral administration, the antibodies may be formulated in a unit dosage injectable form (solution, suspension, emulsion) in association with a pharmaceutically acceptable, parenteral vehicle. Examples of such vehicles include, but are not limited, water, saline, Ringer's solution, dextrose solution, and 5% human serum albumin. Nonaqueous vehicles include, but are not limited to, fixed oils and ethyl oleate. Liposomes can be used as carriers. The vehicle may contain minor amounts of additives such as substances that enhance isotonicity and chemical stability, such as, for example, buffers and preservatives. The antibodies can be formulated in such vehicles at concentrations of about 1 mg/ml to 10 mg/ml.

The dose and dosage regimen depends upon a variety of factors readily determined by a physician, such as the nature of the infection, for example, its therapeutic index, the patient, and the patient's history. Generally, a therapeutically effective amount of an antibody is administered to a patient. In some embodiments, the amount of antibody administered is in the range of about 0.1 mg/kg to about 50 mg/kg of patient body weight. Depending on the type and severity of the infection, about 0.1 mg/kg to about 50 mg/kg body weight (for example, about 0.1-15 mg/kg/dose) of antibody is an initial candidate dosage for administration to the patient, whether, for example, by one or more separate administrations, or by continuous infusion. The progress of this therapy is readily monitored by conventional methods and assays and based on criteria known to the physician or other persons of skill in the art. The above parameters for assessing successful treatment and improvement in the disease are readily measurable by routine procedures familiar to a physician.

Other therapeutic regimens may be combined with the administration of the multispecific antibodies of the present disclosure. The combined administration includes coadministration, using separate formulations or a single pharmaceutical formulation, and consecutive administration in either order, wherein preferably there is a time period while both (or all) active agents simultaneously exert their biological activities. Such combined therapy can result in a synergistic therapeutic effect. The parameters for assessing successful treatment and improvement in the disease are also readily measurable by routine procedures familiar to a physician.

Those in need of treatment include those already with the disorder as well as those prone to have the disorder or those in whom the disorder is to be prevented. A subject or mammal is successfully "treated" for an infection if, after receiving a therapeutic amount of an antibody according to the methods of the present disclosure, the patient shows observable and/or measurable reduction in or absence of one or more of the following: reduction in the number of infected cells or absence of the infected cells; reduction in the percent of total cells that are infected; and/or relief to some extent, one or more of the symptoms associated with the specific infection; reduced morbidity and mortality, and improvement in quality of life issues. The above parameters for assessing successful treatment and improvement in the disease are readily measurable by routine procedures familiar to a physician.

Eliminating the HIV-1 reservoir in chronic infection is key to curing the disease, but direct measurement of the latent reservoir to evaluate therapeutic eradication strategies remains difficult (Siliciano et al, Curr Opin HIV AIDS, 2013. 8(4): p. 318-25). Quantitative viral outgrowth assays and PCR-based assays of integrated DNA yield variable results (Eriksson et al., PLoS Pathog, 2013. 9(2): p. e1003174) in part because PCR cannot distinguish between inactive and permanently disabled proviruses, and outgrowth assays underestimate reservoir size (Ho et al., Cell, 2013. 155(3): p. 540-51). To that end, the most effective way to evaluate the reservoir in vivo is to measure viral rebound after terminating therapy as disclosed in the examples below.

V. Methods of Making

Another aspect of the disclosure is a method of generating a multispecific antibody comprising a first light chain comprising a first light chain variable region (VL) and a first heavy chain comprising a first heavy chain variable region (VH), wherein the first light chain and the first heavy chain are derived from a first antibody or an antigen-binding fragment thereof; and a second light chain comprising a second light chain variable region (VL) and a second heavy chain comprising a second heavy chain variable region (VH), wherein the second light chain and the second heavy chain are derived from a second antibody or an antigen-binding fragment thereof, wherein the first antibody and the second antibody bind non-overlapping epitopes of the envelope protein of human immunodeficiency virus-1 (HIV-1), and wherein the VH from the first light chain and the VL from the second light chain are connected by two or more tetra-glycine serine (G4S) protein linkers or wherein the VL from the first light chain and the VH from the second light chain are connected by two or more tetra-glycine serine (G4S) protein linkers.

In one embodiment, the multispecific antibody is prepared by recombinant methods. Thus, the disclosure also relates to a method for the preparation of a multispecific antibody according to the disclosure, comprising the steps of transforming a host cell with vectors comprising nucleic acids encoding the first light chain comprising a first light chain variable region (VL) and a first heavy chain comprising a first heavy chain variable region (VH), wherein the first light chain and the first heavy chain are derived from a first antibody or an antigen-binding fragment thereof; the second light chain comprising a second light chain variable region (VL) and a second heavy chain comprising a second heavy chain variable region (VH), wherein the second light chain and the second heavy chain are derived from a second antibody or an antigen-binding fragment thereof, and in certain embodiments, a third antibody which specifically binds to a third epitope, culturing said host cell under conditions that allow synthesis of said multispecific antibody; and recovering said multispecific antibody from said host cell culture.

Another object of the disclosure is a multispecific antibody produced by a method according to the disclosure.

In other embodiments, the present disclosure features a host cell comprising a vector comprising nucleic acids according to the disclosure encoding the first light chain derived from a first antibody which specifically binds to a first antigen; a vector comprising nucleic acids according to the disclosure encoding the first heavy chain derived from a first antibody which specifically binds to a first antigen; a vector comprising nucleic acids according to the disclosure encoding the second light chain derived from a second antibody which specifically binds to a second antigen; and a vector comprising nucleic acids according to the disclosure encoding the second heavy chain derived from a second antibody which specifically binds to a second antigen.

In other embodiments, the disclosure features a nucleic acid encoding the multispecific antibody according to the disclosure. In one embodiment, the nucleic acid according to the disclosure is an isolated nucleic acid.

In one embodiment the nucleic acid encodes a first light chain comprising a first light chain variable region (VL) and a first heavy chain comprising a first heavy chain variable region (VH), wherein the first light chain and the first heavy chain are derived from a first antibody or an antigen-binding fragment thereof; and a second light chain comprising a second light chain variable region (VL) and a second heavy chain comprising a second heavy chain variable region (VH), wherein the second light chain and the second heavy chain are derived from a second antibody or an antigen-binding fragment thereof.

Standard recombinant DNA methodologies are used to construct the polynucleotides that encode the polypeptides which form the antibodies, incorporate these polynucleotides into recombinant expression vectors, and introduce such vectors into host cells. See e.g., Sambrook et al., 2001, MOLECULAR CLONING: A LABORATORY MANUAL (Cold Spring Harbor Laboratory Press, 3rd ed.). Enzymatic reactions and purification techniques may be performed according to manufacturer's specifications, as commonly accomplished in the art, or as described herein. Unless specific definitions are provided, the nomenclature utilized in connection with, and the laboratory procedures and techniques of, analytical chemistry, synthetic organic chemistry, and medicinal and pharmaceutical chemistry described herein are those well-known and commonly used in the art. Similarly, conventional techniques may be used for chemical syntheses, chemical analyses, pharmaceutical preparation, formulation, delivery, and treatment of patients.

Other aspects of the present disclosure relate to isolated nucleic acid molecules comprising a nucleotide sequence encoding any of the antibodies described herein. In some embodiments, the isolated nucleic acid is operably linked to a heterologous promoter to direct transcription of the binding protein-coding nucleic acid sequence. A promoter may refer to nucleic acid control sequences which direct transcription of a nucleic acid. A first nucleic acid sequence is operably linked to a second nucleic acid sequence when the first nucleic acid sequence is placed in a functional relationship with the second nucleic acid sequence. For instance, a promoter is operably linked to a coding sequence of a binding protein if the promoter affects the transcription or expression of the coding sequence.

Examples of promoters may include, but are not limited to, promoters obtained from the genomes of viruses (such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), and the like), from heterologous eukaryotic promoters (such as the actin promoter, an immunoglobulin promoter, from heat-shock promoters, and the like), the CAG-promoter (Niwa et al., Gene 108(2):193-9, 1991), the phosphoglycerate kinase (PGK)-promoter, a tetracycline-inducible promoter (Masui et al., Nucleic Acids Res. 33:e43, 2005), the lac system, the trp system, the tac system, the trc system, major operator and promoter regions of phage lambda, the promoter for 3-phosphoglycerate kinase, the promoters of yeast acid phosphatase, and the promoter of the yeast alpha-mating factors. Polynucleotides encoding binding proteins of the present disclosure may be under the control of a constitutive promoter, an inducible promoter, or any other suitable promoter described herein or other suitable promoter that will be readily recognized by one skilled in the art.

In some embodiments, the isolated nucleic acid is incorporated into a vector. In some embodiments, the vector is an expression vector. Expression vectors may include one or more regulatory sequences operatively linked to the polynucleotide to be expressed. The term "regulatory sequence" includes promoters, enhancers and other expression control elements (e.g., polyadenylation signals). Examples of suitable enhancers may include, but are not limited to, enhancer sequences from mammalian genes (such as globin, elastase, albumin, I-fetoprotein, insulin and the like), and enhancer sequences from a eukaryotic cell virus (such as SV40 enhancer on the late side of the replication origin (bp 100-270), the cytomegalovirus early promoter enhancer, the polyoma enhancer on the late side of the replication origin, adenovirus enhancers, and the like). Examples of suitable vectors may include, for example, plasmids, cosmids, episomes, transposons, and viral vectors (e.g., adenoviral, vaccinia viral, Sindbis-viral, measles, herpes viral, lentiviral, retroviral, adeno-associated viral vectors, etc.). Expression vectors can be used to transfect host cells, such as, for example, bacterial cells, yeast cells, insect cells, and mammalian cells. Biologically functional viral and plasmid DNA vectors capable of expression and replication in a host are known in the art, and can be used to transfect any cell of interest.

Other aspects of the present disclosure relate to a vector system comprising one or more vectors encoding a polypeptide chain of any of the antibodies or antibody binding fragments described herein.

Other aspects of the present disclosure relate to a host cell (e.g., an isolated host cell) comprising one or more isolated polynucleotides, vectors, and/or vector systems described herein. In some embodiments, an isolated host cell of the present disclosure is cultured in vitro. In some embodiments, the host cell is a bacterial cell (e.g., an *E. coli* cell). In some embodiments, the host cell is a yeast cell (e.g., an *S. cerevisiae* cell). In some embodiments, the host cell is an insect cell. Examples of insect host cells may include, for example, *Drosophila* cells (e.g., S2 cells), *Trichoplusia ni* cells (e.g., HIGH FIVE cells), and *Spodoptera frugiperda* cells (e.g., Sf21 or Sf9 cells). In some embodiments, the host cell is a mammalian cell. Examples of mammalian host cells may include, for example, human embryonic kidney cells (e.g., 293 or 293 cells subcloned for growth in suspension culture), EXPI293 cells, CHO cells, baby hamster kidney cells (e.g., BHK, ATCC CCL 10), mouse sertoli cells (e.g., TM4 cells), monkey kidney cells (e.g., CV1 ATCC CCL 70), African green monkey kidney cells (e.g., VERO-76, ATCC CRL-1587), human cervical carcinoma cells (e.g., HELA, ATCC CCL 2), canine kidney cells (e.g., MDCK, ATCC CCL 34), buffalo rat liver cells (e.g., BRL 3A, ATCC CRL 1442), human lung cells (e.g., W138, ATCC CCL 75), human liver cells (e.g., Hep G2, HB 8065), mouse mammary tumor cells (e.g., MMT 060562, ATCC CCL51), TM cells, MRC 5 cells, FS4 cells, a human hepatoma line (e.g., Hep G2), and myeloma cells (e.g., NS0 and Sp2/0 cells).

Other aspects of the present disclosure relate to a method of producing any of the antibodies described herein. In some embodiments, the method includes a) culturing a host cell (e.g., any of the host cells described herein) comprising an isolated nucleic acid, vector, and/or vector system (e.g., any of the isolated nucleic acids, vectors, and/or vector systems described herein) under conditions such that the host cell expresses the antibody; and b) isolating the antibody from the host cell. Methods of culturing host cells under conditions to express a protein are well known to one of ordinary skill in the art. Methods of isolating proteins from cultured host cells are well known to one of ordinary skill in the art, including, for example, by affinity chromatography (e.g., two step affinity chromatography comprising protein A affinity chromatography followed by size exclusion chromatography).

All patent applications, issued patents and journal articles disclosed herein are incorporated by reference in their entireties.

EXAMPLES

Example 1. Bi-Specific bNAbs Targeting the CD4 Binding Site and V3-Base Glycan Display Expanded Neutralization Breadth To date, HIV-1 Env bNAbs are classified into five groups depending on their cognate epitopes (1,2): i) PG9/PG16 that recognize the trimer V2 apex; ii) Receptor CD4 binding site (CD4bs) specific bNAbs including VRC01/VRC07 and 3BNC117; iii) 35022 and PGT151 that recognize the gp120/gp41 interface; iv) PGT121/PGT135 that recognize V3 base glycans; and v) 10E8/4E10/2F5 that recognize gp41 membrane proximal external region (MPER). Many bNAbs demonstrated encouraging protective efficacy as both preventive and therapeutic agents in humanized mouse and simian-human immunodeficiency virus (SHIV) rhesus macaque animal models after passive infusion (11-18). However, the outcome of the most recent clinical trials with bNAbs as therapeutic agents strikingly revealed that the antigenically diverse and persistently evolving HIV-1 Env can rapidly acquire mutations that evade bNAbs administered as single agents (19, 20). The quick onset of escaping virus quasi species in these single bNAb agent therapy trials strongly highlights the need to develop combination therapy strategies to control virus rebound.

The advantage of bNAb combination therapy has been demonstrated by a number of in vitro studies (5, 21). There is a substantial gain of neutralization potency and breadth when two bNAbs targeting independent epitopes are combined to test neutralization capacities against a virus panel consisting of 125 diverse tier 2 and 3 viruses. There is further incremental gain of neutralization potency and breadth by combining 3 or 4 bNAbs of different epitope specificity, resulting in a virtual 100% virus coverage (5). The scientific premise of combination therapy is further supported by a number of in vivo animal studies in which dual-, triple-, and penta-combinations of bNAbs resulted in improved protective efficacy compared to mono bNAb therapy (12, 13). The use of a "single" agent consisting of these multiple functional binding moieties as a means of delivering combination therapy is preferred for both regulatory and manufacturing purposes, in addition to the potential of augmented potency resulting from the increased avidity through bi- or multi-valence Env binding and possible synergistic effect between bNAbs (FIG. 1).

Previous bispecific bNAb designs utilizing CrossMab technology to combine two bNAb Fabs first proved the concept that empirical combinations of bNAb functional moieties in bi-valence format could achieve breadth and coverage (94-97%) superior to individual parental bNAbs (70-90%) (22). The experiments described herein propose to further the crosslinking of Env trimer by structure-based rational design that ensures the optimal accommodation of individual bNAb functional moieties that will orchestrate multi-epitope engagement to achieve superior binding avidity and profoundly enhanced viral inhibition breadth and potency.

Figures 2A, 2B:
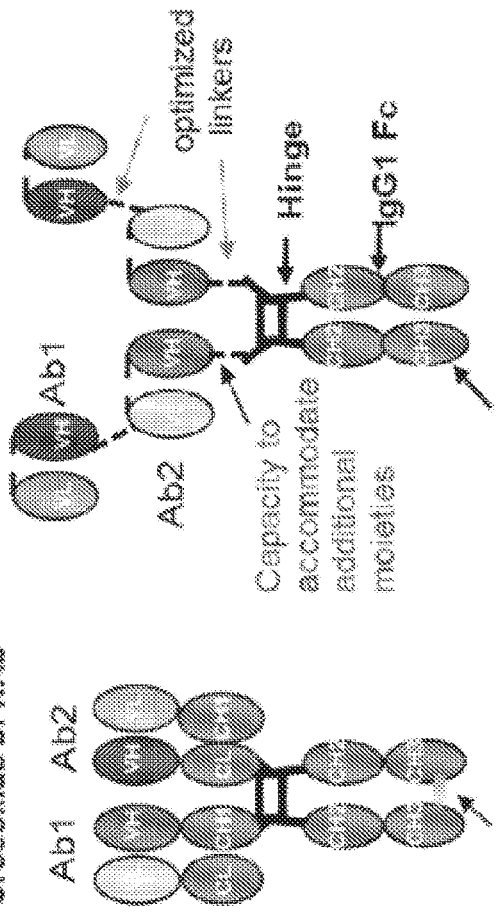
FIG. 2A is a schematic that shows conventional bi-NAb construction.
FIG. 2B is a schematic that shows the proposed modular bi-NAb and multi-NAb in single construct strategy.

As prevention and therapy agents, the bNAb derivatives play major roles in i) inhibiting virus entry by neutralizing the free infectious virus particle, ii) preventing virus cell-to-cell spread, and iii) eliminating virus-infected cells by binding the Env molecules expressed on the surface of the infected cells and triggering antibody-dependent cell-mediated cytotoxicity (ADCC) through interaction between the IgG Fc region and the Fc receptors on effector cells (primarily NK cells) (reviewed in (1)). Thus, the dramatically enhanced viral inhibition breadth and potency associated with the superior binding avidity achieved by Env trimer multi-epitope crosslinking proposed in this study is highly relevant to HIV prevention and therapy efficacy. In addition, the proposed Env trimer multi-epitope crosslinking mechanism will more efficiently combat the emergence of HIV bNAb escaping mutants. Furthermore, modifying the Fc region of bNAb derivatives which will result in bNAb molecules with augmented ADCC effector function, broader effector cell spectra, expanded bio-distribution in HIV reservoir-residing tissues, and longer lasting in vivo half-lives is also proposed. All these features along with selected combinations and permutations will plausibly be applied in optimizing the next generation of prevention and therapeutic agents.

A goal of the studies described herein is to further the crosslinking of Env trimer by structure-based rational design that ensures the optimal accommodation of individual bNAb functional moieties that will orchestrate multi-epitope engagement to achieve superior binding avidity and profoundly enhanced viral inhibition breadth and potency. Conventional bispecific antibodies are formed by empirical combination of Fabs with distinct binding specificity for different molecules or different epitopes within one molecule (FIG. 2A). The empirical combination of Fab functional domains results in compromised biological functions at high frequency, with limited specificities (in most cases, two specificities) combined (22, 23). In contrast, the present studies take a structure-based rational design approach that ensures the optimal accommodation of individual bNAb functional moieties that will orchestrate multi-epitope engagement to achieve superior binding avidity and profoundly enhanced viral inhibition breadth and potency (FIG. 2B). The tandem combination of HIV Env binding moieties allows combinations of up to five epitope specificities, which maximizes the possible ways of multi-epitope targeting in one single construct (FIG. 2B). This single molecule construct configuration is particularly more amenable than conventional CrossMab or "knob-into-holes" configuration requiring more than one construct when advanced to viral expression vectors for further downstream applications.

As the first step toward generating multi-epitope targeting bNAbs, bi-specific single-chain variable fragment (bi-ScFv) consisting of two bNAb epitope binding moieties based on structural information were engineered. The bNAbs VRC01 (CD4bs-directed) (24) and PGT121 (V3-base glycan-directed) (25), which neutralize approximately 90% and 70% of circulating viruses, were chosen, respectively as a model system based on the following criteria: i) both bNAbs display impressive neutralization potency and breadth; ii) structure biology information is available for rational design; and iii) biological relevance: both VRC01 and PGT121 demonstrated impressive protective efficacy in animal models (11, 18, 26), while VRC01 displayed the ability to control viremia as a therapeutic agent in clinical trial (19).

Figure 3A:
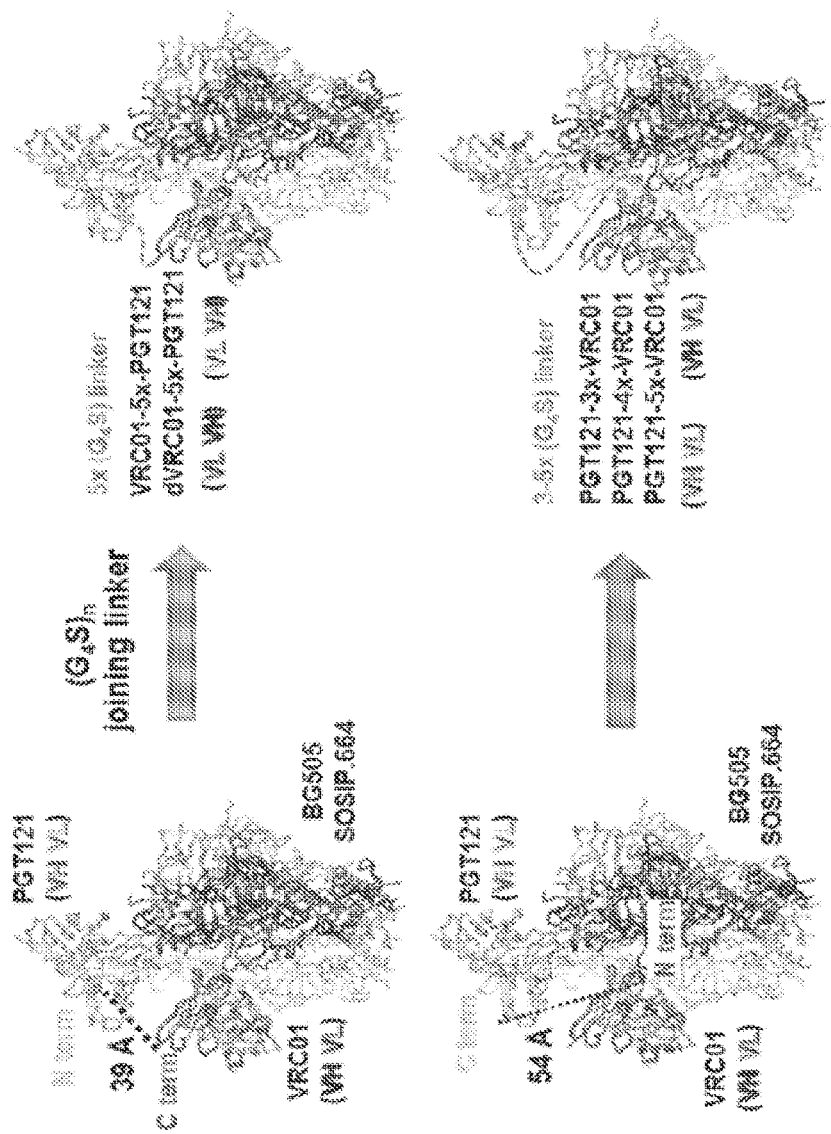
FIG. 3A (left) shows modeling of Env trimer BG505 SOSIP.664 binding to bNAbs VRC01 and PGT121 simultaneously by superimposing individual bNAb Fab-Env complex structure. Only VH-VL regions of Fab are shown. Atomic distance of VRC01 and PGT121 functional domains is shown: 39 Å from VRC01 VH C-terminus to PGT121 VH (upper) and 54 Å from PGT121 VL C-terminus to VRC01 VH N-terminus, respectively.
Figure 3B:
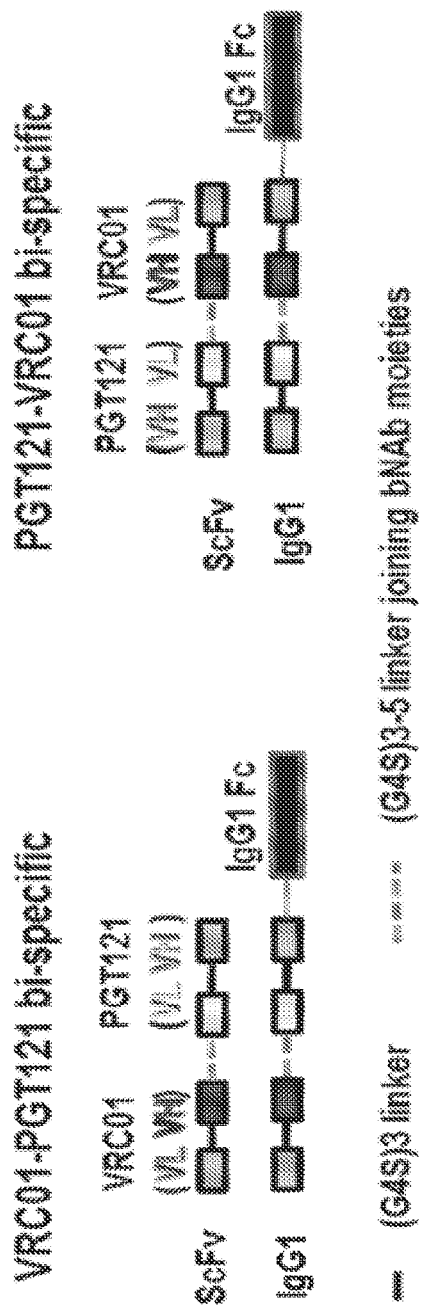
FIG. 3B is a schematic presentation of VRC01-PGT121 ScFv and full length IgG.
Figure 3C:
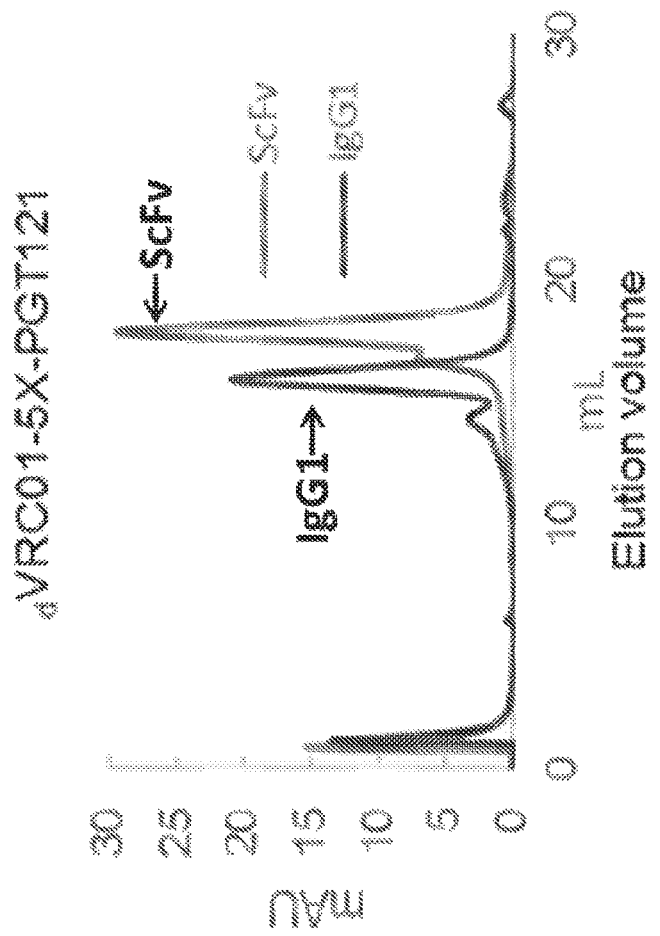
FIG. 3C shows representative size exclusion chromatography profiles of Bi-ScFv and IgG molecules. dVRC01-5x-PGT121 is shown as an example. Both scFV and IgG molecules migrate as a major single peak, free of aggregates.

FIG. 3A-C shows bi-ScFv and bi-IgG1 of VRC01-PGT121 design and expression. As illustrated in FIG. 3A, the bNAb-Env trimer binding mode and the spatial distance between the bNAb variable chains, VH and VL, were taken into account for optimizing the bi-ScFv molecular topology and the means to join individual ScFv moieties. The VRC01 CD4bs epitope is adjacent to that of PGT121 on the Env gp140 BG505 SOSIP.664 trimer, suggesting that it is feasible to engineer a bi-ScFv by joining the variable regions of two bNAbs with flexible linkers. Two different approaches were used to construct VRC01-PGT121 bi-ScFv molecules, based on the following atomic parameters of VRC01 and PGT121 functional variable domains: 1) There is approximately 39 Å distance between the C-terminus of VRC01 VH domain and the N-terminus of PGT121 VL domain (FIG. 3A, upper), which can be joined by 5 G4S linker using the topology of VRC01 (VL-VH) ScFv-linker-PGT121 (VL-VH) ScFv; and 2) There is approximately 55 Å distance between the N-terminus of VRC01 VH and the C-terminus of PGT121 VL (FIG. 3A, lower), which can be bridged by multiple (3 to 5) G4S linkers using the topology of PGT121 (VH-VL) ScFv-linker-VRC01 (VH-VL).

Figure 11A:
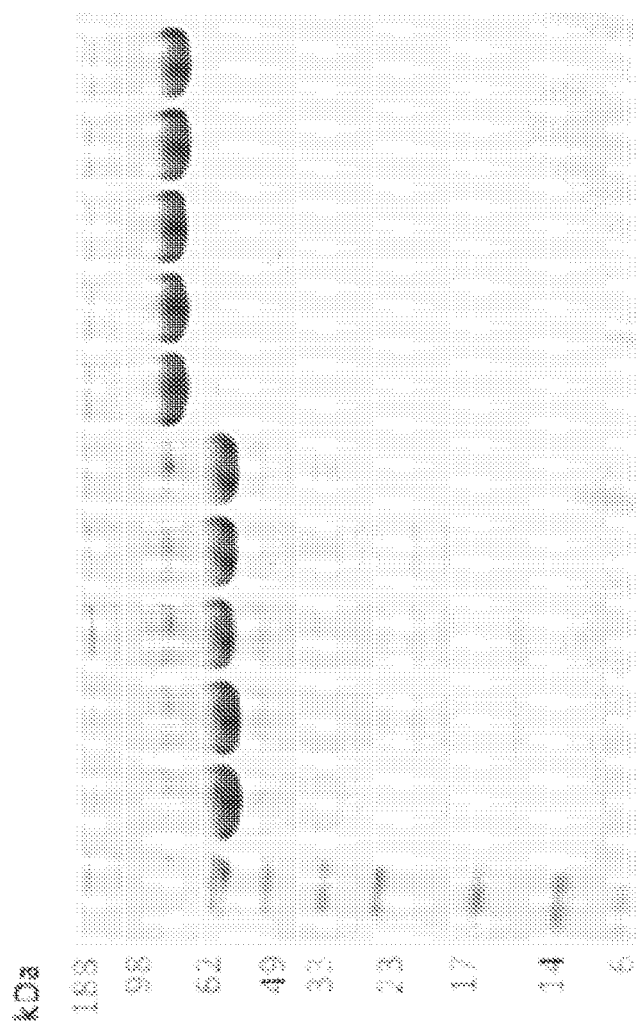
FIG. 11A and FIG. 11B show the expression and purification of bispecific antibodies.

Aa series of VRC01-PGT121 bi-ScFvs and full length IgGs were generated (FIG. 3B), with combinations and permutations of VH-VL orientations and linker length for optimization (SEQ ID NOs 1-27). The nomenclature of these constructs was defined by the VH-VL orientations and linker length. For instance, VRC01-5x-PGT121 refers to VRC01(VL-VH)-(G4S)$_5$-PGT121(VL-VH). A construct was also made containing a 2 amino acid deletion at the N-terminus of VRC01 VL to avoid potential steric clash reported previously, which was designated as $_d$VRC01-5x-PGT121 (FIG. 3B). These bi-ScFvs and full length IgGs were expressed in mammalian 293FreeStyle cells and purified by Ni+ and protein A column, respectively. All the proteins have expected molecular weight, as shown in representative SDS-PAGE gels (FIG. 11A), as well as size exclusion chromatography (FIG. 3C).

Figure 4:
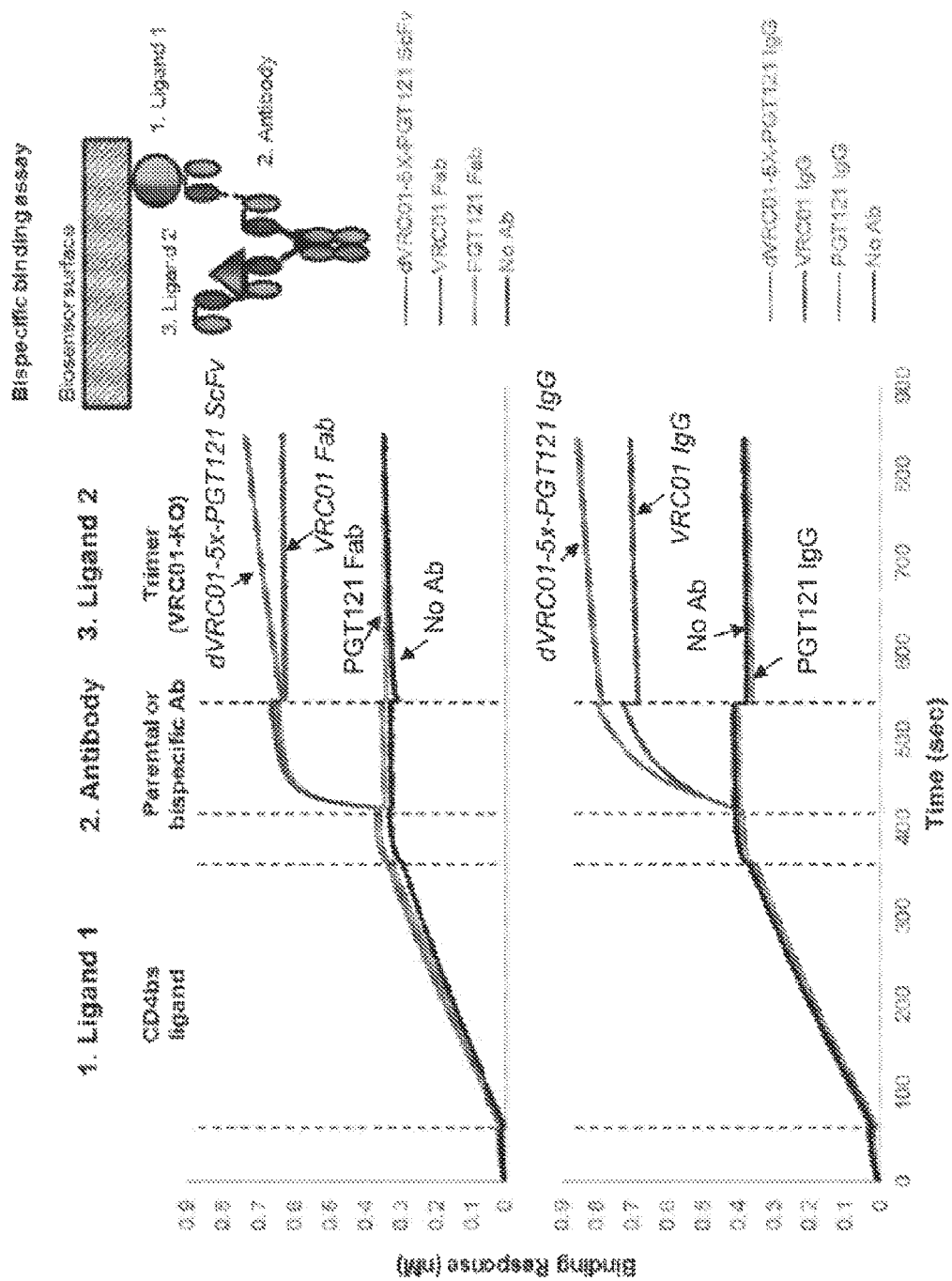
FIG. 4 depicts a set of graphs that show bi-ScFv and bi-IgG1 of VRC01-PGT121 interaction with HIV-1 Env revealed by Bio-Layer Interferometry (BLI), validating the expected bispecific binding feature. dVRC01-5X-PGT121 scFv and dVRC01-5X-PGT121 IgG were able to bind both CD4bs ligand and Env BG505 SOSIP trimer D368R mutant (VRC01-KO).
Figure 12A:
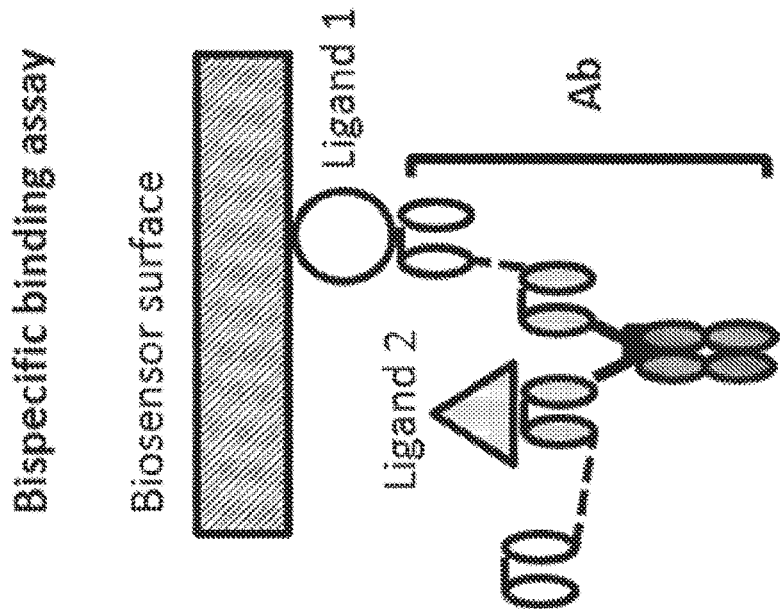
FIG. 12A-C Binding characteristics of anti-Env bispecific antibodies.
Figure 12B:
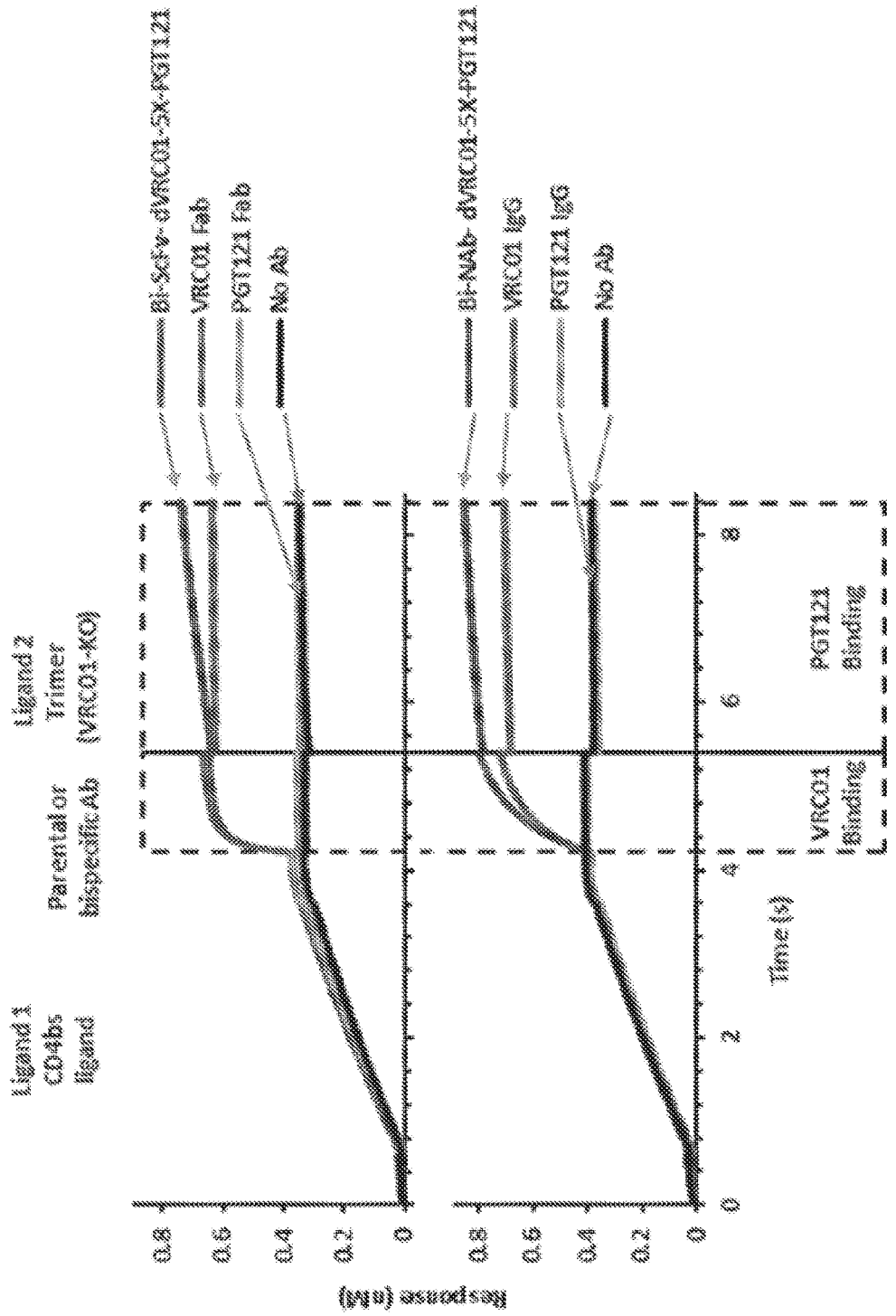
Figure 12C:
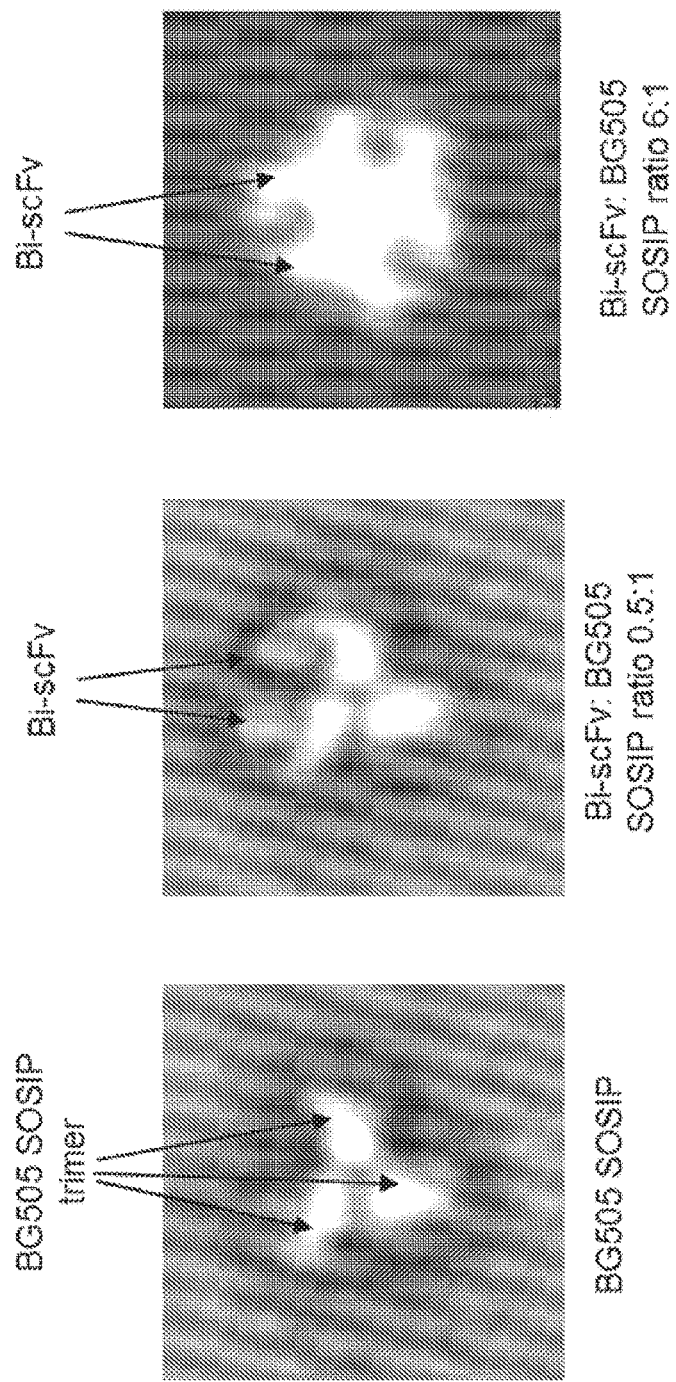

FIG. 4 shows bi-ScFv and bi-IgG1 of VRC01-PGT121 interact with HIV-1 Env trimer in a bispecific manner. The binding specificities of these constructs were validated by ELISA binding assay (not shown) as well as Bio-Layer Interferometry (BLI) which demonstrated that both VRC01 and PGT121 binding moieties are functional (FIG. 4). As shown in FIG. 4, Env CD4bs ligand, RSC3 (Ligand 1), was initially captured to BLI probe, followed by loading the bi-ScFv (upper) and bi-IgG1 (lower) or control antibodies to the probe. The binding signals between the CD4bs ligand RSC3 and the test antibodies were shown as the increased binding response. As expected, only VRC01 and the bi-ScFv or bi-IgG1 demonstrated substantial binding signals. Subsequently, the probe was immersed into buffers containing trimeric Env protein (ligand 2) with CD4bs knockout mutation (VRC01 K/O) but retaining the V3 base glycan epitope for PGT121 recognition. Only the bi-ScFv or bi-IgG1 which recognizes both CD4bs and V3 base glycan epiotipes displayed binding response signal. Furthermore, it was shown using single molecule electron microscopy (EM) analysis that the VRC01-PGT121 bi-ScFv binds Env trimer in a bi-specific manner (FIG. 12C). The well-behaved expression and Env trimer binding phenotypes of the bi-ScFV and IgGs firmly authenticates the rationales of the design.

Figure 5A:
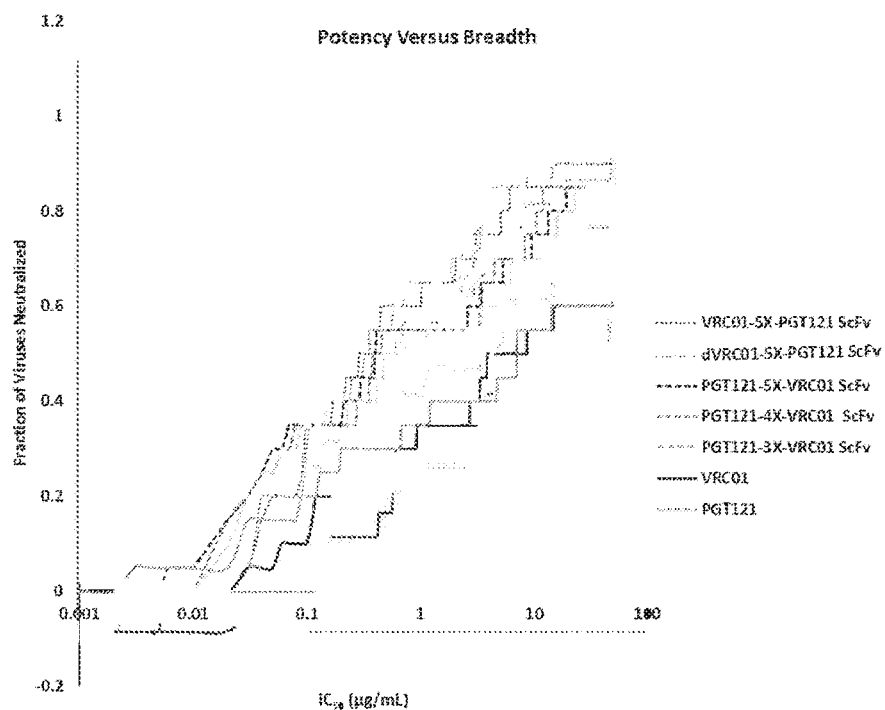
FIG. 5A depicts a graph that shows the potency and breadth curve of Bi-ScFv molecules tested with selected 20 virus panel.
Figure 5B:
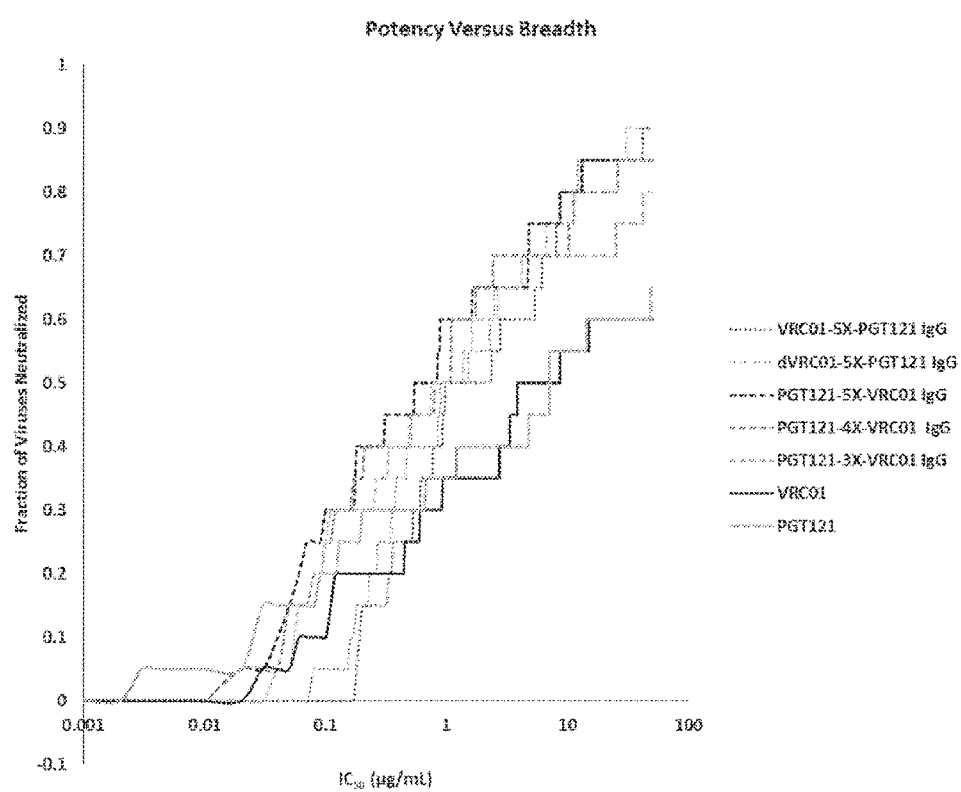
FIG. 5B is a graph that shows the potency and breadth curve of bi-IgG1 molecules tested with selected 20 virus panel.

To assess neutralization capacity of the bi-ScFvs and IgGs, an initial virus panel of high stringency consisting of 20 tier 2 virus strains, including 12 single- and 2 dual-resistant strains was used. The results are shown in FIG. 5A-FIG. 5E. FIG. 5A is a graph that shows the potency and breadth curve of Bi-ScFv molecules tested with selected 20 virus panel. FIG. 5B is a graph that shows the potency and breadth curve of bi-IgG1 molecules tested with selected 20 virus panel. FIG. 5C is a table that shows a summary of the virus neutralization parameters of the bispecific antibody molecules. FIG. 5D-FIG. 5E is a table that shows virus neutralization potency displayed with IC$_{50}$ (ug/ml) values.

Figure 6A:
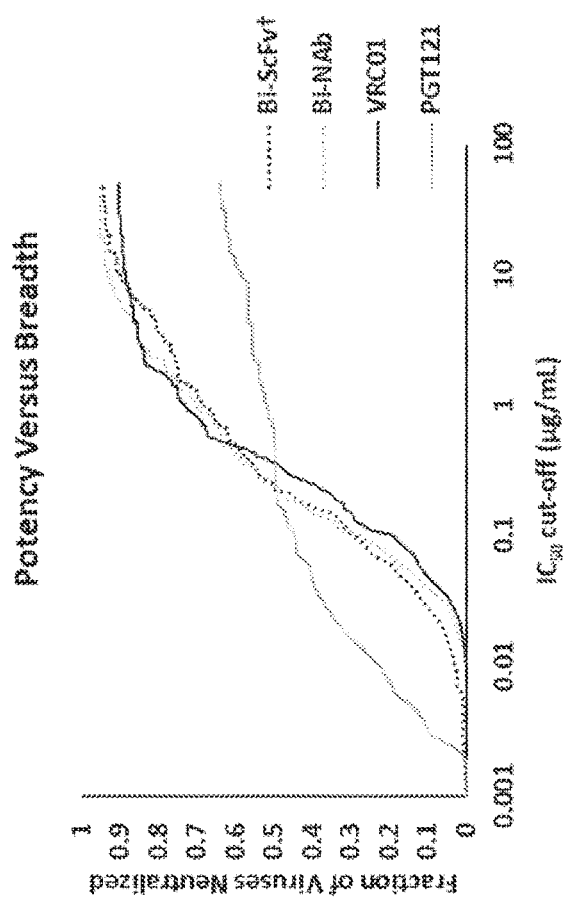
FIG. 6A is a graph that shows potency and breadth curves.
Figure 7A:
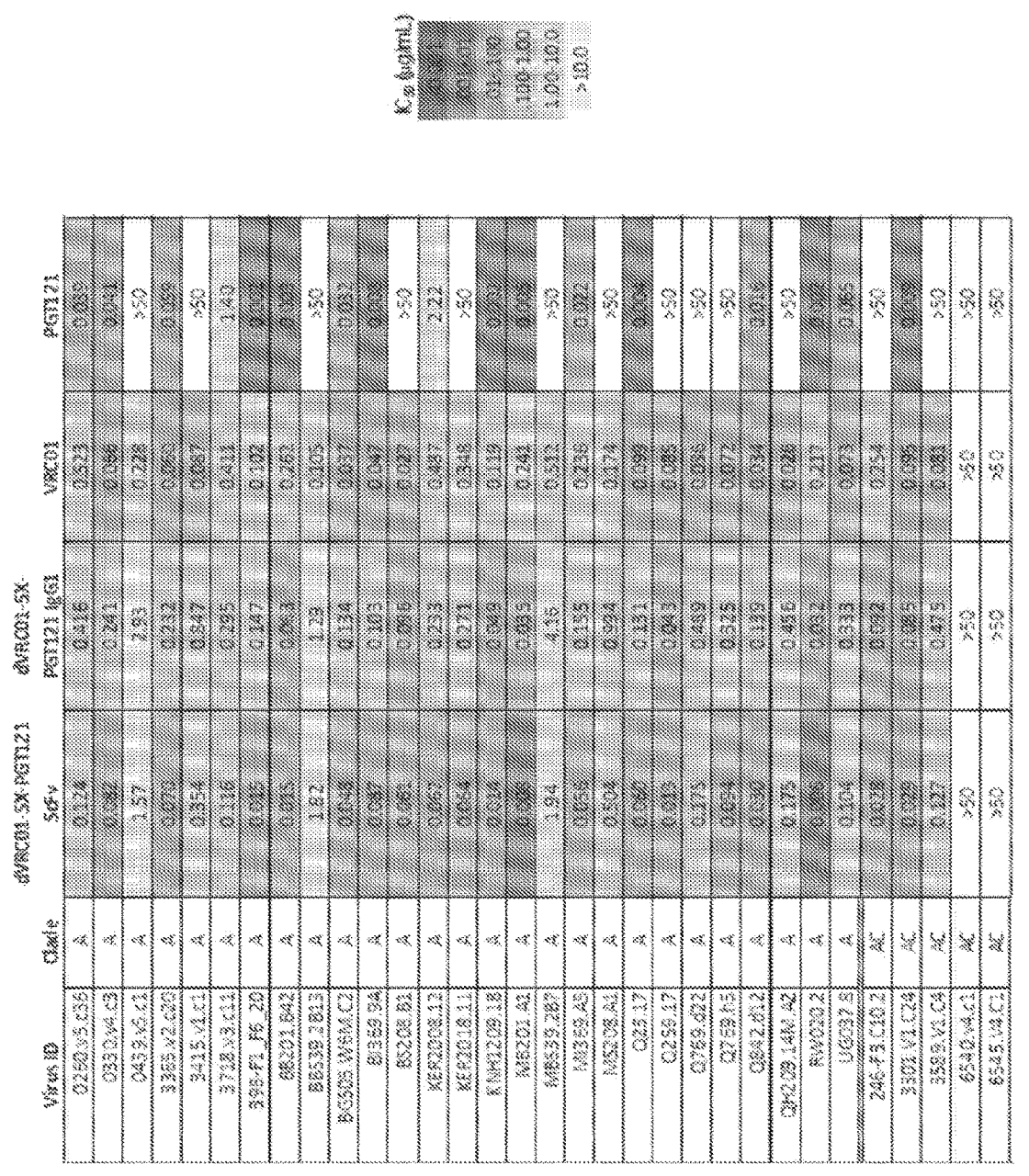
Figure 7B:
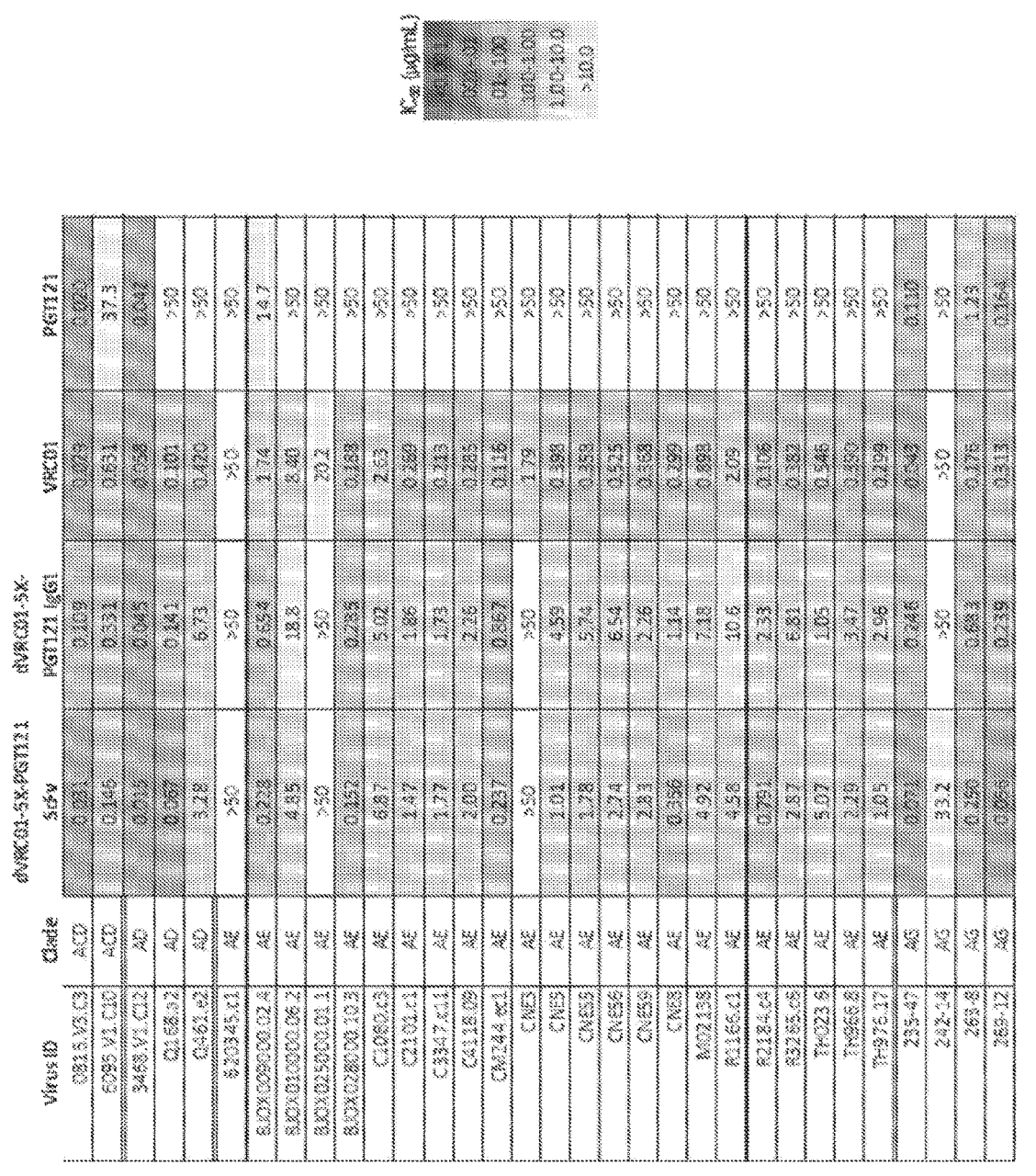
Figure 7C:
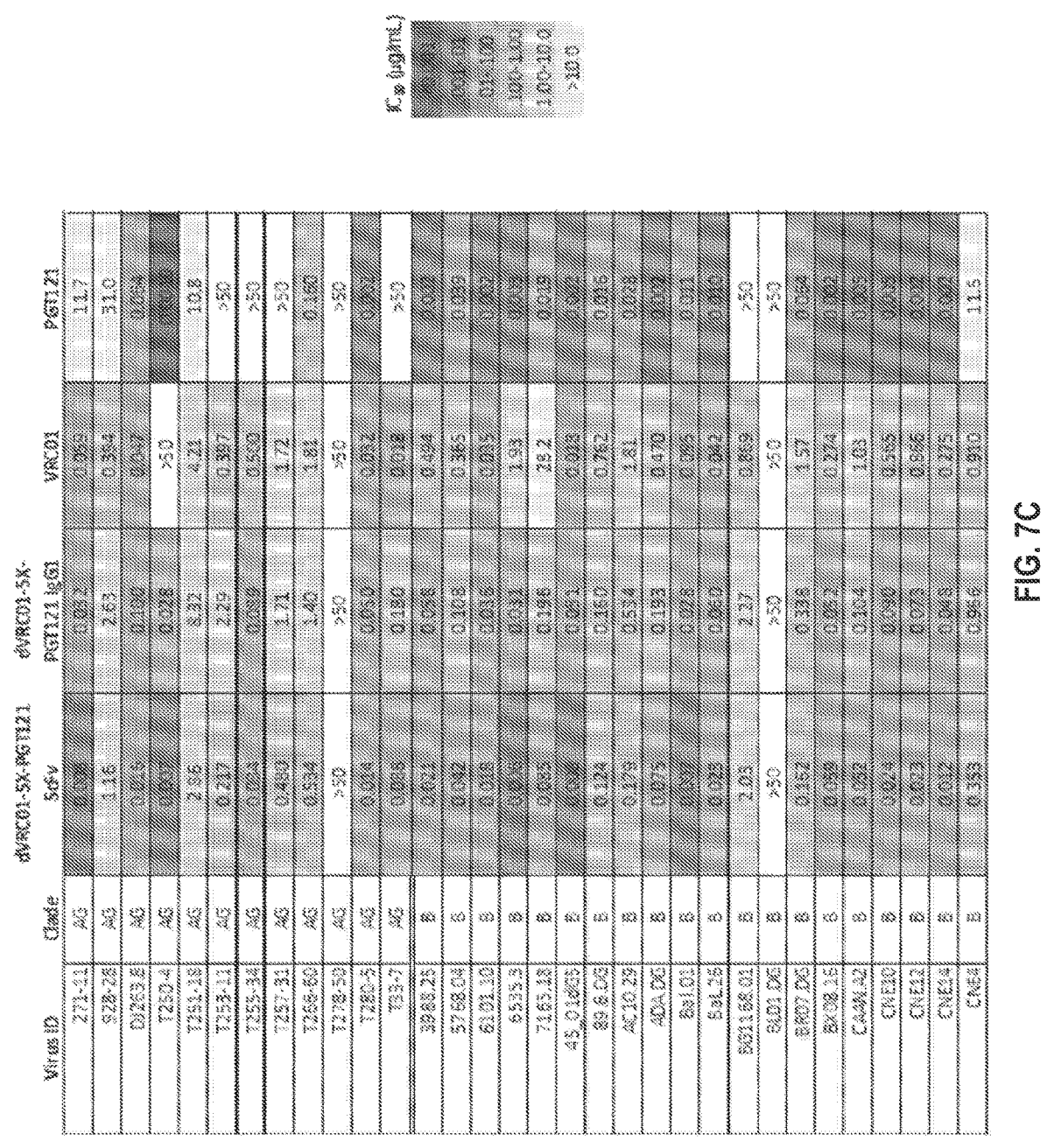
Figure 7D:
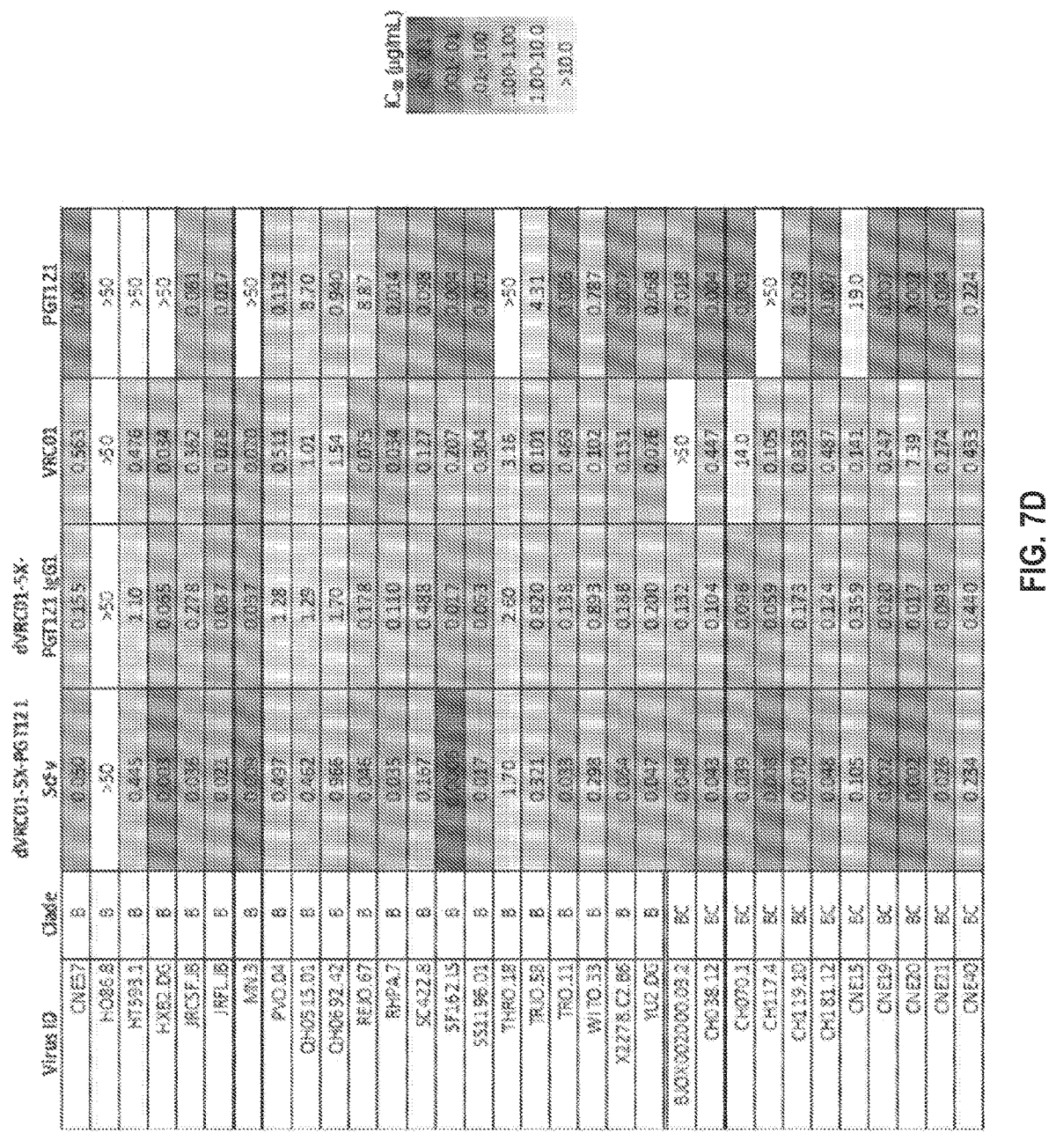
Figure 7F:
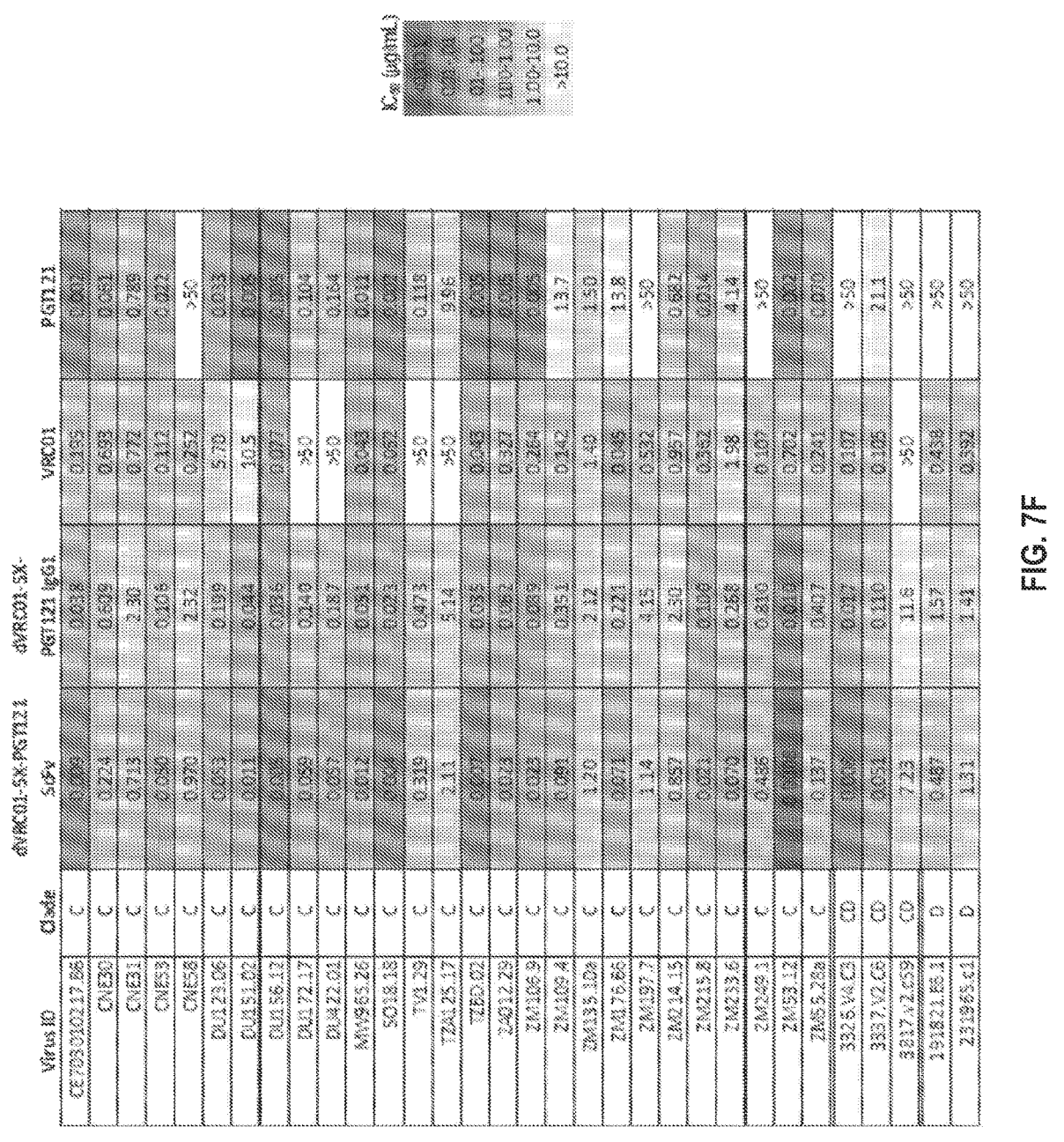
Figure 7G:
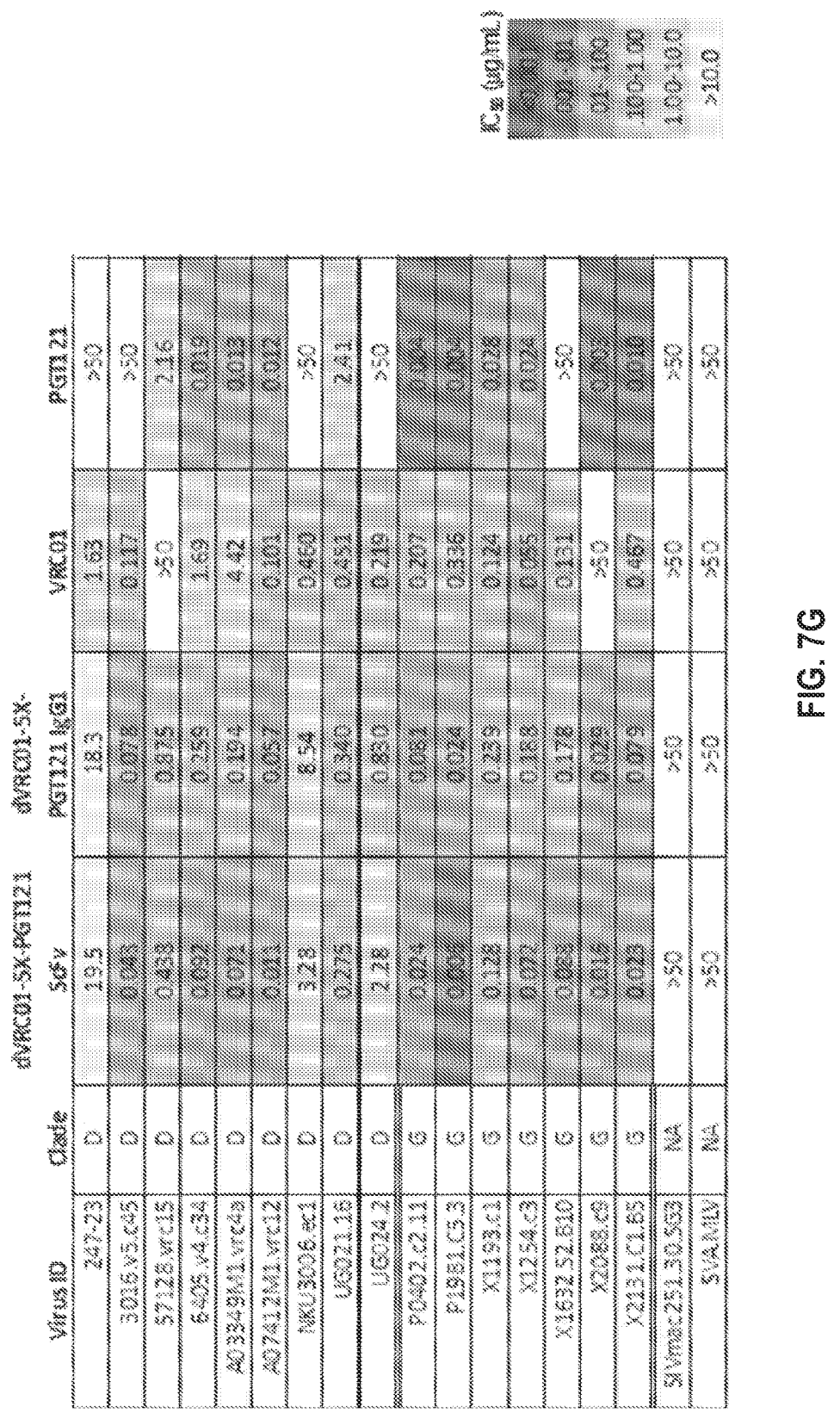

As shown in FIG. 5, most of the VRC01-PGT121 bispecific scFvs and IgGs (N=10) display expanded virus neutralization breadth compared with the parental antibody VRC01 and PGT121, respectively. Of the multiple iterations tested, one combination of VRC01/PGT121, namely $_d$VRC01-5x-PGT121, containing (G4S)$_5$ linker and a 2 amino acid residue deletion in the N-terminus of VRC01 light chain, was found to display improved coverage over the parental antibodies with 100% coverage of neutralization, and potency comparable to the combination of the individual parental antibodies (FIG. 5C and FIG. 5D-FIG. 5E). In IgG1 form, its virus coverage is much higher than PGT121 and slightly higher than VRC01 (FIG. 6 and FIG. 7), when assayed with a more expanded 200 virus panel. FIG. 6A-FIG. 6C shows bi-ScFv and bi-IgG1 of VRC01-PGT121 virus neutralization potency and breadth assessed with a 200 virus panel reflecting the worldwide diversified HIV-1 primary isolates. FIG. 7A-FIG. 7G is a Table that shows neutralization potency and breadth (IC$_{50}$ value, in µg/ml) of $_d$VRC01-PGT bi-ScFv and IgG assessed against a 200-isolate virus panel.

These results suggest that through rational design and iterative optimization, bi-ScFv-based antibodies can achieve superior neutralization breadth and may be candidate moieties for engineering multifunctional anti-viral agents for the prevention and treatment of HIV-1 infection.

Figure 8:
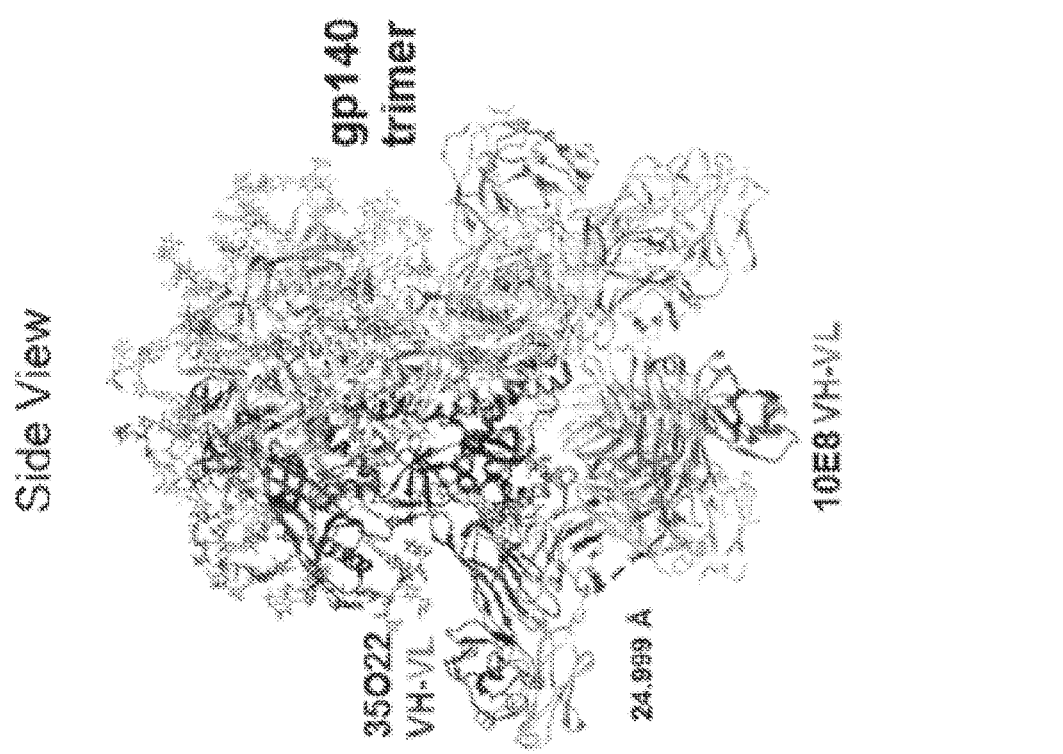
FIG. 8 shows modeling of Env trimer binding to bNAbs 35022 and 10E8 simultaneously by superimposing individual bNAb Fab-Env complex structures. The relatively short distance between the variable chains of 35022 and 10E8 (25 Å) suggests that it is feasible to engineer bi-ScFvs of these bNAbs.

Example 2. Synergistic Effect by Bi-Specific bNAbs Targeting the Gp120/Gp41 Interface and the Gp41 MPER Among the five major bNAb epitope clusters, the gp41 MPER targeted by 10E8, and the gp120/gp41 interface recognized by 35022 (27) are located in proximity on the Env trimer. By superimposing the structures of Env BG505 SOSIP.664 trimer-35022 complex (27) with the more recent fully glycosylated Env trimer-10E8 complex (3), the spatial distance between the variable domains of 35022 and 10E8 (FIG. 8) was determined, and a series of bi-ScFvs were designed in similar manners with the VRC01-PGT121 bi-ScFvs described supra. The sequences of these biScFvs and IgG molecules are shown in SEQ ID NOs 30-53.

The engineered 35022-10E8 bi-ScFv and IgG molecules were initially purified and tested for binding to their cognate epitopes on Env protein variants including MPER peptide (specific for 10E8) and BG505 SOSIP.664 (specific for 35022). As expected, all bi-specific molecules display positive binding to both epitopes (not shown).

Next, virus neutralization capacities were tested against a virus panel of high stringency consisting of 24 tier 2 & 3 viruses similar to that were used for testing the bi-ScFVs of VRC01-PGT121. It is of note that this panel of viruses displays a high degree of resistance to 35022, with only 33% virus coverage but high potency for the sensitive strains, while most of these viruses are sensitive to 10E8 neutralization with 92% coverage and good potency (geometric mean $IC_{50}=0.5$ µg/ml).

Figure 9A:
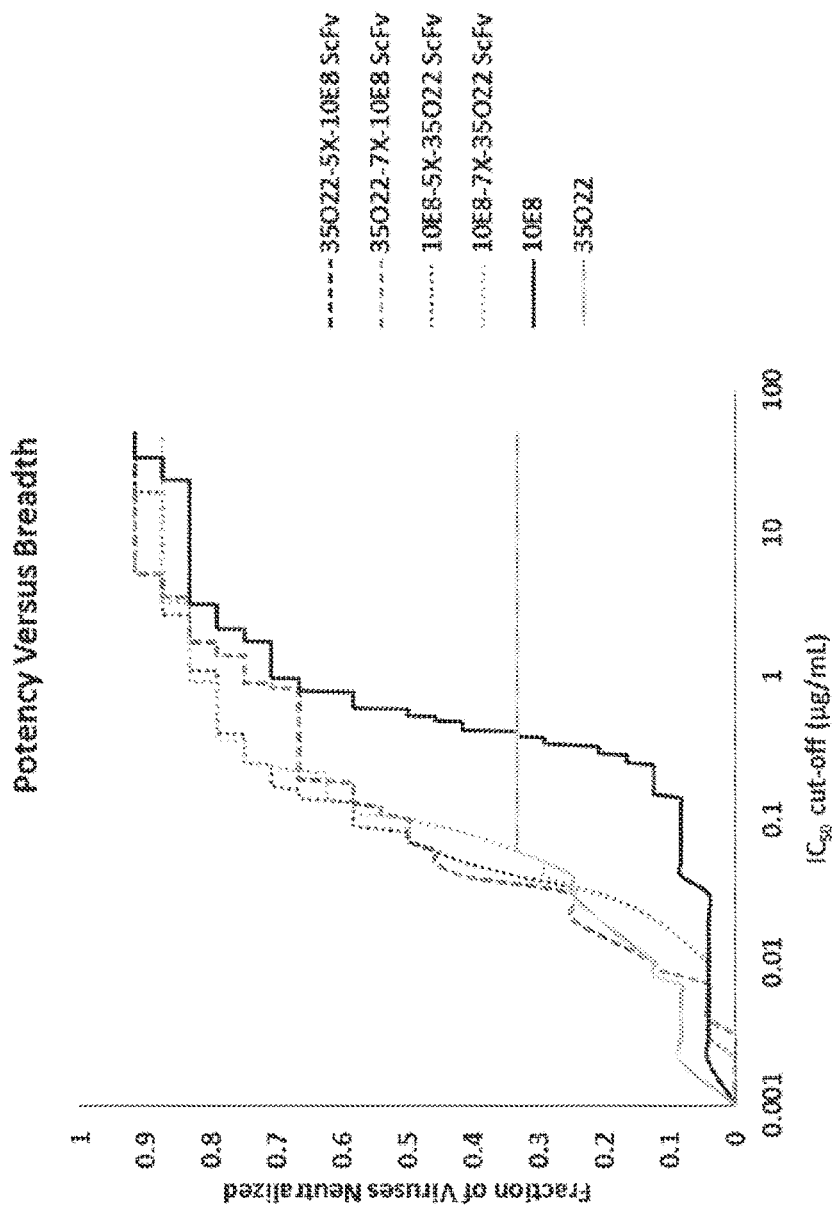
FIG. 9A is a graph that shows neutralization profiles of bi-ScFvs of 10E8 and 35022.
Figure 9B:
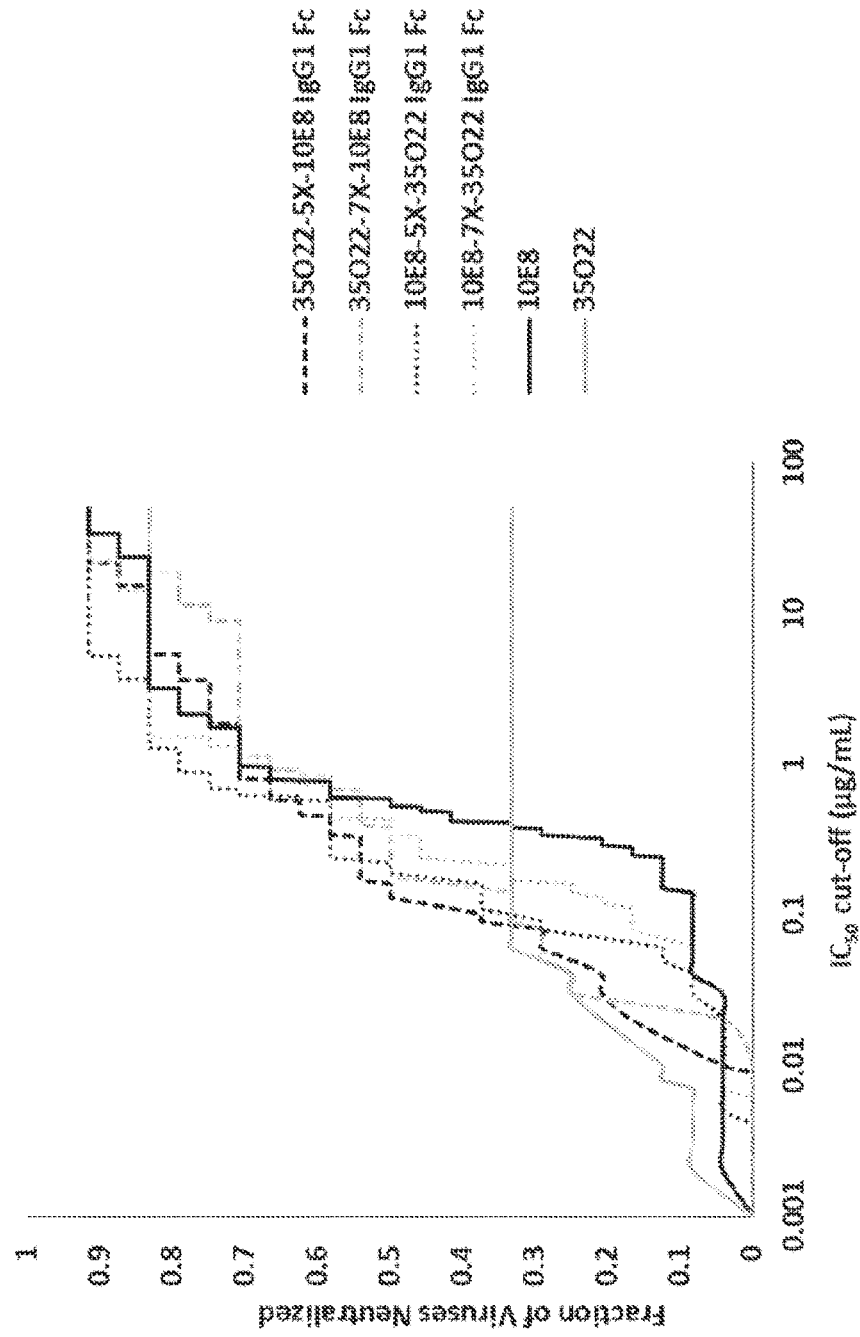
FIG. 9B is a graph that shows neutralization profiles of bi-NAb (IgGs) of 10E8 and 35022.

FIG. 9A-FIG. 9C shows bi-ScFv and IgG of 35022-10E8 virus neutralization potency and breadth tested with selected 24 virus panel. The 35022-10E8 bi-ScFvs and IgGs demonstrated unaltered or slightly improved virus coverage (92-96%) (FIG. 9A and FIG. 9B). Interestingly, substantially increased potencies of the bi-functional molecules was found compared to the parental bNAb 10E8 and 35022 (FIG. 9C), likely caused by synergistic effect, which will be validated in subsequent analysis. An expanded 200 virus panel will also be further tested to confirm the neutralization potency and breadth.

REFERENCES CITED

1. Burton D R, Mascola J R. 2015. Antibody responses to envelope glycoproteins in HIV-1 infection. Nat Immunol 16:571-576.
2. Kwong P D, Mascola J R, Nabel G J. 2013. Broadly neutralizing antibodies and the search for an HIV-1 vaccine: the end of the beginning. Nat Rev Immunol 13:693-701.
3. Lee J H, Ozorowski G, Ward A B. 2016. Cryo-E M structure of a native, fully glycosylated, cleaved HIV-1 envelope trimer. Science 351:1043-1048.
4. Huang J, Kang B H, Pancera M, Lee J H, Tong T, Feng Y, Imamichi H, Georgiev I S, Chuang G Y, Druz A, Doria-Rose N A, Laub L, Sliepen K, van Gils M J, de la Pena A T, Derking R, Klasse P J, Migueles S A, Bailer R T, Alam M, Pugach P, Haynes B F, Wyatt R T, Sanders R W, Binley J M, Ward A B, Mascola J R, Kwong P D, Connors M. 2014. Broad and potent HIV-1 neutralization by a human antibody that binds the gp41-gp120 interface. Nature 515:138-142.
5. Kong R, Louder M K, Wagh K, Bailer R T, deCamp A, Greene K, Gao H, Taft J D, Gazumyan A, Liu C, Nussenzweig M C, Korber B, Montefiori D C, Mascola J R. 2015. Improving neutralization potency and breadth by combining broadly reactive HIV-1 antibodies targeting major neutralization epitopes. J Virol 89:2659-2671.
6. Gallo R C, Salahuddin S Z, Popovic M, Shearer G M, Kaplan M, Haynes B F, Palker T J, Redfield R, Oleske J, Safai B, et al. 1984. Frequent detection and isolation of cytopathic retroviruses (HTLV-III) from patients with AIDS and at risk for AIDS. Science 224:500-503.
7. Barre-Sinoussi F, Chermann J C, Rey F, Nugeyre M T, Chamaret S, Gruest J, Dauguet C, Axler-Blin C, Vezinet-Brun F, Rouzioux C, Rozenbaum W, Montagnier L. 1983. Isolation of a T-lymphotropic retrovirus from a patient at risk for acquired immune deficiency syndrome (AIDS). Science 220:868-871.
8. Kowalski M, Potz J, Basiripour L, Dorfman T, Goh W C, Terwilliger E, Dayton A, Rosen C, Haseltine W, Sodroski J. 1987. Functional regions of the envelope glycoprotein of human immunodeficiency virus type 1. Science 237:1351-1355.
9. Lu M, Blacklow S C, Kim P S. 1995. A trimeric structural domain of the HIV-1 transmembrane glycoprotein. Nat Struct Biol 2:1075-1082.
10. Wyatt R, Sodroski J. 1998. The HIV-1 envelope glycoproteins: fusogens, antigens, and immunogens. Science 280:1884-1888.
11. Barouch D H, Whitney J B, Moldt B, Klein F, Oliveira T Y, Liu J, Stephenson K E, Chang H W, Shekhar K, Gupta S, Nkolola J P, Seaman M S, Smith K M, Borducchi E N, Cabral C, Smith J Y, Blackmore S, Sanisetty S, Perry J R, Beck M, Lewis M G, Rinaldi W, Chakraborty A K, Poignard P, Nussenzweig M C, Burton D R. 2013. Therapeutic efficacy of potent neutralizing HIV-1-specific monoclonal antibodies in SHIV-infected rhesus monkeys. Nature 503:224-228.
12. Shingai M, Nishimura Y, Klein F, Mouquet H, Donau O K, Plishka R, Buckler-White A, Seaman M, Piatak M, Jr., Lifson J D, Dimitrov D S, Nussenzweig M C, Martin M A. 2013. Antibody-mediated immunotherapy of macaques chronically infected with SHIV suppresses viraemia. Nature 503:277-280.
13. Klein F, Halper-Stromberg A, Horwitz J A, Gruell H, Scheid J F, Bournazos S, Mouquet H, Spatz L A, Diskin R, Abadir A, Zang T, Dorner M, Billerbeck E, Labitt R N, Gaebler C, Marcovecchio P M, Incesu R B, Eisenreich T R, Bieniasz P D, Seaman M S, Bjorkman P J, Ravetch J V, Ploss A, Nussenzweig M C. 2012. HIV therapy by a combination of broadly neutralizing antibodies in humanized mice. Nature 492:118-122.
14. Diskin R, Klein F, Horwitz J A, Halper-Stromberg A, Sather D N, Marcovecchio P M, Lee T, West A P, Jr., Gao H, Seaman M S, Stamatatos L, Nussenzweig M C, Bjorkman P J. 2013. Restricting HIV-1 pathways for escape using rationally designed anti-HIV-1 antibodies. J Exp Med 210:1235-1249.
15. Ko S Y, Pegu A, Rudicell R S, Yang Z Y, Joyce M G, Chen X, Wang K, Bao S, Kraemer T D, Rath T, Zeng M, Schmidt S D, Todd J P, Penzak S R, Saunders K O, Nason M C, Haase A T, Rao S S, Blumberg R S, Mascola J R, Nabel G J. 2014. Enhanced neonatal Fc receptor function improves protection against primate SHIV infection. Nature 514:642-645.

16. Balazs A B, Chen J, Hong C M, Rao D S, Yang L, Baltimore D. 2012. Antibody-based protection against HIV infection by vectored immunoprophylaxis. Nature 481:81-84.
17. Balazs A B, Ouyang Y, Hong C M, Chen J, Nguyen S M, Rao D S, An D S, Baltimore D. 2014. Vectored immunoprophylaxis protects humanized mice from mucosal HIV transmission. Nat Med 20:296-300.
18. Pegu A, Yang Z Y, Boyington J C, Wu L, Ko S Y, Schmidt S D, McKee K, Kong W P, Shi W, Chen X, Todd J P, Letvin N L, Huang J, Nason M C, Hoxie J A, Kwong P D, Connors M, Rao S S, Mascola J R, Nabel G J. 2014. Neutralizing antibodies to HIV-1 envelope protect more effectively in vivo than those to the CD4 receptor. Sci Transl Med 6:243ra288.
19. Lynch R M, Boritz E, Coates E E, DeZure A, Madden P, Costner P, Enama M E, Plummer S, Holman L, Hendel C S, Gordon I, Casazza J, Conan-Cibotti M, Migueles S A, Tressler R, Bailer R T, McDermott A, Narpala S, O'Dell S, Wolf G, Lifson J D, Freemire B A, Gorelick R J, Pandey J P, Mohan S, Chomont N, Fromentin R, Chun T W, Fauci A S, Schwartz R M, Koup R A, Douek D C, Hu Z, Capparelli E, Graham B S, Mascola J R, Ledgerwood J E, Team VRCS. 2015. Virologic effects of broadly neutralizing antibody VRC01 administration during chronic HIV-1 infection. Sci Transl Med 7:319ra206.
20. Caskey M, Klein F, Lorenzi J C, Seaman M S, West A P, Jr., Buckley N, Kremer G, Nogueira L, Braunschweig M, Scheid J F, Horwitz J A, Shimeliovich I, Ben-Avraham S, Witmer-Pack M, Platten M, Lehmann C, Burke L A, Hawthorne T, Gorelick R J, Walker B D, Keler T, Gulick R M, Fatkenheuer G, Schlesinger S J, Nussenzweig M C. 2015. Viraemia suppressed in HIV-1-infected humans by broadly neutralizing antibody 3BNC117. Nature 522:487-491.
21. Doria-Rose N A, Louder M K, Yang Z, O'Dell S, Nason M, Schmidt S D, McKee K, Seaman M S, Bailer R T, Mascola J R. 2012. HIV-1 neutralization coverage is improved by combining monoclonal antibodies that target independent epitopes. J Virol 86:3393-3397.
22. Asokan M, Rudicell R S, Louder M, McKee K, O'Dell S, Stewart-Jones G, Wang K, Xu L, Chen X, Choe M, Chuang G, Georgiev I S, Joyce M G, Kirys T, Ko S, Pegu A, Shi W, Todd J P, Yang Z, Bailer R T, Rao S, Kwong P D, Nabel G J, Mascola J R. 2015. Bispecific Antibodies Targeting Different Epitopes on the HIV-1 Envelope Exhibit Broad and Potent Neutralization. J Virol 89:12501-12512.
23. Bournazos S, Gazumyan A, Seaman M S, Nussenzweig M C, Ravetch J V. 2016. Bispecific Anti-HIV-1 Antibodies with Enhanced Breadth and Potency. Cell 165:1609-1620.
24. Wu X, Yang Z Y, Li Y, Hogerkorp C M, Schief W R, Seaman M S, Zhou T, Schmidt S D, Wu L, Xu L, Longo N S, McKee K, O'Dell S, Louder M K, Wycuff D L, Feng Y, Nason M, Doria-Rose N, Connors M, Kwong P D, Roederer M, Wyatt R T, Nabel G J, Mascola J R. 2010. Rational design of envelope identifies broadly neutralizing human monoclonal antibodies to HIV-1. Science 329:856-861.
25. Walker L M, Huber M, Doores K J, Falkowska E, Pejchal R, Julien J P, Wang S K, Ramos A, Chan-Hui P Y, Moyle M, Mitcham J L, Hammond P W, Olsen O A, Phung P, Fling S, Wong C H, Phogat S, Wrin T, Simek M D, Koff W C, Wilson I A, Burton D R, Poignard P. 2011. Broad neutralization coverage of HIV by multiple highly potent antibodies. Nature 477:466-470.
26. Bolton D L, Pegu A, Wang K, McGinnis K, Nason M, Foulds K, Letukas V, Schmidt S D, Chen X, Todd J P, Lifson J D, Rao S, Michael N L, Robb M L, Mascola J R, Koup R A. 2016. Human Immunodeficiency Virus Type 1 Monoclonal Antibodies Suppress Acute Simian-Human Immunodeficiency Virus Viremia and Limit Seeding of Cell-Associated Viral Reservoirs. J Virol 90:1321-1332.
27. Pancera M, Zhou T, Druz A, Georgiev I S, Soto C, Gorman J, Huang J, Acharya P, Chuang G Y, Ofek G, Stewart-Jones G B, Stuckey J, Bailer R T, Joyce M G, Louder M K, Tumba N, Yang Y, Zhang B, Cohen M S, Haynes B F, Mascola J R, Morris L, Munro J B, Blanchard S C, Mothes W, Connors M, Kwong P D. 2014. Structure and immune recognition of trimeric pre-fusion HIV-1 Env. Nature 514:455-461.
28. Huang J, Ofek G, Laub L, Louder M K, Doria-Rose N A, Longo N S, Imamichi H, Bailer R T, Chakrabarti B, Sharma S K, Alam S M, Wang T, Yang Y, Zhang B, Migueles S A, Wyatt R, Haynes B F, Kwong P D, Mascola J R, Connors M. 2012. Broad and potent neutralization of HIV-1 by a gp41-specific human antibody. Nature 491: 406-412.

Example 3. Methods

This example describes the general methods used to carry out the experiments in Examples 4-9. The methods used in Examples 4-9 include, but are not limited to the below described methods.

Analysis of Ab Structures in Complex with SOSIP

The published structure of the two bNAbs PGT122 and VRC01 bound to JR-FL SOSIP.664 (PDB: 5FYK)[40] was used to model bispecific combinations of VRC01 and PGT121 in the program Chimera[41] where PGT122 served as the surrogate for PGT121. Trimers were visualized using the Higher Order Structure-Unit Cell tool. Antibody variable domains were retained for analysis, while antibody residues corresponding to the CL1 and CH1 regions were deleted from the Fab entities. Distances between termini were assessed by selecting the respective terminis' Cβ atoms using the Structure Analysis-Distance tool and measuring the spatial distance.

Antibody Production

Bi-NAbs in a ScFv format were designed utilizing tetraglycine-serine ($G_4S$) peptide linkers[36, 37]. C-terminal His-tagged Bi-ScFvs DNA sequences were synthesized (GenScript, Piscataway, N.J.) and cloned into the pcDNA3.1(−) vector while the Bi-ScFv lacking the C-terminal His tag was subcloned into an IgG1 Fc vector as well as IgG1 Fc vectors carrying knob-and-hole mutations[32]. Bi-NAbs were expressed by transient transfection of either Bi-ScFv or Bi-ScFv-IgG1 Fc plasmids in 293F cells. Tri-NAbs were expressed by transient transfection of the Bi-ScFv$_{dVRC01-5X-PGT121}$ IgG1 Fc "knob", 10E8 HC "hole" and 10E8 LC plasmids in 293F cells. Supernatants were harvested 5 days post transfection, filtrated, followed by affinity purification. Bi-ScFvs with 6-His tag were purified by Complete His-tag purification resin (Sigma-Aldrich). Bi-NAb and Tri-NAb with IgG1 Fc were purified by protein A affinity chromatography. Elutes were dialyzed with phosphate-buffered saline (PBS), and concentrated using an Amicon Ultra 10 kDa molecular weight cut-off concentrator. Antibody purity was analyzed by SDS PAGE.

Protein Purification

BG505 SOSIP.664, an avi-tagged version of BG505 SOSIP.664_D368R, and RSC3 core were expressed in 293F cells, purified using a *Galanthus nivalis* (GN)-lectin column as previously described[57], followed by purifications with size-exclusive chromatography (SEC) with purity confirmed by Blue NativePage. The BirA 500 biotin ligase (AVIDITY AVITAG Technology) was utilized according to the manufacturer's protocol to biotinylate the C-terminal avi-tags of BG505 SOSIP.664_D368R and RSC3.

Ab Binding Affinity

Biolayer light interferometry (BLI) was performed using an Octet RED96 instrument (ForteBio; Pall Life Sciences). Bispecific binding was confirmed by first capturing biotin labeled RSC3 (ligand 1) at 10 µg/ml onto Streptavidin biosensors for 300 seconds. The biosensors were then submerged in binding buffer (PBS/0.2% TWEEN 20) for a wash for 60 seconds followed by immersion in a solution containing 250 nM of either the parental or Bi-NAb antibodies for 180 seconds and an immediate immersion in a solution containing 300 µg/ml of trimeric BG505 SOSIP.664_D368R (ligand 2) for 300 seconds.

Trispecific binding was confirmed by first capturing 10 µg/ml of biotin labeled RSC3 (ligand 1) onto Streptavidin biosensors for 300 seconds. The biosensors were then submerged in binding buffer for a wash of 60 seconds. Then, the biosensors were immersed in a solution containing 250 nM of either the parental or Bi-NAb antibodies for 180 seconds followed by an immediate immersion in a solution containing 300 µg/ml of trimeric BG505 SOSIP.664_D368R (ligand 2) for 300 seconds. Finally, the biosensors were immersed in a solution containing 50 µg/ml of MPER peptide fused to a rabbit Fc (MPER rFc) for 120 seconds. Baselines were established before and after the loading step. All assays were performed in 1× binding buffer.

HIV-1 Neutralization Assays

Ab neutralization assays were performed in a single round of infection using HIV-1 Env-pseudoviruses and TZM-bl target cells, as previously described[58, 59]. Neutralization curves were fitted by nonlinear regression using a five-parameter hill slope equation as previously described[58]. The $IC_{50}$ or $IC_{80}$ titers of Abs were reported as the concentration of Ab required to inhibit infection by 50% and 80%, respectively. The $IC_{50}$ or $IC_{80}$ geometric mean (Geomean) indicating mAb neutralization potency was derived from $IC_{50}$ or $IC_{80}$ values against each individual tier 2 virus for each mAb. When $IC_{50}$ or $IC_{80}$ value is >50 µg/mL for certain viruses (no neutralization), a value of 50 µg/mL is designated for calculation. The number of viruses neutralized by mAb ($IC_{50}$ or $IC_{80}$<50 µg/mL) out of the total number of tested viruses was used to calculate the neutralization breadth. The virus panel for the neutralization profile covers the major genetic subtypes and circulating recombinant forms and consists almost entirely of primary isolate Envs[45].

Electron Microscopy Analysis

To confirm bivalent binding, Bi-ScFv/BG505 SOSIP.664 complexes were generated by incubating 6× molar ScFv with BG505 SOSIP.664 overnight at room temperature, followed by purification of complexes by SEC. To specifically confirm crosslinking of the HIV Env trimer, ScFv/BG505 SOSIP.664 complexes were generated by incubating 0.5× molar ScFv with BG505 SOSIP.664 overnight at room temperature, followed by purification of complexes by SEC. Complexes were then deposited on 400 mesh copper grids and stained with 2% uranyl formate. Negative stain EM images were taken on a 120 kv Tecnai Spirit microscope with a LAB6 filament. Raw micrographs were collected using Leginon[60] and deposited in Appion [61]. DoG picker[62] was performed to select particles in stain. Those particles were stacked and aligned using Iterative MSA/MRA[63]. 2D classes representing the complex are shown in FIG. 12 and FIG. 13. Images were false colored using Photoshop.

Statistical Analysis

Comparisons of antibody neutralization performance was carried out with one-way ANOVA. Statistical evaluation of difference between two groups was performed via non-parametric t test for paired data, determined with Wilcoxon matched-pairs signed rank test, with a two-tailed p value calculated for significance. Statistical significance was determined as *$p<0.05$, $p<0.01$, *$p<0.001$, ****$p<0.0001$. All statistical analysis was performed with GraphPad Prism version 7.

Example 4. Structural Analysis of the Interactions of HIV-1 Env Trimer with bNAbs For the first step towards generating multi-epitope targeting bNAbs, bispecific single-chain variable fragment (Bi-ScFv) were engineered. This construct consists of two bNAb variable fragments (Fv) connected by a flexible amino acid linker whose length was estimated following Env/bNAb structural information[36, 37]. bNAbs VRC01 (CD4bs-directed) [8] and PGT121 (V3-base glycan-directed)[9], which neutralize approximately 90% and 70% of circulating viruses, respectively, were selected as a model system to determine if a Bi-ScFv could improve breadth and potency over the capacities of the individual bNAbs. To guide the design, a bNAb/Env complex structure[40] was used to assess the distance between the bNAbs Fvs and to determine ideal linker lengths[41].

Figures 10A, 10B:
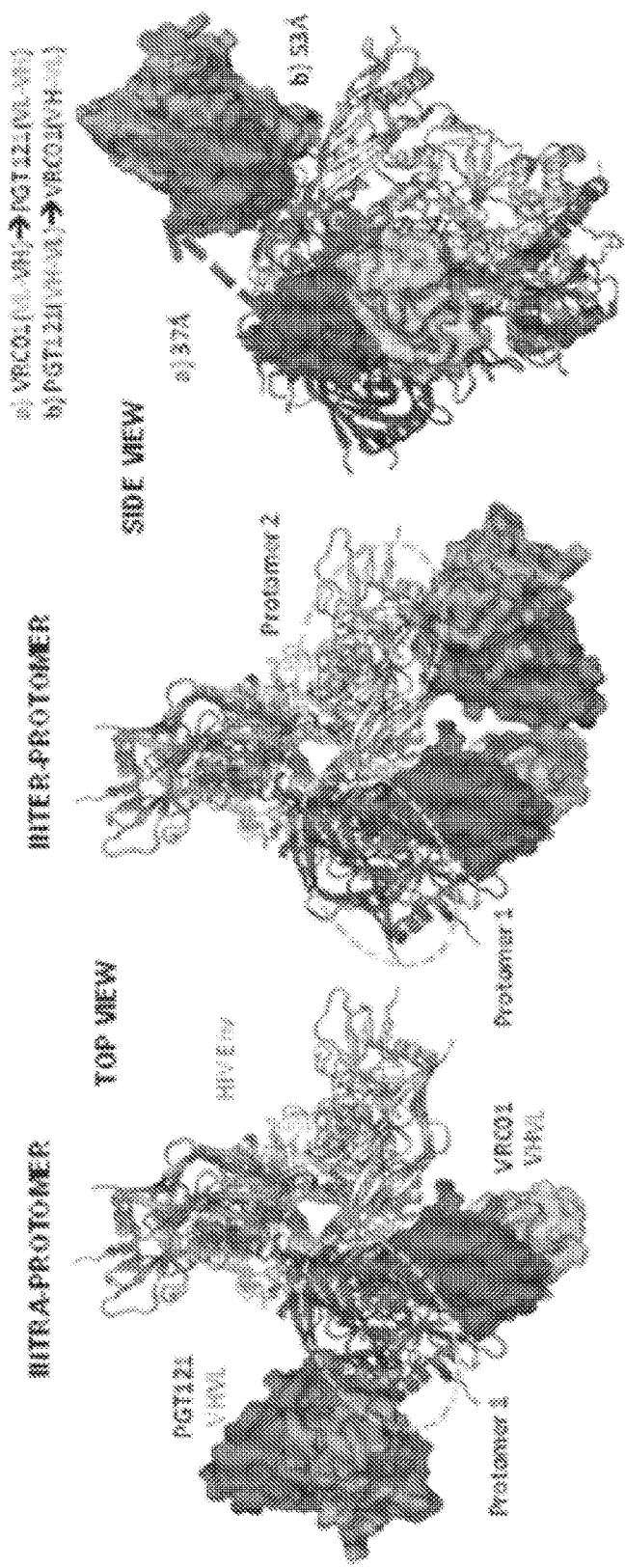
FIG. 10A through D depicts the design of bispecific antibodies.

To determine the distances between the variable domains of VCR01 and PGT121, the PDB structure 5FYK[40] was used, which includes the HIV-1 clade B trimeric Env JR-FL SOSIP.664 bound to bNAbs VRC01 and PGT122. PGT122 is a somatic variant of PGT121 possessing nearly identical Env binding mode[9] that serves as a surrogate for PGT121 in this study (FIG. 10A). Utilizing the distance tool under the structure analysis module in UCSF Chimera, the distances between the C/N-termini of VRC01 and PGT121 VH/VL moieties for all eight termini combinations were examined (Table 2, shown below).

Table 2 shows a summary of distances between the termini of PGT121 and VRC01 when bound to JR-FL SOSIP.664 trimer (inter-monomer and intra monomer) inspected by Chimera, based on antibody-trimer complex structure (PDB: 5FYK). PGT122 serves as a surrogate for PGT121.

TABLE 2

Distance Between PGT121-VRC01 termini

| | | Inter-Monomer Orientation | | |
|---|---|---|---|---|
| VRC01 | PGT121 | VRC01 C-terminus | PGT121 N-terminus | Distance (Å) |
| VH-VL | VH-VL | VAL 106.V CB | GLN 1.H CB | 60.663 |
| VH-VL | VL-VH | VAL 106.V CB | ALA 6.L CB | 48.913 |
| VL-VH | VH-VL | VAL 111.U CB | ALA 6.L CB | 37.171 |
| VL-VH | VH-VL | VAL 111.U CB | GLN 1.H CB | 66.444 |

TABLE 2-continued

Distance Between PGT121-VRC01 termini

Orientation

| PGT121 | VRC01 | PGT121 C-terminus | VRC01 N-terminus | Distance (Å) |
|---|---|---|---|---|
| VH-VL | VH-VL | VAL 106.L CB | GLN 1.U CB | 53.470 |
| VH-VL | VL-VH | VAL 106.L CB | VAL 3.V CB | 63.459 |
| VL-VH | VL-VH | SER 111.H CB | VAL 3.V CB | 96.431 |
| VL-VH | VH-VL | SER 111.H CB | GLN 1.U CB | 77.125 |

Intra-Monomer Orientation

| VRC01 | PGT121 | VRC01 C-terminus | PGT121 N-terminus | Distance (Å) |
|---|---|---|---|---|
| VH-VL | VH-VL | VAL 106.V CB | GLN 1.H CB | 106.920 |
| VH-VL | VL-VH | VAL 106.V CB | PRO 7.L CB | 100.662 |
| VL-VH | VL-VH | VAL 111.U CB | ALA 6.L CB | 73.361 |
| VL-VH | VH-VL | VAL 111.U CB | GLN 1.H CB | 78.762 |

Orientation

| PGT121 | VRC01 | PGT121 C-terminus | VRC01 N-terminus | Distance (Å) |
|---|---|---|---|---|
| VH-VL | VH-VL | VAL 106.L CB | GLN 1.U CB | 96.925 |
| VH-VL | VL-VH | VAL 106.L CB | VAL 3.V CB | 94.519 |
| VL-VH | VL-VH | SER 111.H CB | VAL 3.V CB | 93.620 |
| VL-VH | VH-VL | SER 111.H CB | GLN 1.U CB | 94.350 |

Table 3, shown below, shows the topology of the bi-ScFv and Bi-nAb.

TABLE 3

| | Bi-ScFv | | Bi-nAb | |
|---|---|---|---|---|
| Topology | VRC01→PGT121 | PGT121→VRC01 | VRC01→PGT121 | PGT121→VRC01 |

It was found that in general the distance between these two antibody moieties on two separate but adjacent gp120 protomers (inter-protomer distance) is shorter than that within the same protomer (intra-protomer distance) (FIG. 10A and Table 2). While the maximum intra-protomer distance between PGT121 and VRC01 termini is approximately 100 Å, the minimum inter-protomer distance is 37.171 Å (VRC01 $VH_{C-term}$ to PGT121 $VL_{N-term}$) and 53.470 Å (PGT121 $VL_{C-term}$ to VRC01 $VH_{N-term}$), respectively (FIG. 10B and Table 2). The relatively short VRC01 and PGT121 VH/VL N/C termini inter-protomer distance implies the potential to connect their antibody functional moieties by tandem GGGGS ($G_4S$) linkers without unfavorable steric clash and supports the premise of inter-protomer VRC01/PGT121 Bi-ScFvs to target HIV-1 Env trimer.

Example 5. Design and Expression of Bispecific Antibodies

Figure 10C:
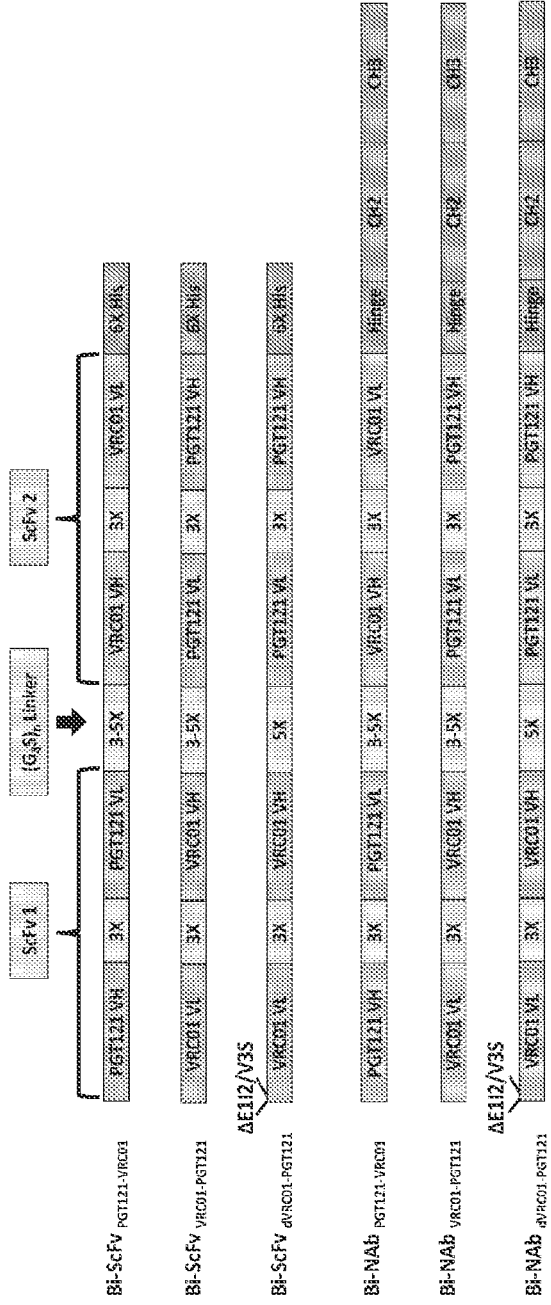

With the rationale stated herein above, the VRC01/PGT121 inter-protomer binding mode was selected (FIG. 10B) and the most favorable molecular topology, including VRC01$_{VL-VH}$→PGT121$_{VL-VH}$ and PGT121$_{VH-VL}$→VRC01$_{VH-VL}$ respectively, to construct Bi-ScFvs (FIG. 10B). First, to derive the individual scFvs, three tandem G4S linkers were used (designated as 3× linker)[42, 43], with each linker estimated to be briefly 18 Å in length, to connect the cognate VH/VL domains within VRC01 and PGT121, respectively (FIG. 10C). 3-5 G4S linkers, namely 3-5× linkers, were then used to connect the individual VRC01 and PGT121 scFvs to form the Bi-ScFv molecule (FIG. 10C). Here, 3-5 $G_4S$ linkers were empirically used to optimize the linkage between individual ScFvs to avoid potential steric hindrance imposed by elements of the HIV-1 Env functional spike. Hence, the nomenclatures of these Bi-ScFv constructs, shown in FIG. 10C included: 1) the molecular topology of the whole Bi-ScFv (e.g., VRC01 ScFv at the N-terminus), and 2) the linker length between each ScFv (e.g. 3 tandem $G_4S$ linker). For instance, Bi-ScFv$_{VRC01-5X-PGT121}$ represents a Bi-ScFv with VRC01$_{VL-VH}$→($G_4S$)$_5$ linkers→PGT121$_{VL-VH}$ topology, while Bi-ScFv$_{PGT121-5X-VRC01}$ ScFv denotes a Bi-ScFv with PGT121$_{VH-VL}$→($G_4S$)$_5$ linkers→VRC01$_{VH-VL}$ topology (FIG. 10C).

Figure 10D:
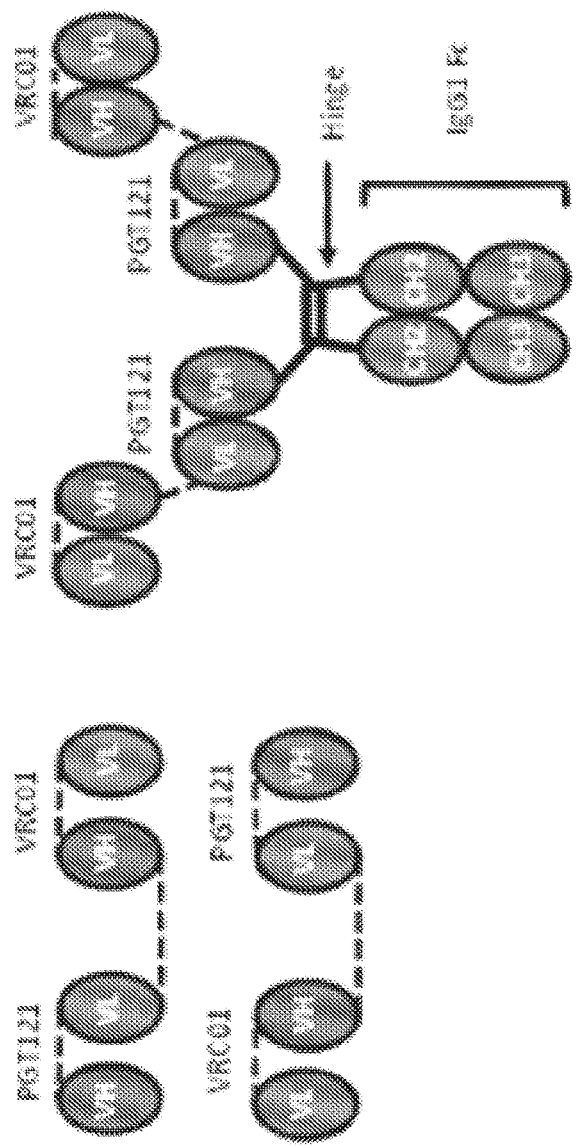

In a previous study, a truncation of the first two amino acid residues E1 and I2 (ΔE1I2) and a V3S mutation at the N-terminus of VRC01 VL increased potency of HIV neutralization[44] by eliminating a steric clash between the VRC01 VL N-terminus and the V5 region of HIV-1 Env. Therefore, such modifications were incorporated into the VRC01 VL moiety of the Bi-ScFv $_{VRC01-5X-PGT121}$, denoted as Bi-ScFv $_{dVRC01-5X-PGT121}$ (FIG. 10C). These ScFvs were also fused to the IgG1 Fc via a glycine-serine-glycine linker to support effector functions[39], thus forming Bi-NAbs (FIG. 10C and FIG. 10D).

Figure 11B:
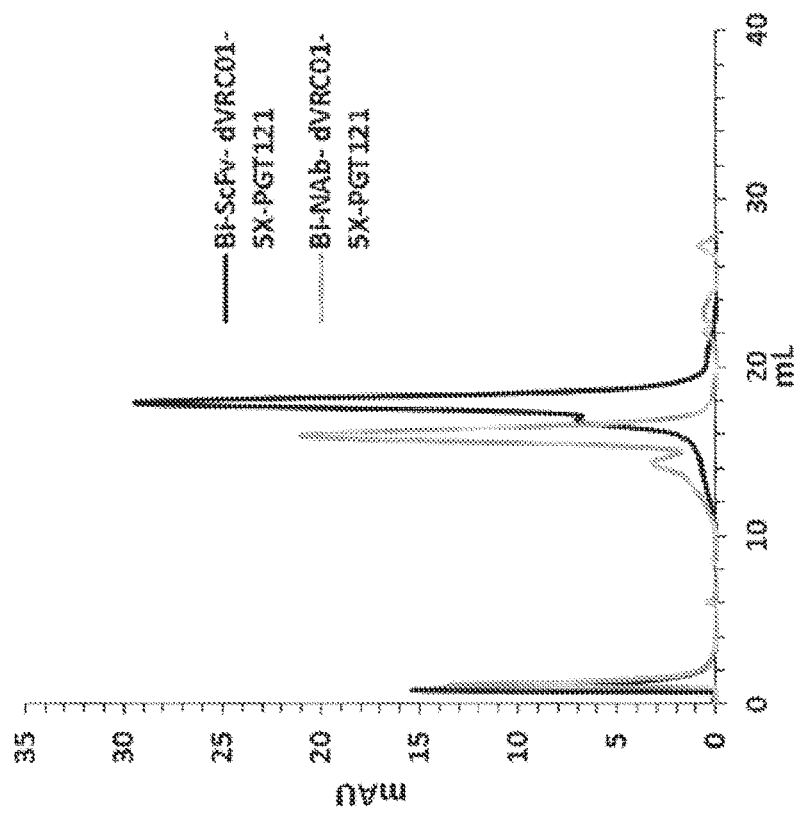

Ten bispecific antibodies of the PGT121/VRC01 Bi-ScFvs and Bi-NAbs iterations in a total were expressed in 293F cells and purified by affinity chromatography. All the antibodies expressed well and ran as a homogeneous species at the expected molecular weight on an SDS-PAGE gel (FIG. 11A) and size exclusion chromatography (SEC), with negligible aggregation forms (FIG. 11B).

Example 6. Binding Properties of Bispecific Antibodies

Bio-Layer Interferometry (BLI) was employed to validate the simultaneous Env trimer engagement of the two arms of the Bi-ScFvs. Env ligands including RSC3 core were used, which selectively displays the CD4bs (VRC01) epitope but not the PGT121 epitope, and the BG505 SOSIP.664_D368R mutant that exclusively exhibits the PGT121 epitope (FIG. 12A). In this assay, biotinylated RSC3 was first loaded as the initial ligand (ligand 1), then the parental or bispecific antibodies, followed by the second ligand BG505 SOSIP.664_D368R (ligand 2) (FIG. 12A), and the antibody binding signals to each of the Env ligands was assessed. As expected, it was found that only antibodies containing the VRC01 moiety including Bi-ScFv$_{dVRC01-5X-PGT121}$ and Bi-NAb$_{dVRC01-5X-PGT121}$ as well as VRC01 Fab and IgG, were able to bind CD4bs ligand, RSC3 (Ligand 1) initially (FIG. 12B). Similarly, bispecific antibodies containing the PGT121 moiety bound the CD4bs knockout trimer (VRC01-KO), BG505 SOSIP.664_D368R, which exclusively presents the PGT121 epitope, while the VRC01 Fab or IgG displayed no binding signal (FIG. 12B). These data confirm that bispecific antibodies including Bi-ScFv$_{dVRC01-5X-PGT121}$ and Bi-NAb $_{dVRC01-5X-PGT121}$ can simultaneously bind both the VRC01 and the PGT121 epitopes, demonstrating that both arms of the bispecific antibody are functional.

Figure 13A:
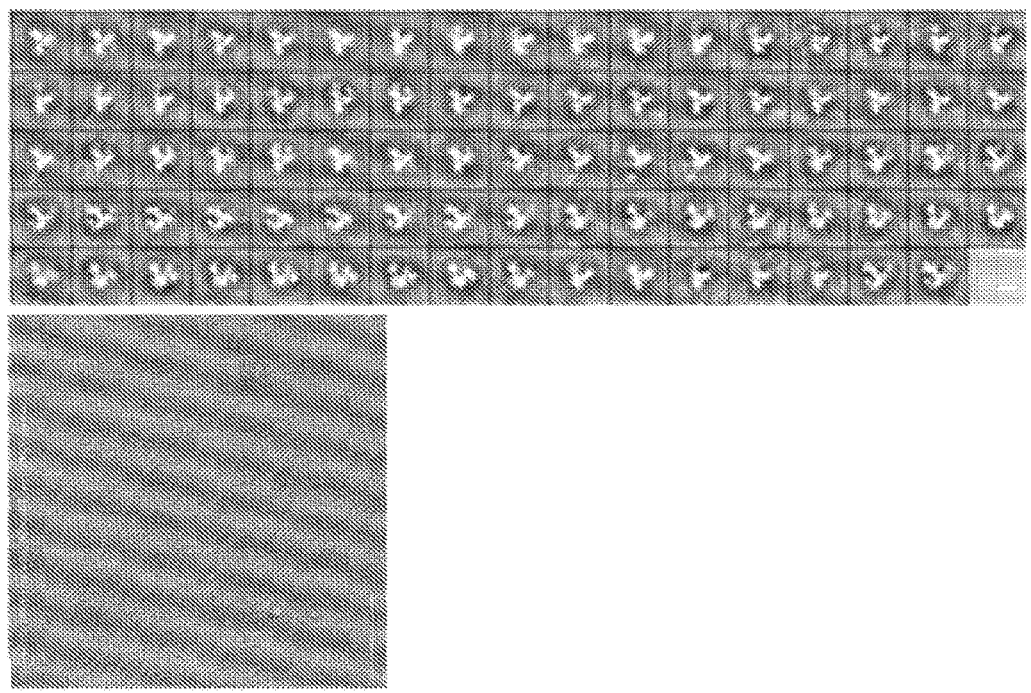
FIGS. 13A and B shows negative stain EM of Bi-ScFv/HIV Env trimer complex.
Figure 13B:
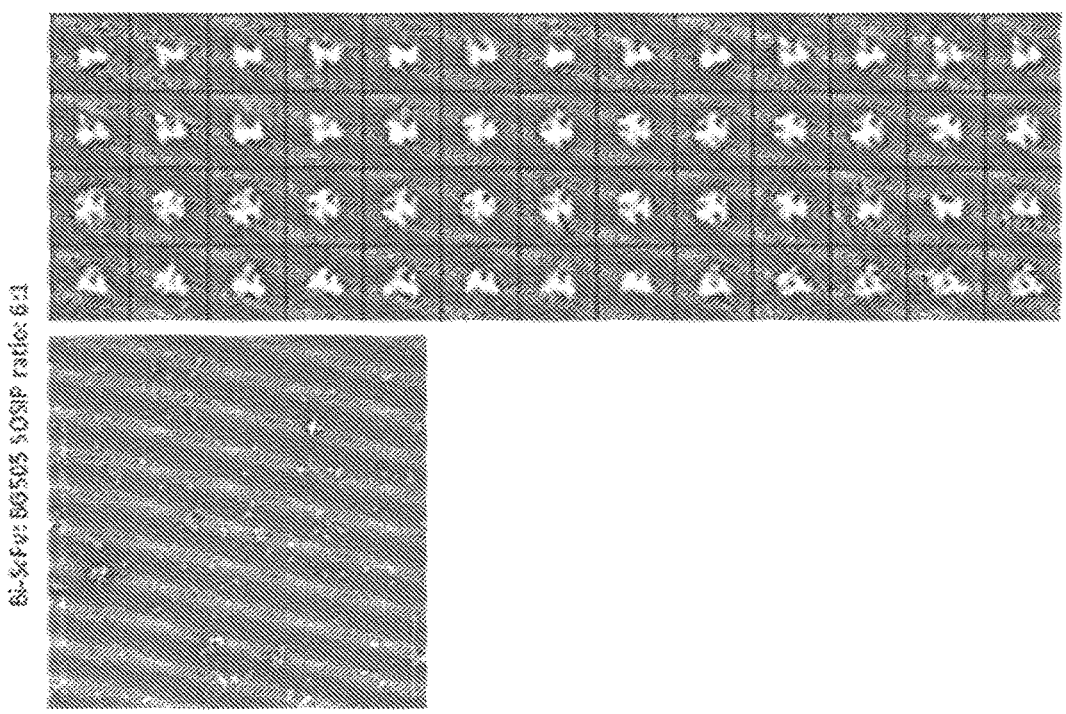
FIG. 13B shows bi-ScFv, dVRC01-5X-PGT121, in complex with BG505.SOSIP.664 at a ratio of 6:1.

As shown in FIG. 10, the bispecific antibodies were designed to cross-link adjacent protomers within the same HIV-1 Env trimer by connecting the CD4bs of one Env protomer (protomer 1) with the glycan patch at the V3 base of the adjacent protomer (protomer 2). To further investigate the bivalency of Bi-ScFv$_{dVRC01-5X-PGT121}$, negative stain electron microscopy (EM) analysis of the Bi-ScFv$_{dVRC01-5X-PGT121}$ and Env trimer BG505 SOSIP.664 complex was performed (FIG. 12C, FIG. 13A and FIG. 13B). The Bi-ScFv$_{dVRC01-5X-PGT121}$ was incubated with the BG505 SOSIP.664 Env trimer at a 1:2 (or 0.5:1) ratio so that each Env trimer would be occupied by a single Bi-ScFv$_{dVRC01-5X-PGT121}$ molecule, in a way that enabled the inter-protomer vs. intra-protomer binding modes depicted in FIG. 10A to be distinguished. As expected, both unbound Env trimer (FIG. 12C, left panel) and Env trimer bound with single Bi-ScFv$_{dVRC01-5X-PGT121}$ were visualized (FIG. 12C, second from left and middle panel), given the sub-saturation ratio between the Bi-ScFv and Env trimer. Importantly, it was found that each Env protomer was only decorated with one of the Bi-ScFv moieties (FIG. 12C, second from left and middle panel), while two adjacent Env protomers were simultaneously decorated by two Bi-ScFv moieties (FIG. 12C, second from left and middle panel). The data corroborated the bivalent nature of the binding event between the Bi-ScFv and Env trimer, as predicted by design. The Bi-ScFv crosslinked both the VRC01 (in purple, FIG. 12C, middle panel) and PGT121 (in green, FIG. 12C, middle panel) epitopes in an inter-protomer mode. When the molar ratio of Bi-ScFv$_{dVRC01-5X-PGT121}$ to BG505 SOSIP.664 trimer was increased to 6:1 to form Bi-ScFv/Env complex, it was observed that all the protomers of Env trimer were fully occupied with Bi-ScFv moieties and each Env trimer bound three Bi-ScFvs (FIG. 12C, second from right and right panel). This observation is consistent with the inter-protomer crosslinking binding mode and suggests that three molecules of Bi-ScFv$_{dVRC01-5X-PGT121}$ can fully occupy the total 6 cognate epitopes on each HIV-1 Env trimer.

Figure 14A-2:
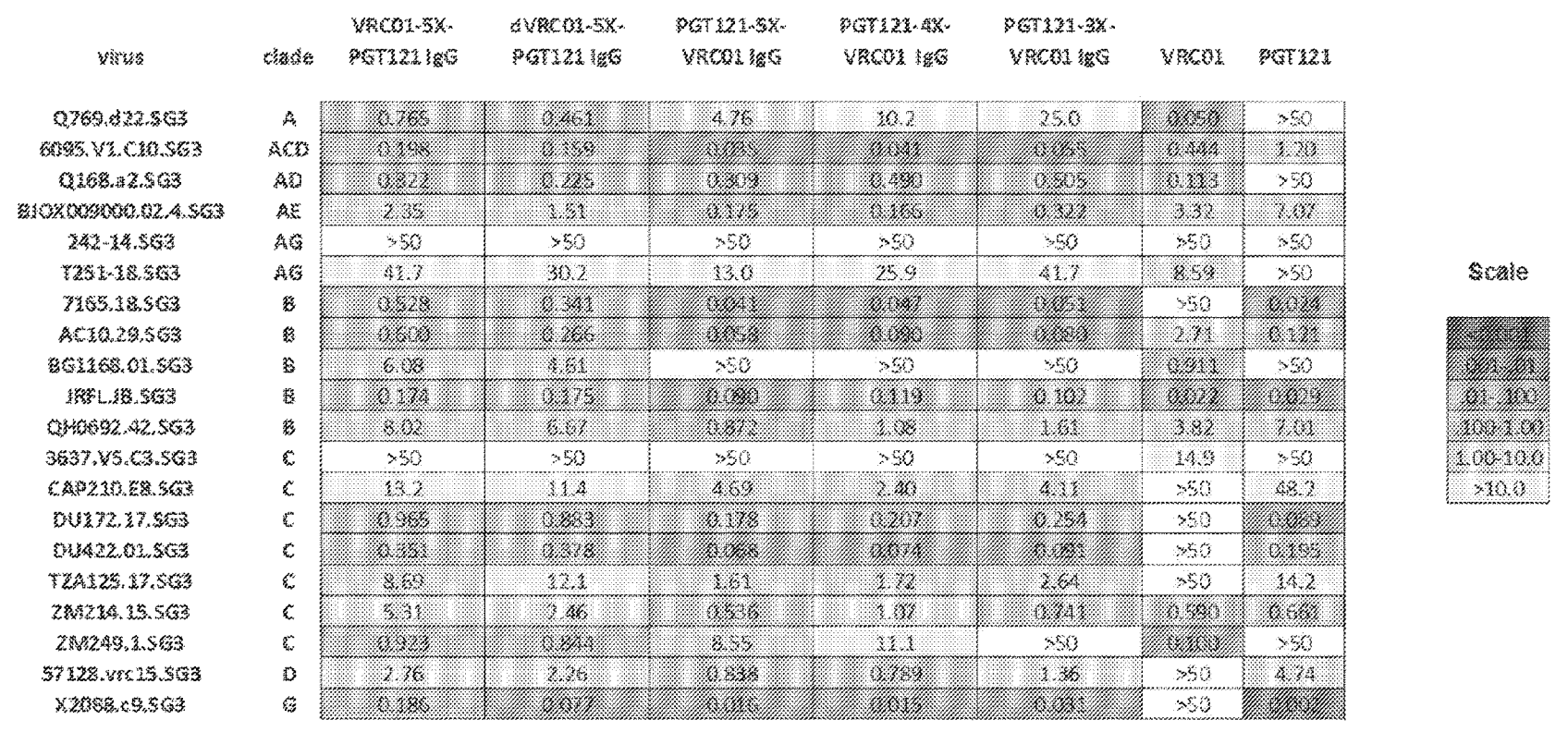
Figure 14B:
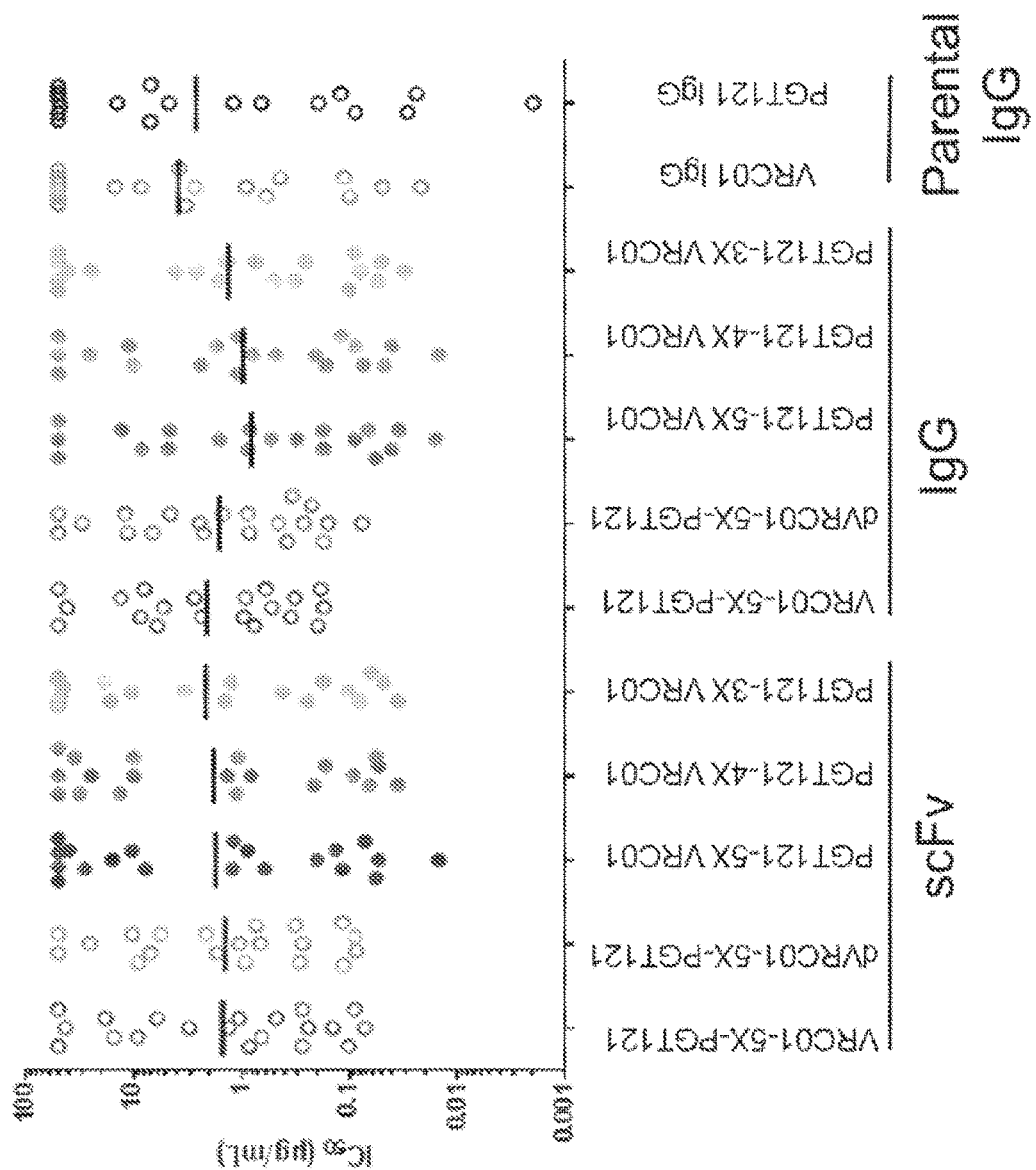
FIG. 14B shows scatter plots of $IC_{50}$ titers in which each virus is represented by an individual circle. († indicates that the $IC_{50}$ was adjusted by a factor of 3 to account for the molarity difference between the lower molecular weight Bi-ScFv and the IgG and Bi-NAb).

Example 7. Bispecific Antibodies Display Expanded Virus Neutralization Breadth Compared to Parental bNAbs To initially assess the virus neutralization capacity of the bispecific antibodies in comparison to their parental bNAbs, VRC01 and PGT121, a small HIV-1 virus panel (N=20) containing Envs of viruses from diverse clades was selected to perform virus neutralization assay (FIG. 14A-1-FIG. 14A-2). This panel included Envs of viruses that were: 1) sensitive to both (dual sensitive) bNAbs (N=6); or 2) resistant to both (dual resistant) bNAbs (N=1); or 3) sensitive to one but resistant to the other parental antibody (N=13) (FIG. 14). It is notable that 70% of the selected viruses (N=14) were resistant to at least one of the parental bNAbs, which represented a high bar for the evaluation of neutralization capacity.

Figure 15A:
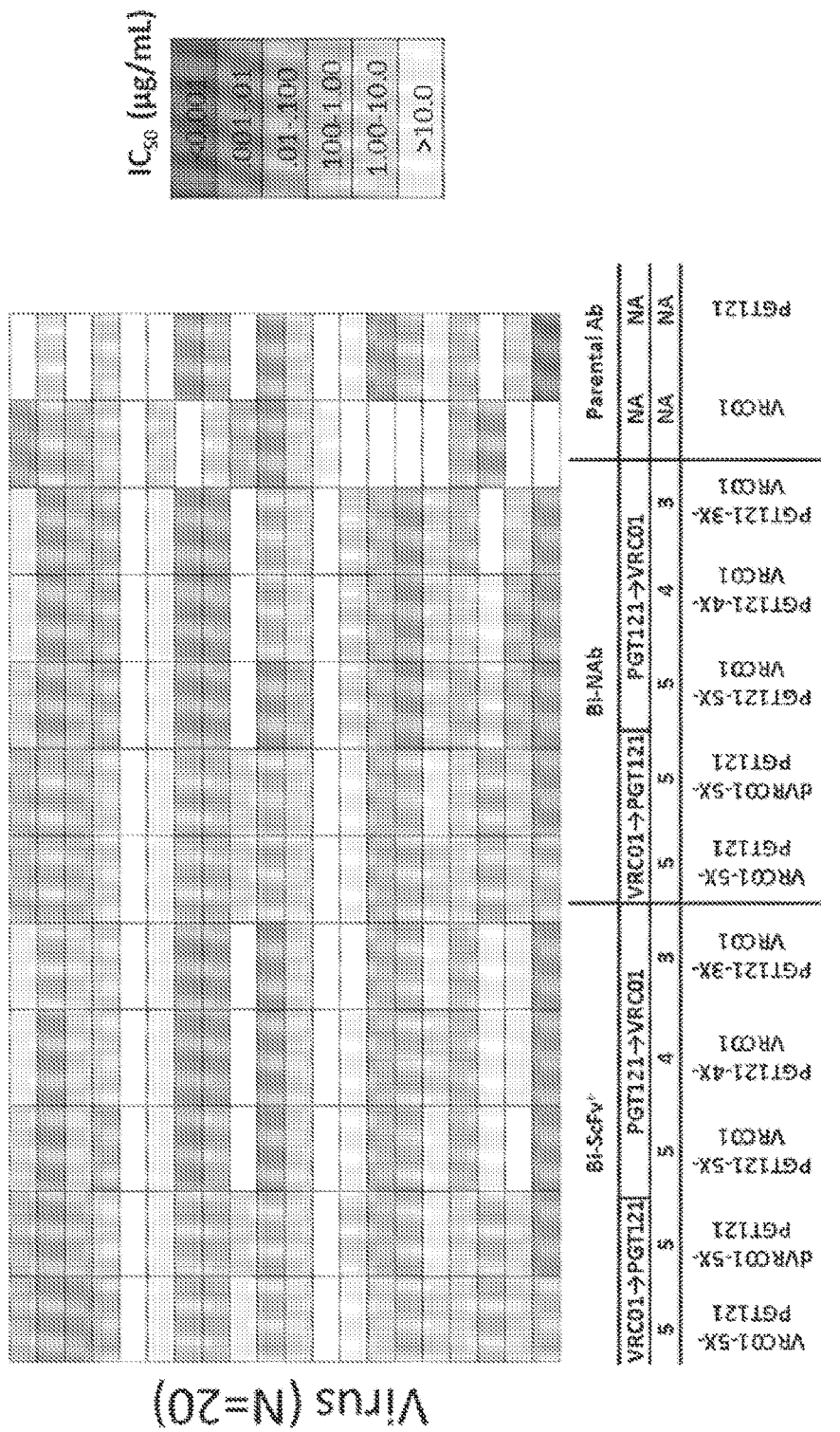
FIGS. 15A through 15C show neutralization breadth and potency of bispecific antibodies.

Using IC$_{50}$ titers (the concentration of antibody at which 50% of virus entry is inhibited) with a cut-off value set at 50 μg/ml, the neutralization capacity of bispecific antibodies was assessed with this initial virus panel. It was found that all the bispecific antibodies displayed substantially improved neutralization breadth, ranging from 80-90% virus coverage, compared to 60-65% virus coverage of their parental bNAbs (FIG. 15A, FIG. 14A-1-FIG. 14A-2 and FIG. 14B). Interestingly, it was observed that the bispecific antibodies with the topology of VRC01$_{VL-VH}$→PGT121$_{VL-VH}$ displayed 90% neutralization breadth, which was better than that with the PGT121$_{VH-VL}$→VC01$_{VH-VL}$ topology (80-85%) (FIG. 15A). It was also noted that the five-tandem G$_4$S linker length (5X) was slightly better than the shorter variants (4X and 3X) (FIG. 15A, FIG. 14A-1-FIG. 14A-2 and FIG. 14B). Finally, the bispecific antibodies, Bi-ScFv$_{dVRC01-5X-PGT121}$ and Bi-NAb$_{dVRC01-5X-PGT121}$ with the optimal VRC01$_{VL-VH}$→PGT121$_{VL-VH}$ topology, the 5X G$_4$S linker and the N-terminus VRC01 VL modifications ΔE1I2/V3S (FIG. 1) displayed the best neutralization breadth (90% virus coverage) (FIG. 15A, FIG. 14A-1-FIG. 14A-2 and FIG. 14B).

Figure 15B:
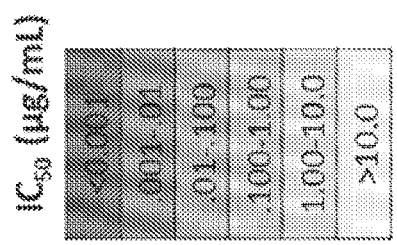
Figure 15B:
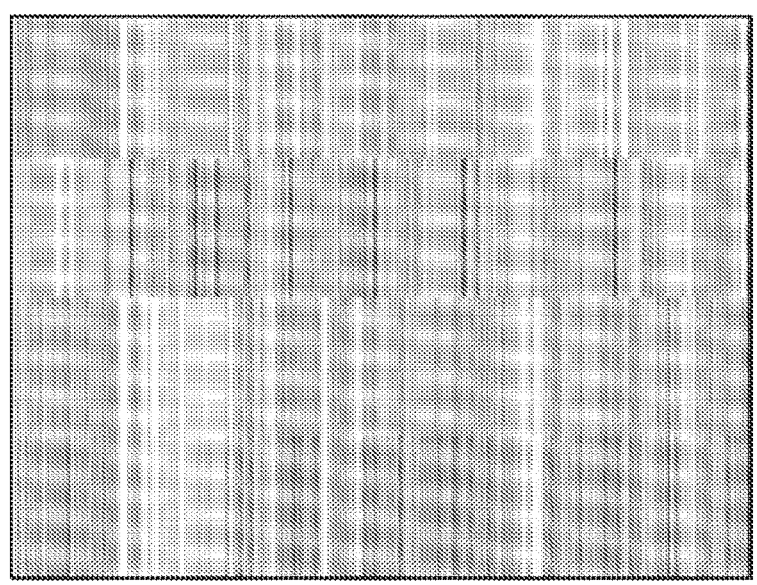
Figure 15C:
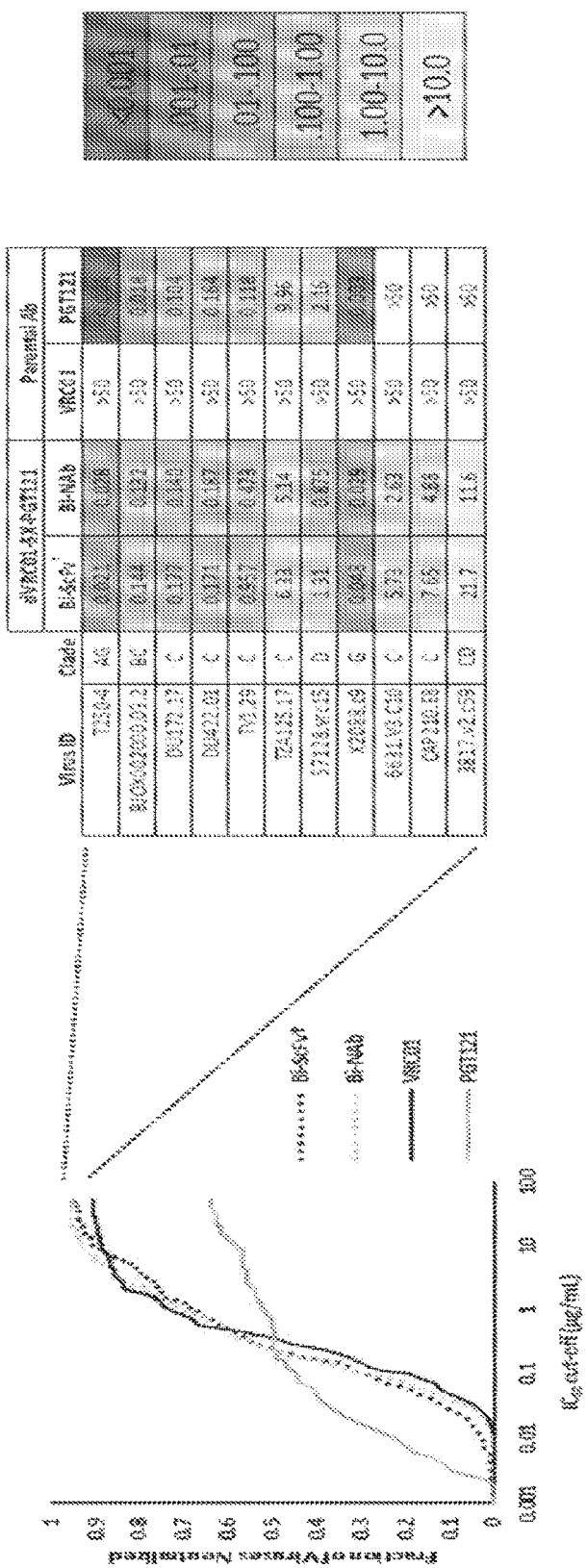

Subsequently, the top bispecific antibodies, Bi-SCFv$_{dVRC01-5x-PGT121}$ and Bi-NAb$_{dVRC01-5x-PGT121}$, were tested against a more comprehensive panel of viruses covering the major genetic subtypes and circulating recombinant forms, and containing almost entirely of primary isolate Envs[45]. In this 208 virus panel, the Bi-SCFv$_{dVRC01-5x-PGT121}$ and Bi-NAb$_{dVRC01-5x-PGT121}$ displayed improved coverage with 94.7% and 95.1% of viruses neutralized, respectively, over the parental antibodies (VRC01=90.4%, and PGT121=64%) (FIG. 15B and FIG. 15C) and with a potency (IC50 geometric mean) comparable to VRC01 (FIG. 15B and FIG. 15C). Interestingly, both Bi-SCFv$_{dVRC01-5x-PGT121}$ and Bi-NAb$_{dVRC01-5x-PGT121}$ were able to neutralize three primary isolates with dual resistance to parental bNAbs (FIG. 15C, right panel, right panel), suggesting a cooperative effect exerted likely by the inter-protomer crosslinking of two distinct epitopes within the HIV-1 Env trimer.

Example 8. Generation and Validation of a Trispecific Antibody

Figure 16A:
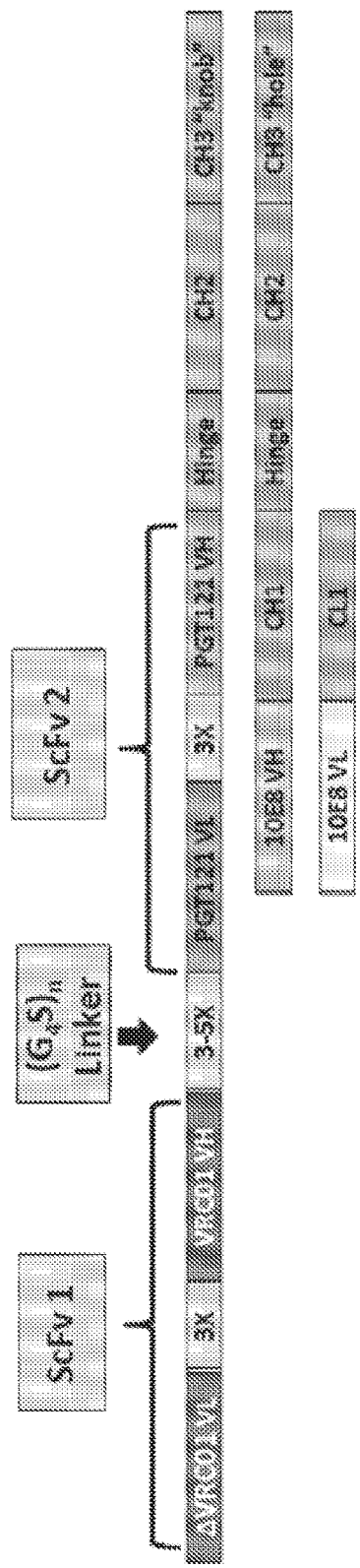
FIGS. 16A though 16E depict Tri-NAb construct, expression, and characterization.
Figure 16B:
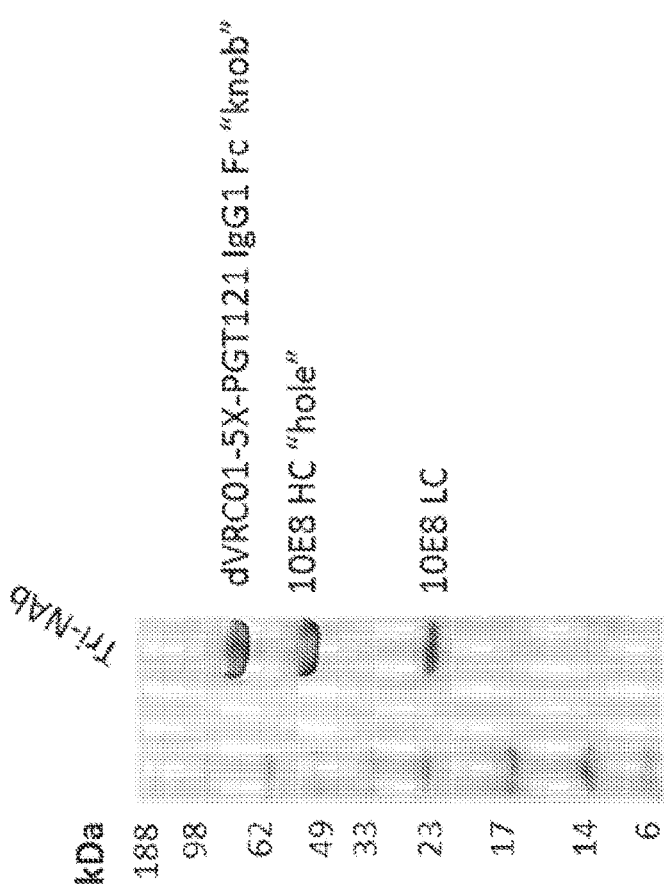
FIG. 16B shows reduced SDS-PAGE analysis of trispecific antibody.

Previous studies indicated that the HIV-1 gp41 MPER-specific bNAb, 10E8, when combined with gp120-specific bNAbs including the CD4bs bNAb VRC01, displayed an additive, and potentially small synergistic/cooperative effect on neutralization[46]. Here, the MPER-specific 10E8 functional moiety was combined with the top lead bispecific antibodies to improve neutralization breadth and potency further. Knob-into-hole technology[32] was used to generate a heterodimeric Tri-NAb consisting of 10E8 and Bi-NAb$_{dVRC01-5x-PGT121}$ moieties (FIG. 16A). The 10E8 was placed on one antibody arm with the Fc containing the "knob" mutation, and the Bi-ScFv$_{dVRC01-5x-PGT121}$ was fused to the IgG1 Fc containing the "hole" mutation on the other arm. To express the Tri-NAb, 293F cells were co-transfected with the plasmid DNA encoding the heavy and light chain genes of 10E8 and the Bi-NAb$_{dVRC01-5x-PGT121}$. The Tri-NAb was then purified via a protein A column and assessed its homogeneity by SDS-PAGE (FIG. 16B).

Figure 16C:
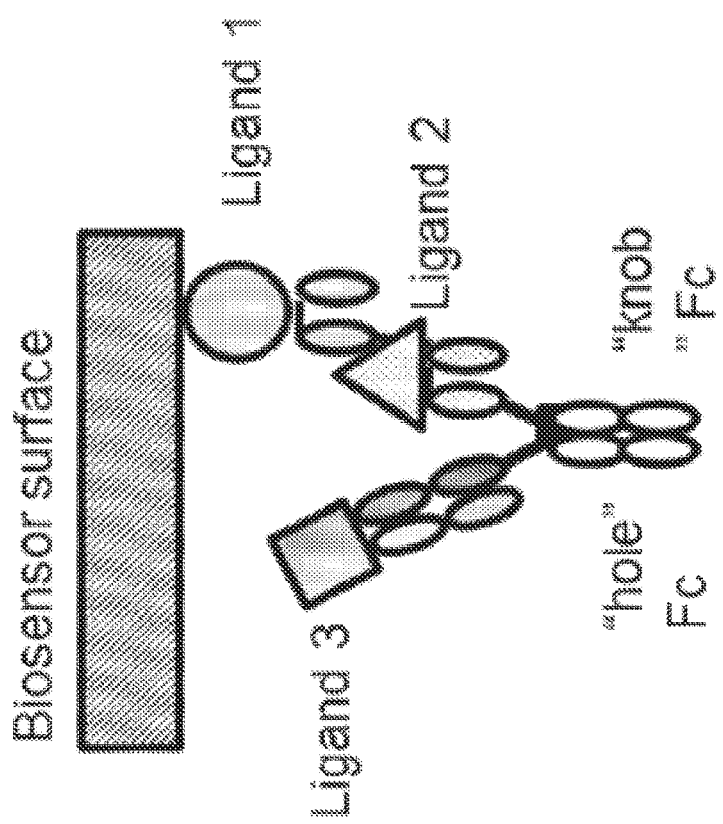
FIG. 16C shows scheme of the trispecific binding assay via biolayer interferometry (BLI).
Figure 16D:
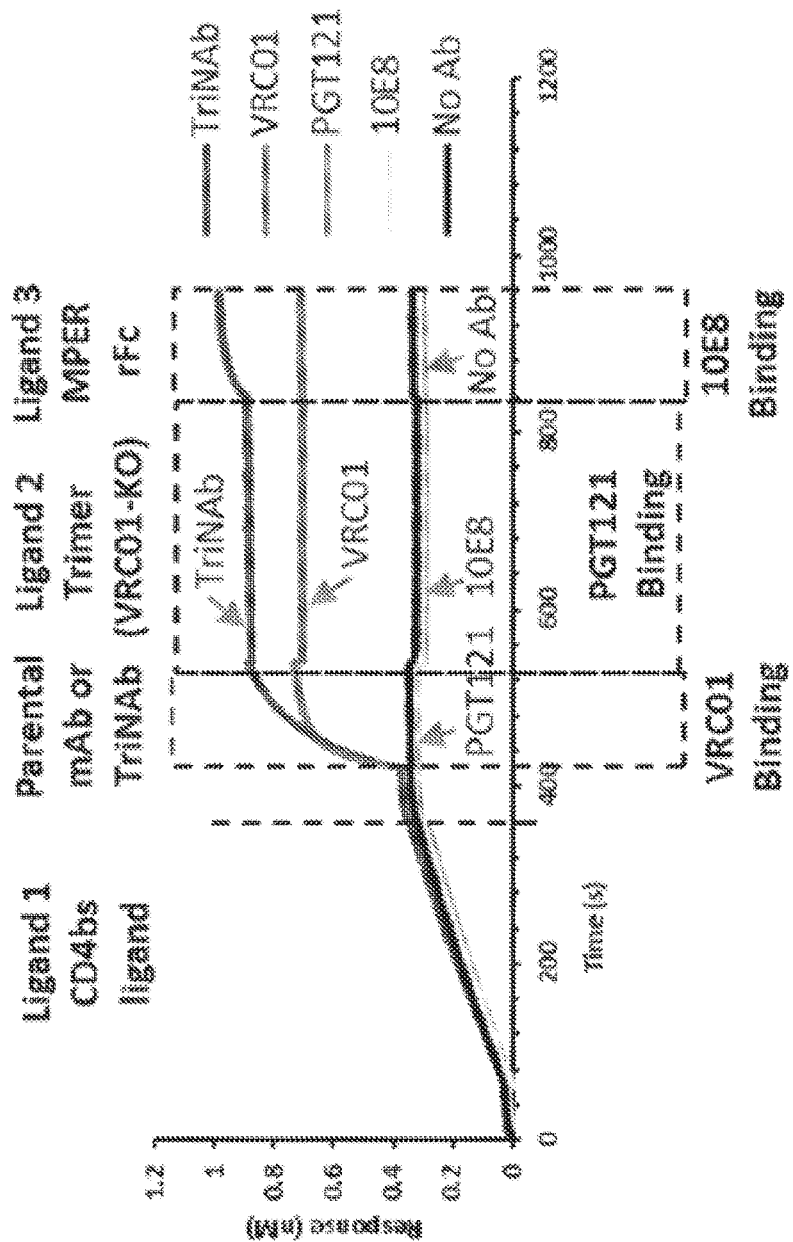
FIG. 16D shows BLI curves of trispecific binding assay. OCTET biosensors were loaded with ligand 1 (biotinylated RSC3) specific for VRC01 epitope (CD4bs), followed by trispecific antibody, ligand 2 (BG505.SOSIP.664_D368R) specific for PGT121 epitope (V3 glycan), and ligand 3 (MPER rFc) specific for 10E8 epitope (MPER). Parental IgGs were used as control.
Figure 16E:
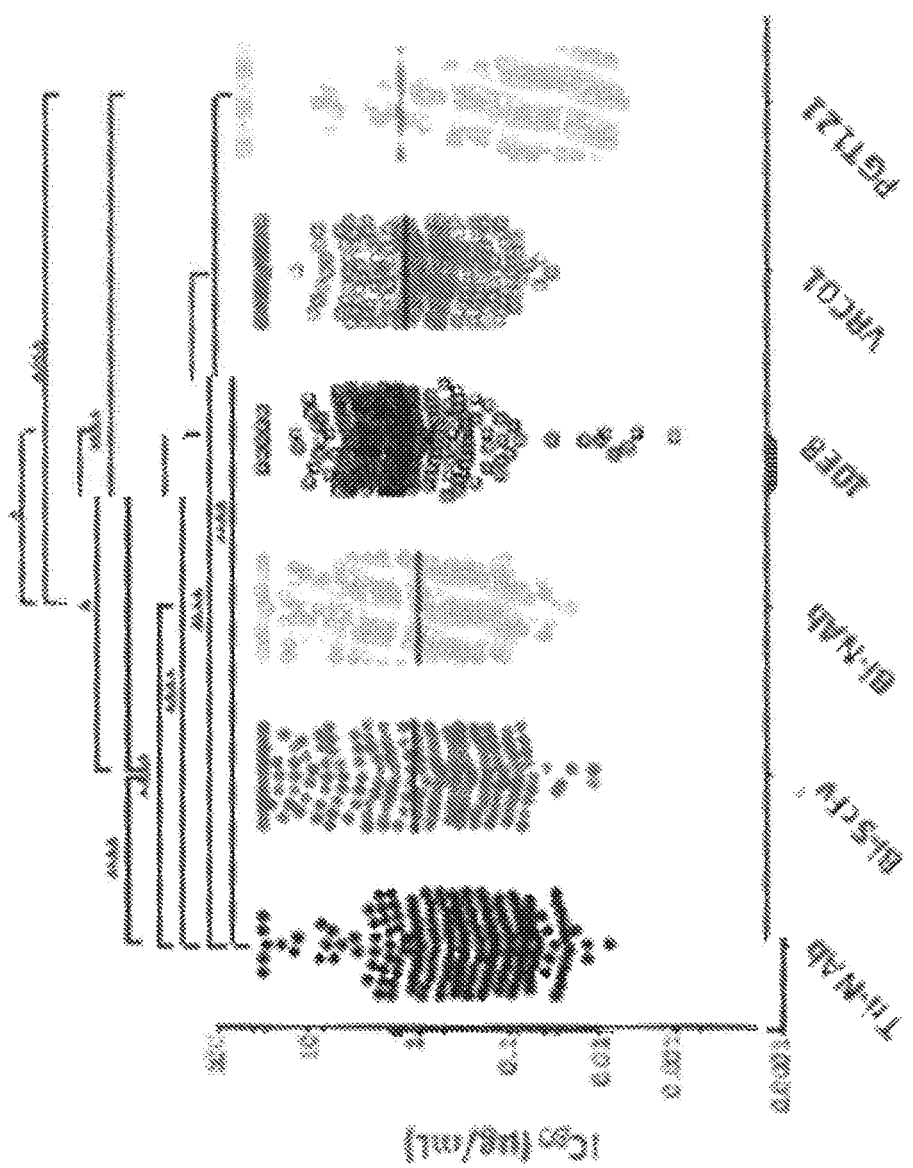
FIG. 16E shows scatter plots of $IC_{80}$ titers in which each virus is represented by an individual circle (Statistical differences in neutralization were evaluated using non-parametric t test (Wilcoxon matched-pairs signed rank test) with *p<0.05, p<0.01, *p<0.001, ****p<0.0001). († indicates that the $IC_{80}$ titer was adjusted by a factor of 3 to account for the molarity difference between the lower molecular weight Bi-ScFv and the IgG, Bi-NAb and Tri-NAb).

BLI was used to assess the triple specificity of the Tri-NAb, with ligands presenting the epitopes of VRC01, PGT121, and 10E8 (FIG. 16C and FIG. 16D), respectively. In a BLI OctetRED96 system, the ligands and antibodies were loaded to the biosensor surface sequentially in the following order: 1) biotinylated RSC3 as the initial ligand (ligand 1) to present VRC01 epitope; 2) the parental bNAbs or Tri-NAb; 3) the second ligand, trimeric BG505.SOSIP.664 D368R with CD4bs/VRC01 epitope knockout to present PGT121 epitope (ligand 2); and finally 4) the third ligand (ligand 3), an MPER peptide fused to a rabbit Fc (MPER rFc) (FIG. 16C and FIG. 16D) to present the 10E8 epitope (FIG. 16D). As expected, it was found that Tri-NAb displayed binding signals for all of the three ligands, while the parental bNAbs only showed binding to ligand 1 with CD4bs epitope (e.g., VRC01) or no binding to any ligands (e.g., PGT121 and 10E8) due to the lack of initial CD4bs ligand 1 engagement in this sequential binding assay. This data confirmed that the Tri-NAb containing the moieties of three bNAbs (VRC01, PGT121, and 10E8) is capable of recognizing all of the three cognate bNAb epitopes on HIV-1 Env molecule.

Example 9. Trispecific Antibody Displays Exceptional Neutralization Capacity

Next, the neutralization capacity of the Tri-NAb against the comprehensive virus panel consisting of Envs of 208 HIV strains [45] was assessed. The Tri-NAb's neutralization capacity (indicated by $IC_{50}$ titers) was extraordinary as it neutralized all but one virus (99.5%) of the panel, with improved neutralization breadth compared to the parental bNAbs and the $\text{Bi-NAb}_{dVRC01\text{-}5x\text{-}PGT121}$ (FIG. 17A). Additionally, the Tri-NAb neutralization potency was superior to that of the individual parental bNAbs or the Bi-NAb (FIG. 17B, **p<0.0001, Wilcoxon matched-pairs signed rank test), with an exceptional $IC_{50}$ geometric mean of 0.069 pg/mL, which is at least four-fold lower than that of the VRC01, 10E8, and $\text{Bi-NAb}_{dVRC01\text{-}5x\text{-}PGT121}$ antibodies (FIG. 17-FIG. 17D, FIG. 18A-FIG. 18H). The $IC_{80}$ titers of the Tri-NAb corroborated its surpassing neutralization potency over both the parental bNAbs and the $\text{Bi-NAb}_{dVRC01\text{-}5x\text{-}PGT121}$ (FIG. 16E, p<0.0001, Wilcoxon matched-pairs signed rank test), neutralizing 98% of all strains with an ICso geometric mean of 0.298 pg/mL (FIG. 16E, FIG. 19A-FIG. 19**H).

Likely, the gain in neutralization breadth exhibited by the Tri-NAb is attributed to the addition of 10E8 moiety to the $\text{Bi-NAb}_{dVRC01\text{-}5x\text{-}PGT121}$ agent (FIG. 17C). In this regard, several PGT121/VRC01 dual resistant strains that are sensitive to 10E8 are also sensitive to Tri-NAb neutralization (FIG. 17C). The only virus strain that showed resistance to the Tri-NAb, 6471.V1.C16, is also highly resistant to both PGT121 and VRC01, and is only moderately sensitive to 10E8 ($IC_{50}$=4.98 pg/mL) (FIG. 18A-FIG. 18H). A bivalent 10E8 moiety such as that found in an IgG molecule may be required for neutralizing viruses moderately sensitive to 10E8, which is absent in the trispecific antibody (FIG. 18A-FIG. 18H).

To evaluate the impact that each antibody contributed to the Tri-NAb neutralization potency, viruses were grouped by their sensitivities to the parental antibodies and assessed the change in potency of neutralization of the multispecific NAbs from that of the parental antibodies (FIG. 17E). Bi-ScFv and Bi-NAb exhibited a 2.1-fold and 1.9-fold increase in neutralization activity compared to VRC01 when measuring activity against VRC01/PGT121 dual sensitive viruses (N=125) accounting for 60% of the 208 tested viruses. With viruses resistant to VRC01 or/and PGT121 (N=73, 40% of the tested viruses), the overall potency of the Bi-ScFv and Bi-NAb decreased compared to the parental bNAbs. When incorporating all viruses in the analysis, the potency of the bispecific antibodies was 1.4- and 1.3-fold greater compared to that of VRC01, respectively (FIG. 17E, upper panel).

Of note, the Tri-NAb neutralized viruses sensitive to two antibody moieties (N=194 or 93% of tested viruses) with a greater potency than that of the parental antibodies (FIG. 17E, lower panel). However, when the viruses were only sensitive to one of the Tri-NAb's moieties (dual resistant, N=14 or 6.7% of tested viruses), the potency was lower than that of the parental antibody (FIG. 17E, lower panel). The Tri-NAb displayed an overall improved potency over VRC01 and 10E8 (4.5-fold and 6.2-fold greater, respectively) for all viruses of the panel (FIG. 17E, lower panel). Therefore, the superior neutralization capacity of Tri-NAb over Bi-NAb and individual parental antibodies is profoundly associated with the Env binding avidity (targeting at least two epitopes) in the face of neutralization resistance.

DISCUSSION

Despite the improved breadth and potency displayed by bNAbs recently isolated, bNAb combinations will likely be necessary to cope with the extensive HIV Env diversity present in circulating virus strains. Recently some Bi-NAbs have been developed that combine receptor- or coreceptor-targeting antibodies or domains such as the anti CD4 receptor Fab ibalizumab (iMab)[47, 48], the anti CCR5 coreceptor Fab PRO140 (P140)[49], or the eCD4Ig containing a fusion protein of human CD4 ectodomain and a CCR5-mimetic sulfopeptide[50]. Although these antibody molecules can exhibit broad and potent HIV neutralization, they are different from the Bi- and Tri-NAb molecules described here, in that they target host receptors or use host receptor derivative, whereas the Bi- and Tri-NAb target only viral Env elements. A number of in vitro studies demonstrated that anti-HIV Env bNAb combinations yield superior neutralization results[45, 46]. This is likely due to the cooperative effect when two bNAbs targeting independent epitopes on the Env trimer are combined. Therefore, combining three or four bNAbs with different epitope specificities may be of significant therapeutic value[46, 51]. Empirical combinations of bNAbs can achieve enhanced potency and breadth over parental bNAbs alone[31, 34, 35] and it has been suggested that some may be capable of crosslinking the Env trimer[31, 34]. Specifically, one study utilized DNA-linkers as "molecular rulers" to construct molecules capable of intra-spike cross-linking with the ultimate goal of enhancing the potency of bNAbs[31] by gain of avidity.

In this study, structure-based antibody rational design was utilized to optimize the multi-epitope engagement of the HIV Env trimer with Bi-ScFvs antibodies. Both the dual engagement of Env epitopes and the enhanced neutralization capacity of the Bi-ScFvs was validated. Furthermore, the experiments described herein confirm that the Bi-NAb engages the CD4bs and the V3 base glycan epitopes through an inter-protomer linkage rather within one Env trimer following the structure-based design (FIG. 10 and FIG. 11, Table 2).

Neutralization analyses of the Bi-NAbs using a panel of viruses with differential resistance profiles illustrated that those possessing both the VRC01 VL at the N-terminus of the bispecific antibody as well as the VRC01 VL N-terminal mutations (ΔE1I2/V3S) had improved neutralization breadth (FIG. 15A, FIG. 14A-1-FIG. 14A2 and FIG. 14B). Conversely, it was observed that Bi-NAbs with PGT121 at the N-terminus had improved potency but reduced neutralization breadth, suggesting that this molecular configuration may present unfavorable steric constraints. Furthermore, it was observed that molecules with shorter linker lengths of 4X or 3X displayed lower neutralization breadth and potency than those with longer (5x) linkers (FIG. 15A-FIG. 15C), suggesting that longer linkers may enable the bispecific antibodies to orchestrate individual functional moieties for simultaneously engaging both cognate epitopes.

Figure 17A:
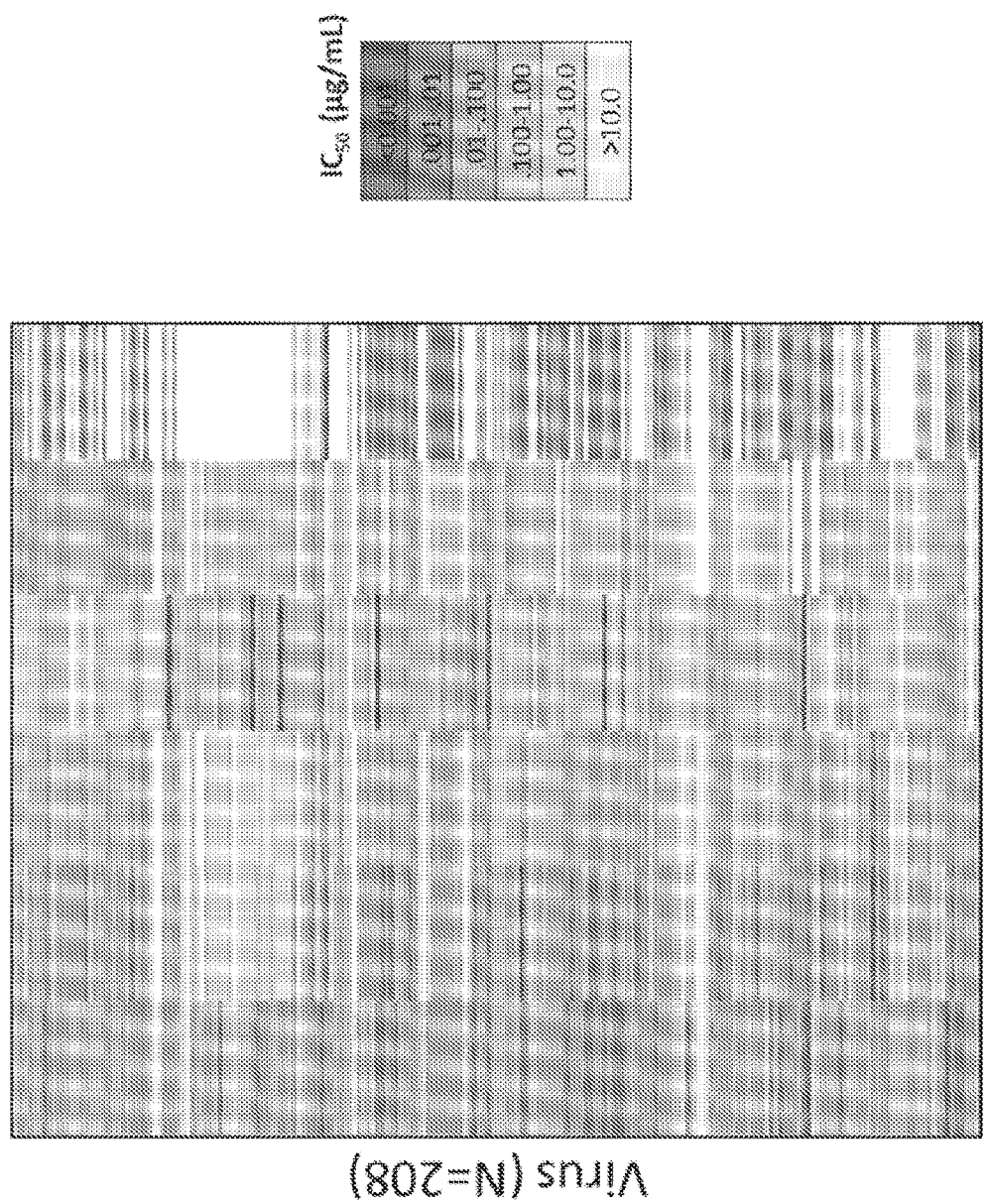
Figure 17B:
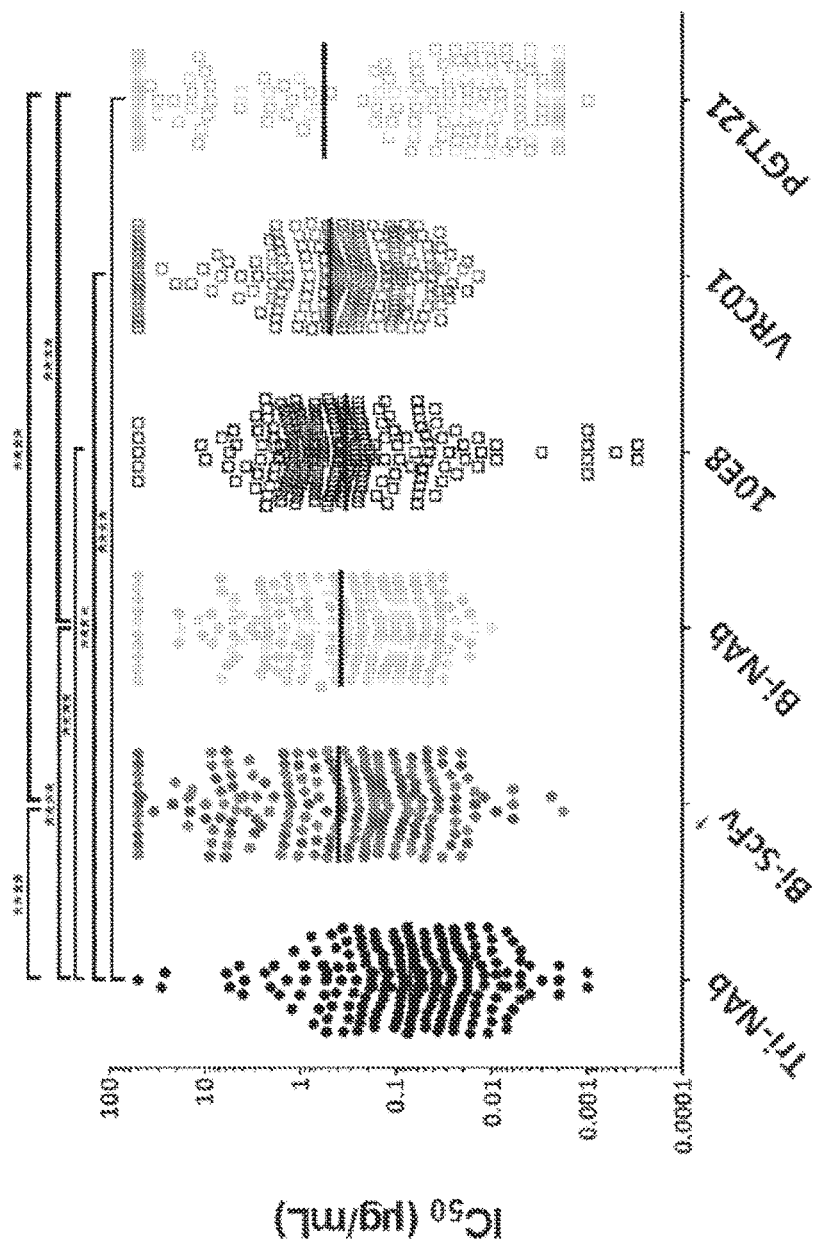
Figure 17C:
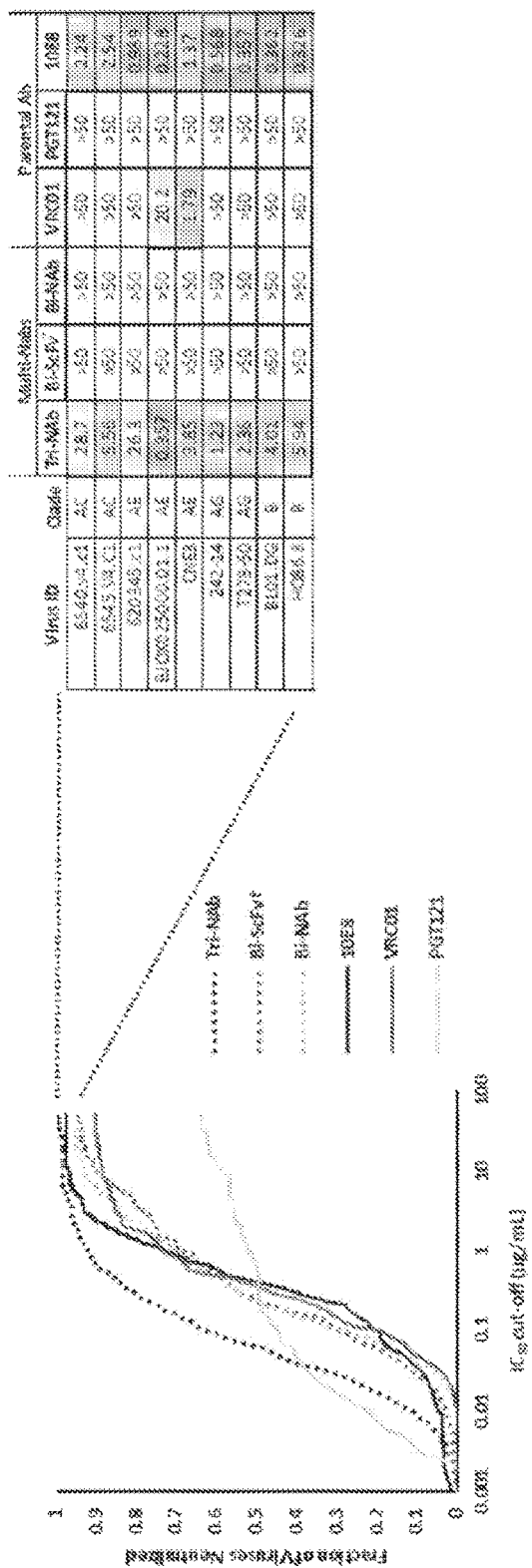
Figure 17D:
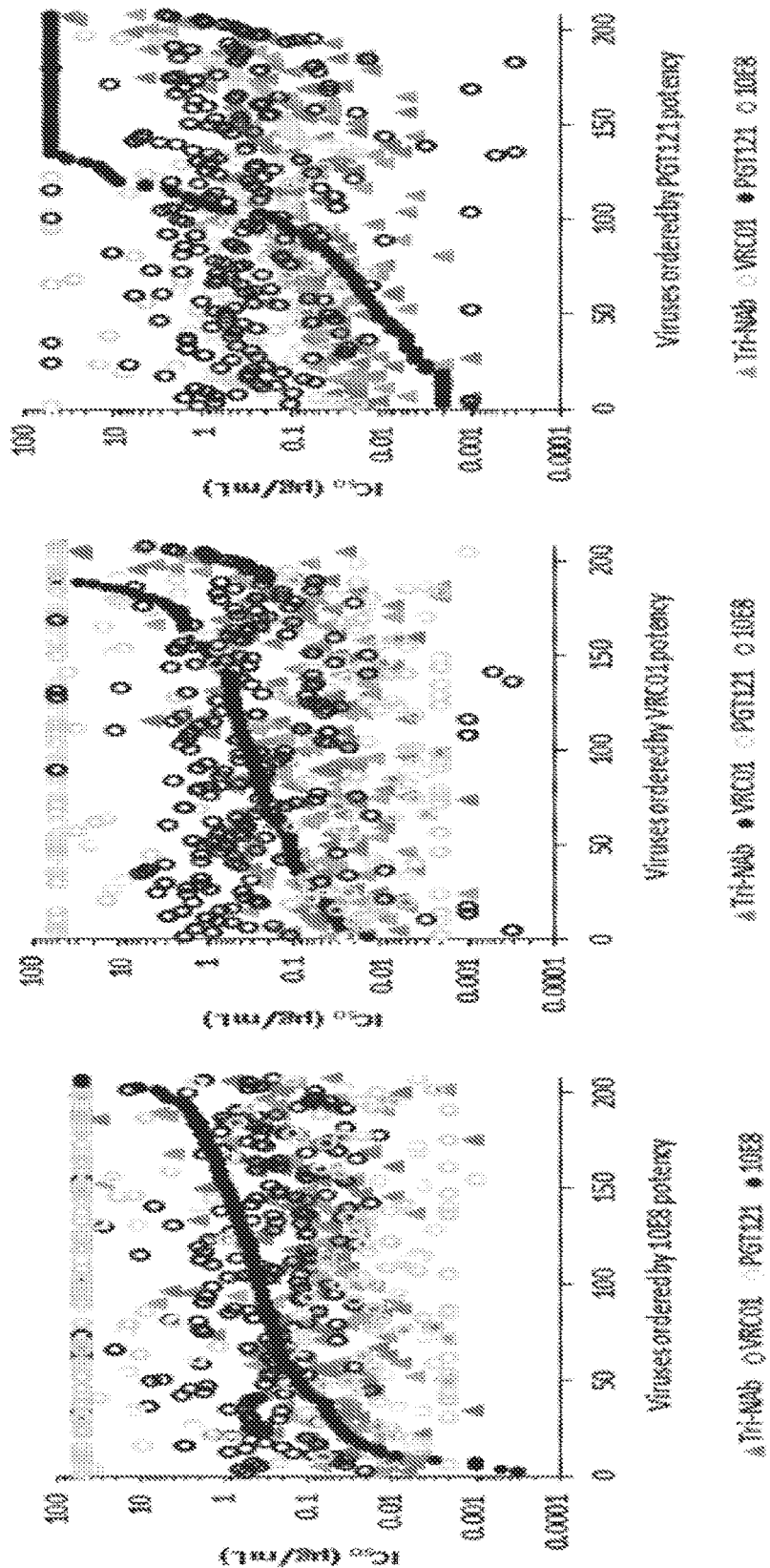
Figure 20:
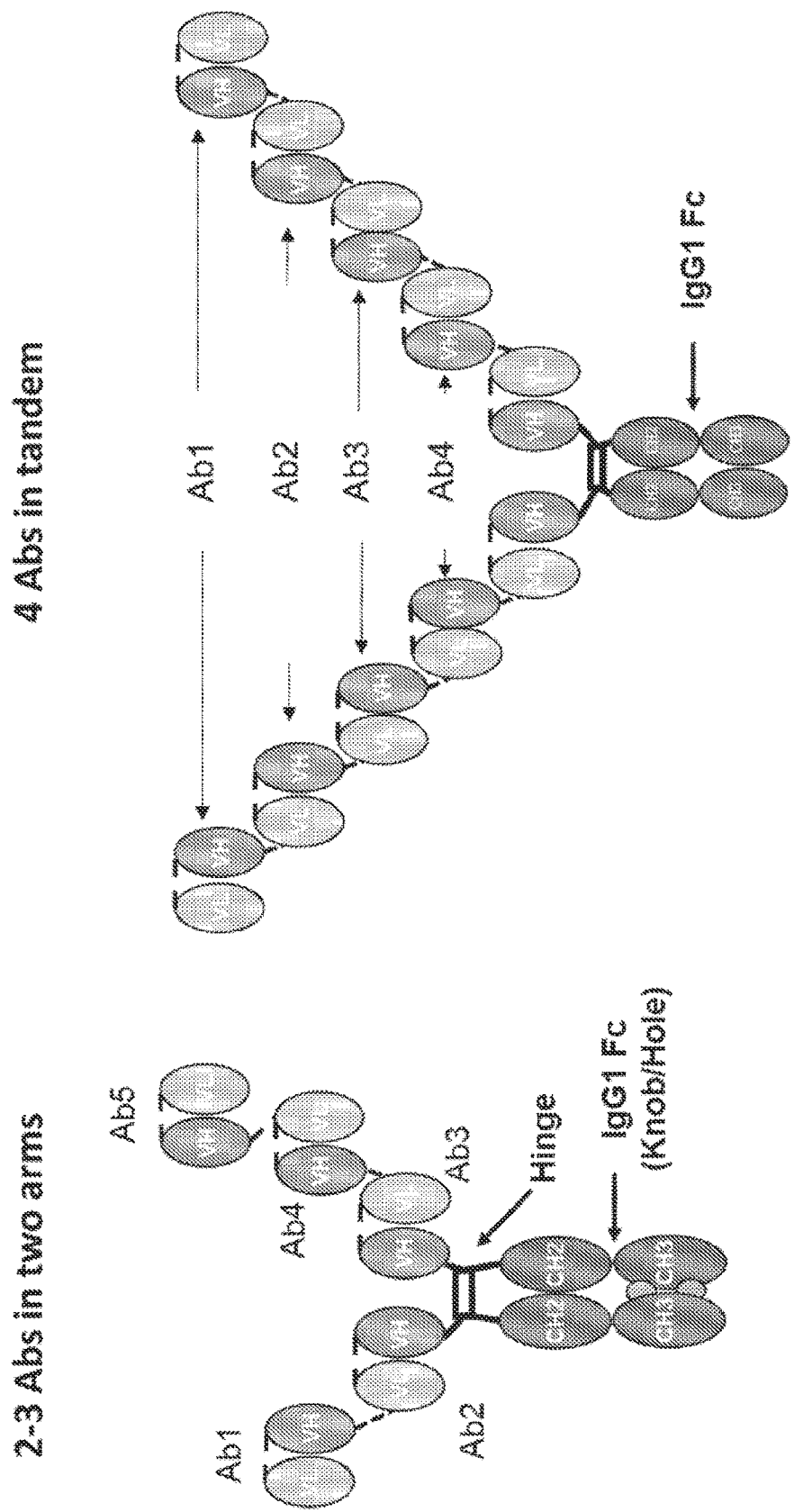
FIG. 20 depicts a schematic of a tri and tetraspecific antibody embodiment of the disclosure.

The Bi-NAb and MPER-specific bNAb 10E8 were combined to form a Tri-NAb with profoundly improved neutralization breadth (FIG. 17A-FIG. 17C, FIG. 16E, FIG. 18A-FIG. 18H and FIG. 19A-FIG. 19H). This gain of breadth most likely attributed to the addition of the 10E8 moiety, as PGT121/VRC01 dual resistant viral strains that are sensitive to 10E8 were sensitive to Tri-NAb neutralization (FIG. 17C). Consistently, the potency of the Tri-NAb ($IC_{50}$ geomean of 0.069 µg/ml, $IC_{80}$ geometric mean of 0.298 µg/mL) increased in comparison with the Bi-NAb (FIG. 17A) and the parental antibodies (FIG. 17A-FIG. 17C, FIG. 17E, FIG. 18A-FIG. 18H). FIG. 20 is a schematic that shows two arrangements for 4 specific antibody binding sites to be accommodated in one antibody. As shown in FIG. 20, the tetra-NAb1 has the configuration of 10E8-5X-35O22/dVRC01-5X-PGT121 and tetra-NAb2 has the configuration of 35O22-5X-10E8/dVRC01-5X-PGT121.

Both Bi- and Tri-NAb outperformed their parental mAbs in neutralization potency when tested with viral isolates that were sensitive to all of the individual bNAbs (FIG. 17E); most likely due to the cooperative effect resulted from simultaneous engagement of multiple epitopes within the same Env trimer. Consistently, the Tri-NAb neutralizes these sensitive viruses more potently than the Bi-NAb (FIG. 17E). The cooperative effect remains for the Tri-NAb when tested with viruses resistant to only one antibody (single-resistance) (FIG. 17E), while this cooperative effect is lost for the Bi-NAb (FIG. 17E). When dual neutralization-resistant viruses were tested, the Tri-NAb showed steady neutralization with slightly lower potency compared to the parental mAbs (FIG. 17E), while the Bi-NAb only occasionally neutralized the viruses with moderate potency (FIG. 17E). The profound improvement of neutralization of the Tri-NAb over Bi-NAb against both sensitive and single-resistant viruses, which represent the majority of the global circulating viruses strongly, highlights the premise of engineering multi-epitope (more than 2 epitopes) targeting antibodies. It can be anticipated that the incorporation of additional bNAb functional moieties to the Tri-NAb will improve its neutralization capacity even further.

The experiments described herein demonstrate the successful combination of three HIV-1 broadly neutralizing antibody specificities into one single trispecific antibody by structure-based rational design. The triple-specificity antibody demonstrated exceptional HIV viral coverage (99.5%) in neutralization assays of a 208 virus panel with remarkable potency (IC50 titer geometric mean below 0.1 µg/ml). With these unprecedented neutralization capacities, the Tri-NAb represents an attractive candidate of the next generation of HIV-1 preventive and therapeutic antibody-based agents. Recently, novel potent antibodies of different specificities have been isolated and modified, which exhibit outstanding neutralization capacities[52, 53, 54]. Furthermore, various Fc mutations, especially the "LS" mutations (M428L/N434S) conferring enhanced affinity for neonatal Fc receptor that improves the in vivo half-life and biodistribution of antibody molecules could be incorporated into the multispecific antibody context to potentially improve the utility of passive immunization[44, 55, 56]. Coordinating combinations of additional antibody entities into multi-NAb designs will become more feasible, and may further the development of strategies for HIV-1 infection prevention, remission, and possible eradication in the future.

REFERENCES

1. Horwitz J A, et al. HIV-1 suppression and durable control by combining single broadly neutralizing antibodies and antiretroviral drugs in humanized mice. *Proc Natl Acad Sci USA* 110, 16538-16543 (2013).
2. Ananworanich J, McSteen B, Robb M L. Broadly neutralizing antibody and the HIV reservoir in acute HIV infection: a strategy toward HIV remission? *Curr Opin HIV AIDS* 10, 198-206 (2015).
3. Barouch D H, Deeks S G. Immunologic strategies for HIV-1 remission and eradication. *Science* 345, 169-174 (2014).
4. Burton D R, Barbas C F, Persson M A, Koenig S, Chanock R M, Lerner R A. A large array of human monoclonal antibodies to type 1 human immunodeficiency virus from combinatorial libraries of asymptomatic seropositive individuals. *Proc Natl Acad Sci USA* 88, 10134-10137 (1991).
5. Buchacher A, et al. Generation of human monoclonal antibodies against HIV-1 proteins; electrofusion and Epstein-Barr virus transformation for peripheral blood lymphocyte immortalization. *AIDS Res Hum Retroviruses* 10, 359-369 (1994).
6. Huang J, et al. Broad and potent neutralization of HIV-1 by a gp41-specific human antibody. *Nature* 491, 406-412 (2012).
7. Scheid J F, et al. Sequence and structural convergence of broad and potent HIV antibodies that mimic CD4 binding. *Science* 333, 1633-1637 (2011).
8. Wu X, et al. Rational design of envelope identifies broadly neutralizing human monoclonal antibodies to HIV-1. *Science* 329, 856-861 (2010).
9. Walker L M, et al. Broad neutralization coverage of HIV by multiple highly potent antibodies. *Nature* 477, 466-470 (2011).
10. Burton D R. Antibodies, viruses and vaccines. *Nat Rev Immunol* 2, 706-713 (2002).
11. Burton D R, Mascola J R. Antibody responses to envelope glycoproteins in HIV-1 infection. *Nat Immunol* 16, 571-576 (2015).
12. Graham B S, Ambrosino D M. History of passive antibody administration for prevention and treatment of infectious diseases. *Curr Opin HIV AIDS* 10, 129-134 (2015).
13. Sullender W M, Mufson M A, Prince G A, Anderson L J, Wertz G W. Antigenic and genetic diversity among the attachment proteins of group A respiratory syncytial viruses that have caused repeat infections in children. *J Infect Dis* 178, 925-932 (1998).
14. Cristina J, Costa-Mattioli M. Genetic variability and molecular evolution of hepatitis A virus. *Virus Res* 127, 151-157 (2007).
15. Lin C L, Kao J H. Hepatitis B virus genotypes and variants. *Cold Spring Harb Perspect Med* 5, a021436 (2015).
16. Dietzschold B, Morimoto K, Hooper D C, Smith J S, Rupprecht C E, Koprowski H. Genotypic and phenotypic diversity of rabies virus variants involved in human rabies: implications for postexposure prophylaxis. *J Hum Virol* 3, 50-57 (2000).
17. Korber B, Gaschen B, Yusim K, Thakallapally R, Kesmir C, Detours V. Evolutionary and immunological implications of contemporary HIV-1 variation. *Br Med Bull* 58, 19-42 (2001).
18. Korber B, et al. Timing the ancestor of the HIV-1 pandemic strains. *Science* 288, 1789-1796 (2000).
19. Caskey M, et al. Viraemia suppressed in HIV-1-infected humans by broadly neutralizing antibody 3BNC117. *Nature* 522, 487-491 (2015).
20. Ledgerwood J E, et al. Safety, pharmacokinetics and neutralization of the broadly neutralizing HIV-1 human 21. Lynch R M, et al. Virologic effects of broadly neutralizing antibody VRC01 administration during chronic HIV-1 infection. *Sci Transl Med* 7, 319ra206 (2015).
22. Bar K J, et al. Effect of HIV Antibody VRC01 on Viral Rebound after Treatment Interruption. *N Engl J Med* 375, 2037-2050 (2016).
23. Caskey M, et al. Antibody 10-1074 suppresses viremia in HIV-1-infected individuals. *Nat Med* 23, 185-191 (2017).
24. Tebit D M, Nankya I, Arts E J, Gao Y. HIV diversity, recombination and disease progression: how does fitness "fit" into the puzzle? *AIDS Rev* 9, 75-87 (2007).
25. Sather D N, et al. Broadly neutralizing antibodies developed by an HIV-positive elite neutralizer exact a replication fitness cost on the contemporaneous virus. *J Virol* 86, 12676-12685 (2012).
26. Lynch R M, et al. HIV-1 fitness cost associated with escape from the VRC01 class of CD4 binding site neutralizing antibodies. *J Virol* 89, 4201-4213 (2015).
27. Pietzsch J, et al. Human anti-HIV-neutralizing antibodies frequently target a conserved epitope essential for viral fitness. *J Exp Med* 207, 1995-2002 (2010).
28. Nishimura Y, et al. Early antibody therapy can induce long-lasting immunity to SHIV. *Nature* 543, 559-563 (2017).
29. Hessell A J, et al. Early short-term treatment with neutralizing human monoclonal antibodies halts SHIV infection in infant macaques. *Nat Med* 22, 362-368 (2016).
30. Hu Q, Sun W, Wang C, Gu Z. Recent advances of cocktail chemotherapy by combination drug delivery systems. *Adv Drug Deliv Rev* 98, 19-34 (2016).
31. Galimidi R P, et al. Intra-spike crosslinking overcomes antibody evasion by HIV-1. *Cell* 160, 433-446 (2015).
32. Ridgway J B, Presta L G, Carter P. 'Knobs-into-holes' engineering of antibody CH3 domains for heavy chain heterodimerization. *Protein Eng* 9, 617-621 (1996).
33. Klein C, Schaefer W, Regula J T. The use of CrossMAb technology for the generation of bi- and multispecific antibodies. *MAbs*, 0 (2016).
34. Bournazos S, Gazumyan A, Seaman M S, Nussenzweig M C, Ravetch J V. Bispecific Anti-HIV-1 Antibodies with Enhanced Breadth and Potency. *Cell* 165, 1609-1620 (2016).
35. Asokan M, et al. Bispecific Antibodies Targeting Different Epitopes on the HIV-1 Envelope Exhibit Broad and Potent Neutralization. *J Virol* 89, 12501-12512 (2015).
36. Kriangkum J, Xu B, Nagata L P, Fulton R E, Suresh M R. Bispecific and bifunctional single chain recombinant antibodies. *Biomol Eng* 18, 31-40 (2001).
37. Ahmad Z A, Yeap S K, Ali A M, Ho W Y, Alitheen N B, Hamid M. scFv antibody: principles and clinical application. *Clin Dev Immunol* 2012, 980250 (2012).
38. Holliger P, Hudson P J. Engineered antibody fragments and the rise of single domains. *Nat Biotechnol* 23, 1126-1136 (2005).
39. Vidarsson G, Dekkers G, Rispens T. IgG subclasses and allotypes: from structure to effector functions. *Front Immunol* 5, 520 (2014).
40. Stewart-Jones G B, et al. Trimeric HIV-1-Env Structures Define Glycan Shields from Clades A, B, and G. *Cell* 165, 813-826 (2016).
41. Pettersen E F, et al. UCSF Chimera—a visualization system for exploratory research and analysis. *J Comput Chem* 25, 1605-1612 (2004).
42. Ainavarapu S R, et al. Contour length and refolding rate of a small protein controlled by engineered disulfide bonds. *Biophys J* 92, 225-233 (2007).
43. Chen X, Zaro J L, Shen W C. Fusion protein linkers: property, design and functionality. *Adv Drug Deliv Rev* 65, 1357-1369 (2013).
44. Rudicell R S, et al. Enhanced potency of a broadly neutralizing HIV-1 antibody in vitro improves protection against lentiviral infection in vivo. *J Virol* 88, 12669-12682 (2014).
45. Doria-Rose N A, et al. HIV-1 neutralization coverage is improved by combining monoclonal antibodies that target independent epitopes. *J Virol* 86, 3393-3397 (2012).
46. Kong R, et al. Improving neutralization potency and breadth by combining broadly reactive HIV-1 antibodies targeting major neutralization epitopes. *J Virol* 89, 2659-2671 (2015).
47. Pace C S, et al. Bispecific antibodies directed to CD4 domain 2 and HIV envelope exhibit exceptional breadth and picomolar potency against HIV-1. *Proc Natl Acad Sci USA* 110, 13540-13545 (2013).
48. Sun M, et al. Rational design and characterization of the novel, broad and potent bispecific HIV-1 neutralizing antibody iMabm36. *J Acquir Immune Defic Syndr* 66, 473-483 (2014).
49. Huang Y, et al. Engineered Bispecific Antibodies with Exquisite HIV-1-Neutralizing Activity. *Cell* 165, 1621-1631 (2016).
50. Gardner M R, et al. AAV-expressed eCD4-Ig provides durable protection from multiple SHIV challenges. *Nature* 519, 87-91 (2015).
51. Wagh K, et al. Optimal Combinations of Broadly Neutralizing Antibodies for Prevention and Treatment of HIV-1 Clade C Infection. *PLoS Pathog* 12, e1005520 (2016).
52. Irimia A, et al. Lipid interactions and angle of approach to the HIV-1 viral membrane of broadly neutralizing antibody 10E8: Insights for vaccine and therapeutic design. *PLoS Pathog* 13, e1006212 (2017).
53. Kwon Y D, et al. Optimization of the Solubility of HIV-1-Neutralizing Antibody 10E8 through Somatic Variation and Structure-Based Design. *J Virol* 90, 5899-5914 (2016).
54. Huang J, et al. Identification of a CD4-Binding-Site Antibody to HIV that Evolved Near-Pan Neutralization Breadth. *Immunity* 45, 1108-1121 (2016).
55. Ko S Y, et al. Enhanced neonatal Fc receptor function improves protection against primate SHIV infection. *Nature* 514, 642-645 (2014).
56. Sievers S A, Scharf L, West A P, Bjorkman P J. Antibody engineering for increased potency, breadth and half-life. *Curr Opin HIV AIDS* 10, 151-159 (2015).
57. Guenaga J, et al. Structure-Guided Redesign Increases the Propensity of HIV Env To Generate Highly Stable Soluble Trimers. *J Virol* 90, 2806-2817 (2015).
58. Seaman M S, et al. Tiered categorization of a diverse panel of HIV-1 Env pseudoviruses for assessment of neutralizing antibodies. *J Virol* 84, 1439-1452 (2010).

59. Li M, et al. Human immunodeficiency virus type 1 env clones from acute and early subtype B infections for standardized assessments of vaccine-elicited neutralizing antibodies. *J Virol* 79, 10108-10125 (2005).
60. Potter C S, et al. Leginon: a system for fully automated acquisition of 1000 electron micrographs a day. *Ultramicroscopy* 77, 153-161 (1999).
61. Lander G C, et al. Appion: an integrated, database-driven pipeline to facilitate E M image processing. *J Struct Biol* 166, 95-102 (2009).
62. Voss N R, Yoshioka C K, Radermacher M, Potter C S, Carragher B. DoG Picker and TiltPicker: software tools to facilitate particle selection in single particle electron microscopy. *J Struct Biol* 166, 205-213 (2009).
63. Ogura T, Iwasaki K, Sato C. Topology representing network enables highly accurate classification of protein images taken by cryo electron-microscope without masking. *J Struct Biol* 143, 185-200 (2003).

| SEQUENCE TABLE | | |
|---|---|---|
| SEQ ID NO | Description | Sequence |
| 1 | VRC01 (VL-3x-VH)-(5X)-PGT121 (VL-3x-VH) ScEv amino acid sequence | EIVLTQSPGTLSLSPGETAIISCRTSQYGSLAWYQQRPGQAPRLVIYS GSTRAAGIPDRFSGSRWGPDYNLTISNLESGDFGVYYCQQYEFFGQGT KVQVDIKGGGGSGGGGSGGGGSQVQLVQSGGQMKKPGESMRISCRASG YEFIDCTLNWIRLAPGKRPEWMGWLKPRGGAVNYARPLQGRVTMTRDV YSDTAFLELRSLTVDDTAVYFCTRGKNCDYNWDFEHWGRGTPVIVSSG GGGSGGGGSGGGGSGGGGSGGGGSSDISVAPGETARISCGEKSLGSRA VQWYQHRAGQAPSLIIYNNQDRPSGIPERFSGSPDSPFGTTATLTITS VEAGDEADYYCHIWDSRVPTKWVFGGGTTLTVLGGGGSGGGGSGGGGS QMQLQESGPGLVKPSETLSLTCSVSGASISDSYWSWIRRSPGKGLEWI GYVHKSGDTNYSPSLKSRVNLSLDTSKNQVSLSLVAATAADSGKYYCA RTLHGRRIYGIVAFNEWFTYFYMDVWGNGTQVTVSSGSGHHHHHH |
| 2 | VRC01 variable light (VL) chain amino acid sequence | EIVLTQSPGTLSLSPGETAIISCRTSQYGSLAWYQQRPGQAPRLVIYS GSTRAAGIPDRFSGSRWGPDYNLTISNLESGDFGVYYCQQYEFFGQGT KVQVDIK |
| 3 | VL-CDR1 | RTSQYGSLA |
| 4 | VL-CDR2 | SGSTRAA |
| 5 | VL-CDR3 | QQYEF |
| 6 | VRC01 variable heavy (VH) chain amino acid sequence | QVQLVQSGGQMKKPGESMRISCRASGYEFIDCTLNWIRLAPGKRPEWM GWLKPRGGAVNYARPLQGRVTMTRDVYSDTAFLELRSLTVDDTAVYFC TRGKNCDYNWDFEHWGRGTPVIVSS |
| 7 | VH-CDR1 | DCTLN |
| 8 | VH-CDR2 | WLKPRGGAVNYARPLQG |
| 9 | VH-CDR3 | GKNCDYNWDFEH |
| 10 | PGT121 variable light (VL) chain amino acid sequence | SDISVAPGETARISCGEKSLGSRAVQWYQHRAGQAPSLIIYNNQDRPS GIPERFSGSPDSPFGTTATLTITSVEAGDEADYYCHIWDSRVPTKWVF GGGTTLTVL |
| 11 | VL-CDR1 | GEKSLGSRAVQ |
| 12 | VL-CDR2 | NNQDRPS |
| 13 | VL-CDR3 | HIWDSRVPTKWV |
| 14 | PGT121 variable heavy (VH) chain amino acid sequence | QMQLQESGPGLVKPSETLSLTCSVSGASISDSYWSWIRRSPGKGLEWI GYVHKSGDTNYSPSLKSRVNLSLDTSKNQVSLSLVAATAADSGKYYCA RTLHGRRIYGIVAFNEWFTYFYMDVWGNGTQVTVSS |
| 15 | VH-CDR1 | DSYWS |
| 16 | VH-CDR2 | YVHKSGDTNYSPSLKS |
| 17 | VH-CDR3 | TLHGRRIYGIVAFNEWFTYFYMDV |
| 18 | dVRC01 (VL(Δ1,2-V3S)-3x-VH)-(5X)-PGT121 (VL-3x-VH) ScEv amino acid sequence | SLTQSPGTLSLSPGETAIISCRTSQYGSLAWYQQRPGQAPRLVIYSGS TRAAGIPDRFSGSRWGPDYNLTISNLESGDFGVYYCQQYEFFGQGTKV QVDIKGGGGSGGGGSGGGGSQVQLVQSGGQMKKPGESMRISCRASGYE FIDCTLNWIRLAPGKRPEWMGWLKPRGGAVNYARPLQGRVTMTRDVYS DTAFLELRSLTVDDTAVYFCTRGKNCDYNWDFEHWGRGTPVIVSSGGG GSGGGGSGGGGSGGGGSGGGGSSDISVAPGETARISCGEKSLGSRAVQ WYQHRAGQAPSLIIYNNQDRPSGIPERFSGSPDSPFGTTATLTITSVE |

SEQUENCE TABLE

| SEQ ID NO | Description | Sequence |
|---|---|---|
| | | AGDEADYYCHIWDSRVPTKWVFGGGTTLTVLGGGGSGGGGSGGGGSQM QLQESGPGLVKPSETLSLTCSVSGASISDSYWSWIRRSPGKGLEWIGY VHKSGDTNYSPSLKSRVNLSLDTSKNQVSLSLVAATAADSGKYYCART LHGRRIYGIVAFNEWFTYFYMDVWGNGTQVTVSSGSGHHHHHH |
| 19 | dVRC01 variable light (VL) chain amino acid sequence | SLTQSPGTLSLSPGETAIISCRTSQYGSLAWYQQRPGQAPRLVIYSGS TRAAGIPDRFSGSRWGPDYNLTISNLESGDFGVYYCQQYEFFGQGTKV QVDIK |
| 20 | PGT121 (VH-3x-VL)-(5X)-VRC01 (VH-3x-VL) ScEv amino acid sequence | QMQLQESGPGLVKPSETLSLTCSVSGASISDSYWSWIRRSPGKGLEWI GYVHKSGDTNYSPSLKSRVNLSLDTSKNQVSLSLVAATAADSGKYYCA RTLHGRRIYGIVAFNEWFTYFYMDVWGNGTQVTVSSGGGGSGGGGSGG GGSSDISVAPGETARISCGEKSLGSRAVQWYQHRAGQAPSLIIYNNQD RPSGIPERFSGSPDSPFGTTATLTITSVEAGDEADYYCHIWDSRVPTK WVFGGGTTLTVLGGGGSGGGGSGGGGSGGGGSGGGGSQVQLVQSGGQM KKPGESMRISCRASGYEFIDCTLNWIRLAPGKRPEWMGWLKPRGGAYN YARPLQGRVTMTRDVYSDTAFLELRSLTVDDTAVYFCTRGKNCDYNWD FEHWGRGTPVIVSSGGGGSGGGGSGGGGSEIVLTQSPGTLSLSPGETA IISCRTSQYGSLAWYQQRPGQAPRLVIYSGSTRAAGIPDRFSGSRWGP DYNLTISNLESGDFGVYYCQQYEFFGQGTKVQVDIKGSGHHHHHH |
| 21 | PGT121 (VH-3x-VL)-(4X)-VRC01 (VH-3x-VL) ScEv amino acid sequence | QMQLQESGPGLVKPSETLSLTCSVSGASISDSYWSWIRRSPGKGLEWI GYVHKSGDTNYSPSLKSRVNLSLDTSKNQVSLSLVAATAADSGKYYCA RTLHGRRIYGIVAFNEWFTYFYMDVWGNGTQVTVSSGGGGSGGGGSGG GGSSDISVAPGETARISCGEKSLGSRAVQWYQHRAGQAPSLIIYNNQD RPSGIPERFSGSPDSPFGTTATLTITSVEAGDEADYYCHIWDSRVPTK WVFGGGTTLTVLGGGGSGGGGSGGGGSGGGGSQVQLVQSGGQMKKPGE SMRISCRASGYEFIDCTLNWIRLAPGKRPEWMGWLKPRGGAVNYARPL QGRVTMTRDVYSDTAFLELRSLTVDDTAVYFCTRGKNCDYNWDFEHWG RGTPVIVSSGGGGSGGGGSGGGGSEIVLTQSPGTLSLSPGETAIISCR TSQYGSLAWYQQRPGQAPRLVIYSGSTRAAGIPDRFSGSRWGPDYNLT ISNLESGDFGVYYCQQYEFFGQGTKVQVDIKGSGHHHHHH |
| 22 | PGT121 (VH-3x-VL)-(3X)-VRC01 (VH-3x-VL) ScEv amino acid sequence | QMQLQESGPGLVKPSETLSLTCSVSGASISDSYWSWIRRSPGKGLEWI GYVHKSGDTNYSPSLKSRVNLSLDTSKNQVSLSLVAATAADSGKYYCA RTLHGRRIYGIVAFNEWFTYFYMDVWGNGTQVTVSSGGGGSGGGGSGG GGSSDISVAPGETARISCGEKSLGSRAVQWYQHRAGQAPSLIIYNNQD RPSGIPERFSGSPDSPFGTTATLTITSVEAGDEADYYCHIWDSRVPTK WVFGGGTTLTVLGGGGSGGGGSGGGGSQVQLVQSGGQMKKPGESMRIS CRASGYEFIDCTLNWIRLAPGKRPEWMGWLKPRGGAVNYARPLQGRVT MTRDVYSDTAFLELRSLTVDDTAVYFCTRGKNCDYNWDFEHWGRGTPV IVSSGGGGSGGGGSGGGGSEIVLTQSPGTLSLSPGETAIISCRTSQYG SLAWYQQRPGQAPRLVIYSGSTRAAGIPDRFSGSRWGPDYNLTISNLE SGDFGVYYCQQYEFFGQGTKVQVDIKGSGHHHHHH |
| 23 | VRC01 (VL-3x-VH)-(5X)-PGT121 (VL-3x-VH) IgG1 amino acid sequence | EIVLTQSPGTLSLSPGETAIISCRTSQYGSLAWYQQRPGQAPRLVIYS GSTRAAGIPDRFSGSRWGPDYNLTISNLESGDFGVYYCQQYEFFGQGT KVQVDIKGGGGSGGGGSGGGGSQVQLVQSGGQMKKPGESMRISCRASG YEFIDCTLNWIRLAPGKRPEWMGWLKPRGGAVNYARPLQGRVTMTRDV YSDTAFLELRSLTVDDTAVYFCTRGKNCDYNWDFEHWGRGTPVIVSSG GGGSGGGGSGGGGSGGGGSGGGGSSDISVAPGETARISCGEKSLGSRA VQWYQHRAGQAPSLIIYNNQDRPSGIPERFSGSPDSPFGTTATLTITS VEAGDEADYYCHIWDSRVPTKWVFGGGTTLTVLGGGGSGGGGSGGGGS QMQLQESGPGLVKPSETLSLTCSVSGASISDSYWSWIRRSPGKGLEWI GYVHKSGDTNYSPSLKSRVNLSLDTSKNQVSLSLVAATAADSGKYYCA RTLHGRRIYGIVAFNEWFTYFYMDVWGNGTQVTVSSGSGPKSCDKTHT CPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKC KVSNKALPAPIEKTISKAKGQPREPQVYTLPPSREEMTKNQVSLTCLV KGFYPSDIAVEWESNGQPENNYKTTPPVLDSDGSFFLYSKLTVDKSRW QQGNVFSCSVMHEALHNHYTQKSLSLSPGK |
| 24 | dVRC01 (VL(Δ1,2-V3S)-3x-VH)-(5X)-PGT121 (VL-3x-VH) IgG1 amino acid sequence | SLTQSPGTLSLSPGETAIISCRTSQYGSLAWYQQRPGQAPRLVIYSGS TRAAGIPDRFSGSRWGPDYNLTISNLESGDFGVYYCQQYEFFGQGTKV QVDIKGGGGSGGGGSGGGGSQVQLVQSGGQMKKPGESMRISCRASGYE FIDCTLNWIRLAPGKRPEWMGWLKPRGGAVNYARPLQGRVTMTRDVYS DTAFLELRSLTVDDTAVYFCTRGKNCDYNWDFEHWGRGTPVIVSSGGG GSGGGGSGGGGSGGGGSGGGGSSDISVAPGETARISCGEKSLGSRAVQ WYQHRAGQAPSLIIYNNQDRPSGIPERFSGSPDSPFGTTATLTITSVE AGDEADYYCHIWDSRVPTKWVFGGGTTLTVLGGGGSGGGGSGGGGSQM QLQESGPGLVKPSETLSLTCSVSGASISDSYWSWIRRSPGKGLEWIGY VHKSGDTNYSPSLKSRVNLSLDTSKNQVSLSLVAATAADSGKYYCART LHGRRIYGIVAFNEWFTYFYMDVWGNGTQVTVSSGSGPKSCDKTHTCP |

| SEQ ID NO | Description | Sequence |
|---|---|---|
| | | PCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKV SNKALPAPIEKTISKAKGQPREPQVYTLPPSREEMTKNQVSLTCLVKG FYPSDIAVEWESNGQPENNYKTTPPVLDSDGSFFLYSKLTVDKSRWQQ GNVFSCSVMHEALHNHYTQKSLSLSPGK |
| 25 | PGT121 (VH-3x-VL)-(5X)-VRC01 (VH-3x-VL) IgG1 amino acid sequence | QMQLQESGPGLVKPSETLSLTCSVSGASISDSYWSWIRRSPGKGLEWI GYVHKSGDTNYSPSLKSRVNLSLDTSKNQVSLSLVAATAADSGKYYCA RTLHGRRIIYGIVAFNEWFTYFMYDVWGNGTQVTVSSGGGGSGGGGSGG GGSSDISVAPGETARISCGEKSLGSRAVQWYQHRAGQAPSLIIYNNQD RPSGIPERFSGSPDSPFGTTATLTITSVEAGDEADYYCHIWDSRVPTK WVFGGGTTLTVLGGGGSGGGGSGGGGSGGGGSGGGGSGVQLVQSGGQM KKPGESMRISCRASGYEFIDCTLNWIRLAPGKRPEWMGWLKPRGGAYN YARPLQGRVTMTRDVYSDTAFLELRSLTVDDTAVYFCTRGKNCDYNWD FEHWGRGTPVIVSSGGGGSGGGGSGGGGSEIVLTQSPGTLSLSPGETA IISCRTSQYGSLAWYQQRPGQAPRLVIYSGSTRAAGIPDRFSGSRWGP DYNLTISNLESGDFGVYYCQQYEFFGQGTKVQVDIKGSGPKSCDKTHT CPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKC KVSNKALPAPIEKTISKAKGQPREPQVYTLPPSREEMTKNQVSLTCLV KGFYPSDIAVEWESNGQPENNYKTTPPVLDSDGSFFLYSKLTVDKSRW QQGNVFSCSVMHEALHNHYTQKSLSLSPGK |
| 26 | PGT121 (VH-3x-VL)-(4X)-VRC01 (VH-3x-VL) IgG1 amino acid sequence | QMQLQESGPGLVKPSETLSLTCSVSGASISDSYWSWIRRSPGKGLEWI GYVHKSGDTNYSPSLKSRVNLSLDTSKNQVSLSLVAATAADSGKYYCA RTLHGRRIIYGIVAFNEWFTYFMYDVWGNGTQVTVSSGGGGSGGGGSGG GGSSDISVAPGETARISCGEKSLGSRAVQWYQHRAGQAPSLIIYNNQD RPSGIPERFSGSPDSPFGTTATLTITSVEAGDEADYYCHIWDSRVPTK WVFGGGTTLTVLGGGGSGGGGSGGGGSGGGGSQVQLVQSGGQMKKPGE SMRISCRASGYEFIDCTLNWIRLAPGKRPEWMGWLKPRGGAVNYARPL QGRVTMTRDVYSDTAFLELRSLTVDDTAVYFCTRGKNCDYNWDFEHWG RGTPVIVSSGGGGSGGGGSGGGGSEIVLTQSPGTLSLSPGETAIISCR TSQYGSLAWYQQRPGQAPRLVIYSGSTRAAGIPDRFSGSRWGPDYNLT ISNLESGDFGVYYCQQYEFFGQGTKVQVDIKGSGPKSCDKTHTCPPCP APELLGGPSVFLFPPKPKDTLMISRTPEVTCVVVDVSHEDPEVKFNWY VDGVEVHNAKTKPREEQYNSTYRVVSVLTVLHQDWLNGKEYKCKVSNK ALPAPIEKTISKAKGQPREPQVYTLPPSREEMTKNQVSLTCLVKGFYP SDIAVEWESNGQPENNYKTTPPVLDSDGSFFLYSKLTVDKSRWQQGNV FSCSVMHEALHNHYTQKSLSLSPGK |
| 27 | PGT121 (VH-3x-VL)-(3X)-VRC01 (VH-3x-VL) IgG1 amino acid sequence | QMQLQESGPGLVKPSETLSLTCSVSGASISDSYWSWIRRSPGKGLEWI GYVHKSGDTNYSPSLKSRVNLSLDTSKNQVSLSLVAATAADSGKYYCA RTLHGRRIIYGIVAFNEWFTYFMYDVWGNGTQVTVSSGGGGSGGGGSGG GGSSDISVAPGETARISCGEKSLGSRAVQWYQHRAGQAPSLIIYNNQD RPSGIPERFSGSPDSPFGTTATLTITSVEAGDEADYYCHIWDSRVPTK WVFGGGTTLTVLGGGGSGGGGSGGGGSQVQLVQSGGQMKKPGESMRIS CRASGYEFIDCTLNWIRLAPGKRPEWMGWLKPRGGAVNYARPLQGRVT MTRDVYSDTAFLELRSLTVDDTAVYFCTRGKNCDYNWDFEHWGRGTPV IVSSGGGGSGGGGSGGGGSEIVLTQSPGTLSLSPGETAIISCRTSQYG SLAWYQQRPGQAPRLVIYSGSTRAAGIPDRFSGSRWGPDYNLTISNLE SGDFGVYYCQQYEFFGQGTKVQVDIKGSGPKSCDKTHTCPPCPAPELL GGPSVFLFPPKPKDTLMISRTPEVTCVVVDVSHEDPEVKFNWYVDGVE VHNAKTKPREEQYNSTYRVVSVLTVLHQDWLNGKEYKCKVSNKALPAP IEKTISKAKGQPREPQVYTLPPSREEMTKNQVSLTCLVKGFYPSDIAV EWESNGQPENNYKTTPPVLDSDGSFFLYSKLTVDKSRWQQGNVFSCSV MHEALHNHYTQKSLSLSPGK |
| 28 | IgG1 Fc (hinge-CH2-CH3) amino acid sequence | PKSCDKTHTCPPCPAPELLGGPSVFLFPPKPKDTLMISRTPEVTCVVV DVSHEDPEVKFNWYVDGVEVHNAKTKPREEQYNSTYRVVSVLTVLHQD WLNGKEYKCKVSNKALPAPIEKTISKAKGQPREPQVYTLPPSREEMTK NQVSLTCLVKGFYPSDIAVEWESNGQPENNYKTTPPVLDSDGSFFLYS KLTVDKSRWQQGNVFSCSVMHEALHNHYTQKSLSLSPGK |
| 29 | signal sequence | MGWSCIILFLVATATGVHS |
| 30 | 35022(VH-3x-VL)-(5X)-10E8(VH-3x-VL) ScEv amino acid sequence | QGQLVQSGAELKKPGASVKISCKTSGYRFNFYHINWIRQTAGRGPEWM GWISPYSGDKNLAPAFQDRVIMTTDTEVPVTSFTSTGAAYMEIRNLKF DDTGTYFCAKGLLRDGSSTWLPYLWGQGTLLTVSSGGGGSGGGGSGGG GSQSVLTQSASVSGSLGQSVTISCTGPNSVCCSHKSISWYQWPPGRAP TLIIYEDNERAPGISPRFSGYKSYWSAYLTISDLRPEDETTYYCCSYT HNSGCVFGTGTKVSVLGGGGSGGGGSGGGGSGGGGSGGGGSEVQLVES GGGLVKPGGSLRLSCSASGFDFDNAWMTWVRQPPGKGLEWVGRITGPG EGWSVDYAAPVEGRFTISRLNSINFLYLEMNNLRMEDSGLYFCARTGK YYDFWSGYPPGEEYFQDWGRGTLVTVSSGGGGSGGGGSGGGGSSYELT |

SEQUENCE TABLE

| SEQ ID NO | Description | Sequence |
|---|---|---|
| | | QETGVSVALGRTVTITCRGDSLRSHYASWYQKKPGQAPILLFYGKNNR PSGVPDRFSGSASGNRASLTISGAQAEDDAEYYCSSRDKSGSRLSVFG GGTKLTVLGSGHHHHHH |
| 31 | 35022 variable light (VL) chain amino acid sequence | QSVLTQSASVSGSLGQSVTISCTGPNSVCCSHKSISWYQWPPGRAPTL IIYEDNERAPGISPRFSGYKSYWSAYLTISDLRPEDETTYYCCSYTHN SGCVFGTGTKVSVL |
| 32 | VL-CDR1 | TGPNSVCCSHKSIS |
| 33 | VL-CDR2 | EDNERAP |
| 34 | VL-CDR3 | CSYTHNSGCV |
| 35 | 35022 variable heavy (VH) chain amino acid sequence | QGQLVQSGAELKKPGASVKISCKTSGYRFNFYHINWIRQTAGRGPEWM GWISPYSGDKNLAPAFQDRVIMTTDTEVPVTSFTSTGAAYMEIRNLKF DDTGTYFCAKGLLRDGSSTWLPYLWGQGTLLTVSS |
| 36 | VH-CDR1 | FYHIN |
| 37 | VH-CDR2 | WISPYSGDKNLAPAFQD |
| 38 | VH-CDR3 | GLLRDGSSTWLPYL |
| 39 | 10E8 variable light (VL) chain amino acid sequence | SYELTQETGVSVALGRTVTITCRGDSLRSHYASWYQKKPGQAPILLFY GKNNRPSGVPDRFSGSASGNRASLTISGAQAEDDAEYYCSSRDKSGSR LSVFGGGTKLTVL |
| 40 | VL-CDR1 | RGDSLRSHYAS |
| 41 | VL-CDR2 | GKNNRPS |
| 42 | VL-CDR3 | SSRDKSGSRLSV |
| 43 | 10E8 variable heavy (VH) chain amino acid sequence | EVQLVESGGGLVKPGGSLRLSCSASGFDFDNAWMTWVRQPPGKGLEWV GRITGPGEGWSVDYAAPVEGRFTISRLNSINFLYLEMNNLRMEDSGLY FCARTGKYYDFWSGYPPGEEYFQDWGRGTLVTVSS |
| 44 | VH-CDR1 | NAWMT |
| 45 | VH-CDR2 | RITGPGEGWSVDYAAPVEG |
| 46 | VH-CDR3 | TGKYYDFWSGYPPGEEYFQD |
| 47 | 35022(VH-3x-VL)-(7X)-10E8(VH-3x-VL) ScEv amino acid sequence | QGQLVQSGAELKKPGASVKISCKTSGYRFNFYHINWIRQTAGRGPEWM GWISPYSGDKNLAPAFQDRVIMTTDTEVPVTSFTSTGAAYMEIRNLKF DDTGTYFCAKGLLRDGSSTWLPYLWGQGTLLTVSSGGGGSGGGGSGGG GSQSVLTQSASVSGSLGQSVTISCTGPNSVCCSHKSISWYQWPPGRAP TLIIYEDNERAPGISPRFSGYKSYWSAYLTISDLRPEDETTYYCCSYT HNSGCVFGTGTKVSVLGGGGSGGGGSGGGGSGGGGSGGGGSGGGGSGG GGSEVQLVESGGGLVKPGGSLRLSCSASGFDFDNAWMTWVRQPPGKGL EWVGRITGPGEGWSVDYAAPVEGRFTISRLNSINFLYLEMNNLRMEDS GLYFCARTGKYYDFWSGYPPGEEYFQDWGRGTLVTVSSGGGGSGGGGS GGGGSSYELTQETGVSVALGRTVTITCRGDSLRSHYASWYQKKPGQAP ILLFYGKNNRPSGVPDRFSGSASGNRASLTISGAQAEDDAEYYCSSRD KSGSRLSVFGGGTKLTVLGSGHHHHHH |
| 48 | 10E8(VH-3x-VL)-(5X)-35022(VH-3x-VL) ScEv amino acid sequence | EVQLVESGGGLVKPGGSLRLSCSASGFDFDNAWMTWVRQPPGKGLEWV GRITGPGEGWSVDYAAPVEGRFTISRLNSINFLYLEMNNLRMEDSGLY FCARTGKYYDFWSGYPPGEEYFQDWGRGTLVTVSSGGGGSGGGGSGGG GSSYELTQETGVSVALGRTVTITCRGDSLRSHYASWYQKKPGQAPILL FYGKNNRPSGVPDRFSGSASGNRASLTISGAQAEDDAEYYCSSRDKSG SRLSVFGGGTKLTVLGGGGSGGGGSGGGGSGGGGSGGGGSQGQLVQSG AELKKPGASVKISCKTSGYRFNFYHINWIRQTAGRGPEWMGWISPYSG DKNLAPAFQDRVIMTTDTEVPVTSFTSTGAAYMEIRNLKFDDTGTYFC AKGLLRDGSSTWLPYLWGQGTLLTVSSGGGGSGGGGSGGGGSQSVLTQ SASVSGSLGQSVTISCTGPNSVCCSHKSISWYQWPPGRAPTLIIYEDN ERAPGISPRFSGYKSYWSAYLTISDLRPEDETTYYCCSYTHNSGCVFG TGTKVSVLGSGHHHHHH |

| SEQ ID NO | Description | Sequence |
|---|---|---|
| 49 | 10E8(VH-3x-VL)-(7X)-35022(VH-3x-VL) ScEv amino acid sequence | EVQLVESGGGLVKPGGSLRLSCSASGFDFDNAWMTWVRQPPGKGLEWV GRITGPGEGWSVDYAAPVEGRFTISRLNSINFLYLEMNNLRMEDSGLY FCARTGKYYDFWSGYPPGEEYFQDWGRGTLVTVSSGGGGSGGGGSGGGG GSSYELTQETGVSVALGRTVTITCRGDSLRSHYASWYQKKPGQAPILL FYGKNNRPSGVPDRFSGSASGNRASLTISGAQAEDDAEYYCSSRDKSG SRLSVFGGGTKLTVLGGGGSGGGGSGGGGSGGGGSGGGGSGGGGSGGG GSQGQLVQSGAELKKPGASVKISCKTSGYRFNFYHINWIRQTAGRGPE WMGWISPYSGDKNLAPAFQDRVIMTTDTEVPVTSFTSTGAAYMEIRNL KFDDTGTYFCAKGLLRDGSSTWLPYLWGQGTLLTVSSGGGGSGGGGSG GGGSQSVLTQSASVSGSLGQSVTISCTGPNSVCCSHKSISWYQWPPGR APTLIIYEDNERAPGISPRFSGYKSYWSAYLTISDLRPEDETTYYCCS YTHNSGCVFGTGTKVSVLGSGHHHHHH |
| 50 | 35022(VH-3x-VL)-(5X)-10E8(VH-3x-VL) IgG1 amino acid sequence | QGQLVQSGAELKKPGASVKISCKTSGYRFNFYHINWIRQTAGRGPEWM GWISPYSGDKNLAPAFQDRVIMTTDTEVPVTSFTSTGAAYMEIRNLKF DDTGTYFCAKGLLRDGSSTWLPYLWGQGTLLTVSSGGGGSGGGGSGGG GSQSVLTQSASVSGSLGQSVTISCTGPNSVCCSHKSISWYQWPPGRAP TLIIYEDNERAPGISPRFSGYKSYWSAYLTISDLRPEDETTYYCCSYT HNSGCVFGTGTKVSVLGGGGSGGGGSGGGGSGGGGSGGGGSEVQLVES GGGLVKPGGSLRLSCSASGFDFDNAWMTWVRQPPGKGLEWVGRITGPG EGWSVDYAAPVEGRFTISRLNSINFLYLEMNNLRMEDSGLYFCARTGK YYDFWSGYPPGEEYFQDWGRGTLVTVSSGGGGSGGGGSGGGGSSYELT QETGVSVALGRTVTITCRGDSLRSHYASWYQKKPGQAPILLFYGKNNR PSGVPDRFSGSASGNRASLTISGAQAEDDAEYYCSSRDKSGSRLSVFG GGTKLTVLGSGPKSCDKTHTCPPCPAPELLGGPSVFLFPPKPKDTLMI SRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVY TLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSP GK |
| 51 | 35022(VH-3x-VL)-(7X)-10E8(VH-3x-VL) IgG1 amino acid sequence | QGQLVQSGAELKKPGASVKISCKTSGYRFNFYHINWIRQTAGRGPEWM GWISPYSGDKNLAPAFQDRVIMTTDTEVPVTSFTSTGAAYMEIRNLKF DDTGTYFCAKGLLRDGSSTWLPYLWGQGTLLTVSSGGGGSGGGGSGGG GSQSVLTQSASVSGSLGQSVTISCTGPNSVCCSHKSISWYQWPPGRAP TLIIYEDNERAPGISPRFSGYKSYWSAYLTISDLRPEDETTYYCCSYT HNSGCVFGTGTKVSVLGGGGSGGGGSGGGGSGGGGSGGGGSGGGGSGG GGSEVQLVESGGGLVKPGGSLRLSCSASGFDFDNAWMTWVRQPPGKGL EWVGRITGPGEGWSVDYAAPVEGRFTISRLNSINFLYLEMNNLRMEDS GLYFCARTGKYYDFWSGYPPGEEYFQDWGRGTLVTVSSGGGGSGGGGS GGGGSSYELTQETGVSVALGRTVTITCRGDSLRSHYASWYQKKPGQAP ILLFYGKNNRPSGVPDRFSGSASGNRASLTISGAQAEDDAEYYCSSRD KSGSRLSVFGGGTKLTVLGSGPKSCDKTHTCPPCPAPELLGGPSVFLF PPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKA KGQPREPQVYTLPPSREEMTKNQVSLTCLVKGFYPSDIAVEWESNGQP ENNYKTTPPVLDSDGSFFLYSKLTVDKSRWQQGNVESCSVMHEALHNH YTQKSLSLSPGK |
| 52 | 10E8(VH-3x-VL)-(5X)-35022(VH-3x-VL) IgG1 amino acid sequence | EVQLVESGGGLVKPGGSLRLSCSASGFDFDNAWMTWVRQPPGKGLEWV GRITGPGEGWSVDYAAPVEGRFTISRLNSINFLYLEMNNLRMEDSGLY FCARTGKYYDFWSGYPPGEEYFQDWGRGTLVTVSSGGGGSGGGGSGGG GSSYELTQETGVSVALGRTVTITCRGDSLRSHYASWYQKKPGQAPILL FYGKNNRPSGVPDRFSGSASGNRASLTISGAQAEDDAEYYCSSRDKSG SRLSVFGGGTKLTVLGGGGSGGGGSGGGGSGGGGSGGGGSQGQLVQSG AELKKPGASVKISCKTSGYRFNFYHINWIRQTAGRGPEWMGWISPYSG DKNLAPAFQDRVIMTTDTEVPVTSFTSTGAAYMEIRNLKFDDTGTYFC AKGLLRDGSSTWLPYLWGQGTLLTVSSGGGGSGGGGSGGGGSQSVLTQ SASVSGSLGQSVTISCTGPNSVCCSHKSISWYQWPPGRAPTLIIYEDN ERAPGISPRFSGYKSYWSAYLTISDLRPEDETTYYCCSYTHNSGCVFG TGTKVSVLGSGPKSCDKTHTCPPCPAPELLGGPSVFLFPPKPKDTLMI SRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVY TLPPSREEMTKNQVSLTCLVKGFYPSDIAVEWESNGQPENNYKTTPPV LDSDGSFFLYSKLTVDKSRWQQGNVESCSVMHEALHNHYTQKSLSLSP GK |
| 53 | 10E8(VH-3x-VL)-(7X)-35022(VH-3x-VL) IgG1 amino acid sequence | EVQLVESGGGLVKPGGSLRLSCSASGFDFDNAWMTWVRQPPGKGLEWV GRITGPGEGWSVDYAAPVEGRFTISRLNSINFLYLEMNNLRMEDSGLY FCARTGKYYDFWSGYPPGEEYFQDWGRGTLVTVSSGGGGSGGGGSGGG GSSYELTQETGVSVALGRTVTITCRGDSLRSHYASWYQKKPGQAPILL FYGKNNRPSGVPDRFSGSASGNRASLTISGAQAEDDAEYYCSSRDKSG SRLSVFGGGTKLTVLGGGGSGGGGSGGGGSGGGGSGGGGSGGGGSGGG GSQGQLVQSGAELKKPGASVKISCKTSGYRFNFYHINWIRQTAGRGPE |

SEQUENCE TABLE

| SEQ ID NO | Description | Sequence |
|---|---|---|
| | | WMGWISPYSGDKNLAPAFQDRVIMTTDTEVPVTSFTSTGAAYMEIRNL KFDDTGTYFCAKGLLRDGSSTWLPYLWGQGTLLTVSSGGGGSGGGGSG GGGSQSVLTQSASVSGSLGQSVTISCTGPNSVCCSHKSISWYQWPPGR APTLIIYEDNERAPGISPRFSGYKSYWSAYLTISDLRPEDETTYYCCS YTHNSGCVFGTGTKVSVLGSGPKSCDKTHTCPPCPAPELLGGPSVFLF PPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKA KGQPREPQVYTLPPSREEMTKNQVSLTCLVKGFYPSDIAVEWESNGQP ENNYKTTPPVLDSDGSFFLYSKLTVDKSRWQQGNVFSCSVMHEALHNH YTQKSLSLSPGK |
| 54 | 10-1074 variable light (VL) chain amino acid sequence | SYVRPLSVALGETARISCGRQALGSRAVQWYQHRPGQAPILLIYNNQD RPSGIPERFSGTPDINFGTRATLTISGVEAGDEADYYCHMWDSRSGFS WSFGGATRLTVL |
| 55 | VL-CDR1 | GRQALGSRAVQ |
| 56 | VL-CDR2 | NNQDRPS |
| 57 | VL-CDR3 | HMWDSRSGFSWS |
| 58 | 10-1074 variable heavy (VH) chain amino acid sequence | QVQLQESGPGLVKPSETLSVTCSVSGDSMNNYYWTWIRQSPGKGLEWI GYISDRESATYNPSLNSRVVISRDTSKNQLSLKLNSVTPADTAVYYCA TARRGQRIYGVVSFGEFFYYYSMDVWGKGTTVTVSS |
| 59 | VH-CDR1 | NYYWT |
| 60 | VH-CDR2 | YISDRESATYNPSLNS |
| 61 | VH-CDR3 | ARRGQRIYGVVSFGEFFYYYSMDV |
| 62 | BG18 variable light (VL) chain amino acid sequence | WASSELTQPPSVSVSPGQTARITCSGAPLTSRFTYWYRQKPGQAPVLI ISRSSQRSSGWSGRFSASWSGTTVTLTIRGVQADDEADYYCQSSDTSD SYKMFGGGTKLTVL |
| 63 | VL-CDR1 | SGAPLTSRFTY |
| 64 | VL-CDR2 | SRSSQRS |
| 65 | VL-CDR3 | QSSDTSDSYKM |
| 66 | BG18 variable heavy (VH) chain amino acid sequence | EQVQLRESGPGLVKPSETLSLSCTVSQDSRPSDHSWTWVRQSPGKALE WIGDIHYNGATTYNPSLRSRVRIELDQSIPRFSLKMTSMTAADTGMYY CARNAIRIYGVVALGEWFHYGMDVWGQGTAVTVSS |
| 67 | VH-CDR1 | SDHSWT |
| 68 | VH-CDR2 | DIHYNGATTYNPSLRS |
| 69 | VH-CDR3 | NAIRIYGVVALGEWFHYGMDV |
| 70 | PGT135 variable light (VL) chain amino acid sequence | EIVMTQSPDTLSVSPGETVTLSCRASQNINKNLAWYQYKPGQSPRLVI FETYSKIAAFPARFVASGSGTEFTLTINNMQSEDVAVYYCQQYEEWPR TFGQGTKVDIK |
| 71 | VL-CDR1 | RASQNINKNLA |
| 72 | VL-CDR2 | ETYSKIA |
| 73 | VL-CDR3 | QQYEEWPRT |
| 74 | PGT135 variable heavy (VH) chain amino acid sequence | QLQMQESGPGLVKPSETLSLSCTVSGDSIRGGEWGDKDYHWGWVRHSA GKGLEWIGSIHWRGTTHYKESLRRRVSMSIDTSRNWFSLRLASVTAAD TAVYFCARHRHHDVFMVPIAGWFDVWGPGVQVTVSS |
| 75 | VH-CDR1 | GGEWGDKDYHWG |
| 76 | VH-CDR2 | SIHWRGTTHYKESLRR |

SEQUENCE TABLE

| SEQ ID NO | Description | Sequence |
|---|---|---|
| 77 | VH-CDR3 | HRHHDVFMVPIAGWFDV |
| 78 | PGT122 variable light (VL) chain amino acid sequence | TFVSVAPGQTARITCGEESLGSRSVIWYQQRPGQAPSLIIYNNNDRPS GIPDRFSGSPGSTFGTTATLTITSVEAGDEADYYCHIWDSRRPTNWVF GEGTTLIVL |
| 79 | VL-CDR1 | GEESLGSRSVI |
| 80 | VL-CDR2 | NNNDRPS |
| 81 | VL-CDR3 | HIWDSRRPTNWV |
| 82 | PGT122 variable heavy (VH) chain amino acid sequence | QVHLQESGPGLVKPSETLSLTCNVSGTLVRDNYWSWIRQPLGKQPEWI GYVHDSGDTNYNPSLKSRVHLSLDKSKNLVSLRLTGVTAADSAIYYCA TTKHGRRIYGVVAFKEWFTYFYMDVWGKGTSVTVSS |
| 83 | VH-CDR1 | DNYWS |
| 84 | VH-CDR2 | YVHDSGDTNYNPSLKS |
| 85 | VH-CDR3 | TKHGRRIYGVVAFKEWFTYFYMDV |
| 86 | PGT128 variable light (VL) chain amino acid sequence | TFVSVAPGQTARITCGEESLGSRSVIWYQQRPGQAPSLIIYNNNDRPS GIPDRFSGSPGSTFGTTATLTITSVEAGDEADYYCHIWDSRRPTNWVF GEGTTLIVL |
| 87 | VL-CDR1 | GEESLGSRSVI |
| 88 | VL-CDR2 | NNNDRPS |
| 89 | VL-CDR3 | HIWDSRRPTNWV |
| 90 | PGT128 variable heavy (VH) chain amino acid sequence | EPQLQESGPTLVEASETLSLTCAVSGDSTAACNSFWGWVRQPPGKGLE WVGSLSHCASYWNRGWTYHNPSLKSRLTLALDTPKNLVFLKLNSVTAA DTATYYCARFGGEVLRYTDWPKPAWVDLWGRGTLVTVSS |
| 91 | VH-CDR1 | ACNSFWG |
| 92 | VH-CDR2 | SLSHCASYWNRGWTYHNPSLKS |
| 93 | VH-CDR3 | FGGEVLRYTDWPKPAWVDL |
| 94 | 10E8v4 variable light (VL) chain amino acid sequence | SELTQDPAVSVALKQTVTITCRGDSLRSHYASWYQKKPGQAPVLLFYG KNNRPSGIPDRFSGSASGNRASLTITGAQAEDEADYYCSSRDKSGSRL SVFGGGTKLTVL |
| 95 | VL-CDR1 | RGDSLRSHYAS |
| 96 | VL-CDR2 | GKNNRPS |
| 97 | VL-CDR3 | SSRDKSGSRLSV |
| 98 | 10E8v4 variable heavy (VH) chain amino acid sequence | EVRLVESGGGLVKPGGSLRLSCSASGFDFDNAWMTWVRQPPGKGLEWV GRITGPGEGWSVDYAESVKGRFTISRDNTKNTLYLEMNNVRTEDTGYY FCARTGKYYDFWSGYPPGEEYFQDWGQGTLVIVSS |
| 99 | VH-CDR1 | NAWMT |
| 100 | VH-CDR2 | RITGPGEGWSVDYAESVKG |
| 101 | VH-CDR3 | TGKYYDFWSGYPPGEEYFQD |
| 94 | 10E8v4 S100cF variable light (VL) chain amino acid sequence | SELTQDPAVSVALKQTVTITCRGDSLRSHYASWYQKKPGQAPVLLFYG KNNRPSGIPDRFSGSASGNRASLTITGAQAEDEADYYCSSRDKSGSRL SVFGGGTKLTVL |

SEQUENCE TABLE

| SEQ ID NO | Description | Sequence |
|---|---|---|
| 95 | VL-CDR1 | RGDSLRSHYAS |
| 96 | VL-CDR2 | GKNNRPS |
| 97 | VL-CDR3 | SSRDKSGSRLSV |
| 106 | 10E8v4 S100cF variable heavy (VH) chain amino acid sequence | EVRLVESGGGLVKPGGSLRLSCSASGFDFDNAWMTWVRQPPGKGLEWV GRITGPGEGWSVDYAESVKGRFTISRDNTKNTLYLEMNNVRTEDTGYY FCARTGKYYDFWFGYPPGEEYFQDWGQGTLVIVSS |
| 107 | VH-CDR1 | NAWMT |
| 108 | VH-CDR2 | RITGPGEGWSVDYAESVKG |
| 109 | VH-CDR3 | TGKYYDFWFGYPPGEEYFQD |
| 110 | DH511.2 k3 variable light (VL) chain amino acid sequence | DIQMTQSPSFLYGSVGDRVTITCRASQNIKDYLNWYQQRPGRAPRLLI YAASNLQSGVPSRFSGSGYGTDFTLIISSLQPEDFATYFCQESYSSTP THIFGLGTKLEK |
| 111 | VL-CDR1 | RASQNIKDYLN |
| 112 | VL-CDR2 | AASNLQS |
| 113 | VL-CDR3 | QESYSSTPTHI |
| 114 | DH511.2 k3 variable heavy (VH) chain amino acid sequence | QVQLVQSGGGLVKPGGSLTLSCSASGFFFDNSWMGWVRQAPGKGLEWV GRIRRLKDGATGEYGAAVKDRFTISRDDSRNMLYHMRTLKTEDSGTY YCTMDEGTPVTRFLEWGYFYYYMAVWGRGTTVIVSS |
| 115 | VH-CDR1 | NSWMG |
| 116 | VH-CDR2 | RIRRLKDGATGEYGAAVKD |
| 117 | VH-CDR3 | DEGTPVTRFLEWGYFYYYMAV |
| 118 | 4E10 variable light (VL) chain amino acid sequence | EIVLTQSPGTQSLSPGERATLSCRASQSVGNNKLAWYQQRPGQAPRLL IYGASSRPSGVADRFSGSGSGTDFTLTISRLEPEDFAVYYCQQYGQSL STFGQGTKVEVK |
| 119 | VL-CDR1 | RASQSVGNNKLA |
| 120 | VL-CDR2 | GASSRPS |
| 121 | VL-CDR3 | QQYGQSLST |
| 122 | 4E10 variable heavy (VH) chain amino acid sequence | VQLVQSGAEVKRPGSSVTVSCKASGGSFSTYALSWVRQAPGRGLEWMG GVIPLLTITNYAPRFQGRITITADRSTSTAYLELNSLRPEDTAVYYCA REGTTGWGWLGKPIGAFAHWGQGTLVTVSS |
| 123 | VH-CDR1 | TYALS |
| 124 | VH-CDR2 | GVIPLLTITNYAPRFQG |
| 125 | VH-CDR3 | EGTTGWGWLGKPIGAFAE |
| 126 | 2F5 variable light (VL) chain amino acid sequence | ALQLTQSPSSLSASVGDRITITCRASQGVTSALAWYRQKPGSPPQLLI YDASSLESGVPSRFSGSGSGTEFTLTISTLRPEDFATYYCQQLHFYPH TFGGGTRVDVR |
| 127 | VL-CDR1 | RASQGVTSALA |
| 128 | VL-CDR2 | DASSLES |
| 129 | VL-CDR3 | QQLHFYPHT |
| 130 | 2F5 variable heavy (VH) chain | RITLKESGPPLVKPTQTLTLTCSFSGFSLSDFGVGVGWIRQPPGKALE WLAIIYSDDDKRYSPSLNTRLTITKDTSKNQVVLVMTRVSPVDTATYF |

SEQUENCE TABLE

| SEQ ID NO | Description | Sequence |
|---|---|---|
| | amino acid sequence | CAHRRGPTTLFGVPIARGPVNAMDVWGQGITVTISS |
| 131 | VH-CDR1 | DFGVGVG |
| 132 | VH-CDR2 | IIYSDDDKRYSPSLNT |
| 133 | VH-CDR3 | RRGPTTLFGVPIARGPVNAMDV |
| 134 | N123-VRC34.01 variable light (VL) chain amino acid sequence | DIQLTQSPSFLSASVGDKVTITCRASQGVRNELAWYQQKPGKAPNLLI YYASTLQSGVPSRFSATGSGTHFTLTVSSLQPEDFATYFCQHMSSYPL TFGGGTKVEIK |
| 135 | VL-CDR1 | RASQGVRNELA |
| 136 | VL-CDR2 | YASTLQS |
| 137 | VL-CDR3 | QHMSSYPLT |
| 138 | N123-VRC34.01 variable heavy (VH) chain amino acid sequence | QEVLVQSGAEVKKPGASVKVSCRAFGYTFTGNALHWVRQAPGQGLEWL GWINPHSGDTTTSQKFQGRVYMTRDKSINTAFLDVTRLTSDDTGIYYC ARDKYYGNEAVGMDVWGQGTSVTVSS |
| 139 | VH-CDR1 | GNALH |
| 140 | VH-CDR2 | WINPHSGDTTTSQKFQG |
| 141 | VH-CDR3 | DKYYGNEAVGMDV |
| 142 | 3BC315 variable light (VL) chain amino acid sequence | QSALTQPASVSASPGQSITISCSGTRSDVGGYDFVSWYQQHPGKVPKL IIYEVTKRPSGIPQRFSGSKSGNTASLTISGLQADDEADYYCCSYANY DKLILGGGTKLTVL |
| 143 | VL-CDR1 | SGTRSDVGGYDFVS |
| 144 | VL-CDR2 | EVTKRPS |
| 145 | VL-CDR3 | CSYANYDKLI |
| 146 | 3BC315 variable heavy (VH) chain amino acid sequence | QVQLVQSGAEMKDPGASVKVSCRASGYKFTDYYMHWVRQAPGQGLEWV GWVNTNGGFTKYGAKFQGRVTVTRDTSTNTVFLELSRLTFGDTAMYFC ARPMRPVSHGIDYSGLFVFQFWGRGTMVTVSS |
| 147 | VH-CDR1 | DYYMH |
| 148 | VH-CDR2 | WVNTNGGFTKYGAKFQG |
| 149 | VH-CDR3 | PMRPVSHGIDYSGLFVFQF |
| 150 | PGT151 variable light (VL) chain amino acid sequence | DIVMTQTPLSLSVTPGQPASISCKSSESLRQSNGKTSLYWYRQKPGQS PQLLVFEVSNRFSGVSDRFVGSGSGTDFTLRISRVEAEDVGFYYCMQS KDFPLTFGGGTKVDLK |
| 151 | VL-CDR1 | KSSESLRQSNGKTSLY |
| 152 | VL-CDR2 | EVSNRFS |
| 153 | VL-CDR3 | MQSKDFPLT |
| 154 | PGT151 variable heavy (VH) chain amino acid sequence | RVQLVESGGGVVQPGKSVRLSCVVSDFPFSKYPMYWVRQAPGKGLEWV AAISGDAWHVVYSNSVQGRFLVSRDNVKNTLYLEMNSLKIEDTAVYRC ARMFQESGPPRLDRWSGRNYYYYSGMDVWGQGTTVTVSS |
| 155 | VH-CDR1 | KYPMY |
| 156 | VH-CDR2 | AISGDAWHVVYSNSVQG |
| 157 | VH-CDR3 | MFQESGPPRLDRWSGRNYYYYSGMDV |

-continued

| SEQ ID NO | Description | Sequence |
|---|---|---|
| 158 | VRC03 variable light (VL) chain amino acid sequence | EIVLTQSPGILSLSPGETATLFCKASQGGNAMTWYQKRRGQVPRLLIYDTSRRASGVPDRFVGSGSGTDFFLTINKLDREDFAVYYCQQFEFFGLGSELEVHR |
| 159 | VL-CDR1 | KASQGGNAMT |
| 160 | VL-CDR2 | DTSRRAS |
| 161 | VL-CDR3 | QQFEF |
| 162 | VRC03 variable heavy (VH) chain amino acid sequence | QVQLVQSGAVIKTPGSSVKISCRASGYNFRDYSIHWVRLIPDKGFEWIGWIKPLWGAVSYARQLQGRVSMTRQLSQDPDDPDWGVAYMEFSGLTPADTAEYFCVRRGSCDYCGDFPWQYWGQGTVVVVSS |
| 163 | VH-CDR1 | DYSIH |
| 164 | VH-CDR2 | WIKPLWGAVSYARQLQG |
| 165 | VH-CDR3 | VRRGSCDYCGDFPWQY |
| 166 | VRC06 variable light (VL) chain amino acid sequence | EIVLTQSPATLSLSPGERATLSCRASQGGNSLNWYQKRRGQTPRLLIYDTSRRASDIPEKFVGSGSGTDFSLTITKVGPEDFAVYYCQQFEFFGLGTTLEIN |
| 167 | VL-CDR1 | RASQGGNSLN |
| 168 | VL-CDR2 | DTSRRAS |
| 169 | VL-CDR3 | QQFEF |
| 170 | VRC06 variable heavy (VH) chain amino acid sequence | EVQLVESGPVMRKPGSSMKISCATSGYNFRDFSIHWVRFNRRYGFEWIGWIKPMWGAVNYARQLQGRVSMSRLFSQDLYYPDRGTAYLEFSGLTSADTADYF CVRRGSSCPHCGDFHFEHWGQGTAVVVSA |
| 171 | VH-CDR1 | DFSIH |
| 172 | VH-CDR2 | WIKPMWGAVNYARQLQG |
| 173 | VH-CDR3 | RGSSCPHCGDFHFEH |
| 2 | VRC07 variable light (VL) chain amino acid sequence | EIVLTQSPGTLSLSPGETAIISCRTSQYGSLAWYQQRPGQAPRLVIYSGSTRAAGIPDRFSGSRWGPDYNLTISNLESGDFGVYYCQQYEFFGQGTKVQVDIK |
| 3 | VL-CDR1 | RTSQYGSLA |
| 4 | VL-CDR2 | SGSTRAA |
| 5 | VL-CDR3 | QQYEF |
| 178 | VRC07 variable heavy (VH) chain amino acid sequence | QVQLVQSGAQVKKPGSSVKVSCKASGYEFINCPINWVRQAPRQRPEWMGWMKPRGGAVSYARQLQGRVTMTRDMYTSTAYLELRSLTSEDTAVYYCARGKYCTARDYYNWDFEHWGPGTPITVSS |
| 179 | VH-CDR1 | NCPIN |
| 180 | VH-CDR2 | WMKPRGGAVSYARQLQG |
| 181 | VH-CDR3 | GKYCTARDYYNWDFEH |
| 182 | 3BNC117 variable light (VL) chain amino acid sequence | DIQMTQSPSSLSASVGDTVTITCQANGYLNWYQQRRGKAPKLLIYDGSKLERGVPSRFSGRRWGQEYNLTINNLQPEDIATYFCQVYEFVVPGTRLDLK |
| 183 | VL-CDR1 | QANGYLN |

SEQUENCE TABLE

| SEQ ID NO | Description | Sequence |
|---|---|---|
| 184 | VL-CDR2 | DGSKLER |
| 185 | VL-CDR3 | QVYEF |
| 186 | 3BNC117 variable heavy (VH) chain amino acid sequence | QVQLLQSGAAVTKPGASVRVSCEASGYNIRDYFIHWWRQAPGQGLQWV GWINPKTGQPNNPRQFQGRVSLTRHASWDFDTFSFYMDLKALRSDDTA VYFCARQRSDYWDFDVWGSGTQVTVSS |
| 187 | VH-CDR1 | DYFIH |
| 188 | VH-CDR2 | WINPKTGQPNNPRQFQG |
| 189 | VH-CDR3 | QRSDYWDFDV |
| 190 | N6 variable light (VL) chain amino acid sequence | YIHVTQSPSSLSVSIGDRVTINCQTSQGVGSDLHWYQHKPGRAPKLLI HHTSSVEDGVPSRFSGSGFHTSFNLTISDLQADDIATYYCQVLQFFGR GSRLHIK |
| 191 | VL-CDR1 | QTSQGVGSDLH |
| 192 | VL-CDR2 | HTSSVED |
| 193 | VL-CDR3 | QVLQF |
| 194 | N6 variable heavy (VH) chain amino acid sequence | RAHLVQSGTAMKKPGASVRVSCQTSGYTFTAHILFWFRQAPGRGLEWV GWIKPQYGAVNFGGGFRDRVTLTRDVYREIAYMDIRGLKPDDTAVYYC ARDRSYGDSSWALDAWGQGTTVVVSA |
| 195 | VH-CDR1 | AHILF |
| 196 | VH-CDR2 | WIKPQYGAVNFGGGFRD |
| 197 | VH-CDR3 | DRSYGDSSWALDA |
| 198 | IOMA variable light (VL) chain amino acid sequence | QSALTQPASVSGSPGQSITISCAGSSRDVGGFDLVSWYQQHPGKAPKL IIYEVNKRPSGISSRFSASKSGNTASLTISGLQEEDEAHYYCYSYADG VAFGGGTKLTVL |
| 199 | VL-CDR1 | AGSSRDVGGFDLVS |
| 200 | VL-CDR2 | EVNKRPS |
| 201 | VL-CDR3 | YSYADGVA |
| 202 | IOMA variable heavy (VH) chain amino acid sequence | EVQLVESGAQVKKPGASVTVSCTASGYKFTGYHMHWVRQAPGRGLEWM GWINPFRGAVKYPQNFRGRVSMTRDTSMEIFYMELSRLTSDDTAVYYC AREMFDSSADWSPWRGMVAWGQGTLVTVSS |
| 203 | VH-CDR1 | GYHMH |
| 204 | VH-CDR2 | WINPFRGAVKYPQNFRG |
| 205 | VH-CDR3 | EMFDSSADWSPWRGMVA |

What is claimed is:

1. A multispecific antibody, or an antigen-binding fragment thereof, comprising:
   a) a first light chain comprising a first light chain variable region (VL) and a first heavy chain comprising a first heavy chain variable region (VH), wherein the first light chain and the first heavy chain are derived from a first antibody or an antigen-binding fragment thereof; and
   b) a second light chain comprising a second light chain variable region (VL) and a second heavy chain comprising a second heavy chain variable region (VH), wherein the second light chain and the second heavy chain are derived from a second antibody or an antigen-binding fragment thereof,
   wherein the first light chain and the second light chain bind non-overlapping epitopes of the envelope protein of human immunodeficiency virus-1 (HIV-1),
   wherein the VH from the first light chain and the VL from the second light chain are connected by one or more linkers or wherein the VL from the first light chain and the VH from the second light chain are connected by one or more linkers, and
wherein the multispecific antibody further includes a modification in the Fc region.

2. The multispecific antibody, or antigen binding fragment thereof, of claim 1, wherein the linker is not a single glycine (Gly) residue; a diglycine peptide (Gly-Gly); a tripeptide (Gly-Gly-Gly); a peptide with four glycine residues (Gly-Gly-Gly-Gly); a peptide with five glycine residues (Gly-Gly-Gly-Gly-Gly); a peptide with six glycine residues (Gly-Gly-Gly-Gly-Gly-Gly); a peptide with seven glycine residues (Gly-Gly-Gly-Gly-Gly-Gly-Gly); a peptide with eight glycine residues (Gly-Gly-Gly-Gly-Gly-Gly-Gly-Gly), the peptide Gly-Gly-Gly-Gly-Ser, the peptide Gly-Gly-Gly-Gly-Ser-Gly-Gly-Gly-Gly-Ser, the peptide Gly-Gly-Gly-Gly-Ser-Gly-Gly-Gly-Gly-Ser-Gly-Gly-Gly-Gly-Ser (SEQ ID NO: 292), a single Ser, a single Va, the dipeptide Arg-Thr, Gln-Pro, Ser-Ser, Thr-Lys, and Ser-Leu; Thr-Lys-Gly-Pro-Ser, Thr-Val-Ala-Ala-Pro, Gln-Pro-Lys-Ala-Ala, Gln-Arg-Ile-Glu-Gly, Ala-Ser-Thr-Lys-Gly-Pro-Ser, Arg-Thr-Val-Ala-Ala-Pro-Ser, Gly-Gln-Pro-Lys-Ala-Ala-Pro, and His-Ile-Asp-Ser-Pro-Asn-Lys.

3. The multispecific antibody of claim 1, wherein the non-overlapping epitopes are located in the CD4-binding site, the V1/V2-glycan region, the V3-glycan region, the gp41 membrane proximal external region (MPER), or the gp120/gp41 interface of the envelope protein.

4. The multispecific antibody of claim 1, further comprising a third antibody which specifically binds to a third epitope.

5. The multispecific antibody of claim 4, wherein the third epitope is located in the CD4-binding site (CD4bs), the V1/V2-glycan region, the V3-glycan region, the gp41 membrane proximal external region (MPER), or the gp120-gp41 interface of the envelope protein of HIV.

6. The multispecific antibody of claim 1, wherein the first antibody binds to an epitope in the CD4-binding site of the of the envelope protein of HIV-1 and the second antibody binds to an epitope in the V3-glycan region of the of the envelope protein of HIV-1; or, wherein the first antibody binds to an epitope in the V3-glycan region of the of the envelope protein of HIV-1 and the second antibody binds to an epitope in the CD4-binding site of the of the envelope protein of HIV-1.

7. The multispecific antibody of claim 1, wherein the first antibody binds to an epitope in the gp120/gp41 interface of the of the envelope protein of HIV-1 and the second antibody binds to an epitope in the WIPER of the of the envelope protein of HIV-1; or wherein the first antibody binds to an epitope in the WIPER of the of the envelop protein of HIV-1 and the second antibody binds to an epitope in the gp120/gp41 interface of the of the envelope protein of HIV-1.

8. The multispecific antibody of claim 1, wherein the variable domain of the first light chain comprises an amino acid sequence that is 95% identical to an amino acid sequence selected from the group consisting of: SEQ ID NO. 2, SEQ ID NO. 10, SEQ ID NO. 19, SEQ ID NO. 31 and SEQ ID NO. 39 and the variable domain of the first heavy chain comprises an amino acid sequence that is 95% identical to an amino acid sequence selected from the group consisting of: SEQ ID NO. 6, SEQ ID NO. 14, SEQ ID NO. 35 and SEQ ID NO. 43; wherein the variable domain of the second light chain comprises an amino acid sequence that is 95% identical to an amino acid sequence selected from the group consisting of: SEQ ID NO. 2, SEQ ID NO. 10, SEQ ID NO. 19, SEQ ID NO. 31 and SEQ ID NO. 39 and the variable domain of the second heavy chain comprises an amino acid sequence that is 95% identical to an amino acid sequence selected from the group consisting of: SEQ ID NO. 6, SEQ ID NO. 14, SEQ ID NO. 35 and SEQ ID NO. 43.

9. The multispecific antibody of claim 1, comprising an amino acid sequence that is 95% identical to an amino acid sequence selected from the group consisting of: SEQ ID NO. 1, SEQ ID NO. 18, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 30, SEQ ID NO. 47, SEQ ID NO. 48, SEQ ID NO. 49, SEQ ID NO. 50, SEQ ID NO. 51, SEQ ID NO. 52 and SEQ ID NO. 53.

10. A multispecific antibody, or an antigen-binding fragment thereof, comprising:
a) a first light chain comprising a first light chain variable region (VL) and a first heavy chain comprising a first heavy chain variable region (VH), wherein the first light chain and the first heavy chain are derived from a first antibody or an antigen-binding fragment thereof; and
b) a second light chain comprising a second light chain variable region (VL) and a second heavy chain comprising a second heavy chain variable region (VH), wherein the second light chain and the second heavy chain are derived from a second antibody or an antigen-binding fragment thereof,
wherein the first light chain and the second light chain bind non-overlapping epitopes of the envelope protein of human immunodeficiency virus-1 (HIV-1),
wherein the VH from the first light chain and the VL from the second light chain are connected by one or more linkers or wherein the VL from the first light chain and the VH from the second light chain are connected by one or more linkers, and
optionally wherein the multispecific antibody further comprises a third antibody which specifically binds to a third epitope, and
wherein the first antibody, the second antibody or the third antibody is an ScFv.

11. The multispecific antibody of claim 1, wherein the multispecific antibody has an IC50 less than 0.1 μg/ml.

12. The multispecific antibody of claim 1, wherein the multispecific antibody has an IC80 less than 0.3 μg/ml.

13. A method of treating or preventing an HIV infection, comprising administering to a subject in need thereof an effective amount of the multispecific antibody of claim 1.

14. A pharmaceutical composition comprising (i) the multispecific antibody of claim 1 and (ii) a pharmaceutically acceptable carrier.

15. A nucleic acid encoding the multispecific antibody of claim 1.

16. A vector comprising the nucleic acid of claim 15.

17. A host cell comprising the vector of claim 16.

18. An immunoconjugate comprising the multi specific antibody of claim 1 coupled to a cytotoxic agent.

* * * * *